United States Patent [19]

Bagley et al.

[11] Patent Number: 5,565,485
[45] Date of Patent: Oct. 15, 1996

[54] BIPHENYL COMPOUNDS USEFUL OR ENDOTHELIN ANTAGONISTS

[75] Inventors: Scott W. Bagley, Groton, Conn.; Theodore P. Broten, Ambler, Pa.; Prasun K. Chakravarty, Edison, N.J.; Daljit S. Dhanoa, Secaucus, N.J.; Kenneth J. Fitch, Scotch Plains, N.J.; William J. Greenlee, Teaneck, N.J.; Nancy J. Kevin, Clifton, N.J.; Douglas J. Pettibone, Chalfont, Pa.; Ralph A. Rivero, Tinton Falls, N.J.; Thomas F. Walsh, Westfield, N.J.; David L. Williams, Jr., Telford, Pa.; Richard B. Toupence, Cranford, N.J.; Jay M. Matthews, Fords, N.J.

[73] Assignee: Merck & Co., Inc., Rahway, N.J.

[21] Appl. No.: 294,232

[22] Filed: Aug. 22, 1994

Related U.S. Application Data

[63] Continuation-in-part of Ser. No. 287,374, Aug. 8, 1994, abandoned, which is a continuation-in-part of Ser. No. 197,467, Feb. 24, 1994, abandoned, which is a continuation-in-part of Ser. No. 34,455, Mar. 19, 1993, abandoned.

[51] Int. Cl.$^6$ .................. A61K 31/335; A61K 31/535; C07D 319/08; C07D 265/30
[52] U.S. Cl. .................. 514/452; 514/146; 514/231; 514/312; 514/347; 514/231.5; 514/381; 514/461; 514/464; 514/465; 514/469; 514/470; 514/869; 544/146; 546/153; 546/293; 548/253; 548/254; 549/220; 549/362; 549/434; 549/469
[58] Field of Search .................. 514/146, 231, 514/312, 347, 381, 452, 461, 464, 465, 466, 469, 470, 869; 549/220, 221, 362, 434, 436, 437, 438, 439, 440, 441, 443, 444, 445, 446, 447, 448, 469, 470, 471; 548/253, 254; 544/146; 546/153, 293

[56] References Cited

PUBLICATIONS

Naim et al., Indian J. Chem. Vol. 19B, pp. 622–623 1980.
Crenshaw et al., J. Org. Chem. vol. 47, pp. 101–104 1982.
Michael E. Jung et al., Heterocycles, vol. 30(2) pp. 839–853, 1990.
Saraiva et al., CA114(19): 185076t, 1990.
"Antihypertensive Effects of the Endothelin Receptor Antagonist BQ-123 n Conscious Spontaneously Hypetensive Rats" E. H. Ohlstein, et al. Journal of Cardiovascular Pharmacology, vol. 22, (Suppl. 8), 1993, pp. S321–S324.
"Direct and Sympathetically Mediated Vasoconstriction in Essential Hypertension" W. G. Haynes, et al. J. Clin. Invest., vol. 94, Oct. 1994, pp. 1359–1364.
"Role of Endothelin in Hypertension" B. K. Krämer, et al. Clin. Investig., vol. 72, (1994), pp. 88–93.
"Potential Role of Endothelin in Hypertension" T. F. Lüscher, et al. Hypertension, vol. 21, No. 6, Part 1, Jun. 1993, pp. 752–757.

"BQ123, An ET(A) Receptor Antagonist, Attenuates Hypoxic Pulmonary–Hypertension in Rats" Bonvallet, S. T., et al. American Journal of Physiology, vol. 266, No. 4, (Apr. 1994), pp. H1327–1331.
"Endothelin–A Receptor Antagonist Prevents Acute Hypoxia–Induced Pulmonary–Hypertension in the Rat" Oparil, S., et al. American Journal of Physiology–Lung Cellular and Molecular Physiology, vol. 12, No. 1, (Jan. 1995), pp. L95–L100.
"Protection from Pulmonary Hypertension with an Orally Active Endothelin Receptor Antagonist in Hypoxic Rats" American Journal of Physiology–Heart and Circulatory Physiology, vol. 37, No. 2, (Feb. 1995), pp. H828–H835.
"Endothelial Dysfunction and Remodeling of the Pulmonary Ciculation in Chronic Hypoxic Pulmonary–Hypertension" Dinhxuan, A. T., et al. ACP—Applied Cardiopulmonary Pathophysiology, vol. 5, No. 2, (1994), pp. 93–99.
"Cyclosporine–Induced Elevation in Circulating Endothelin–1 in Patients with Solid–Organ Transplants" Grieff, M., et al. Transplantation vol. 54, No. 4, (Oct. 1993), pp. 880–884.
"Cyclosporine–Induced Hypertension After Transplantation" Textor, S. C., et al. Mayo Clinical Proceedings, vol. 69, (1994), pp. 1182–1193.
"A Role of Endogenous Endothelin-1 in Neointimal Formation After Rat Carotid Artery Balloon Angioplasty" Douglas S. A., et al. Circulation Research, vol. 75, (1994), pp. 190–197.

(List continued on next page.)

*Primary Examiner*—Yogendra N. Gupta
*Attorney, Agent, or Firm*—Valerie J. Camara; Mark R. Daniel

[57] ABSTRACT

Phenoxyphenylacetic acids and derivatives of the general structural formula I

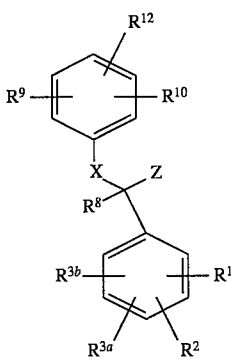

have endothelin antagonist activity and are useful in treating cardiovascular disorders, such as hypertension, postischemic renal failure, vasospasm, cerebral and cardiac ischemia, myocardial infarction, endotoxic shock, benign prostatic hyperplasia, inflammatory diseases including Raynaud's disease and asthma.

23 Claims, No Drawings

PUBLICATIONS

"[125I]–Endothelin–1 Binding to Vasa Vasorum and Regions of Neovascularization in Human and Porcine–Blood Vessels: A Possible Role for Endothelin in Intimal Hyperplasia and Atheroscelerosis" Dashwood, M. R., et al. Journal of Cardiovascular Pharmacology, vol. 22, (Suppl. 8), (1993), pp. S343–347.

"The Endothelin–1 Receptor Antagonist BQ–123 Reduces Infarct Size in a Canine Model of Coronary Occlusion and Reperfusion" Grover, G. J., et al. Cardiovascular Research, vol. 75, No. 9, (Sep. 1993), pp. 1613–1618.

"The Effects of the Endothelin ETa Receptor Antagonist, FR139317, on Infarct Size in a Rabbit Model of Acute Myocardial Ischemia and Reperfusion" McMurdo, L., et al. British Journal of Pharmacology, (1994), vol. 112, pp. 75–80.

"Vasodilator Effects of the Endothelin–1 Receptor Antagonist Bosentan in Patients with Severe Chronic Heart Failure" Kiowski, W., et al. Journal Am. College of Cardiology, Feb. 1995, pp. 296A, abstract No. 779–1.

"Nonpeptide Endothelin Receptor Antagonists. III, Effect of SB 209670 and BQ123 on Acute Renal Failure in Anesthetized Dogs" Brooks, D. P., et al. Journal of Pharmacology and Experimental Therapeutics, vol. 271, (1994), pp. 769–775.

"Reversal of Postischemic Acute Renal Failure with a Selective Endothelin$_A$ Receptor Antagonist in the Rat" Gellai, M., et al. Journal of Clinical Investigator, vol. 93, (1994), pp. 900–906.

"Effects of BQ–123 on Renal–Function and Acute Cyclosporine Induced Renal Dysfunction", Kivlighn, S. D. et al., Kidney International, vol. 45, No. 1, (Jan. 1994), pp. 131–136.

"Endotoxin–Mediated Changes In Plasma Endothelin Concentrations, Renal Endothelin Receptor And Renal–Function", Nambi, P. et al., vol. 48, No. 3, (Mar. 1994), pp. 147–156.

"Effect of Total–Body Cold–Exposure on Plasma–Concentrations of Vonwillebrand–Factor, Endothelin–1 Thrombomodulin in Systemic Lupus–Erythematosus Patients with or without Raynauds–Phenomeon", Matsuda, J.,et al. Acta Haematologica, vol. 88, No. 4, (1992), pp. 189–193.

"Localization of Endothelin–1 and Its Binding–Sites in Scleroderma Skin" Vancheeswaran, R., et al. Journal of Rheumatology, vol. 21, No. 7, (Jul. 1994), pp. 1268–1276.

"Increased Endothelin–1 Production in Fibroblasts Derived from Patients with Systemic–Sclerosis" Kawaguchi, Y., et al. Annals of the Rheumatic Diseases, vol. 53, No. 8, (Aug. 1994), pp. 506–510.

"Characterization of Endothelin–Binding Sites in Human Skin and Their Regulation in Primary Raynauds–Phenomenon and Systemic–Sclerosis" Knock G. A., et al. Journal of Investigative Dermatology, vol. 101, No. 1, (Jul. 1993), pp. 73–78.

"Raynaud–Phenomenon" Coffman, J. D., et al. Current Opinion in Cardiology, vol. 8, No. 5, (Sep. 1993), pp. 821–828.

"Parameters of Vascular Function in Idiopathic and Silica–Induced Systemic–Sclerosis" Haustein, U. F., et al. Hautarzt, vol. 44, No. 11, (Nov. 1993), pp. 717–722.

"Circulating Endothelin–1 Levels in Systemic–Sclerosis Subsets—A Marker of Fibrosis or Vascular Dysfunction" Vancheeswaran, R., et al. Journal of Rheumatology, vol. 21, No. 10, (Oct. 1994), pp. 1838–1844.

"Endothelin and Collagen Vascular Disease: A Review with Special Reference to Raynauds–Phenomenon and Systemic–Sclerosis" Yamane, K. Internal Medicine, vol. 33, No. 10, (Oct. 1994), pp. 579–582.

"A Pathogenic Role for Endothelin in Raynauds–Phenomenon" Bottomley, W., et al. Acta Dermato–Venereologica, vol. 74, No. 6, (Nov. 1994), pp. 433–434.

"BQ 123, A Peptidic Endothelin ETA Receptor Antagonist, Prevents the Early Cerebral Vasospasm Following Subarachnoid Hemorrhage After Interacisternal but not Intravenous–Injection" Clozel, M., et al. Life Sciences, vol. 52, No. 9, (1993), pp. 825–834.

"An Endothelin ET(A) Receptor Antagonist, FR139317, Ameliorates Cerebral Vasospasm in Dogs" Nirei, H., et al. Life Sciences, vol. 52, No. 23, (1993), pp. 1869–1874.

"Reversal of Subarachnoid Hemorrhage–Induced Vasoconstriction with an Endothelin Receptor Antagonist" Foley, P. L. et al. Neurosurgery, vol. 34, No. 1, (Jan. 1994), pp. 108–113.

"Endothelin Levels Increase in Rat Focal and Global–Ischemia" Barone, F. C., et al. Journal of Cerebral Blood Flow and Metabolism, vol. 14, No. 2, (Mar. 1994), pp. 337–342.

"Endothelin ET(A) and ET(B) Receptors in Subarachnoid Hemorrhage–Induced Cerebral Vasospasm" Zuccarello, M., et al. European Journal of Pharmacology, vol. 259, No. 1, (Jun. 23 1994), pp. R1–R2.

"Changes of Endothelin Concentration in Cerebrospinal–Fluid and Plasma of Patients with Aneurysmal Subarachnoid Hemorrhage" Shirakami, G., et al. Acta Anaesthesiologica Scandinavica, vol. 38, No. 5, (Jul. 1994), pp. 457–461.

"Prevention of Delayed Vasospasm by an Endothelin ET(A) Receptor Antagonist, BQ–123—Change of ET(A) Receptor Messenger–RNA Expression in a Canine Subarachnoid Hemorrhage Model" Itoh, S., et al., Journal of Neurosurgery, vol. 81, No. 5, (Nov. 1994), pp. 759–764.

"Endothelin Concentrations in Patients with Aneurysmal Subarachnoid Hemorrhage—Correlation with Cerebral Vasospasm, Delayed Ischemic Neurological Deficits, and Volume of Hematoma" Seifert V., et al. Journal of Neurosurgery, vol. 82, No. 1, (Jan. 1995), pp. 55–62.

BIPHENYL COMPOUNDS USEFUL OR ENDOTHELIN ANTAGONISTS

RELATED APPLICATIONS

The present application is a continuation in part application of Case 18893IB, U.S. Ser. No. 08/287,374 filed Aug. 8, 1994, abandoned, which is a continuation in part application of U.S. Ser. No. 08/197,467 filed Feb. 24, 1994, abandoned, which is a continuation in part application of U.S. Ser. No. 08/034,455 filed on Mar. 19, 1993 (abandoned).

SUMMARY OF THE INVENTION

This invention is concerned with non-peptidic endothelin receptor antagonists represented by the compound of Formula I, pharmaceutical compositions containing these compounds, as well as combination therapies which include a compound of the present invention. The compounds of the present invention are therapeutic agents particularly useful for the treatment of asthma, hypertension, pulmonary hypertension, arteriosclerosis, congestive heart failure, renal failure, particularly post-ischemic renal failure, cyclosporin nephrotoxicity, vasospasm, vascular restenosis, cerebral and cardiac ischemia and other ischemic states, myocardial infarction, Raynaud's disease, benign prostatic hyperplasia, inflammatory bowel diseases, including Crohn's disease and ulcerative colitis, as well as other inflammatory diseases, or endotoxic shock caused by or associated with endothelin.

This invention further constitutes a method for antagonizing endothelin receptors in a mammal, including humans, which comprises administering to a mammal in need of such treatment an effective amount of a compound of Formula I.

BACKGROUND OF THE INVENTION

Endothelin is a 21-amino acid peptide produced by endothelial cells. The peptide is secreted not only by endothelial cells but also by tracheal epithelial cells or from kidney cells. Endothelin (ET-1) has a potent vasoconstrictor effect. The vasoconstricting effect is caused by the binding of endothelin to its receptor on the vascular smooth muscle cells.[1-3]

Endothelin-1 (ET-1) is one of three recently identified potent vasoconstricting peptides which also includes endothelin-2 (ET-2) and endothelin-3 (ET-3) whose sequences differ from ET-1 by two and six amino acids, respectively.[4]

Increased levels of endothelin are found in the blood of patients with essential hypertension, acute myocardial infarction, pulmonary hypertension, Raynaud's disease or atherosclerosis or in the washing fluids of the respiratory tract of patients with asthma compared to normal levels.[5-8]

An experimental model of cerebral vasospasm and a second model of acute renal failure have led to the conclusion that endothelin is one of the mediators causing cerebral vasospasm following a subarachnoid hemorrhage, and renal failure.[9-10]

Endothelin was also found to control the release of many physiological substances such as renin, atrial natriuretic peptide, endothelium-derived relaxing factor (EDRF), thromboxane $A_2$,[14] prostacyclin, norepinephrine, angiotensin II and substance P.[11-16] Further, endothelin causes contraction of the smooth muscle of the gastrointestinal tract[17-19] and the uterine smooth muscle.[17-19] Endothelin has also been shown to promote the growth of rat vascular smooth muscle cells which would suggest a possible relevance to arterial hypertrophy.[20]

Endothelin receptors are present in high concentration in the peripheral tissues and also in the central nervous system, and cerebral administration of endothelin has been shown to induce behavioral changes in animals, suggesting that endothelin may play an important role in controlling neural functions.[21]

Endotoxin has been shown to promote the release of endothelin. This finding has suggested that endothelin is an important mediator for endotoxin-induced diseases.[22-23]

A study has shown that cyclosporin added to a renal cell culture, increased endothelin secretion.[24] Another study has shown that administration of cyclosporin to rats, led to a decrease in the glomerular filtration rate and an increase in the blood pressure, in association with a remarkable increase in the circulating endothelin level. This cyclosporin-induced renal failure can be suppressed by the administration of anti-endothelin antibody.[25] These studies suggest that endothelin is significantly involved in the pathogenesis of cyclosporin-induced renal disease.

A recent study in patients with congestive heart failure demonstrated a good correlation between the elevated levels of endothelin in the plasma and the severity of the disease.[26]

Endothelin is an endogenous substance which directly or indirectly (through the controlled release of various other endogenous substances) induces sustained contraction of vascular or non-vascular smooth muscles. Its excess production or excess secretion is believed to be one of the factors responsible for hypertension, pulmonary hypertension, Raynaud's disease, bronchial asthma, acute renal failure, myocardial infarction, angina pectoris, arteriosclerosis, cerebral vasospasm and cerebral infarction. See A. M. Doherty, *Endothelin: A New Challenge*, J. Med. Chem., 35, 1493–1508 (1992).

Substances which specifically inhibit the binding of endothelin to its receptor are believed to block the physiological effects of endothelin and are useful in treating patients with endothelin related disorders.

The novel compounds of the present invention are useful as a non-peptidic endothelin antagonists, and have not been disclosed in any issued patents or published patent applications. Among the published patent applications disclosing linear and cyclic peptidic compounds as endothelin antagonists are the following: Fujisawa in European Patent Application EP-457,195 and Patent Cooperation Treaty (PCT) International Application No. WO 93/10144, Banyu in EP-436,189 and 460,679, Immunopharmaceutics Inc. in WO 93/225580, Warner Lambert Co. WO 92/20706 and Takeda Chemical Ind. in EP-528,312, EP-543,425, EP-547, 317 and WO 91/13089.

Fujisawa has also disclosed two nonpeptidic endothelin antagonist compounds: anthraquinone derivatives produced by a fermentation process using Streptomyces sp. No. 89009 in EP-405,421 and U.S. Pat. No. 5,187,195; and a 4-phenoxyphenol derivative produced by a fermentation process using *Penicillium citreonigrum* F-12880 in a UK Patent Application GB 2259450. Shionogi and Co. has also disclosed nonpeptidic endothelin antagonist triterpene compounds which were produced by a fermentation process using *Myrica cerifera* in WO 92/12991.

Among the nonopeptidic endothelin antagonist compounds which are known in the patent literature are: 1) a series of substituted (1,4-quinolinoxy)methylbiphenylcarboxylic acids disclosed by Roussel-Uclaf in EP-498,723; 2) a series of of N-(4-pyrimidinyl)benzenesulfonamides with different substitution patterns from Hoffmann-La Roche published in EP-510,526, EP-526,708 and EP-601,386; 3) a series of naphthalenesulfonamides and benzenesulfonamides disclosed by E. R. Squibb & Sons in EP-558,258 and EP-569,193, respectively; 4) a series of compounds represented by 3-(3-indolylmethyl)-1,4-diaza-2,5-dioxobicyclo [4.3.0]nonane-9-carboxylic acid from ImmunoPharmaceutics Inc. in WO 93/23404; 5) a series of fused [1,2,4] thiadiazoles substituted with an iminosulfonyl substituent from Takeda Chemical Ind. has been disclosed in EP-562,599; and 6) a series of indane and indene derivatives from SmithKline Beecham Corp. disclosed in WO 93/08779; and a series of related phenylalkyl derivatives from SmithKline Beecham disclosed in WO 94/02474.

REFERENCES

1 Nature, 332, 411–415 (1988).

2 FEBS Letters, 231, 440–444 (1988).

3 Biochem. Biophys. Res. Commun. 154, 868–875 (1988).

4 TiPS, 13, 103–108, March 1992.

5 Japan J. Hypertension 12, 79 (1989).

6 J. Vascular Medicine Biology, 2, 207 (1990).

7 J. Am. Med. Association, 264, 2868 (1990).

8 The Lancet, ii, 207 (1990) and The Lancet, ii, 747–748 (1989).

9 Japan. Soc. Cereb. Blood Flow & Metabol. 1, 73 (1989).

10 J. Clin. Invest., 83, 1762–1767 (1989).

11 Biochem. Biophys. Res. Comm. 157, 1164–1168 (1988).

12 Biochem. Biophys. Res. Comm. 155, 167–172 (1989).

13 Proc. Natl. Acad. Sci. USA, 85, 9797–9800 (1989).

14 J. Cardiovasc. Pharmacol., 13, 589–592 (1989).

15 Japan. J. Hypertension 12, 76 (1989).

16 Neuroscience Letters, 102, 179–184 (1989).

17 FEBS Letters, 247, 337–340 (1989).

18 Eur. J. Pharmacol. 154, 227–228 (1988).

19 Biochem. Biophys. Res. Commun., 159, 317–323 (1989).

20 Atherosclerosis, 78, 225–228 (1989).

21 Neuroscience Letters, 97, 276–279 (1989).

22 Biochem. Biophys. Res. Commun. 161, 1220–1227 (1989).

23 Acta. Physiol. Scand., 137, 317–318 (1989).

24 Eur. J. Pharmacol., 180, 191–192 (1990).

25 Kidney Int. 37, 1487–1491 (1990).

26 Mayo Clinic Proc., 67, 719–724 (1992).

DETAILED DESCRIPTION OF THE INVENTION

This invention is concerned with novel compounds of structural formula I:

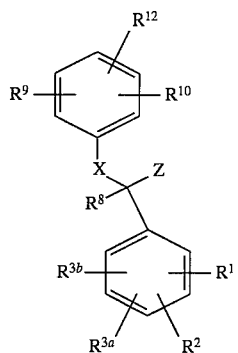

or a pharmaceutically acceptable salt thereof, wherein:
$R^1$, $R^2$, $R^{3a}$ and $R^{3b}$ are independently:
  (a) H,
  (b) F, Cl, Br, or I,
  (c) —$NO_2$,
  (d) —$NH_2$,
  (e) —NH($C_1$–$C_4$)-alkyl,
  (f) —N[($C_1$–$C_4$)-alkyl]$_2$,
  (g) —$SO_2NHR^7$,
  (h) —$CF_3$,
  (i) ($C_1$–$C_6$)-alkyl,
  (j) —$OR^7$,
  (k) —S(O)$_n$—($C_1$–$C_4$)-alkyl,
  (l) —NHCO—($C_1$–$C_4$)-alkyl,
  (m) —NHCO—O($C_1$–$C_4$)-alkyl,
  (n) —$CH_2$O—($C_1$–$C_4$)-alkyl,
  (o) —O—($CH_2$)$_m$—$OR^7$,
  (p) —$CONR^7R^{11}$,
  (q) —$COOR^7$, or
  (r) —phenyl;
$R^1$ and $R^2$ on adjacent carbon atoms can be joined together to form a ring structure:

A represents:
  a) —Y—C($R^4$)=C($R^5$)—,
  b) —Y—C($R^4$)=N—,
  c) —Y—N=C($R^4$)—,
  d) —Y—[C($R^6$)($R^6$)]$_s$—Y—,
  e) —Y—C($R^6$)($R^6$)—C($R^6$)($R^6$)—,
  f) —C($R^4$)=C($R^5$)—Y—,
  g) —N=C($R^4$)—Y—,
  h) —C($R^6$)($R^6$)—C($R^6$)($R^6$)—Y—, or
  i) —C($R^4$)=C($R^5$)—C($R^4$)=C($R^5$)—;
n is 0, 1 or 2;
m is 2, 3 or 4;
s is 1 or 2;
Y is —O—, —S(O)$_n$— and $NR^7$;
$R^4$ and $R^5$ are independently:
  (a) H, (b) $(C_1-C_6)$-alkyl or $(C_2-C_6)$-alkenyl each of which is unsubstituted or substituted with one or two substiments selected from the group consisting of:
  i) —OH,
  ii) —O—$(C_1-C_4)$-alkyl,
  iii) —S(O)$_n$—$(C_1-C_4)$-alkyl,
  iv) —NR$^7$—$(C_1-C_4)$-alkyl,
  v) —NHR$^7$,
  vi) —COOR$^7$,
  vii) —CONHR$^7$,
  viii) —OCOR$^{11}$, or
  ix) —CONR$^7$R$^{11}$,
(c) $(C_3-C_7)$-cycloalkyl,
(d) F, Cl, Br, I,
(e) CF$_3$,
(f) —COOR$^7$,
(g) —CONR$^7$R$^{11}$,
(h) —NR$^7$R$^{11}$,
(i) —NR$^7$CONR$^7$R$^{11}$,
(j) —NR$^7$COOR$^{11}$,
(k) —SO$_2$NR$^7$R$^{11}$,
(l) —O—$(C_1-C_4)$-alkyl,
(m) —S(O)$_n$—$(C_1-C_4)$-alkyl, or
(n) —NHSO$_2$R$^{11}$;

R$^6$ is:
(a) H,
(b) $(C_1-C_4)$-alkyl unsubstituted or substituted with one of the following substituents:
  i) —OH,
  ii) —NR$^7$R$^{11}$,
  iii) —COOR$^7$,
  iv) —CONHR$^7$, or
  v) —CONR$^7$R$^{11}$, or
(c) Cl, or F;

R$^7$ is:
(a) H,
(b) $(C_1-C_6)$-alkyl,
(c) phenyl,
(d) $(C_1-C_6)$-alkylphenyl, or
(e) $(C_3-C_7)$-cycloalkyl;

R$^8$ is:
(a) H,
(b) $(C_1-C_6)$-alkyl, unsubstimted or substituted with a substiment selected from the group consisting of:
  (i) —phenyl,
  (ii) —$(C_3-C_7)$-cycloalkyl,
  (iii) —NR$^7$R$^{11}$,
  (iv) —morpholin-4-yl,
  (v) —OH,
  (vi) —CO$_2$R$^7$, or
  (vii) —CON(R$^7$)$_2$,
(c) phenyl, unsubstimted or substituted with a substituent selected from the group consisting of:
  i) $(C_1-C_4)$-alkyl
  ii) —O—$(C_1-C_4)$-alkyl
  iii) —CONR$^7$R$^{11}$,
  iv) F, Cl, Br or I, or
  v) —COOR$^7$;

R$^9$ and R$^{10}$ are independently:
(a) H,
(b) $(C_1-C_6)$-alkyl, unsubstituted or substituted with $(C_3-C_7)$-cycloalkyl or —CO$_2$R$^7$, (c) $(C_2-C_6)$-alkenyl,
(d) $(C_2-C_6)$-alkynyl,
(e) Cl, Br, F, I,
(f) $(C_1-C_6)$-alkoxy,
(g) perfluoro-$(C_1-C_6)$-alkyl,
(h) $(C_3-C_7)$-cycloalkyl, unsubstituted or substituted with $(C_1-C_6)$-alkyl,
(i) phenyl,
(j) $(C_1-C_6)$-alkyl—S(O)$_n$—(CH$_2$)$_n$—,
(k) hydroxy-$(C_1-C_6)$-alkyl,
(l) —CF$_3$,
(m) —CO$_2$R$^7$,
(n) —OH,
(o) —NR$^7$R$^{11}$,
(p) —[$(C_1-C_6)$-alkyl]NR$^7$R$^{11}$,
(q) —NO$_2$,
(r) —(CH$_2$)$_n$—SO$_2$—N(R$^7$)$_2$,
(s) —NR$^7$CO—$(C_1-C_4)$-alkyl, or
(t) —CON(R$^7$)$_2$;

R$^9$ and R$^{10}$ on adjacent carbons can join together to form a fused phenyl ring, unsubstituted or substituted with a substituent selected from the group consisting of: $(C_1-C_6)$-alkyl, $(C_1-C_6)$-alkoxy, $(C_3-C_7)$-cycloalkyl and $(C_1-C_6)$-alkyl-$(C_3-C_7)$-cycloalkyl, R$^{11}$ is
(a) $(C_1-C_6)$-alkyl, unsubstimted or substituted with a substituent selected from the group consisting of:
  i) —OR$^7$,
  ii) —N[R$^7$]$_2$,
  iii) —NH$_2$,
  iv) —COOR$^7$,
  v) —N[CH$_2$CH$_2$]$_2$Q,
  vi) —CF$_3$, or
  vii) —CON(R$^7$)$_2$;
(b) aryl, wherein aryl is defined as phenyl or naphthyl which is unsubstituted or substituted with one or two substituents selected from the group consisting of:
  i) $(C_1-C_4)$-alkyl,
  ii) —O—$(C_1-C_4)$-alkyl,
  iii) —CO[NR$^7$]$_2$,
  iv) F, Cl, Br or I,
  v) —COOR$^7$,
  vi) —NH$_2$,
  vii) —NH[$(C_1-C_4)$-alkyl],
  viii) —N[$(C_1-C_4)$-alkyl]$_2$, or
  ix) —CON[CH$_2$CH$_2$]$_2$Q;
(c) —$(C_1-C_4)$-alkylaryl, wherein aryl is as defined above,
(d) $(C_3-C_7)$-cycloalkyl, (e) 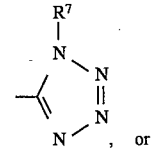, or R$^7$ and R$^{11}$ on the same nitrogen atom they can join together to form a ring selected from the group consisting of: morpholinyl, piperazinyl, or pyrrolyl, or Q is O, S or —NR$^7$;

R$^{12}$ is
(a) H
(b) $(C_1-C_6)$-alkyl, unsubstituted or substituted with one or two substituents selected from the group consisting of:

i) —OH,
ii) —O—($C_1$–$C_4$)-alkyl,
iii) —O—($C_1$–$C_4$)-cycloalkyl,
iv) —S(O)$_n$—($C_1$–$C_4$)-alkyl,
v) —NR$^7$R$^{11}$,
vi) —COOR$^7$,
vii) —CONHR$^7$,
viii) —OCOR$^{11}$,
ix) —CONR$^7$R$^{11}$,
x) —NR$^7$CONR$^7$R$^{11}$,
xi) —NR$^7$COOR$^{11}$,
xii) —C(R$^6$)(OH)—C(R$^6$)(R$^7$)(OH),
xiii) —SO$_2$NR$^7$R$^{11}$,
xiv) CN, or xv) 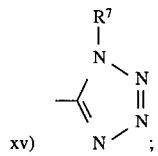

(c) ($C_3$–$C_7$)-cycloalkyl,
(d) —OR$^7$,
(e) —COOR$^7$,
(f) —CONH$_2$,
(g) —CONR$^{16}$OR$^7$,
(h) —CONR$^7$R$^{11}$,
(i) —CONR$^7$CO$_2$R$^7$,
(j) —NH$_2$,
(k) —NR$^7$R$^{11}$,
(l) —NR$^7$CONR$^7$R$^{11}$,
(m) —NR$^7$COOR$^{11}$,
(n) —C(R$^6$)(OH)—C(R$^6$)(R$^7$)(OH),
(o) —SO$_2$NR$^7$R$^{11}$,
(p) —S(O)$_2$NR$^7$COR$^{11}$,
(q) —S(O)$_2$NR$^7$COR$^{11}$,
(r) —S(O)$_2$NR$^7$CONR$^{11}$,
(s) —NHSO$_2$R$^{11}$,
(t) NR$^7$SO$_2$NR$^7$R$^{11}$,
(u) —CONHSO$_2$R$^{11}$,
(v) —CO-amino acid, wherein amino acid is defined as an L- or D-amino acid selected from the group consisting of Ala, Ile, Phe, Asp, Pro and Val and which can be further substituted as a ($C_1$–$C_6$)-alkyl ester or an amide, or (w) 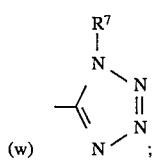

X is:
(a) —O—,
(b) —S(O)$_n$—,
(c) —NR$^7$—,
(d) —CH$_2$O—,
(e) —CH$_2$S(O)$_n$—,
(f) —CH$_2$NR$^7$—,
(g) —OCH$_2$—,
(h) —N(R$^7$)CH$_2$—, (i) —S(O)$_n$CH$_2$—, or
(j) —single bond;

Z is:
(a) —CO$_2$H,
(b) —CO$_2$R$^{13}$,
(c) —CONH-(tetrazol-5-yl),
(d) —CONHSO$_2$OR$^{11}$,
(e) —CONHSO$_2$NR$^7$R$^{11}$,
(f) —CONHSO$_2$-aryl, wherein aryl is defined as phenyl or naphthyl which is unsubstimted or substituted with one, two or three substituents selected from the group consisting of:
  i) ($C_1$–$C_4$)-alkyl,
  ii) —O—($C_1$–$C_4$)-alkyl,
  iii) —CONR$^7$R$^{11}$,
  iv) F, Cl, Br or I,
  v) —COOR$^7$,
  vi) —NH$_2$,
  vii) —NH[($C_1$–$C_4$)-alkyl],
  viii) —N[($C_1$–$C_4$)-alkyl]$_2$,
  ix) —phenyl,
  x) —OH,
  xi) —OCH$_2$CH$_2$OH,
  xii) —CF$_3$;
(g) —CONHSO$_2$—($C_1$–$C_8$)-alkyl, wherein the alkyl group is unsubstituted or substituted as defined in R$^4$(b),
(h) —CONHSO$_2$—($C_1$–$C_4$)-perfluoroalkyl,
(i) —tetrazol-5-yl,
(j) —CONHSO$_2$-heteroaryl, wherein heteroaryl is defined as carbazolyl, furyl, thienyl, pyrrolyl, isothiazolyl, imidazolyl, isoxazolyl, thiazolyl, oxazolyl, pyrazolyl, pyrazinyl, pyridyl, pyrimidyl, purinyl or quinolinyl, which is unsubstituted or substituted with one, two or three substituents selected from the group consisting of:
  i) ($C_1$–$C_4$)-alkyl,
  ii) —($C_1$–$C_4$)-alkyl,
  iii) —CONR$^7$R$^{11}$,
  iv) F, Cl, Br or I,
  v) —COOR$^7$,
  vi) —NR$^7$CONR$^7$R$^{11}$, and
  vii) —NR$^7$COOR$^{11}$;
(k) —SO$_2$NHCO-aryl, wherein aryl is defined in Z(f) above,
(l) —SO$_2$NHCO—($C_1$–$C_8$)-alkyl, wherein the alkyl group is unsubstituted or substituted as defined in R$^4$(b),
(m) —SO$_2$NHCO—($C_1$–$C_4$)-perfluoroalkyl,
(n) —SO$_2$NHCO-heteroaryl, wherein heteroaryl is as defined in Z(j) above,
(o) —SO$_2$NHCON(R$^{11}$)$_2$ wherein the R$^{11}$ groups are the same or different,
(p) —PO(OR$^7$)$_2$, wherein the R$^7$ groups are the same or different, or
(q) —PO(R$^{11}$)OR$^7$;

R$^{13}$ is:
(a) ($C_1$–$C_4$)-alkyl,
(b) CHR$^{14}$—O—COR$^{15}$,
(c) CH$_2$CH$_2$—N[($C_1$–$C_2$)-alkyl]$_2$,
(d) CH$_2$CH$_2$—N[CH$_2$CH$_2$]$_2$O,
(e) (CH$_2$CH$_2$O)$_y$—O—[($C_1$–$C_4$)-alkyl], wherein y is 1 or 2,
(f) phenyl, naphthyl, CH$_2$-phenyl or CH$_2$-naphthyl, where phenyl or naphthyl is substituted or unsubstituted with $CO_2$—$(C_1$–$C_4)$-alkyl, (g) 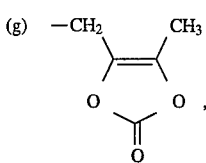

(h) 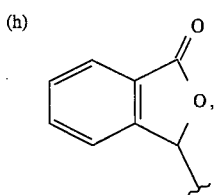

(i) 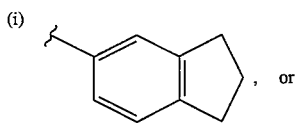, or (j) 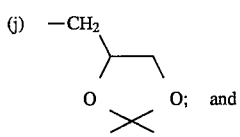

$R^{14}$ and $R^{15}$ independently are $(C_1$–$C_6)$-alkyl or phenyl; and $R^{16}$ is H, $(C_1$–$C_6)$-alkyl or $(C_1$–$C_6)$-alkylphenyl.

An embodiment of the invention is the compound of structural formula II:

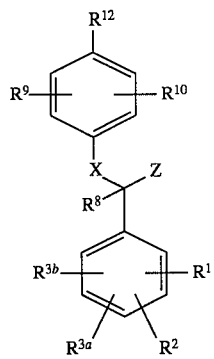    II or a pharmaceutically acceptable salt thereof, wherein:
$R^1$, $R^2$, $R^{3a}$ and $R^{3b}$ are independently:
- (a) H,
- (b) F, Cl, Br, or I,
- (c) —$NO_2$,
- (d) —$NH_2$,
- (e) —$NH(C_1$–$C_4)$-alkyl,
- (f) —$N[(C_1$–$C_4)$-alkyl]$_2$,
- (g) —$SO_2NHR^7$,
- (h) —$CF_3$,
- (i) $(C_1$–$C_6)$-alkyl,
- (j) —$OR^7$,
- (k) —$S(O)_n$—$(C_1$–$C_4)$-alkyl,
- (l) —NHCO—$(C_1$–$C_4)$-alkyl,
- (m) —NHCO—$O(C_1$–$C_4)$-alkyl,
- (n) —$CH_2O$—$(C_1$–$C_4)$-alkyl,
- (o) —O—$(CH_2)_m$—$OR^7$,
- (p) —$CONR^7R^{11}$, or
- (q) —$COOR^7$;

$R^1$ and $R^2$ on adjacent carbon atoms can be joined together to form a ring structure:

A represents:
- a) —Y—$C(R^4)$=$C(R^5)$—,
- b) —Y—$C(R^4)$=N—,
- c) —Y—N=$C(R^4)$—,
- d) —Y—$[C(R^6)(R^6)]_s$—Y—,
- e) —Y—$C(R^6)(R^6)$—$C(R^6)(R^6)$—,
- f) —$C(R^4)$=$C(R^5)$—Y—,
- g) —N=$C(R^4)$—Y—,
- h) —$C(R^6)(R^6)$—$C(R^6)(R^6)$—Y—, or
- i) —$C(R^4)$=$C(R^5)$—$C(R^4)$=$C(R^5)$—;

m is 2, 3 or 4,
n is 0, 1 or 2,
s is 1 or 2,
Y is —O—, —$S(O)_n$— and $NR^7$;
$R^4$ and $R^5$ are independently:
- (a) H,
- (b) $(C_1$–$C_6)$-alkyl or $(C_2$–$C_6)$-alkenyl each of which is unsubstituted or substituted with one or two substituents selected from the group consisting of:
  - i) —OH,
  - ii) —O—$(C_1$–$C_4)$-alkyl,
  - iii) —$S(O)_n$—$(C_1$–$C_4)$-alkyl,
  - iv) —$NR^7$—$(C_1$–$C_4)$-alkyl,
  - v) —$NHR^7$,
  - vi) —$COOR^7$,
  - vii) —$CONHR^7$,
  - viii) —$OCOR^{11}$, or
  - ix) —$CONR^7R^{11}$,
- (c) $(C_3$–$C_7)$-cycloalkyl,
- (d) F, Cl, Br, I,
- (e) $CF_3$,
- (f) —$COOR^7$,
- (g) —$CONR^7R^{11}$,
- (h) —$NR^7R^{11}$,
- (i) —$NR^7CONR^7R^{11}$,
- (j) —$NR^7COOR^{11}$,
- (k) —$SO_2NR^7R^{11}$,
- (l) —O—$(C_1$–$C_4)$-alkyl,
- (m) —$S(O)_n$—$(C_1$–$C_4)$-alkyl, or
- (n) —$NHSO_2R_{11}$;

$R^6$ is:
- (a) H,
- (b) $(C_1$–$C_4)$-alkyl unsubstimted or substituted with one or two substituents selected from the group consisting of:
  - i) —OH,
  - ii) —$NR^7R^{11}$,
  - iii) —$COOR^7$,
  - iv) —$CONHR^7$, or
  - v) —$CONR^7R^{11}$, or
- (c) Cl, or F;

$R^7$ is:
- (a) H,
- (b) $(C_1$–$C_6)$-alkyl,
- (c) phenyl,
- (d) $(C_1$–$C_6)$-alkylphenyl, or (e) $(C_3-C_7)$-cycloalkyl;

$R^8$ is:
(a) H,
(b) $(C_1-C_6)$-alkyl, unsubstituted or substituted with one or two substituents selected from the group consisting of:
(i) —phenyl,
(ii) —$(C_3-C_7)$-cycloalkyl,
(iii) —$NR^7R^{11}$,
(iv) —morpholin-4-yl,
(v) —OH,
(vi) —$CO_2R^7$, or
(vii) —$CON(R^7)_2$, or
(c) phenyl;

$R^9$ and $R^{10}$ are independently:
(a) H,
(b) $(C_1-C_6)$-alkyl, unsubstituted or substituted with $(C_3-C_7)$-cycloalkyl or —$CO_2R^7$,
(c) $(C_2-C_6)$-alkenyl,
(d) $(C_2-C_6)$-alkynyl,
(e) Cl, Br, F, I,
(f) $(C_1-C_6)$-alkoxy,
(g) perfluoro-$(C_1-C_6)$-alkyl,
(h) $(C_3-C_7)$-cycloalkyl, unsubstituted or substituted with $(C_1-C_6)$-alkyl,
(i) phenyl,
(j) $(C_1-C_6)$-alkyl-$S(O)_n$—$(CH_2)_n$—,
(k) hydroxy-$(C_1-C_6)$-alkyl,
(l) —$CF_3$,
(m) —$CO_2R^7$,
(n) —OH,
(o) —$NR^7R^{11}$,
(p) —$[(C_1-C_6)$-alkyl$]NR^7R^{11}$,
(q) —$NO_2$,
(r) —$(CH_2)_n$—$SO_2$—$N(R^7)_2$,
(s) —$NR^7CO$—$(C_1-C_4)$-alkyl, or
(t) —$CON(R^7)_2$;

$R^9$ and $R^{10}$ on adjacent carbons can join together to form a fused phenyl ring, unsubstituted or substituted with a substituent selected from the group consisting of: $(C_1-C_6)$-alkyl, $(C_1-C_6)$-alkoxy, $(C_3-C_7)$-cycloalkyl and $(C_1-C_6)$-alkyl-$(C_3-C_7)$-cycloalkyl, $R^{11}$ is
(a) $(C_1-C_6)$-alkyl, unsubstituted or substituted with a substituent selected from the group consisting of:
i) —$OR^7$,
ii) —$N[R^7]_2$,
iii) —$NH_2$,
iv) —$COOR^7$,
v) —$N[CH_2CH_2]_2Q$,
vi) —$CF_3$, or
vii) —$CON(R^7)_2$;
(b) aryl, wherein aryl is defined as phenyl or naphthyl which is unsubstituted or substituted with one or two substituents selected from the group consisting of:
i) $(C_1-C_4)$-alkyl,
ii) —O—$(C_1-C_4)$-alkyl,
iii) —$CO[NR^7]_2$,
iv) F, Cl, Br or I,
v) —$COOR^7$,
vi) —$NH_2$,
vii) —$NH[(C_1-C_4)$-alkyl],
viii) —$N[(C_1-C_4)$-alkyl$]_2$, or
ix) —$CON[CH_2CH_2]_2Q$;
(c) —$(C_1-C_4)$-alkylaryl, wherein aryl is as defined above,
(d) $(C_3-C_7)$-cycloalkyl,

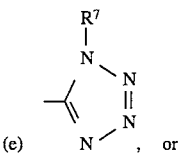
(e)

(f) $CF_3$;

$R^7$ and $R^{11}$ on the same nitrogen atom they can join together to form a ring selected from the group consisting of: morpholinyl, piperazinyl, or pyrrolyl, or Q is O, S or —$NR^7$;

$R^{12}$ is
(a) H
(b) $(C_1-C_6)$-alkyl, unsubstituted or substituted with one or two substituents selected from the group consisting of:
i) —OH,
ii) —O—$(C_1-C_4)$-alkyl,
iii) —O—$(C_1-C_4)$-cycloalkyl,
iv) —$S(O)_n$—$(C_1-C_4)$-alkyl,
v) —$NR^7R^{11}$,
vi) —$COOR^7$,
vii) —$CONHR^7$,
viii) —$OCOR^{11}$,
ix) —$CONR^7R^{11}$,
x) —$NR^7CONR^7R^{11}$,
xi) —$NR^7COOR^{11}$,
xii) —$C(R^6)(OH)$—$C(R^6)(R^7)(OH)$,
xiii) —$SO_2NR^7R^{11}$, or
xiv) CN, or

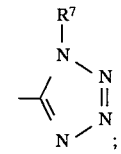
xv)

(c) $(C_3-C_7)$-cycloalkyl,
(d) —$OR^7$,
(e) —$COOR^7$,
(f) —$CONH_2$,
(g) —$CONR^{16}OR^7$,
(h) —$CONR^7R^{11}$,
(i) —$CONR^7CO_2R^7$,
(j) —$NH_2$,
(k) —$NR^7R^{11}$,
(l) —$NR^7CONR^7R^{11}$,
(m) —$NR^7COOR^{11}$,
(n) —$C(R^6)(OH)$—$C(R^6)(R^7)(OH)$,
(o) —$SO_2NR^7R^{11}$,
(p) —$S(O)_2NR^7COR^{11}$,
(q) —$S(O)_2NR^7CO_2R^{11}$,
(r) —$S(O)_2NR^7CONR^7R^{11}$,
(s) —$NHSO_2R^{11}$,
(t) —$NR^7SO_2NR^7R^{11}$,
(u) —$CONHSO_2R^{11}$,
(v) —CO-amino acid, wherein amino acid is defined as an L- or D-amino acid selected from the group consisting of Ala, Ile, Phe, Asp, Pro and Val and which can be further substituted as a $(C_1-C_6)$-alkyl ester or an amide, or

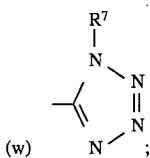

X is
(a) —O—,
(b) —S(O)$_n$—,
(c) —NR$^7$—,
(d) —CH$_2$O—,
(e) —CH$_2$S(O)$_n$—,
(f) —CH$_2$NR$^7$—,
(g) —OCH$_2$—,
(h) —N(R$^7$)CH$_2$—,
(i) —S(O)$_n$CH$_2$—, or
(j) —single bond;

Z is:
(a) —CO$_2$H,
(b) —CO$_2$R$^{13}$,
(c) —CONH-(tetrazo-5-yl),
(d) —CONHSO$_2$OR$^{11}$,
(e) —CONHSO$_2$NR$^7$R$^{11}$,
(f) —CONHSO$_2$-aryl, wherein aryl is defined as phenyl or naphthyl which is unsubstimted or substituted with one, two or three substituents selected from the group consisting of:
  i) $(C_1-C_4)$-alkyl,
  ii) —O—$(C_1-C_4)$-alkyl,
  iii) —CONR$^7$R$^{11}$,
  iv) F, Cl, Br or I,
  v) —COOR$^7$,
  vi) —NH$_2$,
  vii) —NH[$(C_1-C_4)$-alkyl],
  viii) —N[$(C_1-C_4)$-alkyl]$_2$,
  ix) —phenyl,
  x) —OH,
  xi) —OCH$_2$CH$_2$OH,
  xii) —CF$_3$;
(g) —CONHSO$_2$—$(C_1-C_8)$-alkyl, wherein the alkyl group is unsubstimted or substituted as defined in R$^4$(b),
(h) —CONHSO$_2$—$(C_1-C_4)$-perfluoroalkyl,
(i) —tetrazol-5-yl,
(j) —CONHSO$_2$-heteroaryl, wherein heteroaryl is defined as carbazolyl, furyl, thienyl, pyrrolyl, isothiazolyl, imidazolyl, isoxazolyl, thiazolyl, oxazolyl, pyrazolyl, pyrazinyl, pyridyl, pyrimidyl, purinyl or quinolinyl, which is unsubstituted or substituted with one, two or three substituents selected from the group consisting of:
  i) $(C_1-C_4)$-alkyl,
  ii) —O—$(C_1-C_4)$-alkyl,
  iii) —CONR$^7$R$^{11}$,
  iv) F, Cl, Br or I,
  v) —COOR$^7$,
  vi) —NR$^7$CONR$^7$R$^{11}$, and
  vii) —NR$^7$COOR$^{11}$;
(k) —SO$_2$NHCO-aryl, wherein aryl is defined in Z(f) above,
(l) —SO$_2$NHCO—$(C_1-C_8)$-alkyl, wherein the alkyl group is unsubstituted or substituted as defined in R$^4$(b),
(m) —SO$_2$NHCO—$(C_1-C_4)$-perfluoroalkyl,
(n) —SO$_2$NHCO-heteroaryl, wherein heteroaryl is as defined in Z(j) above,
(o) —SO$_2$NHCON(R$^{11}$)$_2$ wherein the R$^{11}$ groups are the same or different,
(p) —PO(OR$^7$)$_2$, wherein the R$^7$ groups are the same or different, or
(q) —PO(R$^{11}$)OR$^7$;

R$^{13}$ is:
(a) $(C_1-C_4)$-alkyl,
(b) CHR$^{14}$—O—COR$^{15}$,
(c) CH$_2$CH$_2$—N[$(C_1-C_2)$-alkyl]$_2$,
(d) CH$_2$CH$_2$—N[CH$_2$CH$_2$]$_2$O,
(e) (CH$_2$CH$_2$O)$_y$—O—[$(C_1-C_4)$-alkyl], wherein y is 1 or 2,
(f) phenyl, naphthyl, CH$_2$-phenyl or CH$_2$-naphthyl, where phenyl or naphthyl is substituted or unsubstituted with CO$_2$—$(C_1-C_4)$-alkyl, (g) 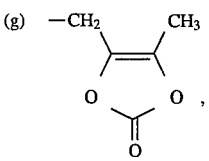

(h) 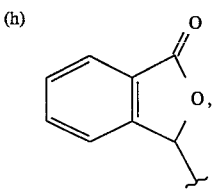

(i) 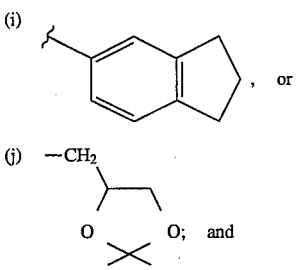, or (j) 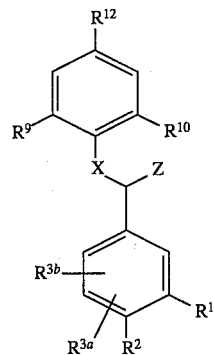; and

R$^{14}$ and R$^{15}$ independently are $(C_1-C_6)$-alkyl or phenyl; and R$^{16}$ is H, $(C_1-C_6)$-alkyl, or $(C_1-C_6)$-alkylphenyl.

An embodiment of the compounds of Formula II are the compounds of Formula III:

III or a pharmaceutically acceptable salt thereof, wherein:
R$^1$, R$^2$, R$^{3a}$ and R$^{3b}$ are independently:
(a) H, (b) F, Cl, Br, or I,
(c) —$NO_2$,
(d) $(C_1-C_6)$-alkyl,
(e) —$OR^7$,
(f) —NHCO—$(C_1-C_4)$-alkyl,
(g) —NHCO—$O(C_1-C_4)$-alkyl,
(h) —O—$(CH_2)_m$—$OR^7$,
(i) —$CONR^7R^{11}$, or
(j) —$COOR^7$;

$R^1$ and $R^2$ on adjacent carbon atoms can be joined together to form a ring structure:

A represents:
a) —Y—$C(R^4)$=$C(R^5)$—,
b) —Y—$C(R^4)$=N—,
c) —Y—N=$C(R^4)$—,
d) —Y—$[C(R^6)(R^6)]_s$—Y—,
e) —Y—$C(R^6)(R^6)$—$C(R^6)(R^6)$—,
f) —$C(R^4)$=$C(R^5)$—Y—,
g) —N=$C(R^4)$—Y—,
h) —$C(R^6)(R^6)$—$C(R^6)(R^6)$—Y—, or
i) —$C(R^4)$=$C(R^5)$—$C(R^4)$=$C(R^5)$—;

m is 2, 3 or 4,
n is 0, 1 or 2,
s is 1 or 2,
Y is —O—, —S— and $NR^7$
$R^4$ and $R^5$ are independently:
(a) H,
(b) $(C_1-C_6)$-alkyl,
(c) $(C_3-C_7)$-cycloalkyl,
(d) F, Cl, Br, I,
(e) —$NR^7COOR^{11}$,
(f) —$SO_2NR^7R^{11}$,
(g) —O—$(C_1-C_4)$-alkyl,
(h) —$S(O)_n$—$(C_1-C_4)$-alkyl, or
(i) —$NHSO_2R^{11}$;

$R^6$ is:
(a) H, or
(b) $(C_1-C_4)$-alkyl, or
(c) Cl, or F;

$R^7$ is:
(a) H,
(b) $(C_1-C_6)$-alkyl,
(c) phenyl, or
(d) benzyl;

$R^8$ is:
(a) H,
(b) $(C_1-C_6)$-alkyl, or
(c) phenyl;

$R^9$ and $R^{10}$ are independently:
(a) H,
(b) $(C_1-C_6)$-alkyl, unsubstituted or substituted with $(C_3-C_7)$-cycloalkyl,
(c) Cl, Br, F, I,
(d) $(C_1-C_6)$-alkoxy, or
(e) hydroxy-$(C_1-C_6)$-alkyl;

$R^{11}$ is
(a) $(C_1-C_6)$-alkyl, unsubstimted or substituted with a substituent selected from the group consisting of:
i) —$OR^7$,
ii) —$N[R^7]_2$,
iii) —$NH_2$,
iv) —$COOR^7$,
v) —$N[CH_2CH_2]_2Q$,
vi) —$CF_3$, or
vii) —$CON(R^7)_2$;
(b) aryl, wherein aryl is defined as phenyl or naphthyl which is unsubstituted or substituted with one or two substituents selected from the group consisting of:
i) $(C_1-C_4)$-alkyl,
ii) —O—$(C_1-C_4)$-alkyl,
iii) —$CO[NR^7]_2$,
iv) F, Cl, Br or I,
v) —$COOR^7$,
vi) —$NH_2$,
vii) —$NH[(C_1-C_4)$-alkyl],
viii) —$N[(C_1-C_4)$-alkyl]$_2$,
ix) —$CON[CH_2CH_2]_2Q$, or
(c) —$(C_1-C_4)$-alkylaryl, wherein aryl is as defined above,
(d) $(C_3-C_7)$-cycloalkyl,

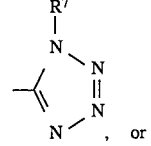

(e)                    , or (f) $CF_3$;

$R^7$ and $R^{11}$ on the same nitrogen atom they can join together to form a ring selected from the group consisting of: morpholinyl, piperazinyl, or pyrrolyl, or Q is O, S or —$NR^7$;

$R^{12}$ is
(a) H,
(b) $(C_1-C_6)$-alkyl, wherein alkyl is defined as unsbustituted or substituted with one or two substituents selected from the group consisting of:
i) —OH,
ii) —O—$(C_1-C_4)$-alkyl,
iii) —O—$(C_1-C_4)$-cycloalkyl,
iv) —$S(O)_n$—$(C_1-C_4)$-alkyl,
iv) —$NR^713$ $(C_1-C_4)$-alkyl,
v) —$NR^7R^{11}$,
vi) —$COOR^7$,
vii) —$CONHR^7$,
viii) —$OCOR^{11}$,
ix) —$CONR^7R^{11}$,
x) —$NR^7CONR^7R^{11}$,
xi) —$NR^7COOR^{11}$,
xii) —$C(R^6)(OH)$—$C(R^6)(R^7)(OH)$,
xiii) —$SO_2NR^7R^{11}$,
xiv) CN, or

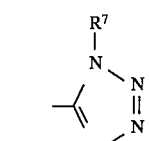

xv)                  ;

(c) —$COOR^7$, (d) —CONH$_2$,
(e) —CONR$^{16}$OR$^7$,
(f) —CONR$^7$R$^{11}$,
(g) —CONR$^7$CO$_2$R$^7$,
(h) —C(R$^6$)(OH)—C(R$^6$)(R$^7$)(OH), or
(i) —CONHSO$_2$R$^{11}$,
(j) —SO$_2$NR$^7$R$^{11}$,
(k) —NR$^7$SO$_2$NR$^7$R$^{11}$,
(l) —CO-amino acid, wherein amino acid is defined as an L- or D-amino acid selected from the group consisting of Ala, Ile, Phe, Asp, Pro and Val and which can be further substituted as a (C$_1$–C$_6$)-alkyl ester or an amide, or (m) 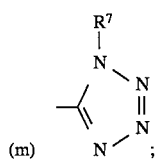;

X is
(a) —O—,
(b) —NR$^7$—, or
(c) —single bond;

Z is:
(a) —CO$_2$H,
(b) —CO$_2$R$^{13}$,
(c) —CONH(tetrazol-5-yl),
(d) —CONHSO$_2$NR$^7$R$^{11}$,
(e) —CONHSO$_2$-aryl, wherein aryl is defined as phenyl or naphthyl which is unsubstituted or substituted with one, two or three substituents selected from the group consisting of:
  i) (C$_1$–C$_4$)-alkyl,
  ii) —O-(C$_1$–C$_4$)-alkyl,
  iii) —CONR$^7$R$^{11}$,
  iv) F, Cl, Br or I,
  v) —COOR$^7$,
  vi) —NH$_2$,
  vii) —NH[(C$_1$–C$_4$)-alkyl],
  viii) —N[(C$_1$–C$_4$)-alkyl]$_2$,
  ix) -phenyl;
(f) —CONHSO$_2$—(C$_1$–C$_8$)-alkyl, wherein alkyl is unsubstituted or substituted as defined in R$^4$(b),
(g) —CONHSO$_2$-heteroaryl, wherein heteroaryl is defined as carbazolyl, furyl, thienyl, pyrrolyl, isothiazolyl, imidazolyl, isoxazolyl, thiazolyl, oxazolyl, pyrazolyl, pyrazinyl, pyridyl, pyrimidyl, purinyl, or quinolinyl, which is unsubstituted or substituted with one, two or three substituents selected from the group consisting of:
  i) (C$_1$–C$_4$)-alkyl,
  ii) —O—(C$_1$–C$_4$)-alkyl,
  iii) -CONR$^7$R$^{11}$,
  iv) F, Cl, Br or I,
  v) —COOR$^7$,
  vi) —NR$^7$CONR$^7$R$^{11}$, and
  vii) —NR$^7$COOR$^{11}$;
(h) —tetrazol-5-yl;

R$^{13}$ is: (C$_1$–C$_4$)alkyl; and
R$^{16}$ is H, (C$_1$–C$_6$)-alkyl, or (C$_1$–C$_6$)-alkylphenyl.

A subclass of the compounds of Formula III are the compounds of Formula IV:

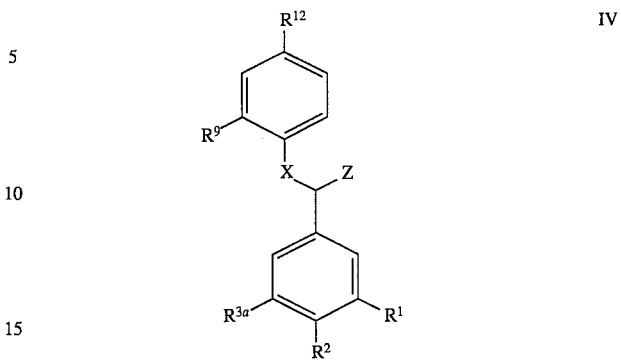

or a pharmaceutically acceptable salt thereof, wherein:
R$^1$ and R$^2$ taken together form the ring structure:

;

A represents:
a) —Y—[C(R$^6$)(R$^6$)]$_s$—Y—, or
b) —C(R$^4$)=C(R$^5$)—C(R$^4$)=C(R$^5$)—;
s is 1 or 2;
Y is —O—;
R$^{3a}$ is:
(a) H,
(b) F, Cl, Br, or I,
(c) (C$_1$–C$_6$)-alkyl,
(d) —OR$^7$,
(e) —O—(CH$_2$)m-OR$^7$,
(f) —CONR$^7$R$^{11}$, or
(g) —COOR$^7$;
m is 2, 3 or 4;
R$^4$ and R$^5$ are independently:
(a) H,
(b) (C$_1$–C$_6$)-alkyl,
(c) (C$_3$–C$_7$)-cycloalkyl,
(d) F, Cl, Br, I,
(e) —NR$^7$COOR$^{11}$,
(f) —SO$_2$NR$^7$R$^{11}$,
(g) —O—(C$_1$–C$_4$)-alkyl,
(h) —S(O)$_n$—(C$_1$–C$_4$)-alkyl, or
(i) —NHSO$_2$R$^{11}$;
n is 0, 1 or 2,
R$^6$ is:
(a) H, or
(b) (C$_1$–C$_4$)-alkyl, or
(c) Cl, or F;
R$^7$ is:
(a) H,
(b) (C$_1$–C$_6$)-alkyl,
(c) phenyl, or
(d) benzyl;
R$^8$ is:
(a) H,
(b) (C$_1$–C$_6$)-alkyl, or
(c) phenyl;
R$^9$ is:

(a) H,
(b) (C$_1$–C$_6$)-alkyl, unsubstituted or substituted with (C$_3$–C$_7$)-cycloalkyl,
(c) Cl, Br, F, I,
(d) (C$_1$–C$_6$)-alkoxy, or
(e) hydroxy-(C$_1$–C$_6$)-alkyl;

R$^{11}$ is
(a) (C$_1$–C$_6$)-alkyl, unsubstituted or substituted with a substituent selected from the group consisting of:
  i) —OR$^7$,
  ii) —N[R$^7$]$_2$,
  iii) —NH$_2$,
  iv) —COOR$^7$,
  v) —N[CH$_2$CH$_2$]$_2$Q,
  vi) —CF$_3$, or
  vii) —CON(R$^7$)$_2$;
(b) aryl, wherein aryl is defined as phenyl or naphthyl which is unsubstituted or substituted with one or two substituents selected from the group consisting of:
  i) (C$_1$–C$_4$)-alkyl,
  ii) —O—(C$_1$–C$_4$)-alkyl,
  iii) —CO[NR$^7$]$_2$,
  iv) F, Cl, Br or I,
  v) —COOR$^7$,
  vi) —NH$_2$,
  vii) —NH[(C$_1$–C$_4$)-alkyl],
  viii) —N[(C$_1$–C$_4$)-alkyl]$_2$, or
  ix) —CON[CH$_2$CH$_2$]$_2$Q;
(c) —(C$_1$–C$_4$)-alkylaryl, wherein aryl is as defined above,
(d) (C$_3$–C$_7$)-cycloalkyl, (e) 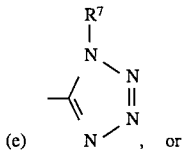, or (f) CF$_3$;

R$^7$ and R$^{11}$ on the same nitrogen atom they can join together to form a ring selected from the group consisting of: morpholinyl, piperazinyl, or pyrrolyl, or Q is O, S or —NR$^7$;

R$^{12}$ is
(a) H,
(b) (C$_1$–C$_6$)-alkyl, wherein alkyl is defined as unsubstituted or substituted with one or two substituents selected from the group consisting of:
  i) —OH,
  ii) —O—(C$_1$–C$_4$)-alkyl,
  iii) —O—(C$_1$–C$_4$)-cycloalkyl,
  iv) —S(O)$_n$—(C$_1$–C$_4$)-alkyl,
  iv) —NR$^7$—(C$_1$–C$_4$)-alkyl,
  v) —NR$^7$R$^{11}$,
  vi) —COOR$^7$,
  vii) —CONHR$^7$,
  viii) —OCOR$^{11}$,
  ix) —CONR$^7$R$^{11}$,
  x) —NR$^7$CONR$^7$R$^{11}$,
  xi) —NR$^7$COOR$^{11}$,
  xii) —C(R$^6$)(OH)—C(R$^6$)(R$^7$)(OH), or
  xiii) —SO$_2$NR$^7$R$^{11}$,
  xiv) CN, or xv) 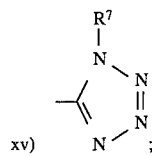;

(c) —COOR$^7$,
  (d) —CONH$_2$,
  (e) —CONR$^{16}$OR$^7$,
  (f) —CONR$^7$R$^{11}$,
  (g) —CONR$^7$CO$_2$R$^7$,
  (h) —C(R$^6$)(OH)—C(R$^6$)(R$^7$)(OH), or
  (i) —CONHSO$_2$R$^{11}$,
  (j) —SO$_2$NR$^7$R$^{11}$,
  (k) —NR$^7$SO$_2$NR$^7$R$^{11}$,
  (l) —CO-amino acid, wherein amino acid is defined as an L- or D-amino acid selected from the group consisting of Ala, Ile, Phe, Asp, Pro and Val and which can be further substituted as a (C$_1$–C$_6$)-alkyl ester or an amide, or (m) 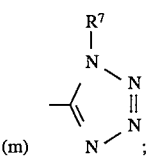;

X is
(a) —O—,
(b) —NR$^7$—, or
(c) —single bond;

Z is:
(a) —CO$_2$H,
(b) —CO$_2$R$^{13}$,
(c) —CO NH—(tetrazol-5-yl),
(d) —CONHSO$_2$NR$^7$R$^{11}$,
(e) —CONHSO$_2$-aryl, wherein aryl is defined as phenyl or naphthyl which is unsubstituted or substituted with one, two or three substituents selected from the group consisting of:
  i) (C$_1$–C$_4$)-alkyl,
  ii) —O—(C$_1$–C$_4$)-alkyl,
  iii) —CONR$^7$R$^{11}$,
  iv) F, Cl, Br or I,
  v) —COOR$^7$,
  vi) —NH$_2$,
  vii) —NH[(C$_1$–C$_4$)-alkyl],
  viii) —N[(C$_1$–C$_4$)-alkyl]$_2$,
  ix) —phenyl;
(f) —CONHSO$_2$—(C$_1$–C$_8$)-alkyl, wherein alkyl is unsubstituted or substituted as defined in R$^4$(b),
(g) —CONHSO$_2$-heteroaryl, wherein heteroaryl is defined as carbazolyl, furyl, thienyl, pyrrolyl, isothiazolyl, imidazolyl, isoxazolyl, thiazolyl, oxazolyl, pyrazolyl, pyrazinyl, pyridyl, pyrimidyl, purinyl, or quinolinyl, which is unsubstituted or substituted with one, two, or three substituents selected from the group consisting of:
  i) (C$_1$–C$_4$)-alkyl,
  ii) —O—(C$_1$–C$_4$)-alkyl, iii) —CONR$^7$R$^{11}$,
iv) F, Cl, Br or I,
v) —COOR$^7$,
vi) —NR$^7$CONR$^7$R$^{11}$, and
vii) —NR$^7$COOR$^{11}$;
(h) —tetrazol-5-yl;
R$^{13}$ is: (C$_1$–C$_4$)-alkyl; and
R$^{16}$ is H, (C$_1$–C$_6$)-alkyl, or (C$_1$–C$_6$)-alkylphenyl.

A second embodiment of the compounds of Formula II are the compounds of Formula V:

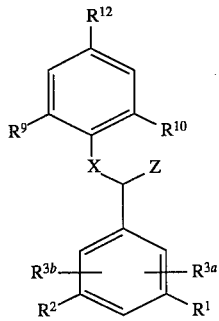

V or a pharmaceutically acceptable salt thereof, wherein: R$^1$, R$^2$, R$^{3a}$ and R$^{3b}$ are independently:
(a) H,
(b) F, Cl, Br, or I,
(c) —NO$_2$,
(d) (C$_1$–C$_6$)-alkyl,
(e) —OR$^7$,
(f) —NHCO—(C$_1$–C$_4$)-alkyl,
(g) —NHCO—O(C$_1$–C$_4$)-alkyl,
(h) —O—(CH$_2$)$_m$—OR$^7$,
(i) —CONR$^7$R$^{11}$, or
(j) —COOR$^7$;
m is 2, 3 or 4,
R$^4$ and R$^5$ are independently:
(a) H,
(b) (C$_1$–C$_6$)-alkyl,
(c) (C$_3$–C$_7$)-cycloalkyl,
(d) F, Cl, Br, I,
(e) —NR$^7$COOR$^{11}$,
(f) —SO$_2$NR$^7$R$^{11}$,
(g) —O—(C$_1$–C$_4$)-alkyl,
(h) —S(O)$_n$—(C$_1$–C$_4$)-alkyl, or
(i) —NHSO$_2$R$^{11}$;
n is 0, 1 or 2,
R$^6$ is:
(a) H,
(b) (C$_1$–C$_4$)-alkyl, or
(c) Cl or F;
R$^7$ is:
(a) H,
(b) (C$_1$–C$_6$)-alkyl,
(c) phenyl, or
(d) benzyl;
R$^8$ is:
(a) H,
(b) (C$_1$–C$_6$)-alkyl, or
(c) phenyl;
R$^9$ and R$^{10}$ are independently:
(a) H,
(b) (C$_1$–C$_6$)-alkyl, unsubstituted or substituted with (C$_3$–C$_7$)-cycloalkyl,
(c) Cl, Br, F, I,
(d) (C$_1$–C$_6$)-alkoxy, or
(e) hydroxy-(C$_1$–C$_6$)-alkyl;
R$^{11}$ is
(a) (C$_1$–C$_6$)-alkyl, unsubstituted or substituted with a substituent selected from the group consisting of:
i) —OR$^7$,
ii) —N[R$^7$]$_2$,
iii) —NH$_2$,
iv) —COOR$^7$,
v) —N[CH$_2$CH$_2$]$_2$Q,
vi) —CF$_3$, or
vii) —CON(R$^7$)$_2$;
(b) aryl, wherein aryl is defined as phenyl or naphthyl which is unsubstituted or substituted with one or two substituents selected from the group consisting of:
i) (C$_1$–C$_4$)-alkyl,
ii) —O—(C$_1$–C$_4$)-alkyl,
iii) —CO[NR$^7$]$_2$,
iv) F, Cl, Br or I,
v) —COOR$^7$,
vi) —NH$_2$,
vii) —NH[(C$_1$–C$_4$)-alkyl],
viii) —N[(C$_1$–C$_4$)-alkyl]$_2$, or
ix) —CON[CH$_2$CH$_2$]$_2$Q;
(c) —(C$_1$–C$_4$)-alkylaryl, wherein aryl is as defined above,
(d) (C$_3$–C$_7$)-cycloalkyl, (e)

$$\begin{array}{c} R^7 \\ | \\ N \diagdown \\ \phantom{N} \diagdown N \\ \phantom{NN} \| \\ \phantom{NNN} N \\ N \diagup \end{array}$$

, or (f) CF$_3$;
R$^7$ and R$^{11}$ on the same nitrogen atom they can join together to form a ring selected from the group consisting of: morpholinyl, piperazinyl, or pyrrolyl, or
Q is O, S or —NR$^7$;
R$^{12}$ is
(a) H,
(b) (C$_1$–C$_6$)-alkyl, wherein alkyl is defined as unsubstituted or substituted with one or two substiuents selected from the group consisting of:
i) —OH,
ii) —O—(C$_1$–C$_4$)-alkyl,
iii) —O—(C$_1$–C$_4$)-cycloalkyl,
iv) —S(O)$_n$—(C$_1$–C$_4$)-alkyl,
iv) —NR$^7$—(C$_1$–C$_4$)-alkyl,
v) —NR$^7$R$^{11}$,
vi) —COOR$^7$,
vii) —CONHR$^7$,
viii) —OCOR$^{11}$,
ix) —CONR$^7$R$^{11}$,
x) —NR$^7$CONR$^7$R$^{11}$,
xi) —NR$^7$COOR$^{11}$,
xii) —C(R$^6$)(OH)—C(R$^6$)(R$^7$)(OH), or
xiii) —SO$_2$NR$^7$R$^{11}$, xiv) CN, or

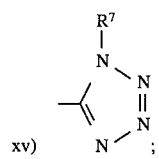

xv)

(c) —COOR$^7$,
(d) —CONH$_2$,
(e) —CONR$^{16}$OR$^7$,
(f) —CONR$^7$R$^{11}$,
(g) —CONR$^7$CO$_2$R$^7$,
(h) —C(R$^6$)(OH)—C(R$^6$)(R$^7$)(OH), or
(i) —CONHSO$_2$R$^{11}$,
(j) —SO$_2$NR$^7$R$^{11}$,
(k) —NR$^7$SO$_2$NR$^7$R$^{11}$,
(l) —CO-amino acid, wherein amino acid is defined as an L- or D-amino acid selected from the group consisting of Ala, Ile, Phe, Asp, Pro and Val and which can be further substituted as a (C$_1$–C$_6$)-alkyl ester or an amide, or

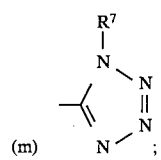

(m)

X is
 (a) —O—,
 (b) —NR$^7$—, or
 (c) —single bond;
Z is:
 (a) —CO$_2$H,
 (b) —CO$_2$R$^{13}$,
 (c) —CONH-(tetrazol-5-yl),
 (d) —CONHSO$_2$NR$^7$R$^{11}$,
 (e) —CONHSO$_2$-aryl, wherein aryl is defined as phenyl or naphthyl which is unsubstituted or substituted with one, two or three substituents selected from the group consisting of:
  i) (C$_1$–C$_4$)-alkyl,
  ii) —O—(C$_1$–C$_4$)-alkyl,
  iii) —CONR$^7$R$^{11}$,
  iv) F, Cl, Br or I,
  v) —COOR$^7$,
  vi) —NH$_2$,
  vii) —NH[(C$_1$–C$_4$)-alkyl],
  viii) —N[(C$_1$–C$_4$)-alkyl]$_2$,
  ix) —phenyl;
 (f) —CONHSO$_2$—(C$_1$–C$_8$)-alkyl, wherein alkyl is unsubstituted or substituted as defined in R$^4$(b),
 (g) —CONHSO$_2$-heteroaryl, wherein heteroaryl is defined as carbazolyl, furyl, thienyl, pyrrolyl, isothiazolyl, imidazolyl, isoxazolyl, thiazolyl, oxazolyl, pyrazolyl, pyrazinyl, pyridyl, pyrimidyl, purinyl, or quinolinyl, which is unsubstituted or substituted with one, two or three substituents selected from the group consisting of:
  i) (C$_1$–C$_4$)-alkyl,
  ii) —O—(C$_1$–C$_4$)-alkyl,
  iii) —CONR$^7$R$^{11}$,
  iv) F, Cl, Br or I,
  v) —COOR$^7$,
  vi) —NR$^7$CONR$^7$R$^{11}$, and
  vii) —NR$^7$COOR$^{11}$;
 (h) —tetrazol-5-yl;
R$^{13}$ is: (C$_1$–C$_4$)-alkyl; and
R$^{16}$ is H, (C$_1$–C$_6$)-alkyl, or (C$_1$–C$_6$)-alkylphenyl.

A third embodiment of compounds of Formula II are the compounds of Formula VI:

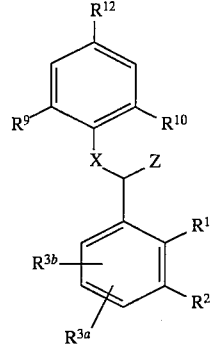

VI or a pharmaceutically acceptable salt thereof, wherein:
R$^1$ and R$^2$ are represented by the following ring structure:

A represents:
 a) —Y—[C(R$^6$)(R$^6$)]$_s$—Y—, or
 b) —C(R$^4$)═C(R$^5$)—C(R$^4$)═C(R$^5$)—;
s is 1 or 2,
Y is —O—, —S— and NR$^7$;
R$^{3a}$ and R$^{3b}$ are independently:
 (a) H,
 (b) F, Cl, Br, or I,
 (c) —NO$_2$,
 (d) (C$_1$–C$_6$)-alkyl,
 (e) —OR$^7$,
 (f) —NHCO—(C$_1$–C$_4$)-alkyl,
 (g) —NHCO-O(C$_1$–C$_4$)-alkyl,
 (h) —O—(CH$_2$)$_m$-OR$^7$,
 (i) —CONR$^7$R$^{11}$, or
 (j) —COOR$^7$;
m is 2, 3 or 4,
R$^4$ and R$^5$ are independently:
 (a) H,
 (b) (C$_1$–C$_6$)-alkyl,
 (c) (C$_3$–C$_7$)-cycloalkyl,
 (d) F, Cl, Br, I,
 (e) —NR$^7$COOR$^{11}$,
 (f) —SO$_2$NR$^7$R$^{11}$,
 (g) —O—(C$_1$–C$_4$)-alkyl,
 (h) —S(O)$_n$—(C$_1$–C$_4$)-alkyl, or
 (i) —NHSO$_2$R$^{11}$;
n is 0, 1 or 2,
R$^6$ is:
 (a) H, or
 (b) (C$_1$–C$_4$)-alkyl, or
 (c) Cl or F;

R⁷ is:
(a) H,
(b) (C₁-C₆)-alkyl,
(c) phenyl, or
(d) benzyl;

R⁸ is:
(a) H,
(b) (C₁-C₆)-alkyl, or
(c) phenyl;

R⁹ and R¹⁰ are independently:
(a) H,
(b) (C₁-C₆)-alkyl, unsubstituted or substituted with (C₃-C₇)-cycloalkyl,
(c) Cl, Br, F, I,
(d) (C₁-C₆)-alkoxy, or
(e) hydroxy-(C₁-C₆)-alkyl;

R¹¹ is
(a) (C₁-C₆)-alkyl, unsubstituted or substituted with a substituent selected from the group consisting of:
i) —OR⁷,
ii) —N[R⁷]₂,
iii) —NH₂,
iv) —COOR⁷,
v) —N[CH₂CH₂]₂Q,
vi) —CF₃, or
vii) —CON(R⁷)₂;
(b) aryl, wherein aryl is defined as phenyl or naphthyl which is unsubstituted or substituted with one or two substituents selected from the group consisting of:
i) (C₁-C₄)-alkyl,
ii) —O—(C₁-C₄)-alkyl,
iii) —CO[NR⁷]₂,
iv) F, Cl, Br or I,
v) —COOR⁷,
vi) —NH₂,
vii) —NH[(C₁-C₄)-alkyl],
viii) —N[(C₁-C₄)-alkyl]₂, or
ix) —CON[CH₂CH₂]₂Q;
(c) —(C₁-C₄)-alkylaryl, wherein aryl is as defined above,
(d) (C₃-C₇)-cycloalkyl,

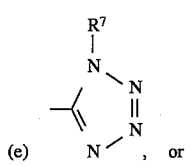
(e)        , or (f) CF₃;

R⁷ and R¹¹ on the same nitrogen atom they can join together to form a ting selected from the group consisting of: morpholinyl, piperazinyl, or pyrrolyl, or Q is O, S or —NR⁷;

R¹² is
(a) H,
(b) (C₁-C₆)-alkyl, wherein alkyl is defined as unsubstituted or substituted with one or two substituents selected from the group consisting of:
i) —OH,
ii) —O—(C₁-C₄)-alkyl,
iii) —O—(C₁-C₄)-cycloalkyl,
iv) —S(O)ₙ—(C₁-C₄)-alkyl,
iv) —NR⁷—(C₁-C₄)-alkyl,
v) —NR⁷R¹¹,
vi) —COOR⁷,
vii) —CONHR⁷,
viii) —OCOR¹¹,
ix) —CONR⁷R¹¹,
x) —NR⁷CONR⁷R¹¹,
xi) —NR⁷COOR¹¹,
xii) —C(R⁶)(OH)-C(R⁶)(R⁷)(OH),
xiii) —SO₂NR⁷R¹¹,
xiv) CN, or

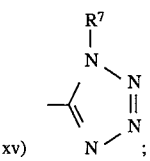
xv)         ;

(c) —COOR⁷,
(d) —CONH₂,
(e) —CONR¹⁶OR⁷,
(f) —CONR⁷R¹¹,
(g) —CONR⁷CO₂R⁷,
(h) —C(R⁶)(OH)—C(R⁶)(R⁷)(OH), or
(i) —CONHSO₂R¹¹,
(j) —SO₂NR⁷R¹¹,
(k) —NR⁷SO₂NR⁷R¹¹,
(l) —CO-amino acid, wherein amino acid is defined as an L- or D-amino acid selected from the group consisting of Ala, Ile, Phe, Asp, Pro and Val and which can be further substituted as a (C₁-C₆)-alkyl ester or an amide, or

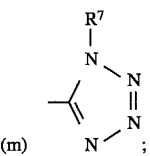
(m)         ;

X is
(a) —O—,
(b) —NR⁷—, or
(c) —single bond;

Z is:
(a) —CO₂H,
(b) —CO₂R¹³,
(c) —CONH-(tetrazol-5-yl ),
(d) —CONHSO₂NR⁷R¹¹,
(e) —CONHSO₂-aryl, wherein aryl is defined as phenyl or naphthyl which is unsubstituted or substituted with one, two or three substituents selected from the group consisting of:
i) (C₁-C₄)-alkyl,
ii) —O—(C₁-C₄)-alkyl,
iii) —CONR⁷R¹¹,
iv) F, Cl, Br or I,
v) —COOR⁷,
vi) —NH₂,
vii) —NH[(C₁-C₄)-alkyl],
viii) —N[(C₁-C₄)-alkyl]₂,
ix) —phenyl;
(f) —CONHSO₂-(C₁-C₈)-alkyl, wherein alkyl is unsubstituted or substituted as defined in R⁴(b),
(g) —CONHSO₂-heteroaryl, wherein heteroaryl is defined as carbazolyl, furyl, thienyl, pyrrolyl, isothiazolyl, imidazolyl, isoxazolyl, thiazolyl, oxazolyl, pyrazolyl, pyrazinyl, pyridyl, pyrimidyl, purinyl, or quinolinyl, which is unsubstituted or substituted with one, two or three substituents selected from the group consisting of:
i) $(C_1-C_4)$-alkyl,
ii) —O—$(C_1-C_4)$-alkyl,
iii) —$CONR^7R^{11}$,
iv) F, Cl, Br or I,
v) —$COOR^7$,
vi) —$NR^7CONR^7R^{11}$, and
Vii) —$NR^7COOR^{11}$;
(h) —tetrazol-5-yl;
$R^{13}$ is: $(C_1-C_4)$-alkyl; and
$R^{16}$ is H, $(C_1-C_6)$-alkyl, or $(C_1-C_6)$-alkylphenyl.

An embodiment of the compounds of Formula I are:

2-[(2,6-dipropyl-4-hydroxymethyl)phenoxy]-2-(3-methylphenyl)acetic acid;
2-[(2,6-dipropyl-4-hydroxymethyl)phenoxy]-2-(4-phenoxyphenyl)acetic acid;
2-[(2,6-dipropyl-4-hydroxymethyl)phenoxy]-2-(4-phenylphenyl)acetic acid;
2-[(2,6-dipropyl-4-hydroxymethyl)phenoxy]-2-(3-carboxyphenyl)acetic acid;
2-[(2,6-dipropyl-4-hydroxymethyl)phenoxy]-2-(3,4-ethylenedioxyphenyl)acetic acid;
2-[(2,6-dipropyl-4-hydroxymethyl)phenoxy]-2-(3,4,5-trimethoxyphenyl)acetic acid;
2-[(2,6-dipropyl-4-hydroxymethyl)phenoxy]-2-(3,4-methylenedioxyphenyl)acetic acid;
2-[(2,6-dipropyl-4-hydroxymethyl)phenoxy]-2-(3,4-dimethoxyphenyl)acetic acid;
2-[(2,6-dipropyl-4-hydroxymethyl)phenoxy]-2-(3,5-dimethoxyphenyl)acetic acid;
2-((2,6-dipropyl-4-tetrazol-5-yl)phenoxy)-2-(3-bromophenyl)acetic acid;
2-[(2,6-dipropyl-4-hydroxymethyl)phenoxy]-2-(3-bromophenyl)acetic acid;
2-[(2,6-dipropyl-4-hydroxymethyl)phenoxy]-2-(2-naphthyl)acetic acid;
2-[(2,6-dipropyl-4-(2-hydroxyethyl)phenoxy]-2-(2-naphthyl)acetic acid;
2-[(2,6-dipropyl-4-(2-hydroxyethyl )phenoxy ]-2-(3,4-methylenedioxyphenyl)acetic acid;
2-[(2,6-dipropyl-4-(2-hydroxyethyl)phenoxy]-2-(3-methoxyphenyl)acetic acid;
2-[(2,6-dipropyl-4-(1,2-dihydroxyethyl)phenoxy)]-2-(2-naphthyl)acetic acid;
2-[(2,6-dipropyl-4-(1-hydroxypentyl)phenoxy]-2-(2-naphthyl)acetic acid;
2-[(4-carboxy-2,6-dipropyl)phenoxy]-2-phenylacetic acid;
2-[(4-carboxy-2,6-dipropyl)phenoxy]-2-(3,4-dichlorophenyl)acetic acid;
2-[(4-carboxy-2,6-dipropyl)phenoxy]-2-(3-bromophenyl)acetic acid;
2-[(4-carboxy-2,6-dipropyl)phenoxy]-2-[3,4-methylenedioxyphenyl]acetic acid;
2-[(4-carboxy-2,6-dipropyl)phenoxy]-2-(3-methoxyphenyl)acetic acid;
(N-benzenesulfonyl)-2-[(4-(N-benzenesulfonyl)carboxamido-2,6-dipropylphenoxy]-2-(3-bromophenyl)acetamide;
(N-4-t-butylbenzenesulfonyl)-2-(4-methoxycarbonyl-2-propylphenoxy)-2-(3,4-methylenedioxyphenly)acetamide;
N-(benzenesulfonyl)-2-(4-methoxycarbonyl-2-propylphenoxy)-2-(3,4-methylenedioxyphenyl)acetamide;
N-(4-phenylbenzenesulfonyl)-2-(4-methoxy carbonyl-2-propylphenoxy)-2-(3,4-methylenedioxyphenyl)acetamide;
N-(4-chlorobenzenesulfonyl)-2-(4-methoxycarbonyl-2-propylphenoxy)-2-(3,4-methylenedioxyphenyl)acetamide;
N-(4-methylbenzenesulfonyl)-2-(4-methoxy carbonyl-2-propylphenoxy)-2-(3,4-methylenedioxyphenyl)acetamide;
N-(5-iso-butylthien-2-ylsulfonyl)-2-(4-methoxycarbonyl-2-propylphenoxy)-2-(3,4-methylenedioxyphenyl)acetamide;
N-(4-methoxybenzenesulfonyl)-2-(4-methoxycarbonyl-2-propylphenoxy)-2-(3,4-methylenedioxyphenyl)acetamide;
N-(4-dimethylaminobenzenesulfonyl)-2-(4-methoxycarbonyl-2-propylphenoxy)-2-(3,4-methylenedioxyphenyl)
N-(2-methylbenzenesulfonyl)-2-(4-methoxycarbonyl-2-propylphenoxy)-2-(3,4-methylenedioxyphenyl)acetamide;
N-(2-methoxycarbonylbenzenesulfonyl)-2-(4-methoxycarbonyl-2-propylphenoxy)-2-(3,4-methylenedioxyphenyl)-acetamide;
N-(2-chlorobenzenesulfonyl)-2-(4-methoxycarbonyl-2-propylphenoxy)-2-(3,4-methylenedioxyphenyl)acetamide;
N-(3-chlorobenzenesulfonyl)-2-(4-methoxycarbonyl-2-propylphenoxy)-2-(3,4-methylenedioxyphenyl )acetamide;
N-(phenylmethanesulfonyl)-2-(4-methoxycarbonyl-2-propylphenoxy)-2-(3,4-methylenedioxyphenyl)acetamide;
N-(dansylsulfonyl)-2-(4-methoxycarbonyl-2-propylphenoxy)-2-(3,4-methylenedioxyphenyl)acetamide;
N-(8-quinolinesulfonyl)-2-(4-methoxycarbonyl-2-propylphenoxy)-2-(3,4-methylenedioxyphenylacetamide;
N-(4-t-butylbenzenesulfonyl)-2-(4-carboxy-2-propylphenoxy)-2-(3,4-methylenedioxyphenyl)acetamide;
N-(benzenesulfonyl)-2-(4-carboxy-2-propylphenoxy)-2-(3, 4-methylenedioxyphenyl)acetamide;
N-(4-phenylbenzenesulfonyl)-2-(4-carboxy-2-propylphenoxy)-2-(3,4-methylenedioxyphenyl)acetamide;
N-(4-chlorobenzenesulfonyl)-2-(4-carboxy-2-propylphenoxy)-2-(3,4-methylenedioxyphenyl)acetamide;
N-(4-methylbenzenesulfonyl)-2-(4-carboxy-2-propylphenoxy)-2-(3,4-methylenedioxyphenyl)acetamide;
N-(5-isobutylthien-2-ylsulfonyl)-2-(4-carboxy-2-propylphenoxy)-2-(3,4-methylenedioxyphenyl)acetamide;
N-(4-methoxybenzenesulfonyl)-2-(4-carboxy-2-propylphenoxy)-2-(3,4-methylenedioxyphenyl)acetamide;
N-(4-dimethylaminobenzenesulfonyl)-2-(4-carboxy-2-propylphenoxy)-3,4-methylenedioxyphenyl)acetamide;
N-(2-methylbenzenesulfonyl)-2-(4-carboxy-2-propylphenoxy)-2-(3,4-methylenedioxyphenyl)acetamide;
N-(2-methoxycarbonylbenzenesulfonyl)-2-(4-carboxy-2-propylphenoxy)-2-(3,4-methylenedioxyphenyl)acetamide;
N-(2-chlorobenzenesulfonyl)-2-(4-carboxy-2-propylphenoxy)-2-(3,4-methylenedioxyphenyl)acetamide;
N-(3-chlorobenzenesulfonyl)-2-(4-carboxy-2-propylphenoxy)-2-(3,4-methylenedioxyphenyl)acetamide;
N-(phenylmethanesulfonyl)-2-(4-carboxy-2-propylphenoxy)-2-(3,4-methylenedioxyphenyl)acetamide;
N-(dansylsulfonyl)-2-(4-carboxy-2-propylphenoxy)-3,4-methylenedioxyphenyl)acetamide;
N-(8-quinolinesulfonyl)-2-(4-carboxy-2-propylphenoxy)-2-(3,4-methylenedioxyphenylacetamide;
N-(8-quinolinesulfonyl)-2-(4-carboxamido-2-propylphenoxy)-2-(3,4-methylenedioxyphenyl)acetamide;
α-(4-carbomethoxy-2-n-propylphenoxy)-3,4-methylenedioxyphenylacetic acid;
N-(4-iso-propylbenzenesulfonyl)-α-(4-carbomethoxy-2-n-propylphenoxy)-3,4-methylenedioxyphenylacetamide;
N-(4-iso-propylbenzenesulfonyl)-α-(4-carboxy-2-n-propylphenoxy)-3,4-methylenedioxyphenylacetamide dipotassium salt;

α-(2-iso-butyl-4-carbomethoxyphenoxy)-3,4-methylene-dioxyphenylacetic acid;

N-(4-iso-propylbenzenesulfonyl)-α-(2-iso-butyl-4-carbomethoxyphenoxy)-3,4-methylenedioxyphenylacetamide;

N-(4-iso-propylbenzenesulfonyl)-α-(2-iso-butyl-4-carboxyphenoxy)-3,4-methylenedioxyphenylacetamide;

N-(4-iso-propylbenzenesulfonyl)-α-(2-n-propyl-4-methoxycarbonylphenoxy)-α-methyl-3,4-methylenedioxyphenylacetamide;

N-(4-iso-propylbenzenesulfonyl)-α-(2-n-propyl-4-carboxyphenoxy)-α-methyl-3,4-methylenedioxyphenylacetamide dipotassium salt;

N-(4-iso-propylbenzenesulfonyl)-α-(2-n-propyl -4-carboxamidophenoxy)-3,4-methylenedioxyphenylacetamide;

N-(4-iso-propylbenzenesulfonyl)-α-(2-n-propyl-4-hydroxymethylphenoxy)-3,4-methylenedioxyphenylacetamide;

N-(4-iso-propylbenzenesulfonyl)-α-(4-formyl-2-n-propylphenoxy)-3,4-methylenedioxyphenylacetamide;

α-(4-acetyl-2-n-propylphenoxy)-3,4-methylenedioxyphenylacetic acid;

N-(4-iso-propylbenzenesulfonyl)-α-(4-acetyl-2-n-propylphenoxy)-3,4-methylenedioxyphenylacetamide;

α-(2-n-propylphenoxy)-3,4-methylenedioxyphenylacetic acid

N-(4-iso-propylbenzenesulfonyl)-α-(2-n-propylphenoxy)-3,4-methylenedioxyphenylacetamide;

α-(3-methoxyphenoxy)-3,4-methylenedioxyphenylacetic acid;

α-(2-(2-hydroxyethyl)phenoxy)-3,4-methylenedioxyphenylacetic acid;

α-(2-(2-carbomethoxyethyl)phenoxy)-3,4-methylenedioxyphenylacetic acid;

α-(4-hydroxymethyl-2-n-propylphenoxy)-3,4-methylenedioxyphenylacetic acid;

α-(4-(2-hydroxyethyl)-2-n-propylphenoxy)-3,4-methylenedioxyphenylacetic acid;

N-(4-iso-propylbenzenesulfonyl)-α-(2-(2-carbomethoxyethyl)phenoxy)-3,4-methylenedioxyphenylacetamide;

N-(4-iso-propylbenzenesulfonyl)-α-(2-(2-carboxyethyl)phenoxy)-3,4-methylenedioxyphenylacetamide;

α-(2-(2-carboxyethyl)phenoxy)-3,4-methylenedioxyphenylacetic acid;

N-(4-iso-propylbenzenesulfonyl)-2-(4-carbomethoxy-2-n-propylphenoxy)-2-(5-methoxy-3,4-methylenedioxyphenyl)acetamide;

N-(4-iso-propylbenzenesulfonyl)-2-(4-carboxy-2-propylphenoxy)-2-(5-methoxy-3,4-methylenedioxyphenyl)acetamide;

N-(4-iso-propylbenzenesulfonyl)-2-(4-(N-(4-iso-propylbenzenesulfonyl)carboxamido)-2-propylphenoxy)-2-(5-methoxy-3,4-methylenedioxyphenyl)acetamide;

N-(4-iso-propylbenzenesulfonyl)-2-(4-carboxamido-2-propylphenoxy)-2-(5-methoxy-3,4-methylenedioxyphenyl)acetamide;

N-(4-iso-propylbenzenesulfonyl)-2-(4-(N-methylcarboxamido)-2-propylphenoxy)-2-(5-methoxy-3,4-methylenedioxyphenyl)acetamide;

N-(4-iso-propylbenzenesulfonyl)-2-(4-(N-2-hydroxyethylcarboxamido)-2-propylphenoxy)-2-(5-methoxy-3,4-methylenedioxyphenyl)acetamide;

N-(4-iso-propylbenzenesulfonyl)-2-(4-(N-morpholinylcarboxamido)-2-propylphenoxy)-2-(5-methoxy-3,4-methylenedioxyphenyl)acetamide;

N-(4-iso-propylbenzenesulfonyl)-2-(4-(N-3-methylbutylcarboxamido)-2-propylphenoxy)-2-(5-methoxy-3,4-methylenedioxyphenyl)acetamide;

N-(4-iso-propylbenzenesulfonyl)-2-(4-(N-carboxymethylcarboxamido)-2-propylphenoxy)-2-(5-methoxy-3,4-methylenedioxyphenyl)acetamide;

N-(4-iso-propylbenzenesulfonyl)-2-(4-(N-(L-Ala-OEt)carboxamido)-2-propylphenoxy)-2-(5-methoxy-3,4-methylenedioxyphenyl)acetamide;

N-(4-iso-propylbenzenesulfonyl)-2-(4-(N-2-ethoxycarbonylethylcarboxamido)-2-propylphenoxy)-2-(5-methoxy-3,4-methylenedioxyphenyl)acetamide;

N-(4-iso-propylbenzenesulfonyl)-2-(4-(N-(L-Ala)carboxamido)-2-prop ylphenoxy)-2-(5-methoxy-3,4-methylenedi oxyphenyl)acetamide;

N-(4-iso-propylbenzenesulfonyl)-2-(4-(N-2-carboxyethylcarboxamido)-2-propylphenoxy)-2-(5-methoxy-3,4-methylenedioxyphenyl)acetamide;

N-(4-iso-propylbenzenesulfonyl)-2-(4-(N-3-hydroxypropylcarboxamido)-2-propylphenoxy)-2-(5-methoxy-3,4-methylenedioxyphenyl)acetamide;

N-(4-iso-propylbenzenesulfonyl)-2-(4 -(N-tetrazol-5-ylcarboxamido)-2-propylphenoxy)-2-(5-methoxy-3,4-methylenedioxyphenyl)acetamide;

N-(4-iso-propylbenzenesulfonyl)-2-(4-(N-3-(morpholin-4-yl)propylcarboxamido)-2-propylphenoxy)-2-(5-methoxy-3,4-methylenedioxyphenyl)acetamide;

N-(4-iso-propylbenzenesulfonyl)-2-(4-(N-(D-Ala-OMe)carboxamido)-2-propylphenoxy)-2-(5-methoxy-3,4-methylenedioxyphenyl)acetamide;

N-(4-iso-propylbenzenesulfonyl)-2-(4-(N-(D-Ala)carboxamido)-2-propylphenoxy)-2-(5-methoxy-3,4-methylenedioxyphenyl)acetamide;

N-(4-iso-propylbenzenesulfonyl)-2-(4-(N-(3-carboxymethylpropyl)-carboxamido)-2-propylphenoxy)-2-(5-methoxy-3,4-methylenedioxyphenyl)acetamide;

N-(4-iso-propylbenzenesulfonyl)-2-(4-(N-(3-carboxypropyl)-carboxamido)-2-n-propylphenoxy)-2-(5-methoxy-3,4-methylenedioxyphenyl)acetamide;

N-(4-iso-propylbenzenesulfonyl)-2-(4-(N-iso-propylcarbamoyl)amino-2-n-propylphenoxy)-2-(3,4-methylenedioxyphenyl)acetamide;

α-(2-n-propyl-4-methylaminosulfonylphenoxy)-3,4-methylenedioxyphenylacetic acid;

N-(4-iso-propylbenzenesulfonyl)-α-(2-n-propyl-4-methylaminosulfonylphenoxy)-3,4-methylenedioxyphenylacetamide potassium salt;

N-(4-iso-propylbenzenesulfonyl)-α-[4-(cyanomethyl)-2-n-propylphenoxy)]-3,4-methylenedioxyphenylacetamide;

N-(4-iso-propylbenzenesulfonyl)-α-[4-(tetrazol-5-ylmethyl)-2-n-propylphenoxy)]-3,4-methylenedioxyphenylacetamide;

N-(4-iso-propylbenzenesulfonyl)-α-[N-(4-carbomethoxyphenylamino)]-3,4-methylenedioxyphenylacetamide;

N-(4-iso-propylbenzenesulfonyl)-α-[N-(4-carboxyphenylamino)]-3,4-methylenedioxyphenylacetamide;

N-(3-pyridinesulfonyl)-2-(4-carboxy-2-propylphenoxy)-2-(3,4-methylenedioxyphenyl)acetamide;

N-(2-methyl-3-quinolinesulfonyl)-2-(4-carboxy-2-propylphenoxy)-2-(3,4-methylenedioxyphenyl)acetamide;

N-(3-quinolinesulfonyl)-2-(4-carboxy-2-propylphenoxy)-2-(3,4-methylenedioxyphenyl)acetamide;

N-(4-hydroxy-3-pyridinesulfonyl)-2-(4-carboxy-2-propylphenoxy)-2-(3,4-methylenedioxyphenyl)acetamide;

N-(4-ethoxybenzenesulfonyl)-2-(4-carboxy-2-propylphenoxy)-2-(3,4-methylenedioxyphenyl)acetamide;

N-(4-carboxamidobenzenesulfonyl)-2-(4-carboxy-2-propylphenoxy)-2-(3,4-methylenedioxyphenyl)acetamide;

N-[4-(N,N-dimethylcarboxamido)benzenesulfonyl]-2-(4-carboxy-2-propylphenoxy)-2-(3,4-methylenedioxyphenyl)acetamide;

N-(4-ethylthio-3-pyridinesulfonyl)-2-(4-carboxy-2-propylphenoxy)-2-(3,4-methylenedioxyphenyl)acetamide;
N-(4-ethoxy-3-pyridinesulfonyl)-2-(4-carboxy-2-propylphenoxy)-2-(3,4-methylenedioxyphenyl)acetamide;
N-[(4-amino-2,5-dimethoxy)benzenesulfonyl]-2-(4-carboxy-2-propylphenoxy)-2-(3,4-methylenedioxyphenyl)acetamide;
N-[(2,5-dimethoxy)benzenesulfonyl]-2-(4-carboxy-2-propylphenoxy)-2-(3,4-methylenedioxyphenyl)acetamide;
N-[(3,4-dimethoxy)benzenesulfonyl]-2-(4-carboxy-2-propylphenoxy)-2-(3,4-methylenedioxyphenyl)acetamide;
N-[2-[5-(morpholin-4-yl)benzothiophene]sulfonyl]-2-(4-carboxy-2-propylphenoxy)-2-(3,4-methylenedioxyphenyl)acetamide;
N-[[2-(4-methoxy)benzothiophene]sulfonyl]-2-(4-carboxy-2-propylphenoxy)-2-(3,4-methylenedioxyphenyl)acetamide;
N-[4-[2-(benzyloxycarbonylamino)ethyl]benzenesulfonyl]-2-(4-carboxy-2-propylphenoxy)-2-(3,4-methylenedioxyphenyl)acetamide;
N-[[2,5-dimethoxy-4-((N-iso-propylcarbamoyl)amino)]benzene-sulfonyl]-2-(4-carboxy-2-propylphenoxy)-2-(3,4-methylenedioxy-phenyl)acetamide;
N-[(2,4-dimethoxy)benzenesulfonyl]-2-(4-carboxy-2-propylphenoxy)-2-(3,4-methylenedioxyphenyl)acetamide;
N-[(2,4,6-trimethoxy)benzenesulfonyl]-2-(4-carboxy-2-propylphenoxy)-2-(3,4-methylenedioxyphenyl)acetamide;
N-(8-quinolinesulfonyl)-2-(4-carboxy-2-propylphenoxy)-2-(3,4-methylenedioxyphenyl)acetamide;
N-(3-quinolinesulfonyl)-2-(4-carboxy-2-propylphenoxy)-2-(3,4-methylenedioxyphenyl)acetamide;
N-(8-quinolinesulfonyl)-2-(4-carboxamido-2-propylphenoxy)-2-(5-methoxy-3,4-methylenedioxyphenyl)acetamide;
N-(4-tert-butylbenzenesulfonyl)-2-(4-carboxamido-2-propylphenoxy)-2-(5-methoxy-3,4-methylenedioxyphenyl)acetamide;
N-(4-amino-2,5-dimethoxybenzenesulfonyl)-2-(4-carboxamido-2-propylphenoxy)-2-(5-methoxy-3,4-methylenedioxyphenyl)acetamide;
N-[4-iso-propylbenzenesulfonyl]-2-(4-carboxy-2-propylphenoxy)-2-(3,4-methylenedioxyphenyl)acetamide;
N-(4-iso-propylbenzenesulfonyl)-2-[[4-[N-[2-(carbethoxy)ethyl]-carbamoyl]]-2-propylphenoxy]-2-(3,4-methylenedioxyphenyl)acetamide;
N-(4-iso-propylbenzenesulfonyl)-2-[[4-[N-(2-carboxyethyl)carbamoyl]]-2-propylphenoxy]-2-(3,4-methylenedioxyphenyl)acetamide;
N-(4-iso-propylbenzenesulfonyl)-2-[[4-[N-(2-carbamoylethyl)-carbamoyl]]-2-propylphenoxy]-2-(3,4-methylenedioxyphenyl)acetamide;
N-(4-iso-propylbenzenesulfonyl)-2-[4-[N-(2,2,2-trifluoroethyl)-carbamoyl]-2-propylphenoxy]-2-(3,4-methylenedioxyphenyl)acetamide;

A perferred embodiment of the compounds of this invention are:
(–)-N-(4-iso-propylbenzenesulfonyl)-α-(4-carboxy-2-n-propylphenoxy)-3,4-methylenedioxyphenylacetamide dipotassium salt;
N-(4-iso-propylbenzenesulfonyl)-α-(4-carboxy-2-n-propylphenoxy)-3,4-methylenedioxyphenylacetamide dipotassium salt;
N-(8-quinolinesulfonyl)-2-(4-carboxy-2-propylphenoxy)-2-(3,4-methylenedioxyphenyl)acetamide;
N-(4-dimethylaminobenzenesulfonyl)-2-(4-carboxy-2-n-propyl-phenoxy)-2-(3,4-methylenedioxyphenyl)acetamide.

The alkyl substituents recited above denote straight and branched chain hydrocarbons of the length specified such as methyl, ethyl, isopropyl, isobutyl, neopentyl, isopentyl, etc.

The alkenyl-substituents denote alkyl groups as described above which are modified so that each contains a carbon to carbon double bond such as vinyl, allyl and 2-butenyl.

Cycloalkyl denotes rings composed of 3 to 8 methylene groups, each of which may be substituted or unsubstituted with other hydrocarbon substituents, and include for example cyclopropyl, cyclopentyl, cyclohexyl and 4-methylcyclohexyl.

The alkoxy substituent represents an alkyl group as described above attached through an oxygen bridge.

The heteroaryl is defined as carbazolyl, furyl, thienyl, pyrrolyl, isothiazolyl, imidazolyl, isoxazolyl, thiazolyl, oxazolyl, pyrazolyl, pyrazinyl, pyridyl, pyrimidyl, purinyl or quinolinyl.

Although the reaction schemes described below are reasonably general, it will be understood by those skilled in the art of organic synthesis that one or more functional groups present in a given compound of Formula I may render the molecule incompatible with a particular synthetic sequence. In such a case an alternative synthetic route, an altered order of steps, or a strategy of protection and deprotection may be employed. In all cases the particular reaction conditions, including reagents, solvent, temperature and time, should be chosen so that they are consistent with the nature of the functionality present in the molecule.

The compounds of Formula I and specifically compounds of Formula III can be synthesized using the reactions and techniques described for the synthesis of the non-heterocyclic components in the patent application WO91/11999 (Merck & Co.; published on Aug. 22, 1991 under the Patent Cooperation Treaty), U.S. Pat. No. 5,177,095 (Merck & Co.; Jan. 5, 1993), and also U.S. Pat. No. 5,240,938 (Merck & Co.; Aug. 31, 1993).

The reaction schemes described below have been generalized for simplicity. It is further to be understood that in the generalized schemes below, unless specified more narrowly in the text, the alkyl and aryl groups represent unfunctionalized or functionalized derivatives as described before. The leaving group Q present in the alkylating agents is either chloro, bromo, iodo, methanesulfonate, p-toluenesulfonate or triflate.

Scheme 1

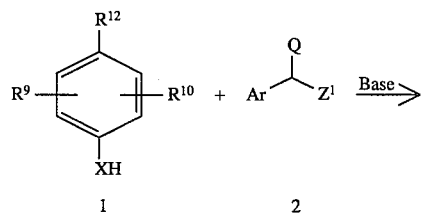

1      2

Scheme 1 -continued

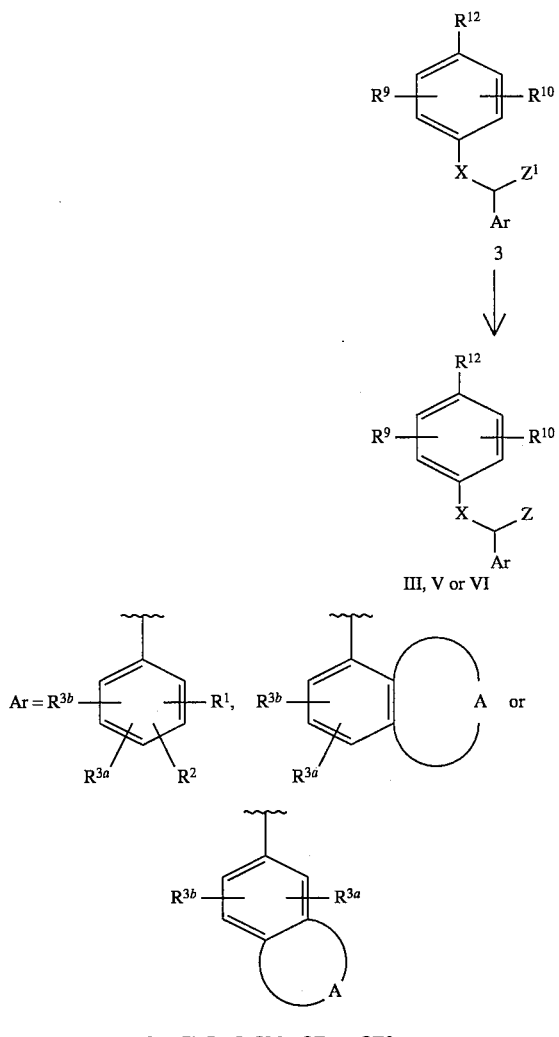

Q = Cl, Br, I, OMs, OTs or OTf $Z^1$ = a precursor to Z

More specifically, the compounds of Formula III, V or VI (where X is oxygen, sulphur or appropriately substituted nitrogen) can be synthesized as outlined in Scheme 1. The substituted compound 1 may be reacted with the alkylating agent 2 in an appropriate solvent such as alcohols (methanol, ethanol, isopropanol and like), dimethylformamide (DMF), dimethylsulfoxide (DMSO), tetrahydrofuran (THF) and acetone in the presence of an alkali metal salt such as alkoxides, carbonates, hydroxides and hydrides, or organic bases such as trialkylamines or alkyl lithiums to provide compound 3. The $Z^1$ group present in compound 3 may then be further transformed to provide the appropriate compounds of Formula III, V or VI.

In general, the alkylating agent 2 can be prepared using methods and techniques outlined in U.S. Pat. No. 5,177,095. More specifically, compound 2 (where $Z^1$ is COOR and Q is Br) can be synthesized from the substituted arylacetic acids 4 as outlined in Scheme 2. The substituted arylacetic acid 4 is converted to the corresponding ester either by refluxing the acid in an appropriate alcohol in the presence of a catalytic amount of conc. sulfufic acid, or using other conventional methods of esterification. The resulting ester is then refluxed in carbon tetrachloride with N-bromosuccinimide and a catalytic amount of a radical initiator (e.g., AIBN or benzoylperoxide) to provide the 2-bromo-arylacetic acid ester 5.

Scheme 2

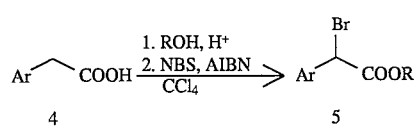

Alternatively, the ester 5 may also be prepared from appropriate aryl aldehydes (Scheme 3). The aldehyde 6 can be reacted with trimethylsilyl cyanide and catalytic amounts of KCN and 18-crown-6 to provide the corresponding trimethylsilyl cyanohydrin 7, which upon further treatment with the gaseous HCl and alcohol affords the 2-hydroxy ester 8. The ester 8 is treated with triphenylphosphine and carbon tetrabromide in methylene chloride to give the 2-bromoarylacetate derivatives 5.

Scheme 3

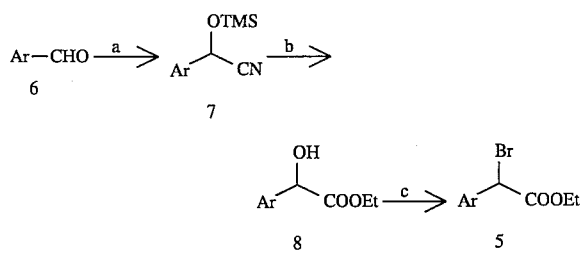

a. TMSCN, Cat. KCN, CH$_2$Cl$_2$, 18-Crown-6;
b. HCl(g), EtOH;
c. CBr$_4$, Ph$_3$P, CH$_2$Cl$_2$ Scheme 4 illustrates a typical synthesis of an alkylating agent 12 (where Ar represents a heterocycle such as an indole). The appropriately substituted cyanoindole 9 (for a general synthesis of substituted indoles refer to, R. K. Brown, *Indoles, Part One*, Ed. W. J. Houlihan, Vol. 25, Chapter II, Wiley-Interscience, New York, 1972) is reduced with DIBAL-H to provide the corresponding aldehyde, which is then converted into the N-Boc derivative 10. Reaction of 10 with the trichloromethide anion [generated from KOH and CHCl$_3$; J. M. Wyvratt et. al., *J. Org. Chem.*, 52, 944–945 (1987)] followed by treatment with aqueous NaOH in DMF provides the alcohol 11. Treatment of 11 with diazomethane followed by the reaction with CBr$_4$/Ph$_3$P yields the alkylating agent 12.

Scheme 4

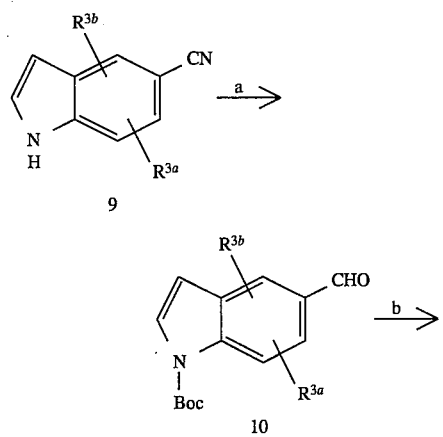

-continued
Scheme 4

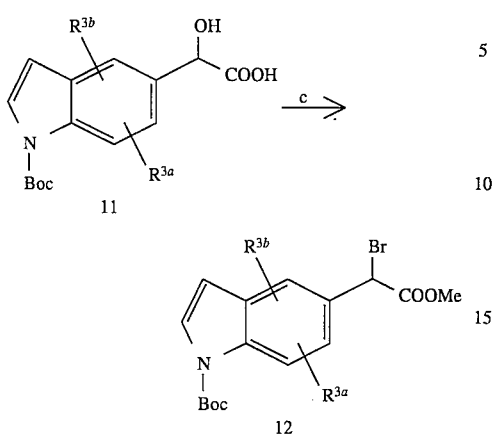

a. (i) DIBALH, Toluene; (ii) Boc₂O, DMAP, CH₂Cl₂
b. (i) CHCl₃, KOH, DMF, 0° C.; (ii) NaOH, DME/H₂O
c. (i) CH₂N₂; (ii) CBr₄/Ph₃P, CH₂Cl₂

A typical synthesis of alkylating agents bearing a substituted benzoxazole or benzthiazole ring is outlined in Scheme 5. The substituted benzoxazole 14 is prepared from the corresponding o-aminophenol 13 by the reaction of an appropriate orthoester under refluxing conditions (for other methods of synthesis of benzoxazoles see, S. A. Lang and Y. Lin, *Comprehensive Heterocyclic Chemistry*, Vol. 6, 1–130, Ed. C. W. Rees; and references cited therein). Reduction of 14 with NaBH₄ provides the alcohol 15 which is then subjected to pyridinium dichromate (PDC) oxidation to yield the corresponding aldehyde 16. Further elaboration of 16 as outlined provides the key intermediate 17. Similarly, the benzothiazole 19 can also be prepared form the appropriately substituted o-aminothiophenol 18.

Scheme 5

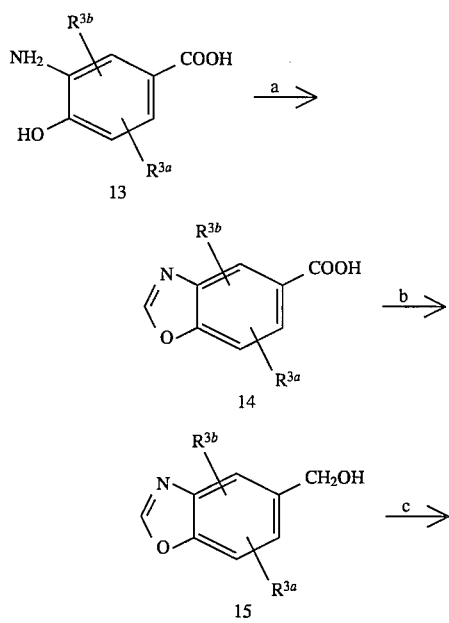

-continued
Scheme 5

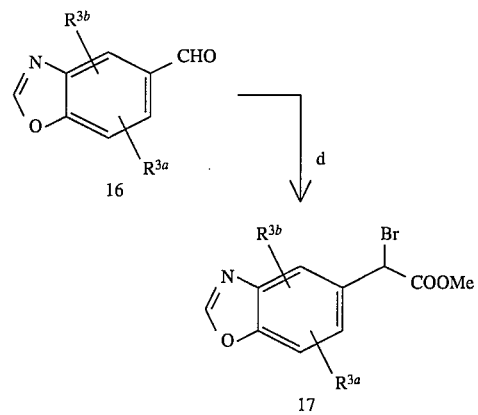

a. CH(OEt)₃, EtOH, reflux
b. (i) ClCOOEt, Et₃N, THF;
   (ii) NaBH₄, THF—H₂O
c. Pyridinium dichromate, CH₂Cl₂
d. (i) CHCl₃, KOH, DMF, 0° C.;
   (ii) NaOH, DME/H₂O;
   (iii) HCl/MeOH;
   (iv) CBr₄/Ph₃P, CH₂Cl₂

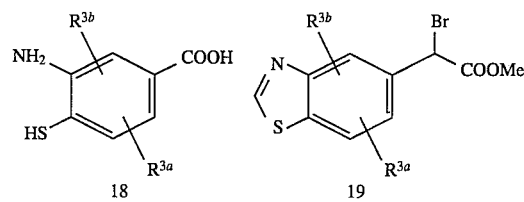

Scheme 6 illustrates the synthesis of benzofuran and dihydrobenzofuran alkylating agents 23 and 25. The benzofuran 21 can be prepared from the α-phenoxy carbonyl compound 20 via a ring closure reaction [Stoermer and Wehln, *Chem. Ber.*, 35, 3549 (1902)](for general methods of synthesis of benzofurans and dihydrobenzofurans see, R. C. Elderfield and V. B. Meyer, *Heterocyclic Compounds*, Vol. 2, Chapter 1, Ed. R. C. Elderfield, Wiley; and references cited therein). The ester 21 is reduced to provide the aldehyde 22 which is then transformed into the corresponding alkylating agent 23. The dihydrobenzofuran ester 24, obtained by catalytic reduction of 21, can also be transformed into the corresponding alkylating agent 25 using the sequence of reactions outlined in Scheme 6.

Benzothiophene 26 may be synthesized from the corresponding aldehyde 26b in a manner similar to that outlined in Scheme 6 for benzofuran 23. Benzothiophene 26b can be prepared by the oxidative cyclization (using an alkaline solution of potassium ferricyanide) of appropriately substituted o-mercaptocinnamic acid 26a [C. Chmelewsky and P. Friedlander, (*Chem. Ber.*, 46, 1903 (1913)]. (For general methods of synthesis of benzothiophene, See, E. Champaigne in *Comprehensive Heterocyclic Chemistry*, vol. 4, Chapter 3–15; Eds. A. Katritzky and C. W. Rees.)

Scheme 7 outlines a typical synthesis of α-bromoarylacetates, 30 and 32, bearing appropriately substituted methylenedioxy or 1,4-dioxane rings. The substituted catechol derivative 27 is treated with an appropriate dibromide (where m is 1 or 2) in the presence of cesium carbonate in dimethylformamide to provide 28. Treatment of 28 with DIBALH yields the aldehyde 29 which is then transformed into the desired alkyl bromide as described.

Scheme 6
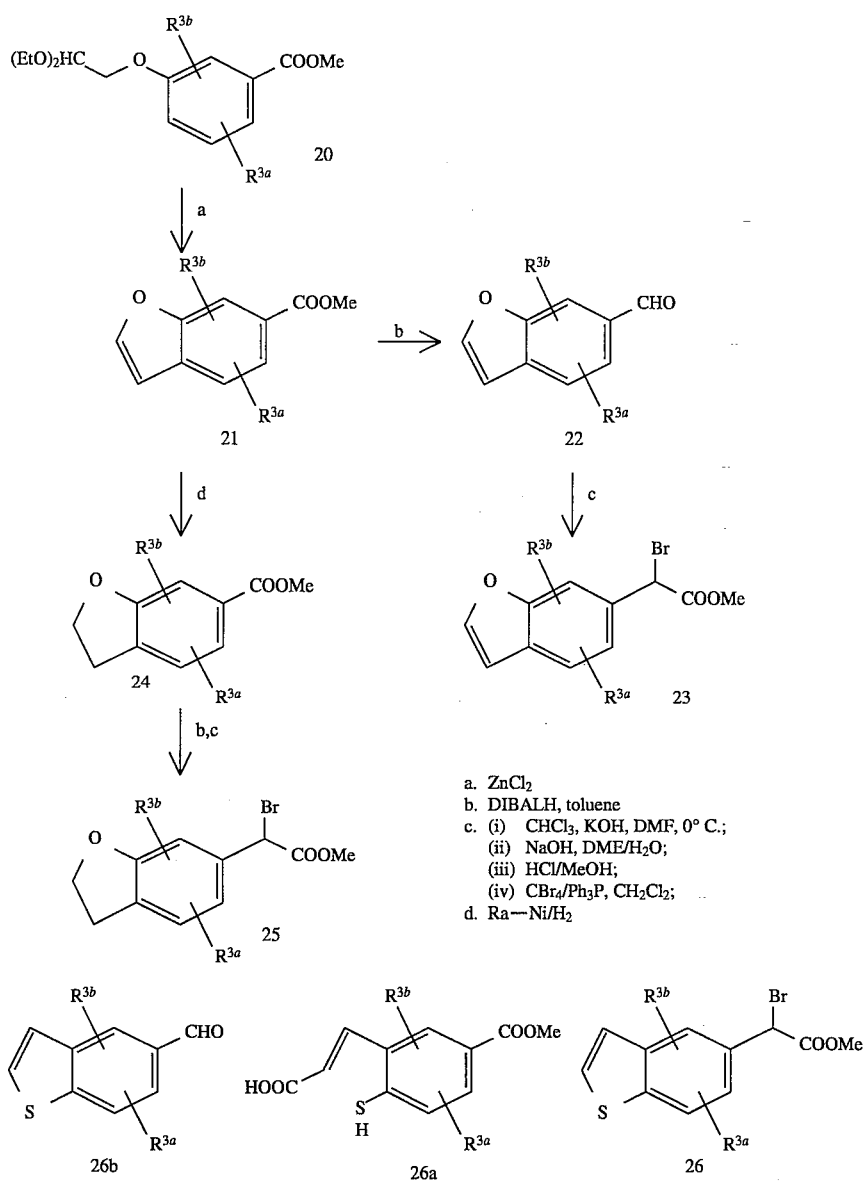

Scheme 7

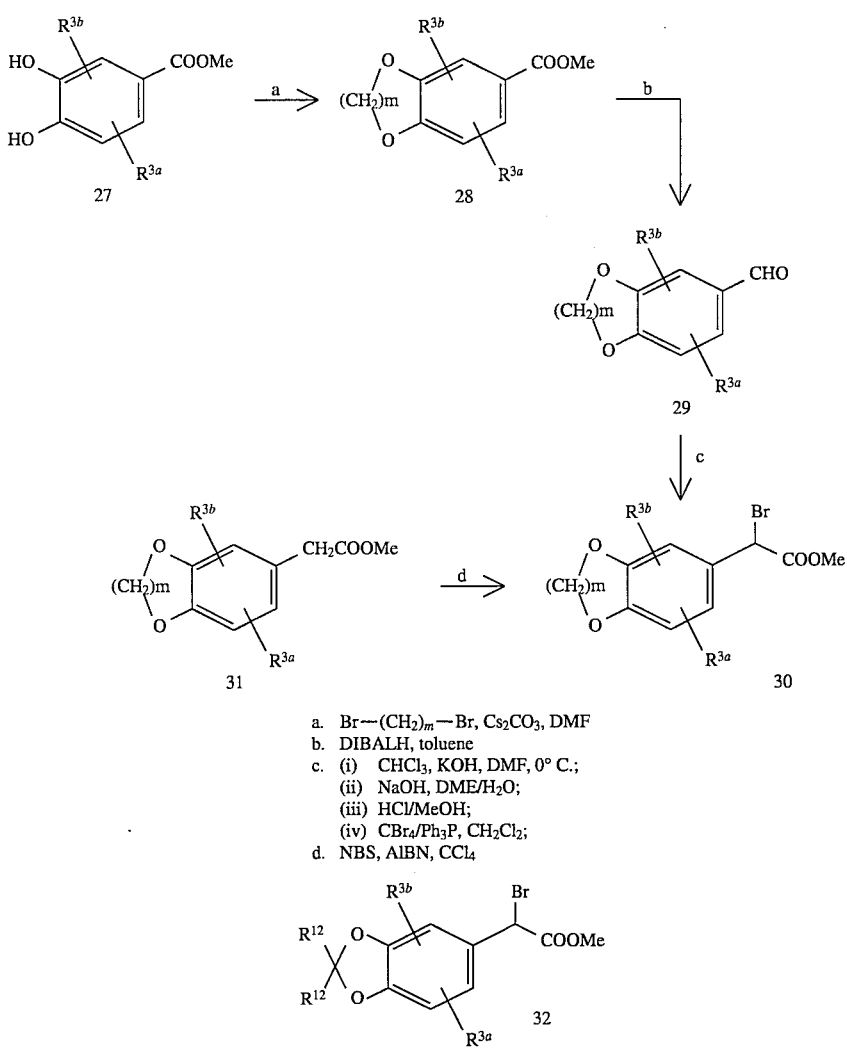

a. Br—(CH₂)ₘ—Br, Cs₂CO₃, DMF
b. DIBALH, toluene
c. (i) CHCl₃, KOH, DMF, 0° C.;
   (ii) NaOH, DME/H₂O;
   (iii) HCl/MeOH;
   (iv) CBr₄/Ph₃P, CH₂Cl₂;
d. NBS, AIBN, CCl₄

Following the synthetic route outlined in Scheme 8 below N-(4-iso-propylbenzenesulfonyl)-α-(4-carboxy-2-n-propylphenoxy)-3,4-methylenedioxyphenylacetamide dipotassium salt, 45 is prepared. Commercially available methyl 4-hydroxybenzoate (33) is O-allylated using allyl bromide in the presence of a suitable base such as potassium carbonate in refluxing acetone. The resulting O-allyl ether (34) then undergoes Claisen rearrangement to afford 35 when heated at elevated temperature, for instance at reflux in a high boiling inert solvent like 1,2-dichlorobenzene. Finally, reduction of 35 with hydrogen at atmospheric or elevated pressures and in the presence of a catalyst such as palladium on carbon provides methyl 4-hydroxy-3-propylbenzoate. The preparation of ethyl α-bromo-3,4-methylenedioxyphenylacetate (39) from piperonal (37) using the general synthetic strategy outlined above in Scheme 3 follows the synthesis of 36. Finally, preparation of 4-iso-propylbenzenesulfonamide (41) from commercially available 4-iso-propylbenzenesulfonyl chloride (40) using ammonium hydroxide solution is also illustrated. The synthesis of compound 45 using the intermediates 36, 39 and 41 is shown at the bottom of Scheme 8. The phenolic hydroxyl group of 36 is alkylated with the α-bromoester 39 in a solvent such as acetone or DMF and in the presence of a suitable base like potassium or cesium carbonate. The reaction is generally conducted at elevated temperatures for instance at the boiling point of acetone (56° C.) or in DMF at at 80° C., and the product is the ether 42. Hydrolysis of the diester 42 using one equivalent of sodium or potassium hydroxide in a solvent such as methanol affords the mono-carboxylic acid 43 with high chemoselectivity. The choice of differentiated alkyl groups in the diester 42 make the assignment of the structure of 43 by NMR spectroscopy unambiguous. The next stage of the synthesis involves activation of the carboxylic acid 43 with a carboxyl-activating agent such as N,N-carbonyldiimidazole (CDI). This reaction is conducted in an aprotic solvent at elevated temperature such as refluxing THF, and an intermediate acyl-imidazole is formed, however this reactive intermediate is not isolated. The reaction mixture is cooled to room temperature briefly and the sulfonamide 41 and a base such as 1,8-diazabicyclo [5.4.0]undec-7-ene (DBU) is added. After reaction at elevated temperature for an additional period (1-6 hours) the coupling of the carboxylic acid 43 and the sulfonamide 41 is generally complete and the reaction mixture is cooled to room temperature. Partitioning the reaction mixture between an organic solvent like ethyl acetate or diethylether followed by extraction of the residual organic bases into dilute aqueous acid affords the semi-purified coupled product in the organic layer. This product can be isolated conveniently as an alkali metal salt (44) by evaporation of the organic layer from the previous step followed by treatment of the residue with one equivalent of sodium or potassium hydroxide in methanol. The synthesis of 45 is then completed by reaction of 44 with excess sodium or potassium hydroxide in a solvent such as methanol at room temperature or at moderately elevated temperatures such as 60° C. Hydrolysis of the remaining ester group in 44 affords the product 45. This organic diacidic compound (45) may also be isolated in pure form by crystallization of the semi-purified product with two equivalents of sodium or potassium hydroxide in a solvent such as methanol or ethanol.

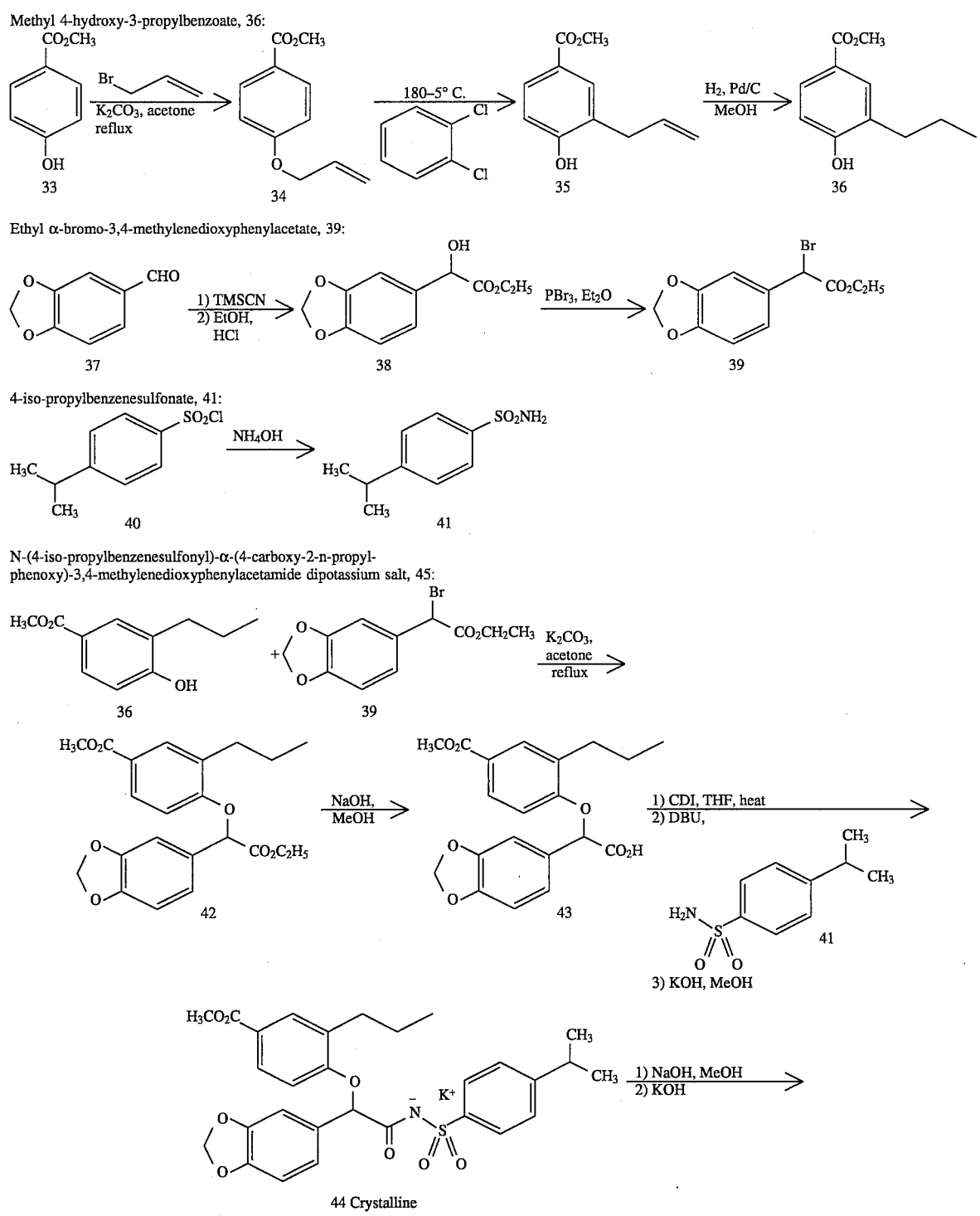

Scheme 8

-continued
Scheme 8

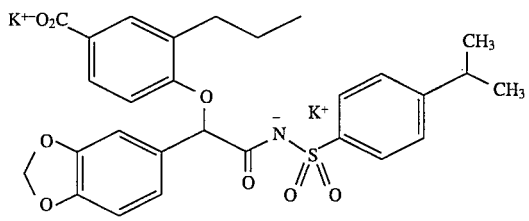

45
Crystalline, $pK_{a1} = 5.4$, $pK_{a2} = 5.8$; MW = 615.8,
logP 2.7; Aqueous solubility > 50 mg/mL Similarly, compounds of general Formula IV wherein —A— is represented by —OCH$_2$O—, $R^{12}$ is CO$_2$H, and X is represented by —NH— are prepared using the route illustrated in Scheme 9. In this synthesis, a generalized 4-aminobenzoic acid ester such as 46 is reacted with an α-bromoester such as 39 which was described above in Schemes 3 and 8, to afford a substituted α-phenylaminophenylacetic ester like 47. This reaction proceeds at elevated temperatures in a polar aprotic solvent such as DMF in the absence of additional bases to provide 47. The diester 47 may be chemoselectively hydrolyzed to give 48 using an alkali metal hydroxide in an alcoholic solvent as was previously illustrated for the conversion of 42 to 43 in Scheme 8. The carboxylic acid group of 48 may then be converted to an acylsulfonamide 49 employing a suitable carboxylic acid activating reagent such as CDI followed by addition of the sulfonamide 41 and DBU as shown above in Scheme 8. Alternatively, acid 48 can be coupled to the sulfonamide 41 using 1-(3-dimethylaminopropyl)-3-ethylcarbodiimide hydrochloride (EDC) in a solvent like methylene chloride in the presence of 4-dimethylaminopyridine (DMAP) as shown in Scheme 9. This reaction produces a compound of general formula IV (49) wherein $R^{12}$ is an ester, A is represented by —OCH$_2$O—, and X is an NH group. Finally, a compound of general formula IV wherein $R^{12}$ is a carboxylic acid, A is represented by —OCH$_2$O—, and X is an NH group is produced when the ester 49 is hydolyzed with an alkali metal hydroxide in a suitable solvent like methanol or ethanol and the acid 50 is the product.

Scheme 9
N-(4-iso-propylbenzenesulfonyl)-α-(4-carboxyphenylamino)-
3,4-methylenedioxyphenylacetamide dipotassium salt, 50:

Scheme 9
N-(4-iso-propylbenzenesulfonyl)-α-(4-carboxyphenylamino)-3,4-methylenedioxyphenylacetamide dipotassium salt, 50:

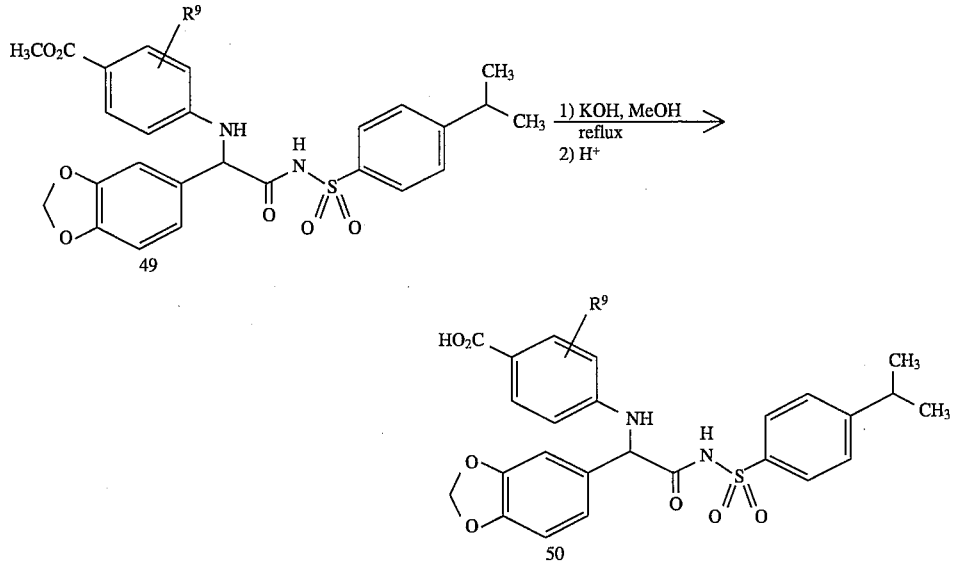

Scheme 10 illustrates the synthetic route to compounds bearing N-acylsulfamides (52) (Z=—CONHSO₂NH—R¹¹). The carboxylic acid 3 (Z₁=—COOH; Scheme 1) is reacted with 1,1'-carbonyldiimidazole (CDI) to provide the acylimidazole which is then reacted with an appropriate sulfamide (51) in the presence of DBU. The sulfamides (R¹¹—NHSO₂NH₂) can be prepared from appropriate primary amines using the literature procedures [W. L. Matier, W. T. Comer and D. Deitchman, *J. Med. Chem.*, 15, 538–541(1972); J. D. Catt and W. L. Maiter, *J. Org. Chem.*, 39, 566–568(1974)].

Scheme 10

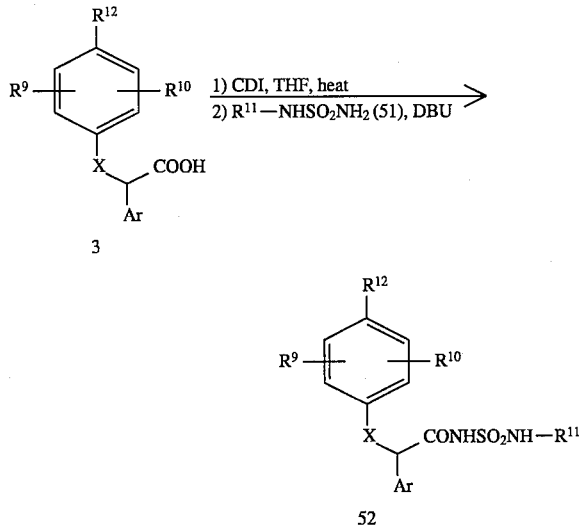

Compounds of general Formula IV in which the $R^{12}$ substituent is a tetrazolyl group can be synthesized as shown in Scheme 11. For this synthesis, a substituted 4-hydroxybenzonitrile (53) is utilized as the starting material. The selected 4-hydroxybenzonitrile 53 may be commercially available, or if it is preferred that one of the substituents $R^9$ or $R^{10}$ be an n-propyl group then 4-hydroxy-3-propylbenzonitrile is first prepared in three steps from 4-hydroxybenzonitrile using the same methods that were illustrated for the synthesis of methyl 4-hydroxy-3-propylbenzoate (36) from methyl 4-hydroxybenzoate (33) at the top of Scheme 8. The substituted or unsubstituted 4-hydroxybenzonitrile 53 is then O-alkylated with an alkyl α-bromo-3,4-methylenedioxyphenylacetate (39) using a base such as cesium carbonate in a solvent like DMF and the ether 54 is the product. Compound 54 is next hydrolyzed with sodium or potassium hyroxide in an alcoholic solvent to yield the acid 55. The carboxylic acid 55 may then be convened to an acylsulfonamide like 56 using CDI activation followed by addition of the sulfonamide 41 and DBU as was decribed previously. The synthesis of a compound of general Formula IV wherein $R^{12}$ is a tetrazolyl group (57) is then completed by reacting the nitrile group of compound 56 with tfirnethyltin azide at elevated temperatures (110° C.) in a solvent like toluene as shown at the bottom of Scheme 11.

Scheme 11

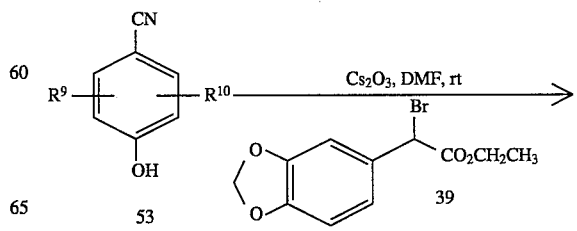

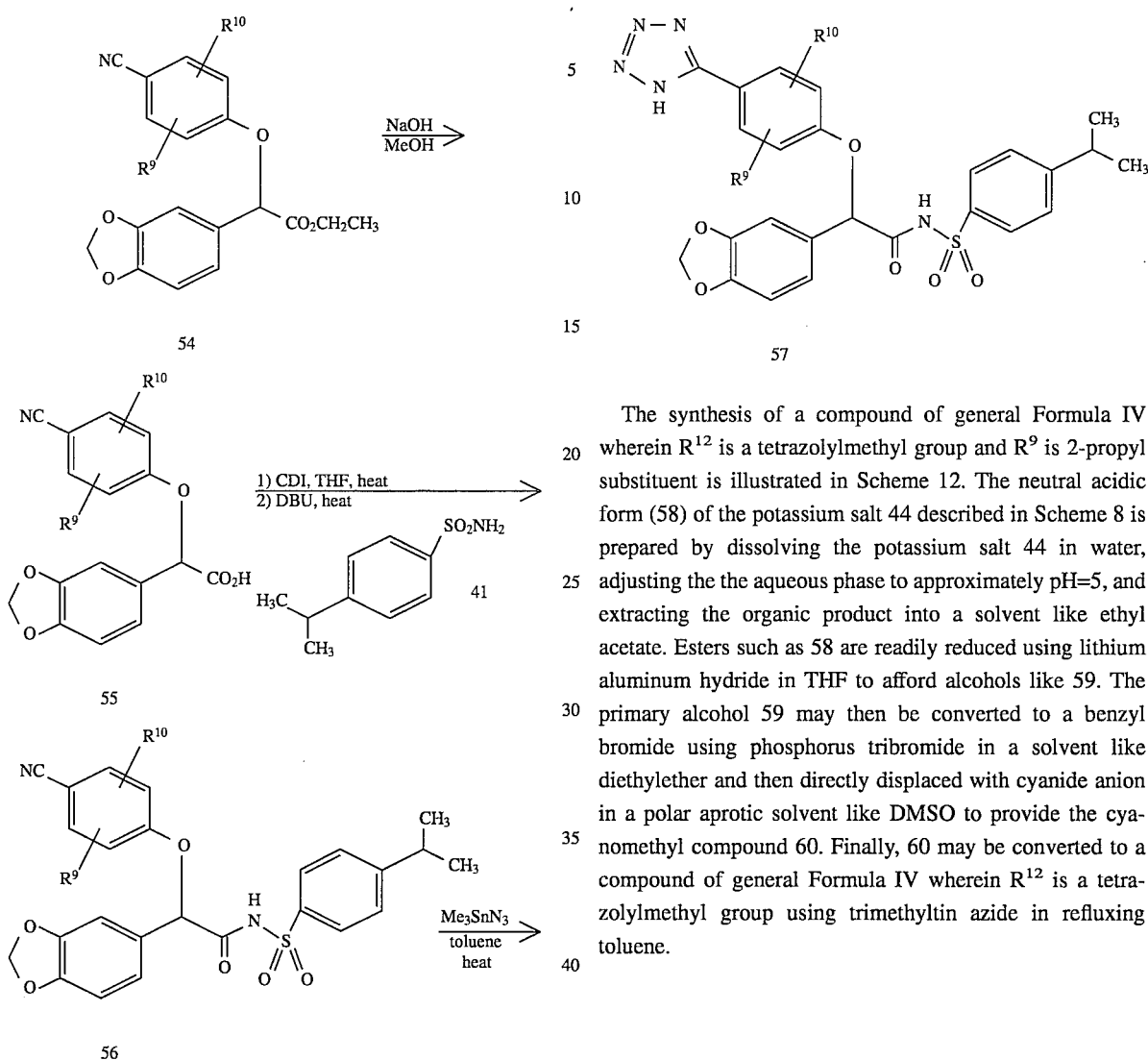

The synthesis of a compound of general Formula IV wherein $R^{12}$ is a tetrazolylmethyl group and $R^9$ is 2-propyl substituent is illustrated in Scheme 12. The neutral acidic form (58) of the potassium salt 44 described in Scheme 8 is prepared by dissolving the potassium salt 44 in water, adjusting the the aqueous phase to approximately pH=5, and extracting the organic product into a solvent like ethyl acetate. Esters such as 58 are readily reduced using lithium aluminum hydride in THF to afford alcohols like 59. The primary alcohol 59 may then be converted to a benzyl bromide using phosphorus tribromide in a solvent like diethylether and then directly displaced with cyanide anion in a polar aprotic solvent like DMSO to provide the cyanomethyl compound 60. Finally, 60 may be converted to a compound of general Formula IV wherein $R^{12}$ is a tetrazolylmethyl group using trimethyltin azide in refluxing toluene.

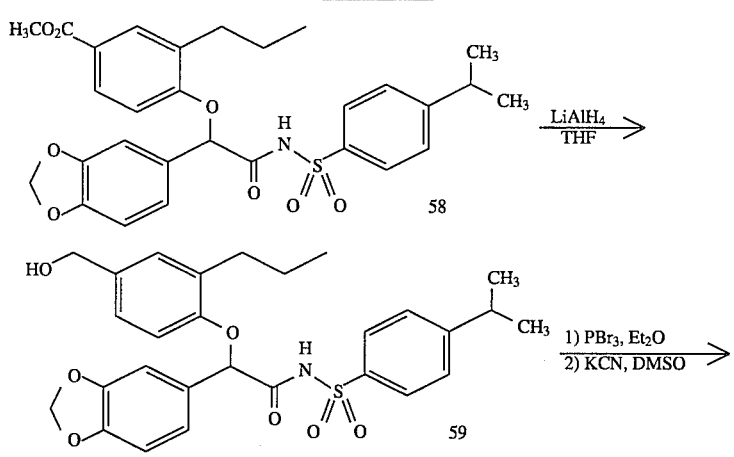

-continued
Scheme 12

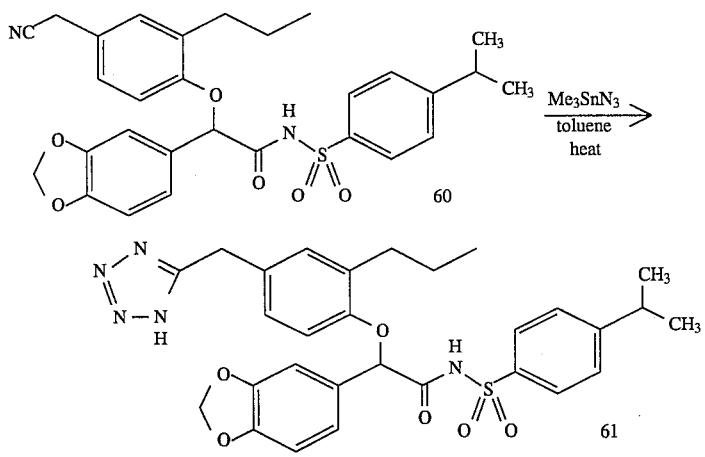

A variety of preferred compounds of general Formula IV wherein X is an oxygen atom, A represents a —OCH$_2$O— group and R$^{12}$ contains a sulfonyl group directly attached to the aromatic ring may be synthesized from commercially available 4-hydroxybenzenesulfonamide (62) as shown in Scheme 13. If it is desired that one of the substituents R$^9$ or R$^{10}$ is an n-propyl group, then it is again possible to utilize the three step protocol for phenol alkylation that was described for the conversion of methyl 4-hydroxybenzoate (33) to methyl 4-hydroxy-3-propylbenzoate (36) that was described in the discussion of Scheme 8. Using the selected substituted or unsubstituted 4-hydroxybenzene sulfonamide 62 the synthesis begins with O-alkylation of the phenolic hydroxyl group of 62 under basic conditions with an α-bromoester like 9, to afford intermediate 63. The ester group of 63 is hydrolyzed under standard conditions and the resulting carboxylic acid (64) is activated (CDI, THF, heat) then condensed with a sulfonamide such as 41. This sequence provides compounds of general Formula IV wherein R$^{12}$ is a primary sulfonamide group (41) and compounds like 41 may be employed as endothelin antagonists or they may be further derivatized at the primary sulfonamide group as shown in Scheme 14.

The primary sulfonamide group of compounds related to 65 may undergo a number of straightforward transformations known to synthetic organic chemists to afford additional examples of endothelin antagonists corresponding to general Formula IV. For instance, 65 reacts readily with a CDI-activated carboxylic acid to provide compound 66 wherein R$^{12}$ is an acylsulfonamide, alternatively 65 reacts with reagents such as di-tert-butyl dicarbonate (BOC)$_2$O to afford the sulfonyl carbamate 66 (R=—O—t-Butyl). The primary sulfonamide 65 may also be reacted with alkyl isocyanates to afford N-alkylsulfonylurea derivatives such as 67 as shown in Scheme 14.

Scheme 13

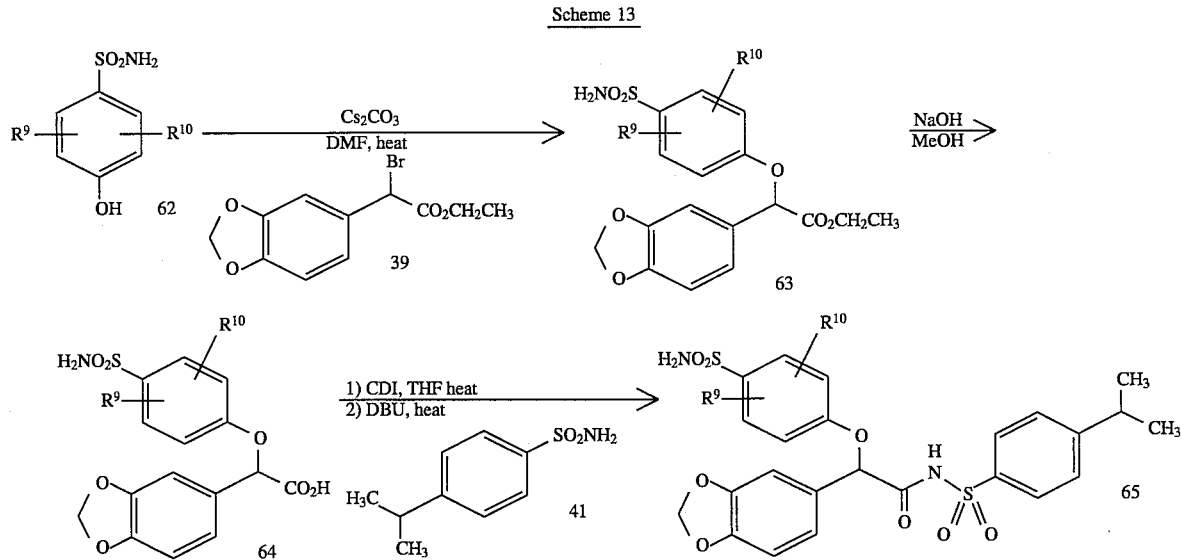

Scheme 14

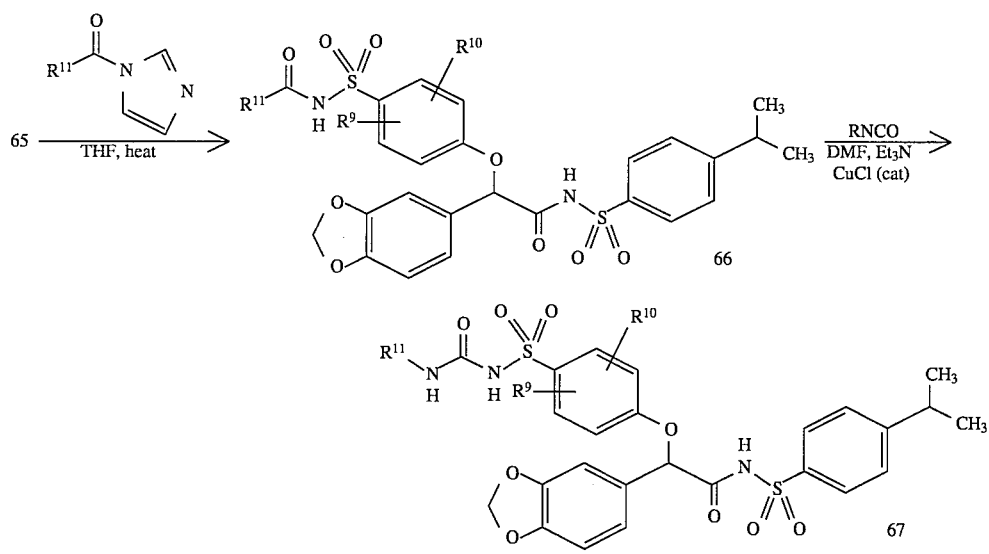

Compounds of general Formula IV may be further derivatized using standard organic functional group manipulation to provide additional examples of endothelin antagonists which are within the scope of this invention. For instance, compounds of Formula IV wherein $R^{12}$ is a carboxylic acid or ester group are useful intermediates for the preparation of compounds wherein $R^{12}$ is a substituted amide, ketone, urea, carbamate or the like. For instance, reaction of compound 45 (Scheme 8) with N,O-dimethylhydroxylamine in the presence of the dehydrating agent EDC provides the N,O-dimethylhydroxylamine 68 as shown in Scheme 15. Amides such as 68 may then be converted into a variety of ketones using methodology described by Weinreb (Nahm, S.; Weinreb, S. M. *Tetrahedron Lett.* 1981, 22, 3815) to provide compounds of general Formula IV (69) wherein $R^{12}$ is an acyl or aroyl group.

Scheme 15

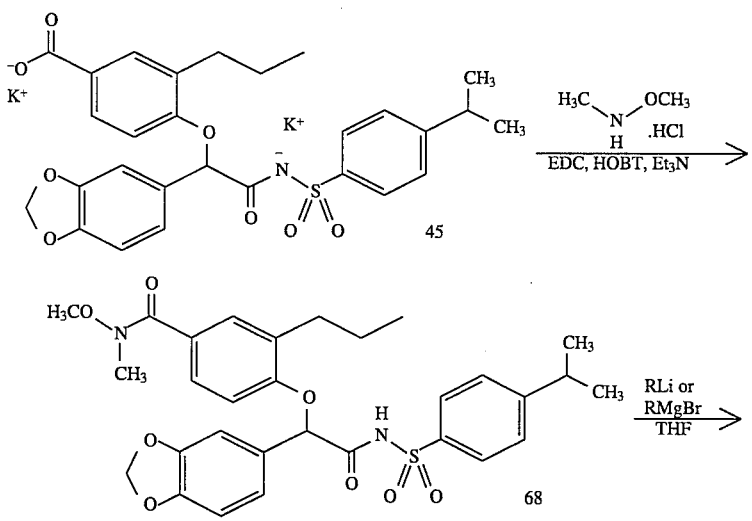

-continued
Scheme 15

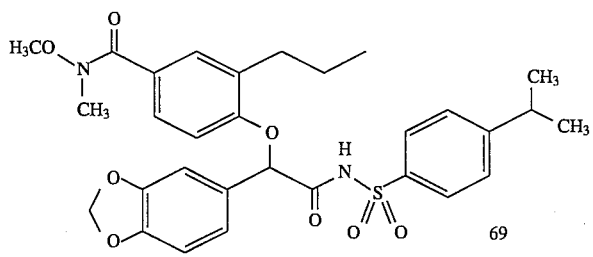

69

The reactions cited above are performed in a solvent appropriate to the reagents and materials employed and suitable for the transformation being effected. It is understood by those skilled in the art of organic synthesis that the functionality present on the heterocycle and in the reactants being employed should be consistent with the chemical transformations being conducted. Depending upon the reactions and techniques employed, optimal yields may require changing the order of synthetic steps or use of protecting groups followed by deprotection.

The compounds useful in the novel method treatment of this invention form salts with various inorganic and organic acids and bases which are also within the scope of the invention. Such salts include ammonium salts, alkali metal salts like sodium and potassium salts, alkaline earth metal salts like the calcium and magnesium salts, salts with organic bases; e.g., dicyclohexylamine salts, N-methyl-D-glucamine salts, salts with amino acids like arginine, lysine, and the like. Also, salts with organic and inorganic acids may be prepared; e.g., HCl, HBr, $H_2SO_4$, $H_3PO_4$, methanesulfonic, toluenesulfonic, maleic, fumaric, camphorsulfonic.

The salts can be formed by conventional means, such as by reacting the free acid or free base forms of the product with one or more equivalents of the appropriate base or acid in a solvent or medium in which the salt is insoluble, or in a solvent such as water which is then removed in vacuo or by freeze-drying or by exchanging the cations of an existing salt for another cation on a suitable ion exchange resin.

It will be appreciated that the compounds of general Formula I in this invention may be derivatised at functional groups to provide prodrug derivatives which are capable of conversion back to the parent compounds in vivo. The concept of prodrug administration has been extensively reviewed (e.g. A. A. Sinkula in *Annual Reports in Medicinal Chemistry*, Vol 10, R. V. Heinzelman, Ed., Academic Press, New York London, 1975, Ch. 31, pp. 306–326, H. Ferres, *Drugs of Today*, Vol 19, 499–538 (1983) and *J. Med. Chem.*, 18, 172 (1975)). Examples of such prodrugs include the physiologically acceptable and metabolically labile ester derivatives, such as lower alkyl (e.g. methyl or ethyl esters), aryl (e.g. 5-indanyl esters), alkenyl (e.g. vinyl esters), alkoxyalkyl (e.g. methoxymethyl esters), alkylthioalkyl (e.g. methylthiomethyl esters), alkanoyloxyalkyl (e.g. pivaloyloxymethyl esters), and substituted or unsubstituted aminoethyl esters (e.g. 2-dimethylaminoethyl esters). Additionally, any physiologically acceptable equivalents of the compounds of general Formula I, similar to the metabolically labile esters, which are capable of producing the parent compounds of general Formula I in vivo, are within the scope of this invention.

It will be further appreciated that the majority of compounds of general Formula I claimed herein are asymmetric and are produced as racemic mixtures of enantiomers and that both the racemic compounds and the resolved individual enantiomers are considered to be within the scope of this invention. The racemic compounds of this invention may be resolved to provide individual enantiomers utilizing methods known to those skilled in the art of organic synthesis. For example, diastereoisomeric salts, esters or imides may be obtained from a racemic compound of general Formula I and a suitable optically active amine, amino acid, alcohol or the like. The diastereoisomeric salts, esters or imides are separated and purified, the optically active enantiomers are regenerated and the preferred enantiomer is the more potent isomer. The resolved enantiomers of the compounds of general Formula I, their pharmaceutically acceptable salts and their prodrug forms are also included within the scope of this invention.

Endothelin (ET-1), and two closely related bioactive peptides, ET-2 and ET-3, are widely distributed in mammalian tissues, and they can induce numerous biological responses in non-vascular as well as vascular tissues by binding to at least two distinct endothelin receptor subtypes. In addition to cardiovascular smooth muscle, neural and atrial sites, endothelin receptors may also be found in brain, gastrointestinal, kidney, lung, urogenital, uteral and placental tissues.

Endothelin is a potent vasoconstrictor peptide and thus plays a role in vivo in arterial pressure-volume homeostasis. Not only peripheral, but coronary vascular resistance as well, is increased by endothelin; cardiac output is decreased, while plasma renin activity is increased. There is a reduction in renal blood flow and glomerular filtration rate, while levels of atrial natriuretic factor, vasopressin, and aldosterone become elevated.

It is also considered, in accordance with the present invention, that antagonists for the endothelin receptor may be useful in preventing or reducing restenosis subsequent to denudation following angioplasty. Such denudation results in myointimal thickening following angioplasty, due to increased endothelin release. Endothelin acts as a growth factor with respect to smooth muscle and fibroblastic cells, and possibly other types of cells, as well.

Endothelin is also a neuropeptide, acting on the posterior pituitary, where it modulates the release of the neurosecretory hormones vasopressin and oxytocin. Endothelin released from the posterior pituitary also acts as a circulating hormone, having a wide range of actions as discussed further above. This includes effects on the endocrine system, especially the adrenal glands. Endothelin increases plasma levels of epinephrine.

Consequently, the novel compounds of the present invention, which are receptor antagonists of endothelin, have therapeutic usefulness in preventing, decreasing or modulating the various physiological effects of endothelin discussed above, by wholly or partially blocking access of endothelin to its receptor.

Endothelin Receptor Binding Assays

The binding of the novel compounds of this invention to the endothelin receptor was determined in accordance with the assay described in detail immediately below. It is similar to the assay described in Ambar et al. (1989) *Biochem. Biophys. Res. Commun.* 158, 195–201; and Khoog et al. (1989) FEBS Letters. 253, 199–202.

The endothelins (ETs) have a number of potent effects on a variety of cells, and exert their action by interacting with specific receptors present on cell membranes. The compounds described in the present invention act as antagonists of ET at the receptors. In order to identify ET antagonists and determine their efficacy in vitro, the following three ligand receptor assays were established.

Receptor binding assay using cow aorta membrane preparation

Thoracic aortae were obtained from freshly slaughtered calves and brought to the lab on wet ice. The adventitia were removed, and the aorta was opened up lengthwise. The lumenal surface of the tissue was scrubbed with cheesecloth to remove the endothelial layer. The tissue was ground in a meat grinder, and suspended in ice-cold 0.25 M sucrose, 5 mM tris-HCl, pH 7.4, containing 0.5 mg/mL leupeptin and 7 mg/mL pepstatin A. Tissue was homogenized twice and then centrifuged for 10 minutes at 750 ×g at 4° C. The supernatant was filtered through cheesecloth and centrifuged again for 30 minutes at 48,000×g at 4° C. The pellet thus obtained was resuspended in the buffer solution described above (including the protease inhibitors), and aliquots were quick-frozen and stored at −70° C. until use. Membranes were diluted into 50 mM potassium. phosphate (KPi), 5 mM EDTA pH 7.5 containing 0.01% human serum albumin. Assays were done in triplicate. Test compounds and 100 pM [$^{125}$I]-endothelin. 1 (2000–2200 Ci/mmole, obtained from New England Nuclear or Amersham) were placed in a tube containing this buffer, and the membranes prepared above were added last. The samples were incubated for 60 min at 37° C. At the end of this incubation, samples were filtered onto prewetted (with 2% BSA in water) glass fiber filter pads and washed with 150 mM NaCl, 0.1% BSA. The filters were assayed for $^{125}$I radioactivity in a gamma counter. Nondisplaceable binding of [$^{125}$I]-endothelin-1 is measured in the presence of 100 nM unlabelled endothelin-1 [Endothelin-1 (ET-1) was purchased from Peptides International (Louisville, Ky.). $^{125}$I-ET-1 (2000 Ci/mMol) was purchased from Amersham (Arlington Heights, Ill.)]. Specific binding is total binding minus nondisplaceable binding. The inhibitory concentration (IC$_{50}$) which gives 50% displacement of the total specifically bound [$^{125}$I]-endothelin-1 was presented as a measure of the efficacy of such compounds as ET antagonists.

Receptor binding assay using rat hippocampal membrane preparation

Rat hippocampi were obtained from freshly sacrificed male Sprague-Dawley rats and placed in ice cold 0.25 M sucrose, 5 mM tris-HCl, pH 7.4 containing 0.5 mg/mL leupeptin, 7 mg/mL pepstatin A. Hippocampi were weighed and placed in a Dounce homogenizer with 25 volumes (wet weight to volume) ice-cold sucrose buffer in the presence of protease inhibitors. Hippocampi were homogenized using a Dounce (glass-glass) homogenizer with type A pestle, with homogenizer in ice. Tissue homogenate was centrifuged at 750×g for 10 min at 4° C. Supernatant was filtered through dampened cheesecloth, and centfifuged again at 48,000 ×g for 30 min at 4° C. Pellets were resuspended in sucrose buffer with protease inhibitors. Aliquots of this preparation were quick frozen and stored at −70° C. until use. Membranes were diluted into 50 mM KPi, 5 mM EDTA pH 7.5 containing 0.01% human serum albumin. Assays were done in triplicate. Test compounds and 25 pM [$^{125}$I]-endothelin-1 (2000–2200 Ci/mmole, obtained from New England Nuclear or Amersham) were placed in a tube containing this buffer, and the membranes prepared above were added last. The samples were incubated for 60 min at 37° C. At the end of this incubation, samples were filtered onto prewetted (with 2% BSA in water) glass fiber filter pads and washed with 150 mM NaCl, 0.1% BSA. The filters were assayed for $^{125}$I radioactivity in a gamma counter. Nondisplaceable binding of [$^{125}$I]-endothelin-1 is measured in the presence of 100 nM unlabelled endothelin-1 [Endothelin-1 (ET-1) was purchased from Peptides International (Louisville, Ky.). $^{125}$I-ET-1 (2000 Ci/mMol) was purchased from Amersham (Arlington Heights, Ill.)]. Specific binding is total binding minus nondisplaceable binding. The inhibitory concentration (IC$_{50}$) which gives 50% displacement of the total specifically bound [$^{125}$I]-endothelin-1 was presented as a measure of the efficacy of such compounds as endothelin antagonists.

Receptor binding assay using cloned human ET receptors expressed in Chinese Hamster Ovary Cells Both endothelin receptor subtypes were cloned from a human cDNA library and were individually expressed in Chinese Hamster Ovary cells. Cells were harvested by addition of 126 mM NaCl, 5 mM KCl, 2 mM EDTA, 1 mM NaH$_2$PO$_4$, 15 mM glucose, 10 mM tris/HEPES pH 7.4 Cells were centrifuged at 250 ×g for 5 minutes. The supernatant was aspirated off, and the cells were resuspended in the 50 mM KPi, 5 mM EDTA pH 7.5 containing 0.01% human serum albumin. Assays were done in triplicate. Test compounds and 25–100 pM [$^{125}$I]-endothelin-1 (2000–2200 Ci/mmole, obtained from New England Nuclear or Amersham) were placed in a tube containing 50 mM KPi, 5 mM EDTA pH 7.5 containing 0.01% human serum albumin, and the cells prepared above were added last. The samples were incubated for 60 min at 37° C. At the end of this incubation, samples were filtered onto prewetted (with 2% BSA in water) glass fiber filter pads and washed with 150 mM NaCl, 0.1% BSA.

The filters were assayed for $^{125}$I radioactivity in a gamma counter. Nondisplaceable binding of [$^{125}$I]-endothelin-1 is measured in the presence of 100 nM unlabelled endothelin-1 [Endothelin-1 (ET-1) was purchased from Peptides International (Louisville, Ky.). $^{125}$I-ET-1 (2000 Ci/mMol) was purchased from Amersham (Arlington Heights, Ill.)]. Specific binding is total binding minus nondisplaceable binding. The inhibitory concentration (IC$_{50}$) which gives 50% displacement of the total specifically bound [$^{125}$I]-endothelin-1 was presented as a measure of the efficacy of such compounds as endothelin antagonists.

The binding assays described above were used to evaluate the potency of interaction of representative compounds of the invention with endothelin receptors. To determine whether these compounds were endothelin antagonists, assays which measure the ability of the compounds to inhibit endothelin-stimulated phosphatidylinositol hydrolysis were established. Rat uterus contains predominantly one of the known endothelin receptor subtypes (ET$_A$).

Phosphatidylinositol hydrolysis assays using rat uterine slices

Diethylstilbestrol primed female Sprague-Dawley rats were sacrificed and their uteri were collected, dissected of fat and connective tissue and minced. Minced tissue was added to oxygenated (95% $O_2$, 5% $CO_2$) 127 mM NaCl, 25 mM $NaHCO_3$, 10 mM Glucose, 2.5 mM KCl, 1.2 mM $KH_2PO_4$, 1.2 mM $MgSO_4$, 1.8 mM $CaCl_2$. To the tissue mince, 1.2 mM myo-[$^3$H]-inositol (Amersham) was added. The mince was incubated 90 min at 37° C., with constant oxygenation. After incubation, the loaded tissue mince was washed five times with the same oxygenated buffer to remove excess radiolabelled inositol. The tissue mince was resuspended in the above buffer, containing 10 mM LiCl, aliquotted into tubes, and 3 nM endothelin-1 with and without test compounds was added to start the assay. Assays were done in quadruplicate. Samples were incubated at 37° C. under blowing $O_2$ in a hooded water bath for 30 minutes. Reaction was stopped by addition of trichloroacetic acid to 6% concentration. Samples were sonicated for 10 min, centrifuged 20 min, then trichloroacetic acid was extracted with water-saturated ethyl ether. An aliquot of each sample was neutralized and diluted by addition of 50 mM tris-HCl pH 7.4. A 100 mL aliquot of this solution was assayed for radioactivity in a beta counter. The diluted neutralized sample was applied to Dowex 1×8-formate columns, washed with water, then washed with 60 mM ammonium formate, 5 mM sodium tetraborate. Samples were eluted with 200 mM ammonium formate, 5 mM sodium tetraborate. The radioactivity of each eluted sample was measured in a beta counter. Radioactivity was normalized by dividing radioactivity in post column sample by radioactivity in precolumn sample. Control values (100% stimulated) are values in the presence of endothelin minus the values in the absence of endothelin (basal). Test sample values are the values in the presence of endothelin and test sample minus basal. Inhibitory concentration ($IC_{50}$) is the concentration of test compound required to give a sample activity of 50% of control value.

Sarafotoxin S6c is a member of the endothelin family which binds preferentially to one of the known endothelin receptor subtypes ($ET_B$).

Phosphatidylinositol hydrolysis assays using rat lung slices

Male Sprague-Dawley rats were sacrificed and their lungs were collected, dissected of fat and connective tissue and minced. Minced tissue was added to oxygenated (95% $O_2$, 5% $CO_2$) 127 mM NaCl, 25 mM $NaHCO_3$, 10 mM glucose, 2.5 mM KCl, 1.2 mM $KH_2PO_4$, 1.2 mM $MgSO_4$, 1.8 mM $CaCl_2$. To the tissue mince, 1.2 μM myo-[$^3$H]-inositol was added. The mince was incubated 60 min at 37° C., with constant oxygenation. After incubation, loaded tissue mince was washed five times with the same oxygenated buffer to remove excess radiolabelled inositol. Tissue mince was resuspended in the above buffer, containing 10 mM LiCl, aliquotted into tubes, and 3 nM sarafotoxin S6c with and without test compounds was added to start the assay. Assays were done in quadruplicate. Samples were incubated at 37° C. under blowing $O_2$ in a hooded water bath for 30 minutes. Reaction was stopped by addition of 0.5 mL 18% trichloroacetic acid to 6% concentration. Samples were sonicated for 10 min, centrifuged 20 min, then trichloroacetic acid was extracted with water-saturated ethyl ether. An aliquot of each sample was neutralized and diluted by addition of 50 mM tris-HCl pH 7.4. A 100 mL aliquot of this solution was assayed for radioactivity in a beta counter. The diluted neutralized sample was applied to Dowex 1×8-formate columns, washed with water, then washed with 60 mM ammonium formate, 5 mM sodium tetraborate. Samples were eluted with 200 mM ammonium formate, 5 mM sodium tetraborate. The radioactivity of each eluted sample was measured in a beta counter. Radioactivity was normalized by dividing radioactivity in post column sample by radioactivity in precolumn sample. Control values (100% stimulated) are values in the presence of sarafotoxin minus the values in the absence of sarafotoxin (basal). Test sample values are the values in the presence of sarafotoxin and test sample minus basal. Inhibitory concentration ($IC_{50}$) is the concentration of test compound required to give a sample activity of 50% of control value.

Phosphatidylinositol hydrolysis assays using cloned human endothelin receptors expressed in Chinese Hamster Ovary cells Endothelin receptors of both receptor subtypes were cloned from a human cDNA library and were individually expressed in Chinese Hamster Ovary cells. Cells were loaded overnight by the addition of 1.2 μM myo-[$^3$H]-inositol to their growth medium. Cells were harvested by addition of 126 mM NaCl, 5 mM KCl, 2 mM EDTA, 1 mM $NaH_2PO_4$, 15 mM glucose, 10 mM tris/HEPES pH 7.4. Cells were washed five times by centrifugation at 250 ×g for 5 minutes to remove excess radiolabelled inositol. The supernatant was aspirated off, and the cells were resuspended in the same oxygenated (95% $O_2$, 5% $CO_2$) buffer containing 10 mM LiCl, aliquotted into tubes, and 0.3 nM endothelin-1 with and without test compounds was added to start the assay. Assays were done in quadruplicate. Samples were incubated at 37° C. under blowing $O_2$ in a hooded water bath for 30 minutes. Reaction was stopped by addition of 0.5 mL 18% trichloroacetic acid to 6% concentration. Samples were sonicated for 10 min, centrifuged 20 min, then trichloroacetic acid was extracted with water-saturated ethyl ether. An aliquot of each sample was neutralized and diluted by addition of 50 mM tris-HCl pH 7.4. A 100 mL aliquot of this solution was assayed for radioactivity in a beta counter. The diluted neutralized sample was applied to Dowex 1×8-formate columns, washed with water, then washed with 60 mM ammonium formate, 5 mM sodium tetraborate. Samples were eluted with 200 mM ammonium formate, 5 mM sodium tetraborate. The radioactivity of each eluted sample was measured in a beta counter. Radioactivity was normalized by dividing radioactivity in post column sample by radioactivity in precolumn sample. Control values (100% stimulated) are values in the presence of endothelin minus the values in the absence of endothelin (basal). Test sample values are the values in the presence of endothelin and test sample minus basal. Inhibitory concentration ($IC_{50}$) is the concentration of test compound required to give a sample activity of 50% of control value.

Using the methodology described above, representative compounds of the invention were evaluated and found to exhibit $IC_{50}$ values of at least <50 μM thereby demonstrating and confirming the utility of the compounds of the invention as effective endothelin antagonists.

Intravenous Effect of Endothelin-1 Antagonist, N-(4-iso-propylbenzene-sulfonyl)-α-(4-carboxy-2-n-propylphenoxy)-3,4-methylenedioxyphenylacetamide dipotassium salt [Example 58] on Endothelin 1-Induced Changes in Diastolic and Urethral Pressures in the Anesthetized Male Dog Methodology for determining whether an ET-1 selective antagonist could inhibit the ET-1 mediated prostatic urethral contractions in a mongrel dog model On separate days, two fasted male mongrel dogs (HRP, Inc.) weighing 11.0 and 12.4 kg, were anesthetized with Sodium Pentobarbital (Steris Laboratories, Inc.) at 35 mg/kg (i.v.) to effect, followed by 4 mg/kg/hr (i.v.) infusion. A cuffed endotracheal tube was inserted and each animal was ventilated with room air using a positive displacement large animal ventilator (Harvard Apparatus) at a rate of 18 breaths/minute and an average tidal volme of 18 ml/kg body weight. Body temperature was maintained with a heating pad and heat lamp using a temperature controller (YSI) and esophageal probe. Two catheters (PE 260) were placed in the aorta via the femoral arteries (one in each artery) for administration of endothelin or phenylephrine and for continuous direct monitoring of blood pressure and heart rate using a Statham blood pressure transducer (Spectramed) and a computer system (Modular Instruments, Inc.). Two other catheters (PE 260) were placed in the vena cava via the femoral veins (one catheter in each vein) for administration of pentobarbital and N-(4-iso-propylbenzenesulfonyl)-α-(4-carboxy-2-n-propylphenoxy)-3,4-methylenedioxyphenyl-acetamide dipotassium salt [Example 58]. A supra-pubic incision approximately one-half inch lateral to the penis was made to expose the ureters, urinary bladder, prostate, and urethra. The dome of the bladder was retracted to facilitate dissection of the ureters. The ureters were cannulated with PE 90 and tied off to the bladder. Umbilical tape was passed beneath the urethra at the bladder neck and another piece of tape was placed approximately 1–2 cm. distal to the prostate. The bladder dome was incised and a Micro-tip® catheter transducer (Millar Instruments, Inc.) was advanced into the urethra. The neck of the bladder was ligated with the umbilical tape to hold the transducer. The bladder incision was sutured with 3-0 silk (purse string suture). The transducer was withdrawn until it was positioned in the prostatic urethra. The position of the Micro-tip® catheter was verified by gently squeezing the prostate and noting the large change in urethral pressure prior to ligating the distal urethra.

Experimental Protocol

Phenylephrine (PE) (10 μg/kg, intra-arterial) was administered and pressor effects on diastolic blood pressure (DBP) and intra-urethral pressure (IUP) were noted. When blood pressure returned to baseline, endothelin-1 (ET-1) (1 nmole/kg, intra-arterial) was administered. Changes in DBP and IUP were monitored for one hour and an ET-1 selective endothelin antagonist, such as the compound of Example 58, N-(4-iso-propylbenzene-sulfonyl)-α-(4-carboxy-2-n-propylphenoxy)-3,4-methylenedioxyphenyl-acetamide dipotassium salt (30 mg/kg, intra-venous) was administered. Ten to fifteen minutes later when blood pressure had stabilized, ET-1 was administered again, and inhibition of ET-1 induced effects were noted. PE was administered at the end of the experiment to verify specificity for ET-1 blockade. The dogs were euthanized with an overdose of pentobarbital followed by saturated KCl.

The drags utilized in the experiment described above were:
1) Phenylephrine, HCl (PE) (Sigma Chemical, Co.) was given at a volume of 0.05 mL/kg;
2) Endothelin-1 (ET-1) (Human, Porcine, Canine, Rat, Mouse, Bovine) (Peninsula Laboratories, Inc.) was given at a volume of 0.05 mL/kg;
3) ET-1 selective antagonist, such as the compound of Example 58, N-(4-iso-propylbenzene-sulfonyl)-α-(4-carboxy-2-n-propylphenoxy)-3,4-methylenedioxyphenylacetamide dipotassium salt, was given at a volume of 0.3 mL/kg.

All drugs were dissolved in isotonic saline solution.

Results

ET-1 elicited an initial depressor effect followed by a longer pressor effect. In one dog, the pressor effect was biphasic. The decrease in DBP in both dogs averaged 13 mmHg, while the peak pressor effect averaged 26 mmHg. The average ET-1 induced increase in IUP was 15 mmHg. Ten to 14 minutes after administration of N-(4-iso-propyl-benzene-sulfonyl)-α-(4-carboxy-2-n-propylphenoxy)-3,4-methylenedioxyphenyl-acetamide dipotassium salt [Example 58], the dogs were challenged with ET-1 again and the depressor and pressor effects on DBP were inhibited 69% and 76%, respectively. The pressor effect on IUP was inhibited 93% (Table 1). Intra-arterial PE-induced increases in DBP and IUP did not change significantly after administration of N-(4-iso-propylbenzene-sulfonyl)-α-(4-carboxy-2-n-propylphenoxy)-3,4-methylenedioxyphenyl-acetamide dipotassium salt [Example 58] in the one dog studied. Increases in DBP and IUP were inhibited 35 and 13%, respectively (Table 2).

TABLE 1

Effects of ET-1 Antagonist, N-(4-iso-propylbenzenesulfonyl)-α-(4-carboxy-2-n-propylphenoxy)-3,4-methylenedioxyphenyl-acetamide dipotassium salt [Example 58], on ET-1 Induced Changes in DBP and IUP in Anesthetized Male Dogs (n = 2)

| DOG # | CHANGE IN DBP (mmHg) | | CHANGE IN IUP (mmHg) |
|---|---|---|---|
| | DEPRESSOR | PRESSOR | PRESSOR |
| ET-1 (i.a.) | | | |
| HG FMJC | −10 | 19 | 18 |
| HG FMHK | −15 | 33 | 11 |
| MEAN | −13 | 26 | 15 |
| SEM | 3 | 7 | 4 |
| ET-1 + Example 58 | | | |
| HG FMJC | −3 | 8 | 1 |
| HG FMHK | −5 | 2 | 1 |
| MEAN | −4 | 5 | 1 |
| SEM | 1 | 3 | 0 |
| % INHIBITION | | | |
| HG FMJC | 70 | 58 | 94 |
| HG FMHK | 67 | 94 | 91 |
| MEAN | 69 | 76 | 93 |
| SEM | 2 | 18 | 2 |

TABLE 2

Effects of ET-1 Antagonist, N-(4-iso-propylbenzenesulfonyl)-α-(4-carboxy-2-n-propylphenoxy)-3,4-methylenedioxyphenyl-acetamide dipotassium salt [Example 58], on PE-Induced Changes in DBP and IUP in Anesthetized Male Dog #HG FMJC

| TREATMENT | INCREASE IN DBP (mmHg) | INCREASE IN IUP (mmHg) |
|---|---|---|
| Phenylephrine | 17 | 31 |
| Phenylephrine + Example 58 | 11 | 27 |
| % Inhibition of Control | 35 | 13 |

Conclusions

ET-1 causes constriction of the prostatic urethra, as well as a complex hemodynamic response comprised of an initial depressor and subsequent pressor response in anesthetized dogs. The hemodynamic and prostatic urethral responses to ET-1 were specifically inhibited by N-(4-iso-propylbenzenesulfonyl)-α-(4-carboxy-2-n-propylphenoxy)-3,4-methylenedioxyphenylacetamide dipotassium salt. The efficacy of the N-(4-iso-propylbenzenesulfonyl)-α-(4-carboxy-2-n-propylphenoxy)-3,4-methylenedioxyphenylacetamide dipotassium salt in inhibiting the prostatic urethral pressor effect of ET-1 suggests that selective antagonists of ET-1 will be useful in the treatment of urinary obstruction in benign prostatic hyperplasia.

In Situ Rat Prostate

Male Sprague-Dawley rats (Taconic Farms) weighing 300–400 grams were anesthetized with urethane (1.75 g/kg, ip), a tracheal cannula was inserted, and the femoral artery was cannulated. Core body temperature was maintained at 37+0.5° C. A 4–5 cm midline abdominal incision was made to expose the bladder and prostate. The prostate was separated from the bladder and surrounding capsule by blunt dissection with a forcep. A length of surgical silk was gently secured around the anterior tips of the prostate lobes. A second length of surgical silk attached to an atraumatic needle was passed through and tied to the base of the prostate approximately 10–12 mm posterior to the first tie. The posterior ligature was secured to an anchor post whereas the anterior ligature was connected to a Grass FT03 transducer (Grass Instruments, Quincy, Mass.) and maintained at a tension of 1 g. Signals from the transducer were amplified and recorded on a polygraph (Hewlett-Packard 8805B amplifiers and 7758A recorder, Palo Alto, Calif.). After equilibrating for approximately 15 min, the rats were administered pretreatment drags (atropine 1 mg/kg, (+) propranolol 1 mg/kg) 10 min apart through the intra-arterial (IA) cannula. Thirty minutes later, ET-1 (0.3 nmoles/kg) was injected intra-arterial every thirty minutes for a total of three times. Five minutes before the third injection of ET-1, vehicle with or without an endothelin antagonist was injected IA. The response of the prostate to ET-1 was quantified by measuring the change (Δ) from baseline tension to the peak of the response during the 5-minute period after the third ET-1 injection.

The in situ rat postate protocol has been utilized to determine the antagonist activity and potency of compounds of this invention to block the direct contractile effects of ET-1 on the rat prostate in vivo. In this protocol, N-(4-iso-propylbenzene-sulfonyl)-α-(4-carboxy-2-n-propylphenoxy)-3,4-methylenedioxyphenylacetamide dipotassium salt was demonstrated to cause a specific inhibition of ET-1 to contract the prostate and will be useful in the treatment of urinary obstruction in benign prostatic hyperplasia.

Accordingly the novel compounds of the present invention are useful in human therapy for treating asthma, hypertension, renal failure particularly post-ischemic renal failure, cyclosporin nephrotoxicity, vasospasm, cerebral and cardiac ischemia, myocardial infarction, or endotoxin shock caused by or associated with endothelin, by adminstration to a patient in need of such treatment of a therapeutically effective amount thereof.

In the management of hypertension and the clinical conditions noted above, the compounds of this invention may be utilized in compositions such as tablets, capsules. or elixirs for oral administration, suppositories for rectal administration, sterile solutions or suspensions for parenteral or intramuscular administration, and the like. The compounds of this invention can be administered to patients (animals and human) in need of such treatment in dosages that will provide optimal pharmaceutical efficacy. Although the dose will vary from patient to patient depending upon the nature and severity of disease, the patient's weight, special diets then being followed by a patient, concurrent medication, and other factors which those skilled in the art will recognize, the dosage range will generally be about 0.5 mg to 1.0 g. per patient per day which can be administered in single or multiple doses. Perferably, the dosage range will be about 0.5 mg to 500 mg. per patient per day; more preferably about 0.5 mg to 200 mg. per patient per day.

The compounds of this invention can also be administered in combination with adenosine $A_2$receptor agonists, α-adrenergic antagonists, angiotensin II antagonists, angiotensin converting enzyme inhibitors, β-adrenergic antagonists, atriopeptidase inhibitors (alone or with ANP), calcium channel blockers, diuretics, potassium channel opening vasodilator, renin inhibitors, sertonin antagonists, sympatholytic agents, as well as other antihypertensive agents. For example, the compounds of this invention can be given in combination with such compounds as A-69729, FK 906, FK 744, UK-73900, CSG 22492C, amiloride, atenolol, atriopeptin, bendroflumethiazide, chlorothalidone, chlorothiazide, clonidine, cromakalim, cryptenamine acetates and cryptenamine tannates, deserpidine, diazoxide, doxazosin, guanabenz, guanethidine, guanethidine sulfate, hydralazine hydrochloride, hydrochlorothiazide, isradipine, ketanserin, losartan, metolazone, metoprolol, metoprolol tartate, methyclothiazide, methyldopa, methyldopate hydrochloride, minoxidil, nadolol, pargyline hydrochloride, pinacidil, pindolol, polythiazide, prazosin, propranolol, rauwolfia serpentina, rescinnamine, reserpine, sodium nitroprusside, spironolactone, terazosin, timolol maleate, trichlormethiazide, trimethaphan camsylate, verapamil, benzthiazide, quinethazone, ticrynafan, triamterene, acetazolamide, aminophylline, cyclothiazide, ethacrynic acid, furosemide, merethoxylline procaine, sodium ethacrynate, captopril, delapril hydrochloride, enalapril, enalaprilat, fosinopril sodium, lisinopril, pentopril, quinapril, quinapril hydrochloride, ramapril, teprotide, zofenopril, zofenopril calcium, difluorinase, diltiazem, felodipine, nicardipine, nifedipine, niludipine, nimodipine, nisoldipine, nitrendipine, and the like, as well as admixtures and combinations thereof. Combinations useful in the management of congestive heart failure include, in addition, compounds of this invention with cardiac stimulants such as dobutamine and xamoterol and phosphodiesterase inhibitors including amrinone and milrinone.

Typically, the individual daily dosages for these combinations can range from about one-fifth of the minimum recommended clinical dosages to the maximum recommended levels for those entities given singly. To illustrate these combinations, one of the endothelin antagonists of this invention effective clinically at a given daily dose range can be effectively combined, at levels which are less than the daily dose range, with the following compounds at the indicated per day dose range: hydrochlorothiazide (6–100 mg), chlorothiazide (125–500 mg), furosemide(5–80 mg), ethacrynic acid (5–200 mg), amiloride (5–20 mg), diltiazem(30–540 mg), felodipine(1–20 mg), nifedipine(5–120 mg), nitrendipine(5–60 mg), timolol maleate (1–20 mg), propanolol (10–480 rag), and methyldopa(125–2000 mg). In addition triple drug combinations of hydrochlorothiazide(6–100 mg) plus amiloride (5–20 mg) plus endothelin antagonists of this invention, or hydrochlorothiazide(6–100 mg) plus timolol maleate (1–20 mg) plus endothelin antagonists of this invention, or hydrochlorothiazide(6–100 mg)

plus nifedipine (5–60 mg) plus endothelin antagonists of this invention are effective combinations to control blood pressure in hypertensive patients. Naturally, these dose ranges can be adjusted on a unit basis as necessary to permit divided daily dosage and the dose will vary depending on the nature and severity of the disease, weight of the patient, special diets and other factors.

The present invention also relates to pharmaceutical compositions for treating asthma, hypertension, renal failure, particularly post-ischemic renal failure, cyclosporin nephrotoxicity, vasospasm, cerebral and cardiac ischemia, benign prostatic hyperplasia, myocardial infarction, or endotoxin shock caused by or associated with endothelin, comprising a therapeutically effective amount of the novel compound of this invention together with a pharmaceutically acceptable carrier therefor.

About 0.5 mg to 1.0 g. of compound or mixture of compounds of Formula I or a physiologically acceptable salt is compounded with a physiologically acceptable vehicle, carrier, excipient, binder, preservative, stabilizer, flavor, etc., in a unit dosage form as called for by accepted pharmaceutical practice. The amount of active substance in these compositions or preparations is such that a suitable dosage in the range indicated is obtained.

Illustrative of the adjuvants which can be incorporated in tablets, capsules and the like are the following: a binder such as gum tragacanth, acacia, corn starch or gelatin; an excipient such as microcrystalline cellulose; a disintegrating agent such as corn starch, pregelatinized starch, alginic acid and the like; a lubricant such as magnesium stearate; a sweetening agent such as sucrose, lactose or saccharin; a flavoring agent such as peppermint, oil of wintergreen or cherry. When the dosage unitform is a capsule, it may contain, in addition to materials of the above type, a liquid carrier such as fatty oil. Various other materials may be present as coatings or to otherwise modify the physical form of the dosage unit. For instance, tablets may be coated with shellac, sugar or both. A syrup or elixir may contain the active compound, sucrose as a sweetening agent, methyl and propyl parabens as preservatives, a dye and a flavoring such as cherry or orange flavor.

Sterile compositions for injection can be formulated according to conventional pharmaceutical practice by dissolving or suspending the active substance in a vehicle such as water for injection, a naturally occurring vegetable oil like sesame oil, coconut oil, peanut oil, cottonseed oil, etc., or a synthetic fatty vehicle like ethyl oleate or the like. Buffers, preservatives, antioxidants and the like can be incorporated as required.

The following examples illustrate the preparation of the compounds of Formula I and their incorporation into pharmaceutical compositions and as such are not to be considered as limiting the invention set forth in the claims appended hereto.

EXAMPLE 1

2-(2,6-Dipropyl-4-hydroxymethyl)phenoxyphenylacetic acids

Step A: Preparation of Alkyl 2-bromo-2-phenylacetates
Method A:
Substituted phenylacetic acid is converted to the corresponding methyl ester by refluxing the acid in methanol in the presence of a catalytic amount of conc. sulfuric acid. The ester thus obtained is then refluxed in carbon tetrachloride with N-bromosuccinimide (1.1 equiv) and AIBN (0.05–0.1 equiv). Upon completion of the reaction, the resulting product is purified by flash column chromatography using silica gel and ethyl acetate in hexane as eluent to provide the desired alkyl bromide.

Method B:
An arylaldehyde is reacted overnight with trimethylsilyl cyanide in the presence of catalytic amounts of KCN and 18-crown-6 in methylene chloride. The reaction mixture is quenched with water and extracted with $CH_2Cl_2$/ethyl acetate/ether (1/2/2) mixture. The organic phase is washed with saturated aq. $NaHCO_3$ solution. After drying and concentration of the organic phase, the resulting trimethylsilyl cyanohydrin is hydrolyzed to give the corresponding hydroxy acid. Treatment with gaseous HCl in methanol or ethanol at 0° C. for 0.5 h and then overnight at room temperature affords the crude 2-hydroxy ester. The ester is then treated with triphenylphosphine and carbon tetrabromide in methylene chloride at 0° C. overnight. Methylene chloride is removed and flash column chromatography of the crude product using silica gel and ethyl acetate/hexane as eluent gives the desired 2-bromophenylacetates.

Step B: Alkylation of the phenol
(2,6-Dipropyl-4-hydroxymethyl)phenol (prepared as described in patent application WO 91/11999) is alkylated with 2-bromo-2-aryl esters in DMF using either cesium carbonate ($Cs_2CO_3$), or potassium carbonate ($K_2CO_3$), or sodium hydride (NaH). The alkylated product is purified by flash column chromatography using silica gel and ethyl acetate/hexane mixture as eluent to provide the desired substituted 2-phenoxy-2-phenylacetic acid esters.

Step C: General procedure for ester hydrolysis
The product of Step C is dissolved in methanol or ethanol and reacted with aqueous NaOH or LiOH, or KOH solution at room temperature for 1–6 hours, neutralized to pH 7 with 1 N HCl and then concentrated in vacuo. The residue is purified on a silica gel flash chromatography column to afford the corresponding carboxylic acid.

The following phenoxyphenylacetic acid derivatives were prepared using the general procedures outlined in Example 1.

EXAMPLE 2

2-[(2,6-Dipropyl-4-hydroxymethyl)phenoxy]-2-(3-methylphenyl)acetic acid $^1$H NMR (400 MHz, $CD_3OD$, ppm): δ7.15–6.95 (m, 4H), 6.86 (s, 2H), 4.92 (br s, 1H), 4.5 (s, 2H), 2.3–2.1 (m, 4H), 2.2 (s, 3H), 1.5–1.35 (m, 2H), 1.32–1.18 (m, 2H), 0.7 (t, 6H).

EXAMPLE 3

2-[(2,6-Dipropyl-4-hydroxymethyl)phenoxy]-2-(4-phenoxyphenyl)-acetic acid $^1$H NMR (400 MHz, $CD_3OD$, ppm): δ7.42 (d, 2H, J=8.4 Hz), 7.33 (dd, 2H, J=7.4 Hz, 8.5), 7.09 (t, 1H, J=7.4 Hz), 6.97–6.95 (m, 4H), 6.91 (d, 2H, J=8.4 Hz), 4.85 (s, 1H), 4.47 (s, 2H), 2.38 (t, 4H, J=8.0 Hz), 1.56 (sx, 2H, J=7.1 Hz), 1.42 (sx, 2H, J=7.1 Hz), 0.85 (t, 6H, J=7.3 Hz). FAB-MS m/e =435 (M+1)

EXAMPLE 4

2-[(2,6-Dipropyl-4-hydroxymethyl)phenoxy]-2-(4-phenylphenyl)acetic acid $^1$H NMR (400 MHz, $CD_3OD$, ppm): δ7.62–7.60 (m, 4H), 7.51 (br, 2H), 7.44 (t, 2H, J=7.5 Hz), 7.34 (t, 1H, J=7.4 Hz), 6.99 (s, 2H), 4.83 (s, 1H), 2.40 (br, 4H), 1.53 (br, 2H), 1.42 (br, 2H), 0.82 (t, 6H, J=6.2 Hz). FAB-MS m/e =419 (M+1)

EXAMPLE 5

2-[(2,6-Dipropyl-4-hydroxymethyl)phenoxy]-2-(3-carboxyphenyl)-acetic acid $^1$H NMR (400 MHz, CD$_3$OD, ppm): δ8.18 (s, 1H) 8.04 (d, 1H, J=7.5 Hz), 7.70 (d, 1H, J=7.4 Hz), 7.51 (d, 1H, J=7.6) Hz, 6.99 (s, 2H), 5.15 (s, 1H), 4.48 (s, 2H), 2.37 (m, 4H), 1.52 (m, 2H), 1.44 (m, 2H), 0.80 (t, 6H, J=7.3 Hz).
FAB-MS m/e =387 (M+1)

EXAMPLE 6

2-[(2,6-Dipropyl-4-hydroxymethyl)phenoxy]-2-(3,4-ethylenedioxyphenyl)acetic acid 1H NMR (200 MHz, CD$_3$OD, ppm): δ6.95 (m, 3H), 6.85 (dd, 1H, J=8.3, 2.0 Hz), 6.72 (d, 1H, J=8.3 Hz), 4.76 (s, 1H), 4.46 (s, 2H), 4.20 (s, 4H), 2.37 (t, 4H, J=7.9 Hz), 1.44 (m, 4H), 0.83 (t, 6H, J=7.3 Hz).
FAB-MS m/e=401 (M+1)

EXAMPLE 7

2-[(2,6-Dipropyl-4-hydroxymethyl)phenoxy]-2-(3,4,5-trimethoxyphenyl)acetic acid $^1$H NMR (400 MHz, CD$_3$OD, ppm): δ6.97 (s, 2H), 6.80 (s, 2H), 4.88 (s, 1H), 4.48 (s, 2H), 3.81 (s, 6H), 3.75 (s, 3H), 2.39 (t, 3H, J=8.1 Hz), 1.55 (m, 2H), 1.41 (m, 2H), 0.82 (t, 6H, J=7.3 Hz).
FAB-MS m/e =433 (M+1)

EXAMPLE 8

2-[2,6-Dipropyl-4-hydroxymethyl)phenoxy]-2-(3,4-methylenedioxyphenyl)acetic acid $^1$H NMR (200 MHz, CD$_3$OD, ppm): δ7.03 (s, 1H), 6.97 (s, 2H), 6.83 (d, 1H, J=7.7 Hz), 6.73 (d, 2H, J=7.7 Hz), 5.94 (s, 2H), 4.84 (s, 1H), 4.48 (s, 2H), 2.38 (t, 4H, J=8.0 Hz), 1.46 (m, 4H), 0.85 (t, 6H, J=7.4 Hz).
FAB-MS m/e =387 (M+1)

EXAMPLE 9

[(2,6-Dipropyl-4-hydroxymethyl)phenoxy]-2-(3,4-dimethoxy-phenyl)acetic acid $^1$H NMR (400 MHz, CD$_3$OD, ppm): δ7.15 (d, 1H), 6.95 (d, 2H), 6.85 (dd, 2H), 4.8 (br s, 1H), 4.46 (br s, 2H), 3.84 (s, 3H), 3.8 (s, 3H), 2.35 (t, 4H), 1.62–1.47 (m, 2H), 1.45–1.3 (m, 2H), 0.85 (t, 6H).

EXAMPLE 10

2-[(2,6-Dipropyl-4-hydroxymethyl)phenoxy]-2-(3,5-dimethoxyphenyl)acetic acid $^1$H NMR (400 MHz, CD$_3$OD, ppm): δ6.954 (s, 2H), 6.66 (d, 2H), 6.39 (t, 1H), 4.747 (s, 1H), 4.47 (s, 2H), 3.74 (s, 6H), 2.39 (t, 4H), 1.60–1.51 (m, 2H), 1.437–1.35 (m, 2H), 0.82 (t, 6H).

EXAMPLE 11

2-((2,6-Dipropyl-4-tetrazol-5-yl)phenoxy)-2-(3-bromophenyl)acetic acid

H NMR (400 MHz, CD$_3$OD, ppm): δ7.73 (s, 2H), 7.67 (t, 1H, J=1.8 Hz), 7.57 (m, 1H), 7.46 (m, 1H), 7.33 (t, 1H, J=7.9 Hz), 5.89 (ddd, 1H, J=1.6, 10.1, 17.1 Hz), 5.41 (s, 1H), 5.08 (dd, 1H, J=10.1, 1.6 Hz), 5.01 (dd, 1H, J=1.7, 17.1 Hz), 4.93 (s, 2H), 3.72 (s, 3H), 3.36–3.30 (m, 2H).
FAB-MS m/e=470 (M+1)

EXAMPLE 12

2-[(2,6-Dipropyl-4-hydroxymethyl)phenoxy]-2-(3-bromophenyl)acetic acid $^1$H NMR (400 MHz, CD$_3$OD/CDCl$_3$,2/1, ppm): δ7.667 (s, 1H), 7.496 (d, 1H), 7.3925 (d, 1H), 7.252 (t, 1H), 6.964 (s, 2H), 4.995 (s, 1H), 4.485 (s, 2H), 2.342 (t, 4H), 1.65–1.35 (m, 2H), 0.803 (t, 6H).

EXAMPLE 13

2-[(2,6-Dipropyl-4-hydroxymethyl)phenoxy]-2-(2-naphthyl)acetic acid $^1$H NMR (400 MHz, CD$_3$OD, ppm): δ8.56–8.52 (m, 1H), 7.86–7.79 (m, 2H), 7.47–7.43 (m, 2H), 7.35–7.32 (m, 1 H), 6.91 (s, 2H), 5.36 (s, 1H), 4.44 (s, 1H), 1.46–1.41 (m, 2 H), 1.2–1.16 (m, 2H), 0.58 (t, J =7.37, 6 H).

EXAMPLE 14

2-[(2,6-Dipropyl-4-(2-hydroxyethyl)phenoxy]-2-(2-naphthyl)acetic acid

STEP A: t-Butyldimethylsilyloxy-2,6-Dipropyl-4-formylbenzene

To a solution of 5.03 g (15.4 mmol)of t-butyl-dimethyl-silyloxy-2,6-dipropyl-4-hydroxymethyl benzene in 30 mL of methylene chloride was added 8.7 g of pyridinium dichromate (PDC). The reaction mixture was stirred for 3 hours and then diluted with 300 mL of ethyl ether. The solution was then filtered through a pad of a 1:1 mixture of florisil and celite. Concentration of the filtrate gave 4.85 g of the title compound.

$^1$H NMR (400 MHz, CDCl$_3$, ppm): δ9.8 (s, 1H), 7.51 (s, 2H), 2.59–2.55 (m, 2H) 1.59–1.55 (m, 2H), 0.99 (s, 9H), 0.91 (t, J=7.28 Hz, 3H), 0.20 (s, 6H).

STEP B: t-Butyldimethylsilyloxy-2,6-dipropyl-4-vinyl benzene

To a solution of 1.0 g (2.80 mmol) of methyl triphenylphosphonium bromide in 5.0 mL of ether at 0° C. was added 1.12 mL (2.5M, 2.80 mmol) of butyllithium. The reaction mixture was stirred for 30 minutes at 0° C. and then 756 mg (2.33 mmol) of the title compound from Example 14 (Step A) was added. After stirring for 1h at room temperature, the reaction mixture was poured into ethyl acetate and washed with water and then saturated aqueous sodium chloride. The organic layer was dried over anhydrous sodium sulfate, filtered and concentrated. Purification by flash chromotography (silica gel, hexane/ethyl acetate 97:3) gave 411 mg of the title compound.

$^1$H NMR (400 MHz, CDCl$_3$, ppm): δ7.02 (s, 2H), 6.6 (dd, J=17.6, J=10.7 Hz, 1H), 5.55 (d,J=17.6 Hz, 1H), 5.08 (d, J=10.7 Hz, 1H), 2.53–2.50 (m, 4 H), 1.59–1.53 (m, 4H), 0.996 (s, 9 H), 0.90 (t, J=7.33 Hz, 6 H), 0.16 (s, 6 H).

STEP C: t-Butyldimethylsilyloxy-2,6-dipropyl-4-(2-hydroxyethyl)-benzene

To a solution of 475 mg (1.48 mmol) of the product of Step B in 3 mL of THF at 0° C. was added 1.6 mL (1.62 mmol) of a 1N borane/THF solution. After 1 hour TLC indicated that the starting material had been consumed. The reaction mixture was quenched with 3 drops of methanol and then 0.70 mL (6.22 mmol) of 30% sodium peroxide and 6.2 mL (6.2 mmol) of 1 N sodium hydroxide were added., After two hours the reaction mixture was diluted with ethyl acetate and washed with water and brine. The organic layer was then dried over sodium sulfate, filtered and concentrated. Flash chromatography (silica gel, hexane/ethyl acetate 4:1) gave 265 mg of the title compound as a clear oil.

$^1$H NMR (400 MHz, CDCl$_3$, ppm): δ6.79 (s, 2 H), 3.79 (m, 2 H), 2.75–2.72 (m, 2 H), 2.51–2.48 (m, 4 H), 1.58–1.51 (m, 6 H), 0.99 (s, 9 H), 0.90 (t, J=7.33, 6 H), 0.16 (s, 6 H).

STEP D: 2,6-Dipropyl-4-(2-hydroxyethyl)phenol

To a solution of 1.0 g (2.98 mmol) of the product of Step C in 3.0 mL of THF was added 3.57 mL (3.57 mmol) of 1.0 N solution of tetrabutylammonium fluoride in THF. After 15 minutes TLC indicated that the reaction was complete. The reaction mixture was concentrated and then purified by flash chromatography (silica gel, hexane/ethyl acetate 3:1) to give 1.13 g of the title compound.

$^1$H NMR (400 MHz, CDCl$_3$, ppm): δ6.8 (s, 2 H), 3.78 (t, J=6.5 Hz, 2 H), 2.73 (t, J=6.5 Hz, 2 H), 2.54–2.50 (m, 4H), 1.66–1.56 (m, 4 H), 0.96 (t , J=7.3 Hz, 6 H).

STEP E: Methyl 2-[(2,6-dipropyl-4-(2-hydroxyethyl)phenoxy]-2-(2-naphthyl)acetate The title compound was prepared from 2,6-dipropyl-4-(2-hydroxyethyl)phenol (Step D) by alkylating with methyl 2-bromo-2-(2-naphthyl)acetate using cesium carbonate or potassium carbonate in DMF. The reaction mixture was filtered through Celite and the filter cake was washed with methylene chloride. The tiltrate was concentrated and the resultant material was purified by flash column chromatography to yield the titled ester.

$^1$H NMR (400 MHz, CDCl$_3$, ppm): δ7.90–7.82 (m, 4 H), 7.69–7.67 (m, 1 H), 7.49–7.47 (m, 2H), 6.8 (s, 2 H), 2.74 (t, J=6.2 Hz, 2 H), 2.36–2.32 (m, 4 H), 1.49–1.41 (m, 4 H), 0.72 (t, J=7.3, 6 H).

STEP F: 2-[(2,6-Dipropyl-4-(2-hydroxyethyl)phenoxy]-2-(2-naphthyl)acetic acid

The title compound was prepared from the product of Step E by saponification with 1N aqueous KOH in methanol as outlined in Step C of Example 1.

$^1$H NMR (400 MHz, CD$_3$OD, ppm) δ7.84–7.7 (m, 4 H), 7.73 (d, J=6.8 Hz, 1 H), 7.45–7.43 (m, 2 H), 6.79 (s, 2 H), 5.01 (s, 2 H), 3.66 (t, J=7.2 Hz, 2 H), 2.68 (t, J=7.2 Hz, 2 H), 2.33–2.29 (m, 4 H), 1.55–1.45 (m, 2H), 1.40–1.28 (M, 2 H), 0.69 (t, J=7.3, 6 H). FAB- MS: m/e=445 (M+K), 429 (M+Na), 407 (M+1).

The following phenoxyphenylacetic acid derivatives were prepared using the general procedures outlined in Example 14.

EXAMPLE 15

2-[(2,6-Dipropyl-4-(2-hydroxyethyl)phenoxy]-2-(3,4-methylenedioxyphenyl)acetic acid $^1$H NMR (200 MHz, CD$_3$OD, ppm): δ7.03 (s, 1H), 6.83 (m, 3H), 6.72 (d, 1H, J=7.8 Hz), 5.93 (s, 2H), 4.80 (s, 1H), 3.68 (t, 2H, J=7.1 Hz), 2.69 (t, 2H, J=7.1 Hz), 2.35 (t, 4H, J=7.9 Hz), 1.42 (m, 4H), 0.83 (t, 6H, J=7.3 Hz).
FAB-MS m/e=401 (M+1)

EXAMPLE 16

2-[(2,6-Dipropyl-4-(2-hydroxyethyl)phenoxy]-2-(3-methoxyphenyl)-acetic acid $^1$H NMR (400 MHz, CD$_3$OD, ppm): δ7.28 (t, 1H, J=7.9 Hz), 7.07 (m, 1H), 7.15 (m, 1H), 6.94 (m, 1H), 6.84 (s, 2H), 4.99 (s, 1H), 3.79 (s, 3H), 3.68 (t, 2H, J=7.1 Hz), 2.70 (t, 2H, J=7.1 Hz), 2.34 (t, 4H, J=8.0 Hz), 1.54–1.40 (m, 4H), 0.80 (t, 3H, J=7.3 Hz).
FAB-MS m/e=387 (M+1)

EXAMPLE 17

2-[(2,6-Dipropyl-4(1,2-dihydroxyethyl)phenoxy)]-2-(2-naphthyl)acetic acid

STEP A: 2,6-dipropyl-4-vinylphenol

The title compound was prepared from t-butyldimethylsilyloxy-2,6-dipropyl-4-vinylbenzene (Step B, Example 14) by treatment with tetrabutylammonium fluoride in THF for a few hours. It was poured into ether/ethyl acetate mixture and washed with brine. After removal of the solvent the crude product was purified by flash column chromatography using ethyl acetate/hexane as eluent.

$^1$H NMR (400 MHz, CDCl$_3$, ppm): δ7.01 (s, 2 H), 6.55 (dd, J=17.6, J=11.0 Hz, 1H), 5.55 (d, J=17.6 Hz, 1 H), 5.06 (d, J=11.0 Hz, 1 H), 2.64 (t, J=7.7 Hz, 4 H), 1.65–1.60 (m, 4 H), 0.96 (t, J=7.2 Hz 6 H).

STEP B: Methyl 2-[(2,6-dipropyl-4-vinyl)phenoxy]-2-(2-naphthyl)-acetate

The title compound was prepared by alkylation of 2,6-dipropyl-4-vinyl phenol (Step A) with methyl 2-bromo-2-(2-naphthyl)acetate using the procedure for alkylation described in Step B of Example 1.

$^1$H NMR (400 MHz, CDCl$_3$, ppm): δ7.9–7.8 (m, 4 H), 7.68 (d, J=6.7 Hz, 1H), 7.50–7.48 (m, 2 H), 7.02 (s, 2 H), 6.57 (dd J=18.4, 10.8 Hz, 1 H), 5.61 (d, J=18.4, 1 H), 5.26 (s, 1 H), 5.14 (d, J=10.8, 1 H), 3.73 (s, 1 H), 2.38–2.34 (m, 4 H), 1.54–1.43 (m, 4 H), 0.74 (t, J =7.33 Hz, 6 H).

STEP C: Methyl 2-[(2,6-dipropyl-4-(1,2-dihydroxyethyl)phenoxy]-2-(2-naphthyl)acetate To a solution of 6 mg (0.024 mmol) of OsO$_4$ and 31 mg (0.263 mmol) of N-methylmorpholine-N-oxide (NMO) in 3 mL of acetone and 2 drops of water was added 96 mg (0.239 mmol) of the product of Step B. After 90 minutes the reaction mixture was poured into a mixture of ether and water. The layers were separated and the aqueous layer was extracted twice with ether. The combined aqueous layers were washed with saturated sodium chloride, dried over anhydrous magnesium sulfate, filtered and concentrated. Purification by flash chromatography (silica gel, hexane/ ethyl acetate 1:1) gave 63 mg of the title compound.

$^1$H NMR (400 MHz, CDCl$_3$, ppm): δ7.89–7.80 (m, 4 H), 7.67 (d, J=8.4 Hz, 1 H), 7.50–7.48 (m, 2 H), 6.9 (s, 2 H), 5.25 (s, 1 H), 4.75–4.68 (m, 1 H), 3.72 (s, 3 H), 3.75–3.61 (m, 2 H), 2.38–2.34 (m, 4 H), 1.53–1.46 (m, 4 H), 0.75–0.71 (m, 6 H).

STEP D: 2-[(2,6-Dipropyl-4-(1,2-dihydroxyethyl)phenoxy]-2-(2-naphthyl)acetic acid The title compound was prepared from the product of Step C by saponification with 1N aqueous KOH solution as described above.

$^1$H NMR (400 MHz, CD$_3$OD, ppm): δ7.84–7.71 (m, 5 H), 7.46–7.42 (m, 2 H), 6.96 (s, 2 H), 5.03 (s, 1 H), 4.55 (t, J=7.2 Hz, 1 H), 3.54 (d, J=7.2 Hz, 2 H), 2.34 (t, J=7.9 Hz, 4 H), 1.51–1.30 (m, 4 H), 0.70 (t, J=7.3 Hz, 6 H).

EXAMPLE 18

2-[(2,6-Dipropyl-4-(1-hydroxypentyl)phenoxy]-2-(2-naphthyl)acetic acid

STEP A: Methyl 2-[(2,6-dipropyl-4-formyl)phenoxy]-2-(2-naphthyl)acetate

To a solution of 262 mg (0.645 mmol) of methyl 2-[(2, 6-dipropyl-4-hydroxymethyl)phenoxyl]-2-(2-naphthyl)acetate in 2 mL of methylene chloride was added 404 mg (0.968 mmol) of PDC. After 4 hours the reaction mixture was diluted with 20 mL of ether and filtered through a pad of florisil/celite and concentrated to give 235 mg of the title compound.

$^1$H NMR (400 MHz, CDCl$_3$, ppm): δ9.86 (s, H), 7.89–7.80 (m, 4 H), 7.65 (m, 1 H), 7.52–7.49 (m, 4 H), 5.35 (s, 1 H), 3.73 (s, 3 H), 2.47–2.43 (m, 4 H), 1.54–1.43 (m, 4 H), 0.77 (t, J=7.3 Hz, 6 H).

STEP B: Methyl 2-[(2,6-dipropyl-4-(1-hydroxypentyl)phenoxy]-2-(2-naphthyl)acetate o To a solution of 56 mg (0.143 mmol) of the product of Step A in 1 mL of THF at −78° C. was added 0.075 mL (2.0 M in THF, 0.150 mmol) of n-butyl magnesium chloride. TLC analysis showed that the starting material remained unconsumed so 0.020 mL of n-butyl magnesium chloride was added. After 1 h the reaction mixture was diluted with saturated aqueous ammonium chloride solution and then extracted twice with ethyl acetate. The organic layers were dried over anhydrous sodium sulfate, filtered and concentrated. Purification by flash column chromatography (silica gel, hexane/ethyl acetate 6:1) gave 32 mg of the title compound.

$^1$H NMR (400 MHz, CDCl$_3$, ppm): δ7.89–7.82 (m, 4 H), 7.67 (m, 1 H), 7.49–7.47 (m, 2 H), 6.9 (s, 2 H), 5.26 (s, 1 H), 2.36 (t, J=8.0 Hz, 4 H), 1.75–1.2 (m, 8 H), 0.86 (t, J=7.2 Hz, 3 H), 0.72 (t, J=7.3 Hz, 6 H).

STEP C: 2-[(2,6-Dipropyl-4-(1-hydroxypentyl)phenoxy)]-2-naphthylacetic acid

The title compound was prepared from the product of Step B by saponification with aqueous 1N KOH in methanol as described above.

1H NMR (400 MHz, CD$_3$OD, ppm): δ7.84–7.72 (m, 5 H), 7.45–7.43 (m, 2 H), 6.91 (s, 2 H), 5.03 (s, 1 H), 4.45 (t, 1 H), 2.36–2.32 (m, 4 H), 1.75–1.45 (m, 4 H), 1.35–1.29 (m, 4 H), 0.87 (t, J=7.2 Hz, 3 H), 0.70 (t, J=7.2 Hz, 6 H).

FAB-MS :m/e=487 (M+K), 469 (M+Na).

EXAMPLE 19

2-[(4-Carboxy-2,6-dipropyl)phenoxy]-2-phenylacetic acid

STEP A: t-Butyl 2-[(4-carbomethoxy-2,6-dipropyl)phenoxy]-2-phenylacetate

Methyl 2,6-dipropyl-4-hydroxybenzoate (1.5 g, 6.383 mmol) was refluxed with K$_2$CO$_3$ (1.5 equiv) and t-butyl α-bromophenylacetate (2.4 g, 8.856 mmol) in acetone for 16 h. The reaction mixture was filmred through Celite, the filter cake was washed with acetone and the combined tiltrate and washings were concentrated. The resulting crude oil was chromatographed (flash column) using silica gel and 10% ethyl acetate in hexane to give the titled compound (2.7 g).

$^1$H NMR (400 MHz, CD$_3$OD, ppm): δ7.665 (s, 2H), 7.443 (dd, 2H), 7.345 (dd, 3H), 5.019 (s, 1H), 3.851 (s, 3H), 2.49–2.335 (m, 4H), 1.63–1.4 (m, 4H), 1.364 (s, 9H), 0.803 (t, 6H).

STEP B: t-Butyl 2-[(4-carboxy-2,6-dipropyl)phenoxy]-2-phenyl acetate

Saponification of the above t-butyl 2-[(4-carbomethoxy-2,6-dipropyl)phenoxy]-2-phenylacetate (200 mg, 0.47 mmol) with 1N aqueous solution of LiOH in methanol gave the titled compound (125 mg).

1H NMR (400 MHz, CD$_3$OD, ppm): δ7.66 (s, 2H), 7.5–7.4 (dd, 2H), 7.43–7.36 (dd, 3H) 4.88 (s, 1H), 2.5–2.35 (m, 4H), 1.63–1.33 (m, 4H), 1.38 (t, 9H), 0.83 (t, 6H).

STEP C: 2-[(4-Carbomethoxy-2,6-dipropyl)phenoxy]-2-phenylacetic acid t-Butyl 2-[(4-carbomethoxy-2,6-dipropyl)phenoxy]-2-phenylacetate (Step A) (125 mg, 0.293 mmol) was treated with 3 mL of trifluoroacetic acid (TFA) in methylene chloride for 2 h. The volatiles were removed to give the titled compound (90 mg).

1H NMR (400 MHz, CD$_3$OD, ppm): δ7.67 (s, 2H), 7.463–7.44 (m, 2H), 7.387–7.362 (m, 3H), 5.177 (s, 1H), 3.856 (s, 3H), 2.377 (t, 4H), 1.6–1.366 (m, 4H), 0.773 (t, 6H).

STEP D: 2-[(4-Carboxy:2,6-dipropyl)phenoxy]-2-phenylacetic acid

The product of Step C (70 mg, 0.19 mmol) was treated with 1N aqueous solution of LiOH in methanol. The reaction was monitored by TLC. When the starting material was completely consumed, the mixture was acidified at 0° C. to pH 5 by addition of 1N HCl. The aqueous phase was extracted with ethyl acetate, dried over anhydrous magnesium sulfate and filtered. The tiltrate was concentrated to yield the titled compound (25 mg).

$^1$H NMR (400 MHz, CD$_3$OD, ppm): δ7.68 (s, 2H), 7.52–7.45 (m, 2H), 7.43–7.365 (m, 3H), 5.175 (s, 1H), 2.43 (t, 4H), 1.64–1.4 (m, 4H), 0.83 (t, 6H).

EXAMPLE 20

2-[(4-Carboxy-2,6-dipropyl)phenoxy]-2-(3,4-dichlorophenyl)acetic acid

The titled compound was prepared using procedures similar to that described in Example 19.

$^1$H NMR (200 MHz, CD$_3$OD, ppm): δ7.72 (d, 1H, J=2.0 Hz) 7.69 (s, 2H), 7.56 (d, 1H, J=8.3 Hz), 7.43 (dd, 1H, J=8.3, 1.9 Hz), 5.18 (s, 1H), 2.45 (m, 4H), 1.58–1.43 (m, 4H), 0.84 (t, 6H, J=7.3 Hz).

FAB-MS m/e=426 (M+1)

EXAMPLE 21

2-[(4-Carboxy-2,6-dipropyl)phenoxy]-2-(3-bromophenyl)acetic acid

The titled compound was prepared using procedures similar to that described in Example 19.

$^1$H NMR (200 MHz, CD$_3$OD, ppm): δ7.73 (d, 1H, J=1.8 Hz), 7.69 (s, 2H), 7.56 (dd, 1H, J=7.8, 1.9 Hz), 7.46 (d, 1H, J=7.9 Hz), 7.32 (t, 1H, J=7.8 Hz), 5.19 (s, 1H), 2.44 (t, 4H, J=7.6 Hz), 1.70–1.34 (m, 4H), 0.84 (t, 6H, J=7.3 Hz).

FAB-MS m/e=436 (M+1)

EXAMPLE 22

2-[(4-Carboxy-2,6-dipropyl)phenoxy]-2-[3,4-methylenedioxyphenyl]acetic acid

The titled compound was prepared using procedures similar to that described in Example 19.

$^1$H NMR (200 MHz, CD$_3$OD, ppm): δ7.68 (s, 2H), 7.02 (d, 1H, J=1.6 Hz), 6.84 (m, 2H), 5.98 (s, 2H), 5.08 (s, 1H), 2.44 (t, 4H, J=7.9 Hz), 1.52 (m, 4H), 0.86 (t, 6H, J=7.3 Hz).

FAB-MS m/e=401 (M+1)

EXAMPLE 23

2-[(4-Carboxy-2,6-dipropyl)phenoxy]-2-(3-methoxyphenyl)acetic acid

The titled compound was prepared using procedures similar to that described in Example 19.

$^1$H NMR (200 MHz, CD$_3$OD, ppm) δ7.68 (s, 2H), 7.29 (t, 1H, J=7.9 Hz), 7.08 (d, 1H, J=2.3 Hz), 7.03 (d, 1H, J=7.7 Hz), 6.95 (dd, 1H, J=0.9, 8.3 Hz), 5.14 (s, 1H), 3.79 (s, 3H), 2.43 (t, 4H, J=7.9 Hz), 1.58–1.42 (m, 4H), 0.82 (t, 6H, J=7.3 Hz).

FAB-MS m/e=387 (M+1)

EXAMPLE 24

(N-Benzenesulfonyl)-2-[(4-(N-benzenesulfonyl)carboxamido-2,6-dipropylphenoxy]-2-(3-bromophenyl)acetamide.

The titled compound was prepared using the procedure described for the synthesis of N-sulfonylcarboxamides in U.S Pat. No. 5,177,095. The diacid 2-[(4-carboxy-2,6-dipropyl)phenoxy]-2-(3-bromophenyl)acetic acid (200 mg, 0.46 mmol; from Example 21 ) was refluxed with carbonyldiimidazole (1.5 equiv) in THF for 3–4 h. At room temperature, a mixture of 1.5 equiv of benzenesulfonamide and 1.5 equiv DBU in THF was added to the above reaction mixture, and the mixture was stirred overnight. The reaction mixture was diluted with ethyl acetate and washed with 5% aq. solution of citric acid. The solvent was removed and the crude product was purified by flash column chromatography to provide 238 mg of the titled compound.

$^1$H NMR (400 MHz, CD$_3$OD, ppm): δ8.07 (dd, 2H, J=1.4, 7.2 Hz), 7.91–7.88 (m, 2H), 7.67–7.49 (m,8H), 7.46 (s, 2H), 7.28–7.25 (m, 2H), 5.01 (s, 1H), 2.28–2.23 (m, 4H), 1.49–1.29 (m, 4H); 0.71 (t, 6H, J=7.4 Hz).

FAB-MS m/e=713 (M+1).

EXAMPLE 25

N-(4-t-butylbenzenesulfonyl)-2-(4-methoxycarbonyl-2-propylphenoxy)-2-(3,4-methylenedioxyphenyl)acetamide Step A: Preparation of 2-(4-carbomethoxy-2-propylphenoxy)-3,4-methylenedioxyphenylacetic acid To ethyl 2-(4-carbomethoxy-2-propylphenoxy)-3,4-methylenedioxyphenylacetate (Step A of Example 56) (2.04 g, 5.10 mmol) in MeOH (40 mL) was added 5 N NaOH (8 mL). The rapid reaction was followed immediately by TLC to monitor mono deesterification. The reaction was quenched with 9 N HCl (4.5 mL) after loss of the ethyl ester and before methyl ester saponification. A saturated solution of NaHCO$_3$ was added to the reaction until it was basic and the MeOH was removed in vacuo. The residue was partitioned between Et$_2$O and water collecting the product in the aqueous phase and removing impurities with the organic phase. The aqueous phase was then acidified with 9 N HCl (pH=1) and the product extracted into EtOAc. The solution was dried over MgSO$_4$, filtered and the solvent removed. yield=1.78 g (4.78 mmol, 94%) rf=0.16 (80:10:1/CHCl$_3$:MeOH:NH$_4$OH).

Step B: Preparation of the precursor sulfonamide

To a dichloromethane solution of the sulfonyl chloride (1eq) cooled to 0° C. was added t-butylamine (3 eq). After 3–5 hrs the CH$_2$Cl$_2$ was removed and replaced with EtOAc. The reaction solution was washed with 1 N HCl, water, 1 N NaOH and brine. The resulting solution was dried over MgSO$_4$ and filtered. The solvent was removed. To the resulting solid was added a couple of drops of anisole and then TFA to remove the t-butyl group. After all of the sulfonamide had been deprotected, the TFA was removed in vacuo and the residue taken up in EtOAc/Et$_2$O. The solution was washed with saturated NaHCO3 solution to remove any residual TFA, then with brine, dried over MgSO$_4$, filtered and the solvent removed.

The sulfonamide precursors used in the preparation of the compounds of Examples 28, 29, 31, 32, 37, 38, and 39 were prepared from the corresponding sulfonyl chlorides utilizing the procedure described above. The sulfonamide precursors used in the preparation of the compounds of Examples 26 and 33-36 are commercially available.

The sulfonamide precursors used in Examples 27, 30 and 32, whose sulfonyl chlorides are not commercially available, were prepared using standard chemistry:

Preparation of precursor Sulfonamide for Example 27

The t-butylsulfonamide of 4-bromobenzenesulfonyl chloride was prepared using the procedure described above. The t-butylsulfonamide was then coupled to phenylboronic acid in a palladium catalyzed cross-coupling reaction with NaOH, EtOH, toluene, and Pd(PPh$_3$)$_4$ at 100° C. to afford the biphenylsulfonamide. Deprotection of the t-butylsulfonamide with TFA and anisole yielded the free sulfonamide.

Preparation of precursor sulfonamide for Example 30

The t-butylsulfonamide of 2-thiophenesulfonyl chloride was prepared using the procedure described above. Treatment of the t-butylsulfonamide with BuLi then isobutyl iodide afforded the 5-isobutyl-2-thiophene-t-butylsulfonamide which was then deprotected with TFA and anisole to yield the free sulfonamide.

Preparation of precursor sulfonamide for Example 32

The t-butylsulfonamide of p-nitrobenzenesulfonyl chloride was prepared using the procedure described above. Reduction of the nitro group to the amine was accomplished with hydrogen in MeOH over Pd-C. Treatment of the free amine with LiBr and (MeO)$_3$PO and then NaOH afforded the dimethylamine and the t-butylsulfonamide was deprotected with TFA and anisole to yield the free sulfonamide.

Step C: Preparation of N-(4-t-butylbenzenesulfonyl)-2-(4-carbomethoxy-2-propylphenoxy)-3,4-methylenedioxyphenylacetamide To the product of Step A (57.2 mg, 0.154 mmol) in dry THF (0.75 mL) was added CDI (76.0 mg, 0.469 mmol) and the reaction heated to 50° C. for 2.5 hr. To this solution was added a solution of p-t-butylphenyl-sulfonamide (131.7 mg, 0.618 mmol) and DBU (92.1 μL, 0.594 mmol) in dry THF (0.75 mL). The reaction continued to be stirred at 50° C. monitoring by thin layer chromatography until all of the mono-acid was consumed (approx. 3 hr). The reaction was concentrated in vacuo and the residue was taken up in 50:50/Et$_2$O:EtOAc. The organic phase was washed with 10% citric acid (2×), water and brine then dried over MgSO$_4$, filtered and the solvent removed. Purification was accomplished by radial chromatography eluting with 3:2/ Hex:EtOAc. yield =74.3 mg (0.131 mmol, 85%) rf=0.32 (80:10:1/CHCl$_3$:MeOH:NH$_4$OH) FAB mass spectrum, m/e 590.0 (M+Na calculated for C$_{30}$H$_{33}$NSO$_8$ 590). See Drummond, J. T.; Johnson, G. Tetrahedron Lett., 1988, 29, 1653.

EXAMPLES 26–39

Examples 26 through 39 were prepared following the procedures described above in Example 25.

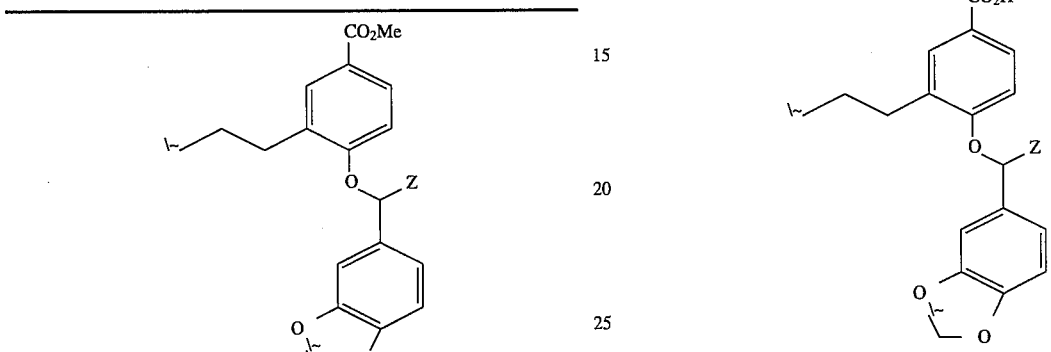

| Ex. # | Z | Mass Spectrum |
|---|---|---|
| 26 | CONHSO$_2$Ph | (M+1) 512.0 |
| 27 | CONHSO$_2$-(p-phenyl)Ph | (M+Na) 610.0 |
| 28 | CONHSO$_2$-(p-Cl)Ph | (M+) 546.0 |
| 29 | CONHSO$_2$-(p-Me)Ph | |
| 30 | CONHSO$_2$-(5-iBu)thiophene | (M+Na) 596.4 |
| 31 | CONHSO$_2$-(p-MeO)Ph | (M+1) 542.0 |
| 32 | CONHSO$_2$-(p-NMe$_2$)Ph | (M+1) 555.1 |
| 33 | CONHSO$_2$-(o-Me)Ph | (M+1) 526.1 |
| 34 | CONHSO$_2$-(o-CO$_2$Me)Ph | (M+) 570.0 |
| 35 | CONHSO$_2$-(o-Cl)Ph | (M+) 546.0 |
| 36 | CONHSO$_2$-(m-Cl)Ph | (M+) 546.0 |
| 37 | CONHSO$_2$CH$_2$Ph | (M+1) 526.1 |
| 38 | CONH-damsyl | (M+1) 605.1 |
| 39 | CONHSO$_2$-8-quinoline | (M+1) 563.4 |

The proton NMR data for Example 29 is given below:

EXAMPLE 29

N-(4-methylbenzenesulfonyl)-2-(4-methoxycarbonyl-2-propylphenoxy)-2-(3,4-methylenedioxyphenyl)acetami de $^1$H NMR (400 MHz, CD$_3$OD, ppm): δ0.89 (t, 3H), 1.59 (m, 2H), 2.34 (s, 3H), 2.63 (m, 2H), 3.85 (s, 3H), 5.49 (s, 1H), 5.97 (s, 2H), 6.55 (d, 1H), 6.79 (d, 1H), 6.91 (d, 1H), 6.96 (dd, 1H), 7.26 (d, 2H), 7.58 (dd, 1H), 7.70 (d, 2H), 7.74 (d, 1H).

EXAMPLE 40

N-(4-t-butylbenzenesulfonyl)-2-(4-carboxy-2-propylphenoxy)-2-(3,4-methylenedioxyphenyl)acetamide To the product of Example 25 (51.1 mg, 0.090 mmol) in MeOH (2 mL) was added 5 N NaOH (0.5 mL). The reaction was monitored by TLC. When the reaction was complete the MeOH was removed and the residue partitioned between water and Et$_2$O:EtOAc. The water layer was acidified with HCl solution and the product extracted into the organic phase. The organic phase was washed with brine then dried over MgSO$_4$, filtered and the solvent removed. Trituration with Et$_2$O/Hex provided a white solid. yield=25.8 mg (0.047 mmol, 52%) FAB mass spectrum, m/e 554.2 (M+1 calculated for C$_{29}$H$_{31}$NSO$_8$ 554).

EXAMPLES 41–54

Examples 41 through 54 were prepared following the procedures described above in Example 40.

| Ex. # | Z | Mass Spectrum |
|---|---|---|
| 41 | CONHSO$_2$Ph | (M+1) 498.0 |
| 42 | CONHSO$_2$-(p-phenyl)Ph | (M+) 573.5 |
| 43 | CONHSO$_2$-(p-Cl)Ph | (M+) 532.0 |
| 44 | CONHSO$_2$-(p-Me)Ph | (M+K) 549.9 |
| 45 | CONHSO$_2$-(5-iBu)thiophene | (M+Na) 582.0 |
| 46 | CONHSO$_2$-(p-MeO)Ph | (M+1) 528.0 |
| 47 | CONHSO$_2$-(p-NMe$_2$)Ph | (M+1) 541.1 |
| 48 | CONHSO$_2$-(o-Me)Ph | (M+1) 512.0 |
| 49 | CONHSO$_2$-(o-CO$_2$Me)Ph | (M+1) 542.1 |
| 50 | CONHSO$_2$-(o-Cl)Ph | (M+1) 532.2 |
| 51 | CONHSO$_2$-(m-Cl)Ph | (M+1) 532.4 |
| 52 | CONHSO$_2$CH$_2$Ph | (M+1) 512.1 |
| 53 | CONH-damsyl | (M+1) 591.0 |
| 54 | CONHSO$_2$-8-quinoline | (M+1) 549.2 |

The proton NMR data for several of the Examples is given below:

EXAMPLE 47

N-(4-dimethylaminobenzenesulfonyl)-2-(4-carboxy-2-propylphenoxy)-2-(3,4-methylenedioxyphenyl)acetamide $^1$H NMR (300 MHz, CD$_3$OD, ppm): δ0.89 (t, 3H), 1.59 (m, 2H), 2.62 (m, 2H), 3.03 (s, 6H), 5.48 (s, 1H), 5.96 (s, 2H), 6.43 (d, 1H), 6.64 (dd, 2H), 6.79 (d, 1H), 6.91 (m, 2H), 7.55 (dd, 1H), 7.64 (dd, 2H), 7.74 (d, 1H).

EXAMPLE 49

N-(2-carboxybenzenesulfonyl)-2-(4-carboxy-2-propylphenoxy)-2-(3,4-methylenedioxyphenyl)acetamide $^1$H NMR (400 MHz, CD$_3$OD, ppm): δ0.92 (t, 3H), 1.62 (m, 2H), 2.67 (m, 2H), 5.66 (s, 1H), 5.95 (s, 2H), 6.74 (d, 1H), 6.77 (d, 1H), 6.93 (d, 1H), 6.98 (dd, 1H), 7.60 (m, 2H), 7.69 (m, 1H), 7.75 (m, 2H), 8.09 (d, 1H).

EXAMPLE 53

N-(dansylsulfonyl)-2-(4-carboxy-2-propylphenoxy)-2-(3,4-methylenedioxyphenyl)acetamide $^1$H NMR (400 MHz, CD$_3$OD, ppm): δ0.83 (t, 3H), 1.51 (m, 2H), 2.57 (m, 2H), 2.88 (s, 6H), 5.40 (s, 1H), 5.95 (dd, 2H), 6.26 (d, 1H), 6.65 (d, 1H), 6.79 (d, 1H), 6.85 (dd, 1H), 7.19 (dd, 1H), 7.25 (d, 1H), 7.48 (t, 1H), 7.54 (t, 1H), 7.66 (d, 1H), 8.13 (d, 1H), 8.30 (dd, 1H), 8.53 (d, 1H).

EXAMPLE 54

N-(8-quinolinesulfonyl)-2-(4-carboxy-2-propylphenoxy)-2-(3,4-methylenedioxyphenyl)acetamide $^1$H NMR (300 MHz, CD$_3$OD, ppm): δ0.85 (t, 3H), 1.54 (m, 2H), 2.59 (m, 2H), 5.57 (s, 1H), 5.94 (s, 2H), 6.47 (d, 1H), 6.66 (d, 1H), 6.71 (d, 1H), 6.87 (dd, 1H), 7.34 (dd, 1H), 7.58 (dd, 1H), 7.68 (m, 2H), 8.20 (dd, 1H), 8.39 (dd, 1H), 8.47 (dd, 1H), 8.83 (dd, 1H).

EXAMPLE 55

N-(8-quinolinesulfonyl)-2-(4-carboxamido-2-propylphenoxy)-2-(3,4-methylenedioxyphenyl)acetamide To N-(8-quinolinesulfonyl)-2-(4-carboxy-2-propylphenoxy)-2-(3,4-methylenedioxyphenyl)acetamide, Example 54, (25.8 mg, 0.047 mmol) in dry DMF (0.5 mL) was added 1-(3-dimethylaminopropyl)-3-ethylcarbodiimide hydrochloride, also referred to as EDC, (18.4 mg, 0.096 mmol), NH$_4$Cl (6.7 mg, 0.125 mmol), and TEA (17.5 mL, 0.125 mmol). Reaction was followed by thin layer chromatography (100:15: 1.5/CH$_2$Cl$_2$:MeOH:HOAc). When the reaction was completed the DMF was removed in vacuo and the residue taken up in Et$_2$O/EtOAc. The solution was washed with 10% citric acid, water and brine then dried over MgSO$_4$, filtered and the solvent removed. The product was purified by chromatography eluting with 200:5:1.5/ CH$_2$Cl$_2$:MeOH:HOAc. rf=0.35 (100:5:1.5/ CH$_2$Cl$_2$:MeOH:HOAc) FAB mass spectrum, m/e 548.0 (M+1 calculated for C$_{28}$H$_{25}$N$_3$SO$_7$ 548).

EXAMPLE 56

α-(4-carbomethoxy-2-n-propylphenoxy)-3,4-methylenedioxyphenyl)acetic acid

Step A: Preparation of ethyl α-(4-carbomethoxy-2-n-propylphenoxy)-3,4-methylenedioxyphenylacetate To a 2 L three necked 24/40 round bottom flask equipped with a mechanical stirrer, a nitrogen inlet and a dropping funnel was first added a solution of 36.0 g (0.185 mol) of methyl 4-hydroxy-3-n-propylbenzoate dissolved in 700 mL of anhydrous DMF followed by 66.4 g (0.204 mol) of cesium carbonate. The flask was purged with nitrogen and the reaction mixture was stirred at room temperature for 2 hours. A solution of 58.5 g (0.204 mol) of ethyl α-bromo-3,4-methylenedioxyphenylacetated dissolved in 100 mL of DMF was then added via an addition funnel over a 15 minute period. The reaction mixture was stirred an additional 1 hour at room temperature then quenched by addition to 5 L of a 5% aqueous citric acid solution. The organic product was extracted into diethylether (2×4 L), the organic layers were separated, washed with saturated aqueous NaCl, dried (MgSO$_4$), filtered, and evaporated. The residue was applied to a silica gel (2 kg; 70–230 mesh) column equilibrated in 10% CH$_2$Cl$_2$-hexane. The column was then eluted successively with 12 L of 10% CH$_2$Cl$_2$-hexane, 12 L of 5% EtOAc-hexane, 4 L of 7.5% EtOAc-hexane, 12 L of 10% EtOAc-hexane, and finally 8 L of 20% EtOAc-hexane. Combination of the purified fractions and evaporation in vacuo afforded 76.3 g (74.2 theoretical) of the title compound as a pale yellow oil which was used without further purification in the next step.

Step B: Preparation of α-(4-carbomethoxy-2-n-propylphenoxy)-3,4-methylenedioxyphenylacetic acid A 1 L 3 necked 24/40 round bottom flask equipped with a mechanical stirrer, a dropping funnel, and a nitrogen inlet was charged with a solution of 76.3 g 0.185 mol) of the semi-purified product of Step A dissolved in 500 mL of methanol. The flask was purged with nitrogen, the stirrer was started, and 37 mL of a 5.0 N aqueous solution of sodium hydroxide was added over a 30 minute period via an addition funnel. The reaction mixture was stirred at room temperature for an additional 30 minutes at which point TLC analysis (CH$_2$Cl$_2$—MeOH—NH$_4$OH90:10:1) indicated that the starting material had been consumed. The reaction mixture was adjusted to pH=4 with 6 N HCl, and the bulk of the organic solvent was removed in vacuo. The precipitated organic product and the aqueous layer were next partitioned between CH$_2$Cl$_2$ (1 L) and water (1 L) which produced a copious emulsion. The reaction mixture was then aged overnight in a refrigerator which resulted in crystallization of the organic product. The crystalline solid was separated from the two phase mixture by filtration and washed with CH$_2$Cl$_2$. The solid was slurried again in diethylether, filtered, washed with hexane, and then dried in a vacuum to afford 65 g (94%) of the title compound as a white crystalline solid. $^1$H-NMR (400 MHz, CD$_3$OD, ppm): δ0.93 (t, J=7.20 Hz, 3H), 1.62–1.75 (m, 2H), 2.63–2.70 (m, 1H), 2.77–2.81 (m, 1H), 3.84 (s, 3H), 5.54 (s, 1H), 5.94 (s, 2H), 6.81 (d, J=7.60 Hz, 1H), 6.89 (d, J=9.20 Hz, 1H), 7.08 (d, J=1.60 Hz, 1H), 7.11 (br s, 1H), 7.78–7.81 (m, 2H).

EXAMPLE 57

N-(4-iso-propylbenzenesulfonyl)-α-(4-carbomethoxy-2-n-propylphenoxy)-3,4-methylenedioxyphenylacetamide Step A: Preparation of N-(4-iso-propylbenzenesulfonyl)-α-(4-carbomethoxy-2-n-propylphenoxy)-3,4-methylenedioxyphenylacetamide An oven dried three-necked 24/40 1 L round-bottom flask was equipped with a mechanical stirrer, a nitrogen inlet, and a septum. The flask was flushed with nitrogen, then charged with 20.06 g (53.9 mmol) of the product of Example 56, 400 mL of anhydrous THF, and 9.76 mL (70.0 mmol) of triethylamine. The flask and its contents were stirred and cooled to −78° C. with an external dry ice-acetone bath and then 7.30 mL (59.3 mmol) of trimethylacetyl chloride was added slowly via a syringe. After the addition was complete, the dry ice-acetone bath was replaced with an ice-water bath and the reaction was stirred at 0° C. for 1 hour. A separate oven dried 3 necked 24/40 2 L round-bottom flask was equipped with a mechanical stirrer, a septum and a nitrogen inlet. The flask was flushed with nitrogen then charged with 16.102 g (80.8 mmol) of 4-iso-propylbenzenesulfonamide and 300 mL of anhydrous methyl sulfoxide. The stirrer was started and a 162 mL of a 1.0 M solution of lithium bis(trimethylsilylamide) in THF was slowly (mildly exothermic) added via a syringe through the septum. After the addition was complete, the reaction mixture was stirred at room temperature for an additional 30 minutes. The contents of the first reaction mixture including a fine white precipitate that was suspended in the reaction mixture were then slowly transfered to the stirred solution of the deprotonated sulfonamide in the second flask via a wide diameter cannula. The combined reaction mixture was then stirred for an additional 14 hours under a nitrogen atmosphere. The reaction was the quenched with 1.0 N HCl and the majority of the volatile solvents were removed in vacuo. The residue was partitioned between EtOAc and 1.0 N HCl, then organic layer was separated, washed with saturated aqueous NaCl, dried (MgSO$_4$), filtered and evaporated in vacuo. The residue was purified on a silica gel (3 kg; 70–230 mesh) chromatography column (15 cm×150 cm) eluted with (90:10:1 CH$_2$Cl$_2$—MeOH—NH$_4$OH). Combination of the purified fractions and evaporation in vacuo afforded 18.367 g (62%) of the title compound.

$^1$H-NMR (400 MHz, CD$_3$OD, ppm): a δ0.88 (t, J=7.60 Hz, 3H), 1.24 (d, J=7.00 Hz, 3H), 1.25 (t, J=7.00 Hz, 3H), 1.55–1.60 (m, 2H), 2.59–2.66 (m, 2H), 2.97 (sept, J=7.00 Hz, 1H), 3.83 (s, 3H), 5.52 (s, 1H), 5.97 (s, 2H), 6.50 (d, J=8.80 Hz, 1H), 6.80 (d, J=8.00 Hz, 1H), 6.89 (d, J=1.60 Hz, 1H), 6.94 (dd, J=2.00, 8.00 Hz, 1H), 7.14 (d, J=8.80 Hz, 2H), 7.59 (dd, J=2.20, 8.80 Hz, 1H), 7.75 (d, J=2.20, 1H), 7.79 (d, J=8.80 Hz, 2H).

EXAMPLE 58

N-(4-iso-propylbenzenesulfonyl)-α-(4-carboxy-2-n-propylphenoxy)-3,4-methylenedioxyphenylacetamide dipotassium salt Step A: Preparation of N-(4-iso-propylbenzenesulfonyl)-α-(4-carboxy-2-n-propylphenoxy)-3,4-methylenedioxyphenylacetamide dipotassium salt To a solution of 18.367 g (33.2 mmol) of the product of Example 57 dissolved in 100 mL of methanol was added a solution of 6.56 g (116.9 mmol) of potassium hydroxide in 25 mL of water and the reaction mixture was stirred at 60° C. under a nitrogen atmosphere. After 6 hours TLC analysis (80:15:1 CHCl$_3$—MeOH—NH$_4$OH) indicated that ester hydrolysis was complete. The reaction mixture was cooled to room temperature, diluted with 100 mL water, filtered through a 0.45 micron filter and then divided into two equal volume portions. The fractions were individually desalted and purified on a Waters Millipore Delta Prep 3000 liquid chromatograph equipped with an M1000 Prep-Pak module containing a 47×300 mm Delta-Pak C18 15 μm 100A column cartridge. Two solvent resevoirs were employed: solvent system A (95–5 water-acetonitrile), and solvent system B (5–95 water-acetonitrile), and the column effluent was monitored simultaneously at 210 and 280 nm with a Waters model 490 UV-visible detector. Each fraction was pump-injected onto the column and desalted by elution (50 mL/min) with several colunto volumes of solvent system A. A gradient elution was then begun which had as initial conditions 100% solvent system A-0% solvent system B and reached after 30 minutes 50% solvent system A-50% solvent system B, and the fractions were collected with an ISCO Foxy 200 fraction collector. The purified fractions were combined in round bottom flasks, frozen in a –78° C. dry ice-acetone bath, and lyophilized. Combination of the purified product afforded 18.719 g (92%) of the title compound as a white lyophilized powder.

$^1$H-NMR (400 MHz, CD$_3$OD, ppm): δ0.88 (t, J=7.20 Hz, 3H), 1.21 (d, J=7.00 Hz, 3H), 1.22 (d, J=7.00 Hz, 3H), 1.56–1.63 (m, 2H), 2.52–2.59 (m, 1H), 2.67–2.74 (m, 1H), 2.91 (sept, J=7.00 Hz, 1H), 5.33 (s, 1H), 5.92 (d, J=1.20 Hz, 1H), 5.93 (d, J=1.20 Hz, 1H), 6.72 (d, J=8.50 Hz, 1H), 6.76 (d, J=8.50 Hz, 1H), 7.04 (d, J=7.50 Hz, 1H), 7.05 (s, 1H), 7.21 (d, J=8.50 Hz, 2H), 7.64 (dd, J=2.00, 8.50 Hz, 1H), 7.67 (d, J=8.50 Hz, 2H), 7.73 (d, J=2.00 Hz, 1H).

Microanalysis for C$_{28}$H$_{27}$NSO$_8$K$_2$·H$_2$O.

Calc'd: C=53.06; H=4.61; N=2.21; K=12.34. Found: C=52.81; H=4.56; N=2.17; K=12.02.

EXAMPLE 59

α-(2-iso-butyl-4-carbomethoxyphenoxy)-3,4-methylenedioxyphenylacetic acid

Step A: Preparation of ethyl α-(2-iso-butyl-4-carbomethoxy-phenoxy)-3,4-methylenedioxyphenylacetate To a solution of 1.008 g (4.84 mmol) of methyl 3-iso-butyl-4-hydroxybenzoate and 1.737 g (6.05 mmol) of ethyl α-bromo-3,4-methylenedioxyphenylacetate in 10 mL of acetone was added 1.338 g (10 mmol) of finely powdered potassium carbonate. The reaction mixture was magnetically stirred and refluxed for 4 hours, then cooled to room temperature, filtered and evaporated. The residue was purified on a silica gel flash chromatography column eluted with 10% EtOAc-hexane; combination of the purified fractions and drying in vacuo afforded 1.518 g (76%) of the title compound as an amorphous powder.

$^1$H-NMR (400 MHz, CDCl$_3$, ppm): δ0.90 (d, J=6.60 Hz, 3H), 0.94 (d, J=6.60 Hz, 3H), 1.17 (t, J=7.20 Hz, 3H), 2.02–2.08 (m, 1H), 2.55 (dd, J=7.20, 13.20 Hz, 1H), 2.64 (dd, J=7.20, 13.20 Hz, 1H), 3.85 (s, 3H), 4.11–4.19 (m, 2H), 5.56 (s, 1H), 5.96 (s, 2H), 6.70 (d, J=9.20 Hz, 1H), 6.68 (d, J=7.60 Hz, 1H), 7.02 (dd, J=1.60, 8.00 Hz, 1H), 7.05 (d, J=2.00 Hz, 1H), 7.78–7.81 (m, 2H).

Step B: Preparation of α-(2-iso-butyl-4-carbomethoxyphenoxy)-3,4-methylenedioxyphenylacetic acid To a solution of 1.518 g (3.66 mmol) of the product of Step A dissolved in 8.0 mL of methanol was added 1.0 mL of a 5.0 M solution of aqueous sodium hydroxide. The reaction was stirred at room temperature and monitored by TLC (80:15:1 CHCl$_3$—MeOH—NH$_4$OH). After 1.5 hours the reaction was judged to be complete and the reaction mixture was adjusted to pH=5 with 1.0 N HCl. The reaction mixture was then partitioned between EtOAc and water, separated, dried (MgSO$_4$), filtered, and evaporated. The residue was purified on a silica gel flash chromatography column eluted with CHCl$_3$—MeOH—NH$_4$OH (80:15:1); evaporation of the purified fractions and drying in vacuo afforded the title compound as an amorphous foam.

$^1$H—NMR (400 MHz, CD$_3$OD, ppm): δ0.86 (d, J=6.80 Hz, 3H), 0.89 (d, J=6.80 Hz, 3H), 1.96–2.04 (m, 1H), 2.49 (dd, J=7.20, 12.80 Hz, 1H), 2.69 (dd, J=7.20, 12.80 Hz, 1H), 3.84 (s, 3H), 5.49 (s, 1H), 5.92 (d, J=1.20 Hz, 1H), 5.93 (d, J=1.20 Hz, 1H), 6.79 (d, J=8.00 Hz, 1H), 6.89 (d, J=8.80 Hz, 1H), 7.08 (dd, J=1.60, 8.00 Hz, 1H), 7.11 (d, J=1.60 Hz, 1H), 7.74 (d, J=2.40 Hz, 1H), 7.78 (dd, J=2.40, 8.80 Hz, 1H).

CI-MS m/e=386.2 (M$^+$).

EXAMPLE 60

N-(4-iso-propylbenzenesulfonyl)-α-(2-iso-butyl-4-carbomethoxyphenoxy)-3,4-methylenedioxyphenylacetamide Step A: Preparation of N-(4-iso-propylbenzenesulfonyl)-α-(2-iso-butyl-4-carbomethoxyphenoxy)-3,4-methylenedioxyphenylacetamide To a solution of 0.727 g (1.88 mmol) of the product of Step B in Example 58 dissolved in 4 mL of anhydrous THF was added 0.458 g (2.82 mmol) of 1,1'-carbonyldiimidazole and the mixture was magnetically stirred and refluxed for 2 hours. The reaction mixture was then cooled to room temperature, and 0.562 g (2.82 mmol) of 4-iso-propylbenzenesulfonamide and 0.42 mL (2.82 mmol) of 1,8-diazabicyclo [5.4.0]undec-7-ene were added. The reaction mixture was stirred an additional 3 hours at room temperature, then was evaporated in vacuo. The residue was partitioned between EtOAc and 1.0 N HCl and extracted. The organic layer was separated, dried ($MgSO_4$), filtered, and evaporated and the residue was purified on a silica gel flash chromatography column eluted with $CHCl_3$—MeOH—$NH_4OH$ (80:15:1). Evaporation of the purified fractions and drying in vacuo afforded 0.666 g (63%) of the title compound.

$^1$H-NMR (400 MHz, $CD_3OD$, ppm): δ0.81 (d, J=6.80 Hz, 3H), 0.84 (d, J=6.80 Hz, 3H), 1.23 (d, J=6.80 Hz, 3H), 1.24 (d, J=6.80 Hz, 3H), 1.88–1.94 (m, 1H), 2.45 (dd, J=7.00, 13.00 Hz, 1H), 2.58 (dd, J=7.00, 13.00 Hz, 1H), 2.95 (sept, J=6.80 Hz, 1H), 3.84 (s, 3H), 5.46 (s, 1H), 5.95 (d, J=1.20 Hz, 1H), 5.96 (d, J=1.20 Hz, 1H), 6.59 (d, J=8.60 Hz, 1H), 6.79 (d, J=8.00 Hz, 1H), 6.98 (br s, 1H), 6.99 (dd, J=1.60, 8.00 Hz, 1H), 7.30 (d, J=8.40 Hz, 2H), 7.60 (dd, J=2.00, 8.60 Hz, 1H), 7.70 (d, J=2.00 Hz, 1H), 7.72 (d, J=8.40 Hz, 2H).

EXAMPLE 61

N-(4-iso-propylbenzenesulfonyl)-α-(2-iso-butyl-4-carboxyphenoxy)-3,4-methylenedioxyphenylacetamide Step A: Preparation of N-(4-iso-propylbenzenesulfonyl)-α-(2-iso-butyl-4-carboxyphenoxy)-3,4-methylenedioxyphenylacetamide To a solution of 0.294 g (0.52 mmol) of the product of Example 60 dissolved in 3.0 mL of methanol was added 1.0 mL of a 5.0 N aqueous solution of sodium hydroxide. The reaction mixture was magnetically stirred at 60° C. After 3 hours TLC analysis ($CHCl_3$—MeOH—$NH_4OH$ 80:15:1) indicated complete hydrolysis of the ester. The reaction was cooled to room temperature, adjusted to pH=5 with dropwise addition of 1.0 N HCl, then partitioned between EtOAc and water. The organic layer was separated, washed with saturated aqueous NaCl, dried ($MgSO_4$), filtered and evaporated. The residue was dried in vacuo to afford 0.238 g (83%) of the title compound as an amorphous powder.

$^1$H-NMR (400 MHz, $CD_3OD$, ppm): δ0.82 (d, J=6.80 Hz, 3H), 0.85 (d, J=6.80 Hz, 3H), 1.24 (d, J=7.20 Hz, 3H), 1.25 (d, J=7.20 Hz, 3H), 1.91 (sept, J=6.80 Hz, 1H), 2.48 (dd, J=7.20, 13.20 Hz, 1H), 2.56 (dd, J=7.20, 13.20 Hz, 1H), 2.97 (sept, J=7.20 Hz, 1H), 5.51 (s, 1H), 5.97 (s, 1H), 6.50 (d, J=8.40 Hz, 1H), 6.81 (d, J=8.00 Hz, 1H), 6.91 (d, J=1.60 Hz, 1H), 6.95 (dd, J=1.60, 8.00 Hz, 1H), 7.36 (d, J=8.40 Hz, 2H), 7.62 (dd, J=2.20, 8.40 Hz, 1H), 7.72 (d, J=2.20 Hz, 1H), 7.79 (d, J=8.40 Hz, 2H).

FAB-MS m/e=554 (M+1).

EXAMPLE 62

N-(4-iso-propylbenzenesulfonyl)-α-(2-n-propyl-4-methoxycarbonylphenoxy)-α-methyl-3,4-methylenedioxyphenylacetamide Step A: Preparation of N-(4-iso-propylbenzenesulfonyl)-α-(2-n-propy-4-methoxycarbonylphenoxy)-α-methyl-3,4-methylenedioxyphenylacetamide To a solution of 0.516 g (0.93 mmol) of the product of Example 57 dissolved in 1.0 mL of anhydrous THF was added 2.80 mL (2.80 mmol) of a 1.0 M solution of lithium bis(trimethylsilylamide) in THF at −78° C. under a nitrogen atmosphere. The reaction mixture was magnetically stirred at −78° C. for 1 hour, then 174 μL (2.80 mmol) of iodomethane was added via syringe. The reaction was allowed to warm to room temperature and was stirred an additional 14 hours. The reaction was next quenched with excess 10% aqueous NaHSO4 and partitioned between EtOAc and water. The organic layer was washed with saturated aqueous NaCl, dried ($MgSO_4$), filtered and evaporated. The residue was purified on a silica gel flash chromatography column eluted with $CHCl_3$—MeOH—$NH_4OH$ (90:10:1). Evaporation of the purified fractions and drying in vacuo afforded 0.293 g (55%) of the title compound as an amorphous solid.

$^1$H-NMR (400 MHz, $CD_3OD$, ppm): δ0.99 (t,J=7.20 Hz, 3H), 1.31 (d, J=6.80 Hz, 6H), 1.64–1.72 (m, 2H), 1.66 (s, 3H), 2.64–2.73 (m, 1H), 2.81–2.88 (m, 1H), 3.02 (sept, J=6.80 Hz, 1H), 3.85 (s, 3H), 5.96 (s, 2H), 6.36 (d, J=8.40, 1H), 6.77 (d, J=8.40 Hz, 2H), 6.99 (m, 1H), 7.05 (br s, 1H), 7.37 (d, J=7.60 Hz, 1H), 7.43 (dd, J=2.40, 8.60 Hz, 1H), 7.76 (d, J=8.40 Hz, 2H), 7.81 (br s, 1H).

FAB-MS m/e=568 (M+1).

EXAMPLE 63

N-(4-iso-propylbenzenesulfonyl)-α-(2-n-propyl-4-carboxyphenoxy)-α-methyl-3,4-methylenedioxyphenylacetamide dipotassium salt Step A: Preparation of N-(4-iso-propylbenzenesulfonyl)-α-(2-n-propyl-4-carboxyphenoxy)-α-methyl-3,4-methylenedioxyphenylacetamide dipotassium salt To a solution of 0.293 g (0.52 mmol) of the product of Example 62 dissolved in 2.0 mL of methanol was added a solution of 0.143 g (2.54 mmol) of potassium hydroxide dissolved in 1.0 mL of water. The reaction mixture was magnetically stirred at 60° C. for 4 hours until TLC anlysis ($CHCl_3$—MeOH—$NH_4OH$ 80:15:1) indicated complete hydrolysis of the starting material. The reaction mixture was then cooled to room temperature, diluted with 5.0 mL of water and filtered through a 0.45 micron filter. The filtrate was then purified on a Waters Millipore Delta Prep 3000 liquid chromatograph equipped with two DuPont Zorbax® 21.2 mm×25 cm ODS reversed phase HPLC columns connected in series. Two solvent resevoirs were employed: solvent system A (95–5 water-acetonitrile), and solvent system B (5–95 water-acetonitrile), and the column effluent was monitored simultaneously at 210 and 280 nm with a Waters model 490 UV-visible detector. The reaction mixture was injected onto the column and desalted by elution (50 mL/min) with approximately 1L of solvent system A. A gradient elution was then begun which had as initial conditions 100% solvent system A-0% solvent system B and reached after 30 minutes 50% solvent system A-50% solvent system B, and the fractions were collected with an ISCO Foxy 200 fraction collector. The purified fractions were combined in round bottom flasks, frozen in a −78° C. dry ice acetone bath, and lyophilized. Combination of the purified product afforded 0.273 g (84%) of the title compound as a white lyophilized powder.

$^1$H-NMR (400 MHz, $CD_3OD$, ppm): δ0.96 (t, J=7.20 Hz, 3H), 1.25 (d, J=7.20 Hz, 3H), 1.26 (d, J=7.20 Hz, 3H), 1.64–1.71 (m, 2H), 1.67 (s, 3H), 2.58–2.65 (m, 1H), 2.74–2.82 (m, 1H), 2.96 (sept, J=7.20 Hz, 1H), 5.91 (d, J=1.20 Hz, 1H), 5.92 (d, J=1.20 Hz, 1H), 6.52 (d, J=8.40 Hz, 1H), 6.72 (d, J=8.00 Hz, 1H), 7.12 (dd, J=1.80, 8.00 Hz, 1H), 7.17 (d, J=2.00 Hz, 1H), 7.28 (d, J=8.80 Hz, 2H), 7.50 (dd, J=2.20, 8.40 Hz, 1H), 7.72 (d, J=8.80 Hz, 2H), 7.74 (d, J=2.00 Hz, 1H).

FAB-MS m/e=591.6 (M+K$^+$).

EXAMPLE 64

N-(4-iso-propylbenzenesulfonyl)-α-(2-n-propyl-4-carboxamidophenoxy)-3,4-methylenedioxyphenylacetamide Step A: Preparation of N-(4-iso-propylbenzenesulfonyl)-α-(2-n-propyl-4-carboxamidophenoxy)-3,4-methylenedioxyphenylacetamide To a solution of 0.162 g (0.30 mmol) of N-(4-iso-propylbenzenesulfonyl)-α-(4-carboxy-2-n-propylphenoxy)-3,4-methylenedioxyphenylacetamide (free acidic form of the product of Example 58) dissolved in 1.5 mL of anhydrous THF was added 0.073 g (0.45 mmol) of 1,1'-carbonyldiimidazole and the resulting mixture was magnetically stirred and refluxed for 50 minutes. The reaction mixture was cooled to room temperature, and then added at 0° C. to excess THF that had been previously saturated with anhydrous gaseous ammonia. The reaction mixture was sealed and then stirred at room temperature for 14 hours. The reaction mixture was then poured into water (70 mL) and extracted with EtOAc (150 mL). The organic layer was separated, washed with saturated aqueous NaCl, dried (MgSO$_4$), filtered, and evaporated in vacuo to afford the title compound as an amorphous solid.

$^1$H-NMR (400 MHz, CD$_3$OD, ppm): δ0.88 (t, J=7.60 Hz, 3H), 1.21 (d, J=6.80 Hz, 6H), 1.55–1.66 (m, 2H), 2.54–2.62 (m, 1H), 2.70–2.77 (m, 1H), 2.89 (sept, J=6.80 Hz, 1H), 5.36 (s, 1H), 5.93 (d, J=1.20 Hz, 1H), 5.94 (d, J=1.20 Hz, 1H), 6.75 (d, J=8.40 Hz, 1H), 6.78 (d, J=8.80 Hz, 1H), 7.02–7.04 (m, 2H), 7.06 (br s, 2H), 7.20 (d, J=8.40 Hz, 2H), 7.55 (dd, J=2.20, 8.60 Hz, 1H), 7.62–7.66 (m, 2H), 7.71 (s, 1H). FAB-MS m/e=539 (M+1).

EXAMPLE 65

N-(4-iso-propylbenzenesulfonyl)-α-(2-n-propyl-4-hydroxymethylphenoxy)-3,4-methylenedioxyphenylacetamide Step A: Preparation of methyl α-(4-hydroxymethyl-2-n-propylphenoxy)-3,4-methylenedioxyphenylacetate To a solution of 3.84 g (23.13 mmol) of 4-hydroxy-3-n-propylbenzyl alcohol dissolved in 70 mL of anhydrous DMF was added 9.04 g (27.7 mmol) of cesium carbonate and the reaction mixture was magnetically stirred at room temperature for 15 minutes. Methyl α-bromo-3,4-methylenedioxyphenylacetate (7.58 g; 27.7 mmol) was added and the reaction mixture was then stirred for an additional 14 hours at room temperature under a nitrogen atmosphere. The reaction was then partitioned between 5% aqueous citric acid (700 mL) and EtOAc (100 mL) and extracted. The organic layer was separated, washed with saturated aqueous NaCl, dried (MgSO$_4$), filtered and evaporated. The residue was purified on a silica gel flash chromatography column eluted with 40% EtOAc-hexane. The purified fractions were combined, evaporated, and dried in vacuo to afford 6.74 g (81%) of the title compound as a yellow oil.

$^1$H-NMR (200 MHz, CDCl$_3$, ppm): δ0.97 (t, J=7.60 Hz, 3H), 2.55–2.75 (m, 2H), 2.71 (t, J=7.20 Hz, 2H), 3.71 (s, 3H), 4.59 (s, 2H), 5.55 (s, 1H), 5.97 (s, 2H), 6.69 (d, J=8.20 Hz, 1H), 6.82 (d, J=7.80 Hz, 1H), 7.02–7.28 (m, 4H). FAB-MS m/e=359 (M+1).

Step B: Preparation of methyl α-(4-tert-butyldimethylsilyloxy-methyl-2-n-propylphenoxy)-3,4-methylenedioxyphenylacetate To a solution of 2.50 g (6.98 mmol) of the product of Step A dissolved in 20 mL of dichloromethane was added 1.95 mL (14.0 mmol) of triethylamine, 1.26 g (8.38 mmol) of tert-butyldimethylchlorosilane, 85 mg (0.1 eq) of 4-dimethylaminopyridine and the reaction mixture was stirred at room temperature for 30 minutes under a nitrogen atmosphere. The reaction was then diluted with 100 mL EtOAc, washed with water, 1.0 N HCl, saturated aqueous NaHCO$_3$, saturated NaCl, dried (MgSO$_4$), filtered and evaporated in vacuo to afford 3.20 g (97%) of the title compound. EI-MS m/e=472 (M$^+$).

Step C: Preparation of α-(4-tert-butyldimethylsilyloxymethyl-2-n-propylphenoxy)-3,4-methylenedioxyphenylacetic acid To a solution of 3.20 g (6.78 mmol) of the product of Step B dissolved in 10 mL of methanol and 3 mL of dichloromethane was added 1.42 mL (7.12 mmol) of a 5.0 N aqueous solution of sodium hydroxide and the reaction mixture was magnetically stirred at room temperature. After 4 hours TLC analysis (CHCl$_3$—MeOH—NH$_4$OH 80:15:1) indicated complete hydrolysis and the reaction mixture was adjusted to pH=4 with 1.0 N HCl. The reaction mixture was then completely evaporated and dried in vacuo to afford the crude product which was used directly in the next step. FAB-MS m/e=481 (M+Na$^+$).

Step D: Preparation of N-(4-iso-propylbenzenesulfonyl)-α-(4-tert-butyldimethylsilyloxymethyl-2-n-propylphenoxy)-3,4-methylenedioxyphenylacetamide To a solution of 3.30 g (7.21 mmol) of the crude product from Step C dissolved in 40 mL of anhydrous THF was added 1.75 g (10.8 mmol) of 1,1'-carbonyldiimidazole and the reaction mixture was magnetically stirred and heated at reflux for 10 minutes. The reaction was then cooled to room temperature, 2.15 g (10.8 mmol) of 4-iso-propylbenzenesulfonamide and 1.61 mL (10.8 mmol) of 1,8-diazabicyclo [5.4.0]undec-7-ene were added and the reaction was stirred for an additional 30 minutes at room temperature. The mixture was then diluted with EtOAc (80 mL), washed with 10% aqueous citric acid, saturated aqueous NaCl, dried (MgSO$_4$), filtered and evaporated. The residue was partially purified on a silica gel flash chromatography column eluted with CHCl$_3$—MeOH—NH$_4$OH (92:8:0.5). The semi-purified material was combined and repurified on a second silica gel flash chromatography column eluted initially with 35% EtOAc-hexane, later with 50% EtOAc-hexane, and finally with 70% EtOAc-hexane. Combination of the purified fractions and evaporation afforded 3.20 g (69%) of the title compound as a yellow oil. FAB-MS m/e=678 (M+K$^+$).

Step E: Preparation of N-(4-iso-propylbenzenesulfonyl)-α-(4-hydroxymethyl-2-n-propylphenoxy)-3,4-methylenedioxyphenylacetamide To a solution of 3.20 g (5.01 mmol) of the product of Step D dissolved in 5.0 mL of anhydrous THF was added 5.06 mL (5.06 mmol) of a 1.0 M solution of tetrabutylammonium fluoride in THF and the reaction mixture was stirred at room temperature under a nitrogen atmosphere. After 2.5 hours 1.0 mL additional tetrabutylammonium fluoride in THF was added and the reaction mixture was stirred for an additional 14 hours. The reaction mixture was then concentrated in vacuo and applied to a silica gel flash chromatography column and eluted with 60% EtOAc-hexane. Combination of the purified fractions and drying in vacuo afforded 0.691 g (26%) of the title compound as an amorphous powder.

1H-NMR (400 MHz, CD$_3$OD, ppm): δ0.87 (t, J=7.60 Hz, 3H), 1.26 (d, J=6.80 Hz, 3H), 1.27 (d, J=6.80 Hz, 3H), 1.51–1.63 (m, 2H), 2.54–2.68 (m, 2H), 2.98 (sept, J=6.80 Hz, 1H), 4.46 (s, 2H), 5.37 (s, 1H), 5.95 (s, 1H), 6.51 (d, J=8.40 Hz, 1H), 6.77 (d, J=8.00 Hz, 1H), 6.88–6.95 (m, H), 7.10 (d, J=2.00 Hz, 1H), 7.36 (d, J=8.40 Hz, 2H), 7.77 (d, J=8.40 Hz, 2H). FAB-MS m/e=548 (M+Na$^+$).

EXAMPLE 66

N-(4-iso-propylbenzenesulfonyl)-α-(4-formyl-2-n-propylphenoxy)-3,4-methylenedioxyphenylacetamide Step A: Preparation of N-(4-iso-propylbenzenesulfonyl)-α-(4-formyl-2-n-propylphenoxy)-3,4-methylenedioxyphenylacetamide To a solution of 0.573 g (1.09 mmol) of the product of Example 65 dissolved in 5.0 mL of dichloromethane was added 2.86 g (32.9 mmol) of manganese dioxide and 1.15 g of finely powdered 3A molecular sieves and the reaction mixture was magnetically stirred at room temperature for 14 hours. The reaction mixture was then filtered through a bed of celite and $MgSO_4$ and the flitrate was evaporated in vacuo. The residue was dissolved in dichloromethane and applied to a silica gel flash chromatography column and then eluted with 3% MeOH—$CH_2Cl_2$. Evaporation of the purified fractions and drying in vacuo afforded 0.149 g (26%) of the title compound.

$^1$H-NMR (400 MHz, $CD_3OD$, ppm): δ0.89 (t, J=7.60 Hz, 3H), 1.24 (d, J=7.20 Hz, 3H), 1.25 (d, J=7.20 Hz, 3H), 1.57–1.68 (m, 2H), 2.63–2.74 (m, 2H), 2.96 (sept, J=7.20 Hz, 1H), 5.56 (s, 1H), 5.97 (s, 2H), 6.70 (d, J=8.40 Hz, 1H), 6.80 (d, J=8.00 Hz, 1H), 6.91 (d, J=1.60 Hz, 1H), 6.96 (dd, J=1.60, 8.00 Hz, 1H), 7.34 (d, J=8.40 Hz, 2H), 7.53 (dd, J=2.00, 8.40 Hz, 1H), 7.66 (d, J=2.00 Hz, 1H), 7.76 (d, J=8.40 Hz, 2H), 9.77 (s, 1H).

FAB-MS m/e=546 (M+Na$^+$).

EXAMPLE 67

α-(4-acetyl-2-n-propylphenoxy)-3,4-methylenedioxyphenylacetic acid

Step A: Preparation of 4-hydroxy-2-n-propylacetophenone

A Parr hydrogenation apparatus flask was charged with a solution of 2.00 g (11.36 mmol) of 3-allyl-4-hydroxyacetophenone dissolved in 10 mL of ethanol and 200 mg of a 10% palladium on carbon catalyst. The flask was mounted in the Parr apparatus and shaken under a 46 psig hydrogen atmosphere for 15 minutes. At the end of this period TLC analysis (15% EtOAc-hexane) indicated that the starting material had been completely consumed, and the reaction mixture was filtered and evaporated. The residue was purified on a silica gel flash chromatography column eluted with 25% EtOAc-hexane. Evaporation of the purified fractions and drying in vacuo afforded 1.83 g (91%) of the title compound.

$^1$H-NMR (200 MHz, $CDCl_3$, ppm): δ0.98 (t, J=7.40 Hz, 3H), 1.56–1.78 (m, 2H), 2.57 (s, 3H), 2.63 (t, J=7.20 Hz, 2H), 6.08 (br s, 1H), 6.84 (d, J=8.20 Hz, 1H), 7.74 (dd, J=2.20, 8.20 Hz, 1H), 7.79 (d, J=2.20 Hz, 1H).

FAB-MS m/e=178 (M$^+$).

Step B: Preparation of methyl α-(4-acetyl-2-n-propylphenoxy)-3,4-methylenedioxphenylacetate To a solution of 0.250 g (1.40 mmol) of the product of Step A dissolved in 3.0 mL of DMF was added 0.504 g (1.54 mmol) of cesium carbonate and the reaction mixture was magnetically stirred at room temperature under a nitrogen atmosphere for 15 minutes. Methyl α-bromo-3,4-methylenedioxyphenylacetate (0.422 g, 1.54 mmol) was then added and the resulting mixture was stirred at room temperature for an additional 24 hours. The reaction mixture was then partitioned between 10% aqueous citric acid and EtOAc. The organic layer was washed with saturated aqueous $NaHCO_3$, saturated aqueous NaCl, dried ($MgSO_4$), filtered and evaporated in vacuo to afford the title compound.

$^1$H-NMR (300 MHz, $CDCl_3$, ppm): δ0.96 (t, J=7.50 Hz, 3H), 1.62–1.74 (m, 2H), 2.52 (s, 3H), 2.68–2.75 (m, 2H), 3.71 (s, 3H), 5.61 (s, 1H), 5.98 (s, 2H), 6.71 (d, J=8.60 Hz, 1H), 6.81 (d, J=8.20 Hz, 1H), 7.02 (dd, J=1.80, 8.20 Hz, 1H), 7.04 (d, J=1.80 Hz, 1H), 7.73 (dd, J=2.20, 8.60 Hz, 1H), 7.79 (d, J=2.20 Hz, 1H).

FAB-MS m/e=371 (M+1).

Step C: Preparation of α-(4-acetyl-2-n-propylphenoxy)-3,4-methylenedioxyphenylacetic acid To a solution of 0.556 g (1.50 mmol) of the product of Step B dissolved in 4.0 mL of methanol was added 0.45 mL (2.25 mmol) of a 5.0N aqueous solution of sodium hydroxide. The reaction mixture was stirred at room temperature and monitored by TLC ($CHCl_3$—MeOH—$NH_4OH$ 80:15:1). After 4 hours the reaction was judged to be complete and the reaction mixture was adjusted to pH=7 with 6.0N HCl. The mixture was then evaporated in vacuo and the residue was purified on a silica gel flash chromatography column eluted with $CHCl_3$—MeOH—$NH_4OH$ (80:15:1). Evaporation of the purified fractions and drying in vacuo afforded 0.416 g (78%) of the title compound.

$^1$H-NMR (400 MHz, $CD_3OD$, ppm): δ0.94 (t, J=7.60 Hz, 3H), 1.62–1.70 (m, 2H), 2.53 (s, 3H), 2.61–2.69 (m, 1H), 2.80–2.88 9m, 1H), 5.39 (s, 1H), 5.93 (d, J=1.20 Hz, 1H), 5.94 (d, J=1.20 Hz, 1H), 6.79 (d, J=8.00 Hz, 1H), 6.91 (d, J=8.80 Hz, 1H), 7.10 (dd, J=1.60, 8.00 Hz, 1H), 7.15 (d, J=1.60 Hz, 1H), 7.78 (d, J=2.40 Hz, 1H), 7.81 (dd, J=2.40, 8.80 Hz, 1H).

EXAMPLE 68

N-(4-iso-propylbenzenesulfonyl)-α-(4-acetyl-2-n-propylphenoxy)-3,4-methylenedioxyphenylacetamide Step A: Preparation of N-(4-iso-propylbenzenesulfonyl)-α-(4-acetyl-2-n-propylphenoxy)-3,4-methylenedioxyphenylacetamide To a solution of 0.181 g (0.51 mmol) of the product of Example 67 dissolved in 2.5 mL of anhydrous DMF was added 0.248 g (1.53 mmol) of 1,1'-carbonyldiimidazole and the reaction mixture was magnetically stirred and heated at 80° C. under a nitrogen atmosphere in an oil bath. After 20 minutes the reaction mixture was cooled to room temperature and 0.152 g (0.77 mmol) of 4-iso-propylbenzenesulfonamide and 381 μL (2.55 mmol) was added. The reaction mixture was heated at 800° C. for an additional 10 minutes then cooled again to room temperature and partitioned between EtOAc and 10% aqueous citric acid. The organic layer was separated, washed with saturated aqueous $NaHCO_3$, saturated aqueous NaCl, dried ($MgSO_4$), filtered and evaporated. The residue was purified on a silica gel flash chromatography column eluted with $CHCl_3$—MeOH—$NH_4OH$ (80:15:1); evaporation of the purified fractions and drying in vacuo afforded 0.128 g (47%) of the title compound as an amorphous solid.

$^1$H-NMR (400 MHz, $CD_3OD$, ppm): δ0.88 (t, J=7.60 Hz, 3H), 1.21 (d, J=6.80 Hz, 3H), 1.22 (d, J=6.80 Hz, 3H), 1.55–1.65 (m, 2H), 2.51 (s, 3H), 2.54–2.64 (m, 1H), 2.67–2.75 (m, 1H), 2.92 (sept, J=6.80 Hz, 1H), 5.43 (s, 1H), 5.94 (s, 2H), 6.75 (d, J=8.80 Hz, 1H), 6.77 (d, J=8.40 Hz, 1H), 7.01–7.03 (m, 2H), 7.23 (d, J=8.40 Hz, 2H), 7.66 (dd, J=2.40, 8.80 Hz, 1H), 7.67 (d, J=8.40 Hz, 2H), 7.73 (d, J=2.40 Hz, 1H).

FAB-MS m/e=538 (M+1).

EXAMPLE 69

α-(2-n-propylphenoxy)-3,4-methylenedioxyphenylacetic acid

FAB-MS for $C_{18}H_{18}O_5$: m/e=337 (M+Na$^+$).

EXAMPLE 70

N-(4-iso-propylbenzenesulfonyl)-α-(2-n-propylphenoxy)-3,4-methylenedioxyphenylacetamide FAB-MS for $C_{27}H_{29}NSO_6$: m/e=534 (M+K$^+$).

EXAMPLE 71

α-(3-methoxyphenoxy)-3,4-methylenedioxyphenylacetic acid

EI-MS for $C_{16}H_{14}O_6$: m/e=302 (M$^+$).

EXAMPLE 72

α-(2-(2-hydroxyethyl)phenoxy)-3,4-methylenedioxyphenylacetic acid

FAB-MS for $C_{17}H_{16}O_6$: m/e=317 (M+1).

EXAMPLE 73

α-(2-(2-carbomethoxyethyl)phenoxy)-3,4-methylenedioxyphenylacetic acid

CI-MS for $C_{19}H_{18}O_7$: m/e=359 (M+1).

EXAMPLE 74

α-(4-hydroxymethyl-2-n-propylphenoxy)-3,4-methylenedioxyphenylacetic acid

CI-MS for $C_{19}H_{20}O_6$: m/e=326 (M$^+$—H$_2$O).

EXAMPLE 75

α-(4-(2-hydroxyethyl)-2-n-propylphenoxy)-3,4-methylenedioxyphenylacetic acid

CI-MS for $C_{20}H_{22}O_6$: m/e=359 (M+1).

EXAMPLE 76

N-(4-iso-propylbenzenesulfonyl)-α-(2-(2-carbomethoxyethyl)phenoxy)-3,4-methylenedioxyphenylacetamide ESI-MS for $C_{28}H_{29}NSO_8$: m/e=540 (M+1).

EXAMPLE 77

N-(4-iso-propylbenzenesulfonyl)-α-(2-(2-carboxyethyl)phenoxy)-3,4-methylenedioxyphenylacetamide CI-MS for $C_{27}H_{27}NSO_8$: m/e=526 (M+1).

EXAMPLE 78

α-(2-(2-carboxyethyl)phenoxy)-3,4-methylenedioxyphenylacetic acid

CI-MS for $C_{18}H_{16}O_7$: m/e=345 (M+1).

EXAMPLE 79

N-(4-iso-propylbenzenesulfonyl)-2-(4-carbomethoxy-2-n-propylphenoxy)-2-(5-methoxy-3,4-methylenedioxyphenyl)acetamide Step A: Ethyl 2-(4-carbomethoxy-2-n-propylphenoxy)-2-(5-methoxy-3,4-methylenediolxyphenyl)acetate To a mixutre of methyl 4-hydroxy-3-n-propylbenzoate (3.0 g, 15.46 mmol) and Cs$_2$CO$_3$ (5.1 g, 16 mmol) in dry dimethylformamide (50 mL) was added ethyl 2-bromo-2-(5-methoxy-3,4-methylenedioxy)phenylacetate (4.3 g, 15.56 mmol), and the resulting mixture was stirred at room temperature for 6 h. At the end of this period, the reaction mixture was diluted with ice water (300 mL) and extracted with ethyl acetate (3×60 mL). The combined organic phase was washed with water and brine, and then dried over anhydrous MgSO$_4$, filtered and solvent removed to give the crude product. Purification of the crude product by silica-gel flash column chromatography using ethyl acetate-hexane (1:9) afforded the titled product as an oil (5.1 g). $^1$H NMR (200 MHz, CDCl$_3$, ppm) δ7.82 (m, 2H); 6.75 (m, 3H); 6.61 (d, 1H, J=1.5 Hz); 5.93 (s, 2H); 5.54 (s, 1H); 4.15 (m, 2H); 3.84 (s, 3H); 3.83 (s, 3H); 2.68 (m, 2H); 1.69 (m, 2H); 1.20 (t, 3H, J=7.4 Hz); 0.90 (t, 3H, J=7.4 Hz).

Step B: 2-(4-carbomethoxy-2-n-propylphenoxy)-2-(5-methoxy-3,4-methylenedioxyphenyl)acetic acid To a solution of the product of Step A (4.3 g, 12 mmol) in methanol (25 mL) was added aqueous 2N NaOH (10 mL) and the reaction mixture was stirred at room temperature. The rapid progress of mono-deesterification was monitored by TLC analysis using CHCl$_3$—MeOH—NH$_4$OH:(80:15:1). After 15 min, the reaction mixture was cooled to 0° C. and neutralized with aqueous 2N HCl. Methanol was removed in vacuo and the resulting mixture was acidified with aqueous 2N HCl. The oily product which precipitated was extracted into methylene chloride (3×40 mL) and the combined organic phase was washed with water, brine and then dried over MgSO$_4$. Removal of the solvent in vacuo afforded the crude product which was then purified by flash-chromatography on silica gel using CHCl$_3$—MeOH—NH$_4$OH:(80:10:1) to give desired product as the ammonium salt. The salt was treated with aqueous 1N HCl (20 mL) to provide the titled compound as a white solid (3.4 g).
$^1$H NMR (200 MHz, CD$_3$OD, ppm) δ7.78 (m, 2H), 6.77 (m, 3H), 6.61 (d, 1H, J=1.5 Hz), 5.93 (s, 2H), 5.54 (s, 1H), 3.84 (s, 3H), 3.83 (s, 3H), 2.68 (m, 2H), 1.69 (m, 2H), 0.90 (t, 3H, J=7.4 Hz).

Step C: N-(4-iso-Propylbenzenesulfonyl)-2-(4-carbomethoxy-2-n-propylphenoxy)-2-(5-methoxy-3,4-methylenedioxyphenyl)acetamide To the product of Step B (0.12 g, 0.30 mmol) in dry THF (1.5 mL) was added 1,1'-carbonyldiimidazole (0.1 g, 0.61 mmol) and the reaction stirred at 50° C. for 3 hr. To this solution was added a solution of 4-iso-propylbenezenesulfonamide (0.17 g, 0.9 mmol) and DBU (0.14 mL, 0.94 mmol) in dry THF (1.5 mL), and the reaction continued at 50° C. for 4 hr. The reaction was diluted with ice water and acidified with aqueous 1N HCl. The precipitated material was taken up in EtOAc and the organic phase was washed with water, brine, and then dried over MgSO$_4$, filtered and the solvent removed. The product was purified by flash-chromatography on silica-gel using CHCl$_3$:MeOH:NH$_4$OH (80:10:1) as the eluting solvent to yield the titled product as the ammonium salt. Acidification of the ammonium salt afforded the titled product as a white solid (0.14 g).

¹H NMR (400 MHz, CD₃OD, ppm): δ7.78 (d, 2H, J=8.4 Hz), 7.76 (d, 1H, J=2.3 Hz), 7.62 (dd, 1H, J=8.6, 2.2 Hz), 7.37 (d, 2H, J=8.4 Hz), 6.70 (d, 1H, J=1.4 Hz), 6.61 (d, 1H, J=1.5 Hz), 5.97 (s, 2H), 5.49 (s, 1H), 3.84 (s, 3H), 3.83 (s, 3H), 2.98 (sept, 1H, J=6.9 Hz), 2.65 (m, 2H), 1.59 (m, 2H), 1.25 (dd, 6H, J=7.0, 2.5 Hz), 0.90 (t, 3H, J=7.4 Hz).

C₃₀H₃₂NO₉N: Calc: C 59.50 H 5.33 N 2.31. Found: C 59.60 H 5.34 N 2.59

EXAMPLE 80

N-(4-iso-propylbenzenesulfonyl)-2-(4-carboxy-2-propylphenoxy)-2-(5-methoxy-3,4-methylenedioxyphenyl)acetamide To the product of Example 79 (0.6 g, 1.02 mmol) in MeOH (15 mL) was added aqueous 2N NaOH (5 mL) and the reaction was stirred at 60° C. for 3 h. When the reaction was complete the MeOH was removed in vacuo and the aqueous phase was acidified with 2N HCl. The product precipitated was extracted into methylene chloride (3×50 mL) and the combined organic phase was washed with brine then dried over MgSO₄, filtered and the solvent removed. The residue upon trituration with ether provided the titled product as a white solid (0.45 g).

¹H NMR (400 MHz, DMSO-d₆, ppm): δ12.67 (br, 1H), 12.63 (br, 1H), 7.70 (d, 2H, J=8.4 Hz), 7.66 (d, 1H, J=2.1 Hz), 7.58 (dd, 1H, J=8.5, 2.2 Hz), 7.40 (d, 2H, J=8.4 Hz), 6.78 (d, 1H, J=1.2 Hz), 6.66 (d, 1H, J=1.2 Hz), 6.51 (d, 1H, J=8.5 Hz), 6.02 (d, 2H, J=3.1 Hz), 5.69 (s, 1H), 3.79 (s, 3H), 2.93 (sept, 1H, J=6.9 Hz), 2.56 (m, 2H), 1.53 (m, 2H), 1.17 (d, 6H, J=6.9 Hz), 0.83 (t, 3H, J=7.4 Hz).

FAB mass spectrum: m/e 570 (M+1). C₂₉H₃₁NO₉S: Calc: C 61.15 H 5.49 N 2.46 Found: C 60.86 H 5.64 N 2.71.

EXAMPLE 81

N-(4-iso-propylbenzenesulfonyl)-2-(4-(N-(4-iso-propylbenzenesulfonyl)carboxamido)-2-propyl-phenoxy)-2-(5-methoxy-3,4-methylene-dioxyphenyl)acetamide The titled compound was prepared from N-(4-iso-propylbenzenesulfonyl)-2-(4-carboxy-2-propylphenoxy)-5-methoxy-3,4-methylenedioxyphenyl)acetamide (Example 80) using a procedure similar to that described in Step C of Example 79.

FAB mass spectrum :m/e 751 (M+1).

C₃₈H₄₂N₂O₁₀S₂·0.5 H₂O: Calc.: C 60.06; H 5.70; N 3.69. Found: C 60.15; H 5.73; N 3.58.

EXAMPLE 82

N-(4-iso-propylbenzenesulfonyl)-2-(4-carboxamido-2-propylphenoxy)-2-(5-methoxy-3,4-methylenedioxyphenyl)acetamide To N-(4-iso-propylbenzenesulfonyl)-2-(4-carboxy-2-propylphenoxy)-2-(5-methoxy-3,4-methylenedioxyphenyl)acetamide (Example 80) (0.12 g, 0.21 mmol) in dry THF (1.5 mL) was added 1,1'-carbonyldiimidazole (0.1 g, 0.61 mmol) and the mixture was stirred at 50° C. for 2h. The reaction was cooled to room temperature and was saturated with dry NH₃. The reaction mixture was stirred at room temperature for 1 h and then acidified. The crude product isolated was purified by silica-gel flash column chromatography using CHCl₃—MeOH—NH₄OH: (40:10:1) to give the product as the ammonium salt. Acidification provided the desired titled product as a white solid (0.06 g).

¹H NMR (300 MHz, DMSO-d₆, ppm): δ7.76 (br, 1H), 7.68 (d, 2H, J=8.4 Hz), 7.64 (d, 1H, J=2.1 Hz), 7.55 (dd, 1H, J=8.6, 2.3 Hz), 7.40 (d, 2H, J=8.4 Hz), 7.16 (br, 1H), 6.76 (s, 1H), 6.65 (d, 1H, J=1.2 Hz), 6.53 (d, 1H, J=8.7 Hz), 6.01 (d, 2H, J=2.9 Hz), 5.67 (s, 1H), 3.78 (s, 3H), 2.93 (sept, 1H, J=6.8 Hz), 2.55 (m, 2H), 1.54 (m, 2H), 1.17 (d, 6H, J=6.9 Hz), 0.84 (t, 3H, J=7.3 Hz).

FAB mass spectrum: m/e 569 (M+1).

EXAMPLE 83

N-(4-iso-propylbenzenesulfonyl)-2-(4-(N-methyl)carboxamido-2-propylphenoxy)-2-(5-methoxy-3,4-methylenedioxyphenyl)acetamide The titled compound was prepared using procedures similar to those described in Example 82.

¹H NMR (300 MHz, DMSO-d₆, ppm): δ8.21 (q, 1H, J=4.7 Hz), 7.68 (d, 2H, J=8.4 Hz), 7.59 (d, 1H, J=1.9 Hz), 7.49 (dd, 1H, J=8.6, 2.1 Hz), 7.40 (d, 2H, J=8.4 Hz), 6.77 (s, 1H), 6.65 (s, 1H), 6.53 (d, 1H, J=8.7 Hz), 6.01 (d, 2H, J=2.9 Hz), 5.67 (s, 1H), 3.78 (s, 3H), 2.93 (sept, 1H, J=6.8 Hz), 2.73 (d, 3H, J=4.4 Hz), 2.56 (m, 2H), 1.54 (m, 2H), 1.16 (d, 6H, J=6.9 Hz), 0.84 (t, 3H, 7.3 Hz).

C₃₀H₃₄N₂O₈S: Calc: C 61.84; H 5.88; N 4.81. Found: C 61.84; H 6.03; N 4.59.

EXAMPLE 84

N-(4-iso-propylbenzenesulfonyl)-2-(4-(N-2-hydroxyethylcarboxamido)-2-propylphenoxy)-2-(5-methoxy-3,4-methylenedioxyphenyl)acetamide The titled compound was prepared using procedures similar to those described in Example 82.

¹H NMR (400 MHz, CD₃OD, ppm): δ7.77 (d, 2H, J=8.4 Hz), 7.64 (d, 1H, J=2.3 Hz), 7.51 (dd, 1H, J=8.5, 2.4 Hz), 7.36 (d, 2H, J=8.5 Hz), 6.68 (d, 1H, J=1.4 Hz), 6.60 (m, 2H), 5.96 (s, 2H), 5.48 (s, 1H), 3.82 (s, 3H), 3.68 (t, 2H, J=5.9 Hz), 3.46 (t, 2H, J=5.9 Hz), 2.97 (sept, 1H, J=6.9 Hz), 2.66 (m, 2H), 1.62 (m, 2H), 1.25 (dd, 6H, J=6.9, 1.2 Hz), 0.90 (t, 3H, J=7.4 Hz).

C₃₁H₃₆N₂O₉S: Calc: C 60.77; H 5.92; N 4.57. Found: C 60.49; H 6.04; N 4.45

EXAMPLE 85

N-(4-iso-propylbenzenesulfonyl)-2-(4-(N-morpholinylcarboxamido)-2-propylphenoxy)-2-(5-methoxy-3,4-methylenedioxyphenyl)acetamide The titled compound was prepared using procedures similar to those described in Example 82.

¹H NMR (400 MHz, CD₃OD, ppm): δ7.77 (d, 2H, J=8.5 Hz), 7.37 (d, 2H, J=8.4 Hz), 7.22 (d, 1H, J=2.1 Hz), 7.09 (dd, 1H, J=8.4, 2.2 Hz), 6.66 (d, 1H, J=1.5 Hz), 6.62 (d, 1H, J=8.5 Hz), 6.57 (d, 1H, J=1.5 Hz), 5.95 (s, 2H), 5.46 (s, 1H), 3.81 (s, 3H), 3.65 (m, 8H), 2.98 (m, 1H), 2.66 (m, 2H), 1.60 (m, 2H), 1.26 (d, 6H, J=7.1 Hz), 0.90 (t, 3H, J =7.4 Hz).

C₃₃H₃₈N₂O₉S: Calc: C 62.05; H 6.00; N 4.39. Found: C 61.96; H 5.98; N 4.55.

EXAMPLE 86

N-(4-iso-propylbenzenesulfonyl)-2-(4-(N-3-methylbutylcarboxamido)-2-propylphenoxy)-2-(5-methoxy-3,4-methylenedioxyphenyl)acetamide The titled compound was prepared using procedures similar to those described in Example 82.
$^1$H NMR (400 MHz, CD$_3$OD, ppm): δ7.77 (d, 2H, J=8.5 Hz), 7.60 (d, 1H, J=2.3 Hz), 7.47 (dd, 1H, J=2.3, 8.5 Hz), 7.36 (d, 2H, J=8.5 Hz), 6.68 (d, 1H, J=1.5 Hz), 6.59 (d, 1H, J=1.4 Hz), 6.58 (d, 1H, J=8.6 Hz), 5.96 (s, 2H), 5.48 (s, 1H), 3.82 (s, 3H), 3.36 (t, 2H, J=7.5 Hz), 2.97 (m, 1H), 2.66 (m, 2H), 1.62 (m, 3H), 1.49 (q, 2H, J=7.2 Hz), 1.25 (dd, 2H, J=1.2, 6.9 Hz), 0.95 (d, 6H, J=6.6 Hz), 0.90 (t, 3H, J=7.4 Hz).
$C_{34}H_{42}N_2O_8S$: Calc: C 63.93; H 6.63; N 4.39. Found: C 63.81; H 6.73; N 4.44.

EXAMPLE 87

N-(4-iso-propylbenzenesulfonyl)-2-(4-(N-carboxymethylcarboxamido)-2-propylphenoxy)-2-(5-methoxy-3,4-methylenedioxyphenyl)acetamide Step A: N-(4-iso-propylbenzenesulfonyl)-2-(4-(N-t-butoxycarbonylmethylcarboxamido)-2-propylphenoxy)-2-(5-methoxy-3,4-methylenedioxyphenyl)acetamide The titled compound was prepared using procedures similar to those described in Example 82, where glycine-t-butyl ester was the amine starting material.
$^1$H NMR (300 MHz, CDCl$_3$ ppm): δ7.70 (d, 2H, J=8.2 Hz), 7.66 (d, 1H, J=1.3 Hz), 7.56 (m, 1H), 7.41 (d, 2H, J=8.2 Hz), 6.79 (s, 1H), 6.67 (s, 1H), 6.59 (d, 1H, J=8.5 Hz), 6.03 (s, 2H), 5.71 (s, 1H), 3.88 (d, 2H, J=5.5 Hz), 3.80 (s, 3H), 2.95 (sept, 1H, J=6.9 Hz), 2.78 (m, 2H), 1.56 (m, 2H), 1.32 (s, 9H), 1.17 (d, 6H, J=6.8 Hz), 0.86 (t, 3H, J=7.3 Hz).

Step B: N-(4-iso-propylbenzenesulfonyl)-2-(4-(N-carboxymethylcarboxamido)-2-propylphenoxy)-2-(5-methoxy-3,4-methylenedioxyphenyl)acetamide A solution of the product of Step A (0.069 g, 0.1 mmol) in anhydrous trifluoroacetic acid (1.5 mL) was stirred at room tempature for 4 h. The excess reagent was evaporated in vacuo and the resulting residue was triturated with dry ether to give the titled product as white solid (0.6 g).
$^1$H NMR (300 MHz, DMSO-d$_6$, ppm): δ7.70 (d, 2H, J=8.2 Hz), 7.66 (d, 1H, J=1.3 Hz), 7.56 (m, 1H), 7.41 (d, 2H, J=8.2 Hz), 6.79 (s, 1H), 6.67 (s, 1H), 6.59 (d, 1H, J=8.5 Hz), 6.03 (s, 2H), 5.71 (s, 1H), 3.88 (d, 2H, J=5.5 Hz), 3.80 (s, 3H), 2.95 (sept, 1H, J=6.9 Hz), 2.58 (m, 2H), 1.56 (m, 2H), 1.17 (d, 6H, J=6.8 Hz), 0.86 (t, 3H, J=7.3 Hz).
$C_{31}H_{34}N_2O_{10}S$0.4 H$_2$O: Calc: C 58.74; H 5.53; N 4.42. Found: C 58.79; H 5.83; N 4.37.

EXAMPLE 88

N-(4-iso-propylbenzenesulfonyl)-2-(4-(N-(L-Ala-OEt)carboxamido)-2-propylphenoxy)-2-(5-methoxy-3,4-methylenedioxyphenyl)acetamide The titled compound was prepared using procedures similar to those described in Example 82, where L-alanine ethyl ester was the amine starting material.
$^1$H NMR (400 MHz, DMSO-d$_6$, ppm): δ8.55 (d, 1H, J=6.1 Hz), 7.69 (m, 3H), 7.57 (q, 1H, J=9.2 Hz), 7.40 (m, 2H), 6.78 (d, 1H, J=3.8 Hz), 6.63 (s, 1H), 6.55 (m, 1H), 6.02 (s, 2H), 5.70 (s, 1H), 4.39 (m, 1H), 4.08 (q, 2H, J=6.8 Hz), 3.79 (d, 3H, J=2.9 Hz), 2.93 (sept, 1H, J=6.9 Hz), 2.57 (m, 2H), 1.55 (m, 2H), 1.37 (d, 3H, J=5.5 Hz), 1.16 (m, 9H), 0.85 (t, 3H, J=7.5 Hz).

EXAMPLE 89

N-(4-iso-propylbenzenesulfonyl)-2-(4-(N-2-ethoxycarbonylethylcarboxamido)-2-propylphenoxy)-2-(5-methoxy-3,4-methylenedioxyphenyl)acetamide The titled compound was prepared using procedures similar to those described in Example 82, where β-alanine ethyl ester was the amine starting material.
$^1$H NMR (400 MHz, DMSO-d$_6$, ppm): δ8.34 (t, 1H, J=5.4 Hz), 7.68 (d, 2H, J=8.3 Hz), 7.58 (d, 1H, J=2.2 Hz), 7.49 (dd, 1H, J=8.6, 2.3 Hz), 7.39 (d, 2H, J=8.4 Hz), 6.77 (d, 1H, J=1.4 Hz), 6.65 (d, 1H, J=1.3 Hz), 6.53 (d, 1H, J=8.8 Hz), 6.01 (s, 2H), 5.67 (s, 1H), 4.05 (q, H, J=7.1 Hz), 3.78 (s, 3H), 3.44 (m, 2H), 2.92 (sept, 1H, J=6.9 Hz), 2.53 (m, 2H), 1.54 (m, 2H), 1.16 (m, 9H), 0.84 (t, 3H, J=7.4 Hz).

EXAMPLE 90

N-(4-iso-propylbenzenesulfonyl)-2-(4-(N-(L-Ala)carboxamido)-2-propylphenoxy)-2-(5-methoxy-3,4-methylenedioxyphenyl)acetamide The product from Example 88 was saponified to give the titled product.
$^1$H NMR (400 MHz, DMSO-d$_6$, ppm): δ12.64 (br, 1H), 12.51 (br, 1H), 8.44 (dd, 1H, J=7.1, 2.7 Hz), 7.69 (m, 3H), 7.56 (m, 1H), 7.40 (m, 2H), 6.77 (d, 1H, J=1.6 Hz), 6.66 (d, 1H, J=1.7 Hz), 6.55 (m, 1H), 6.01 (d, 2H, J=2.6 Hz), 5.69 (s, 1H), 4.37 (pn, 1H, J=7.4 Hz), 3.79 (d, 3H, J=1.9 Hz), 2.93 (sept, 1H, J=6.9 Hz), 2.57 (m, 2H), 1.54 (m, 2H), 1.36 (dd, 3H, J=7.3, 2.7 Hz), 1.16 (d, 6H, J=6.8 Hz), 0.85 (t, H, J=7.2 Hz).

EXAMPLE 91

N-(4-iso-propylbenzenesulfonyl)-2-(4-(N-2-carboxyethylcarboxamido)-2-propylphenoxy)-2-(5-methoxy-3,4-methylenedioxyphenyl)acetamide The product from Example 89 was saponified to give the titled product.
$^1$H NMR (400 MHz, DMSO-d$_6$, ppm): δ12.64 (br, 1H), 12.21 (br, H), 8.32 (t, 1H, J=5.5 Hz), 7.68 (d, 2H, J=8.4 Hz), 7.59 (d, 1H, J=1.9 Hz), 7.49 (dd, 1H, J=8.5, 2.1 Hz), 7.40 (d, 2H, J=8.4 Hz), 6.77 (s, 1H), 6.65 (d, 1H, J=1.2 Hz), 6.01 (d, 2H, J=2.9 Hz), 5.68 (s, 1H), 3.79 (s, 3H), 3.39 (m, 2H), 2.93 (sept, 1H, J=6.8 Hz), 2.55 (m, 2H), 1.54 (m, 2H), 1.16 (d, 6H, J=6.9 Hz), 0.84 (t, 3H, J=7.3 Hz).
$C_{32}H_{36}N_2O_{10}S$: Calc: C 59.99; H 5.66; N 4.37. Found: C 59.72; H 5.77; N 4.49.

EXAMPLE 92

N-(4-iso-propylbenzenesulfonyl)-2-(4-(N-3-hydroxypropyl-carboxamido)-2-propylphenoxy)-2-(5-methoxy-3,4-methylenedioxy-phenyl)acetamide The titled compound was prepared using procedures similar to those described in Example 82, where 3-aminopropanol was the amine starting material.
$^1$H NMR (400 MHz, CD$_3$OD, ppm): δ8.33 (m, 1H), 7.77 (d, 2H, J=8.5 Hz), 7.60 (d, 1H, J=2.3 Hz), 7.48 (dd, 1H, J=8.5, 2.3 Hz), 7.36 (d, 2H, J=8.4 Hz), 6.68 (d, 1H, J=1.5 Hz), 6.60 (d, 1H, J=1.4 Hz), 6.59 (d, 1H, J=8.6 Hz), 5.96 (s, 2H), 5.48

(s, 1H), 3.82 (s, 3H), 3.63 (t, 2H, J=6.3 Hz), 3.43 (t, 2H, J=5.8 Hz), 2.97 (sept, 1H, J=7.0 Hz), 2.66 (m, 2H), 1.80 (pn, 2H, J=6.7 Hz), 1.61 (m, 2H), 1.25 (dd, 6H, J=6.9, 1.3 Hz), 0.90 (t, 3H, J=7.4 Hz).

$C_{32}H_{38}N_2O_9S$: Calc: C 61.33; H 6.11; N 4.47. Found: C 61.07; H 6.09; N 4.48.

EXAMPLE 93

N-(4-iso-propylbenzenesulfonyl)-2-(4-(N-tetrazol-5-ylcarboxamido)-2-propylphenoxy)-2-(5-methoxy-3,4-methylenedioxyphenyl)acetamide The titled compound was prepared using procedures similar to those described in Example 82, where 5-aminotetrazole was the amine starting material.
FAB-MS m/e=640 (M+1)

EXAMPLE 94

N-(4-iso-propylbenzenesulfonyl)-2-(4-(N-3-(morpholin-4-yl)propylcarboxamido)-2-propyl-phenoxy)-2-(5-methoxy-3,4-methylenedioxyphenyl)acetamide The titled compound was prepared using procedures similar to those described in Example 82, where 3-(N-morpholinyl)-aminopropane was the amine starting material.
$^1$H NMR (400 MHz, CD$_3$OD, ppm) δ7.65 (d, 2H, J=8.3 Hz), 7.65 (s, 1H), 7.58 (dd, 1H, J=2.4, 8.6 Hz), 7.24 (d, 2H, J=8.4 Hz), 6.81 (d, 1H, J=8.6 Hz), 6.78 (d, 1H, J=1.4 Hz), 6.69 (d, 1H, J=1.4 Hz), 5.94 (s, 2H), 5.40 (s, 1H), 3.82 (s, 7H), 3.54 (m, 2H), 3.12 (m, 6 H), 2.92 (sept, 1H, J=6.9 Hz), 2.66 (m, 2H), 1.62 (m, 2H), 1.22 (d, 6H, J=6.9 Hz), 0.90 (t, 3H, J=7.4 Hz).

$C_{35}H_{43}N_3O_9 \cdot 0.75 H_2O$: Calc.: C 60.46; H 6.45; N 6.04. Found: C 60.39; H 6.43; N 5.93.

EXAMPLE 95

N-(4-iso-propylbenzenesulfonyl)-2-(4-(N-(D-Ala-OMe)carboxamido)-2-propylphenoxy)-2-(5-methoxy-3,4-methylenedioxyphenyl)acetamide The titled compound was prepared using procedures similar to those described in Example 82, where D-alanine methyl ester was the amine starting material.
$^1$H NMR (400 MHz, CD$_3$OD, ppm): δ8.54 (d, 1H, J=6.8 Hz); 7.77 (d, 2H, J=8.3 Hz), 7.66 (s, 1H), 7.53 (m, 1H), 7.36 (d, 2H, J=8.3 Hz), 6.68 (s, 1H), 6.60 (m, 2H), 5.96 (s, 2H), 5.49 (s, 1H), 4.57 (m, 1H), 3.82 (s, 3H), 3.73 (s, 3H), 2.97 (sept, 1H, J=6.8 Hz), 2.67 (m, 2H), 1.62 (m, 2H), 1.47 (d, 3H, J=7.4 Hz), 1.24 (d, 6H, J=7.0 Hz), 0.91 (t, 3H, J=7.4 Hz).

EXAMPLE 96

N-(4-iso-propylbenzenesulfonyl)-2-(4-(N-(D-Ala)carboxamido)-2-propylphenoxy)-2-(5-methoxy-3,4-methylenedioxyphenyl)acetamide The product from Example 95 was saponified to give the titled product.
$^1$H NMR (400 MHz, DMSO-d$_6$, ppm) δ12.64 (br, 1H), 12.48 (br, 1H), 8.44 (dd, 1H, J=7.3, 2.6 Hz), 7.68 (m, 3H), 7.56 (m, 1H), 7.40 (dd, 2H, J=4.0, 8.4 Hz), 6.77 (d, 1H, J=2.3 Hz), 6.66 (m, 1H), 6.55 (dd, 2H, J=21.0, 8.8 Hz), 6.01 (d, 2H, J=3.6 Hz), 5.70 (d, 1H, J=3.8 Hz), 4.37 (pn, 1H, J=7.3 Hz), 3.78 (d, 3H, J=1.8 Hz), 2.93 (sept, 1H, J=7.0 Hz), 2.57 (m, 2H), 1.55 (m, 2H), 1.36 (dd, 3H, J=7.3, 2.7 Hz), 1.16 (d, 6H, J=6.9 Hz), 0.85 (t, 3H, J=7.3 Hz).

EXAMPLE 97

N-(4-iso-propylbenzenesulfonyl)-2-(4-(N-(3-carboxymethylpropyl)-carboxamido)-2-propyl-phenoxy)-2-(5-methoxy-3,4-methylenedioxyphenyl)acetamide The titled compound was prepared using procedures similar to those described in Example 82, where methyl T-aminobutyrate was the amine starting material.
$^1$H NMR (400 MHz, CD$_3$OD, ppm): δ7.77 (d, 2H, J=8.5 Hz), 7.61 (d, H, J=2.2 Hz), 7.48 (dd, 1H, J=8.5, 2.3 Hz), 7.36 (d, 2H, J=8.5 Hz), 6.68 (s, 1H), 6.59 (s, 1H), 6.59 (d, 1H, J=8.3 Hz), 5.95 (s, 2H), 5.48 (s, 1H), 4.09 (q, 2H, J=7.1 Hz), 3.82 (s, 3H), 3.37 (m, 2H), 2.97 (sept, 1H, J=6.9 Hz), 2.66 (m, 2H), 2.38 (t, 2H, J=7.4 Hz), 1.89 (pn, 2H, J =7.1 Hz), 1.61 (m, 2H), 1.23 (d, 6H, J=6.9 Hz), 0.90 (t, 3H, J=7.3 Hz).

EXAMPLE 98

N-(4-iso-propylbenzenesulfonyl)-2-(4-(N-(3-carboxypropyl)-carboxamido)-2-n-propylphenoxy)-2-(5-methoxy-3,4-methylenedioxy-phenyl)acetamide The product from Example 97 was saponified to give the titled product.
$^1$H NMR (400 MHz, DMSO-d$_6$, ppm): δ12.63 (br, 1H), 12.06 (br, 1H), 8.27 (t, 1H, J=5.5 Hz), 7.68 (d, 2H, J=8.4 Hz), 7.60 (d, 1H, J=2.2 Hz), 7.50 (dd, 1H, J=8.5, 2.2 Hz), 7.40 (d, 2H, J=8.4 Hz), 6.77 (d, 1H, J=1.2 Hz), 6.66 (d, 1H, J=1.3 Hz), 6.52 (d, 1H, J=8.8 Hz), 6.01 (d, 2H, J=2.9 Hz), 5.68 (s, 1H), 3.79 (s, 3H), 3.22 (q, 2H, J=6.5 Hz), 2.92 (sept, 6.8 Hz), 2.54 (m, 2H), 2.25 (t, 2H, J=7.4 Hz), 1.71 (pn, 7.1 Hz), 1.54 (m, 2H), 1.16 (d, 6H, J=6.8 Hz), 0.84 (t, 3H, J=7.3 Hz).

$C_{33}H_{38}N_2O_{10}S$: Calc: C 60.54; H 5.85; N 4.28. Found: C 60.26; H 6.17; N 4.02.

EXAMPLE 99

N-(4-iso-propylbenzenesulfonyl)-2-(4-(N-iso-propyl-carbamoyl)amino-2-n-propylphenoxy)-2-(3,4-methylenedioxyphenyl)acetamide Step A: 4-Nitro-2-(propen-3-yl)phenol
A mixture of 4-nitrophenoxyallyl ether (4.0 g, 22.35 mmol) and 1,2-dichlorobenzene (15 mL) was heated to reflux for 6 h. The reaction mixture was cooled and purified by silica-gel flash column chromatography using hexanes and EtOAc-hexanes (1:6) as eluents, respectively. The pure product was obtained as an yellow oil (2.6 g).
$^1$H NMR (200 MHz, CDCl$_3$, ppm): δ 8.05 (d, 2H), 6.92 (d, 1H), 6.01 (m, 1H), 5.18 (m, 2H), 3.42 (d, 2H, J=7.3 Hz).
Step B: Methyl 2-(4-nitro-2-(propen-3-yl)phenoxy)-2-(3,4-methylenedioxyphenyl)acetate
The titled compound was prepared using the procedures similar to that described in Step A of Example 79. Methyl 2-bromo-2-(3,4-methylenedioxyphenyl)acetate was used as the alkylating agent. Purification of the crude product was accomplished by silica-gel flash column chromatography using ethyl acetate-hexane (1:5).
$^1$H NMR (200 MHz, CDCl$_3$, ppm): δ 8.05 (m, 2H), 7.02 (m, 2H), 6.78 (m, 2H), 5.96 (s, 2H), 5.6 (s, 1H), 5.15 (m, 2H), 4.15 (m, 2H), 3.75 (s, 3H), 3.47 (m, 2H).

Step C: 2-(4-(N-iso-propylcarbamoyl)amino-2-n-propylphenoxy)-2-(3,4-methylenedioxyphenyl)acetic acid To a solution of the product of Step B (0.5 g) in methanol (6 mL) was added Pd-C(10%)(0.05g), and the reaction mixture was stirred at room temperature for 6 h under an atmosphere of hydrogen gas. The catalyst was filtered off and the filtrate was concentrated in vacuo to give the desired methyl α-(4-amino-2-n-propylphenoxy)-2-(3,4-methylenedioxyphenyl)acetate (0.5 g) as a solid. This material without further purification was dissolved in dry THF (5 mL) and reacted with N-iso-propylisocyanate (0.1 mL) at room temperature for 12 h. Purification of the crude product by flash chromatography using EtOAc-hexanes (1:2) gave the titled compound as white solid (0.36 g).

$^1$H NMR (300 MHz, CDCl$_3$, ppm): δ 7.1–6.77 (m, 6H), 6.61 (d, 1H, J=1.5 Hz), 5.93 (s, 2H), 5.54 (s, 1H), 3.98 (m, 1H), 3.78 (s, 3H), 3.63 (m, 1H) 2.68 (m, 2H), 1.69 (m, 2H), 1.15 (dd, 6H, J=7.0, 2.5 Hz), 0.90 (t, 3H, J=7.4 Hz).

Step D: N-(4-iso-propylbenzenesulfonyl)-2-(4-(N-iso-propylcarbamoyl)amino-2-n-propylphenoxy)-2-( 3,4-methylenedioxyphenyl)acetamide The titled product was prepared from the product obtained in Step C using procedures similar to those described in Steps B and C of Example 79.

$^1$H NMR (300 MHz, CD$_3$OD, ppm): δ 7.78 (d, 2H, J=8.4 Hz), 7.76 (m, 1H), 7.52 (m, 1H), 7.32 (d, 2H, J=8.4 Hz), 7.07 (d, 1H,J=1.4 Hz), 6.75–6.90 (m, 2H), 6.75 (d, 1H, J=8.2 Hz), 6.42 (d, 1H, J=8.2 Hz), 5.97 (s, 2H), 5.21 (s, 1H), 3.88 (m, 1H), 2.82 (m, 1H), 2.54 (m, 2H), 1.69 (m, 2H), 1.26 (dd, 6H, J=7.0, 2.5 Hz), 1.15 (dd, 6H, J=7.0, 2.5 Hz), 0.90 (t, 3H, J=7.4 Hz). FAB-MS: m/e 596 (M+1).

EXAMPLE 100

α-(2-n-propyl-4-methylaminosulfonylphenoxy)-3,4-methylenedioxyphenylacetic acid

Step A: preparation of 3-allyl-4-hydroxybenzenesulfonamide

To a solution of 5.00 g (28.9 mmol) of 4-hydroxybenzenesulfonamide dissolved in 30 mL of anhydrous DMF was added 10.36 g (31.8 mmol) of cesium carbonate and the reaction mixture was magnetically stirred at room temperature under a nitrogen atmosphere for 10 minutes. Allyl bromide (2.75 mL, 31.8 mmol) was added and the reaction mixture was then stirred for an additional 14 hours. The reaction mixture was then partitioned between EtOAc (60 mL) and 10% aqueous citric acid (200 mL) and extracted. The organic layer was separated, washed with saturated aqueous NaHCO$_3$, saturated aqueous NaCl, dried (MgSO$_4$), filtered, evaporated and dried in vacuo to afford 5.40 g (88%) of a yellow solid. The crude O-allyl ether (5.36, 25.2 mmol) was then dissolved in 10 mL of 1,2-dichlorobenzene in a 50 mL round bottom flask and magnetically stirred at reflux under a nitrogen atmosphere for 15 hours. The reaction mixture was then cooled to room temperature and diluted with methanol. The 1,2-dichlorobenzene was removed by extraction of the methanol layer with hexane, the methanol layer was separated, then evaporated. The residue was then purifed on a silica gel flash chromatography column eluted with 5% MeOH-CH$_2$Cl$_2$. Combination of the purified fractions, evaporation and drying in vacuo afforded 3.04 g (57%) of the title compound.

$^1$H-NMR (400 MHz, CD$_3$OD, ppm): δ 3.38 (d, J=6.40 Hz, 2H), 5.02–5.10 (m, 2H), 5.94–6.04 (m, 1H), 6.84 (d, J=8.40 Hz, 1H), 7.58 (dd, J=2.40, 8.40 Hz, 1H), 7.61 (d, J=2.40 Hz, 1H). CI-MS m/e=213 (M$^+$).

Step B: Preparation of 4-hydroxy-3-n-propylbenzenesulfonamide

A Parr hydrogenation flask was charged with a solution of 3.04 g (14.30 mmol) of the product of Step A dissolved in 25 mL of ethanol and 0.300 g of a 10% palladium on carbon catalyst was added. The flask was mounted in the hydrogenation apparatus, freed of air, pressurized with hydrogen (40 psig) and shaken for 15 minutes. At the end of this period TLC analysis (3% MeOH-CH$_2$Cl$_2$, 2 elutions) indicated that the reaction was complete and the reaction mixture was filtered and evaporated. The product was dried in vacuo to afford 3.06 g (99%) of the title compound. $^1$H-NMR (400 MHz, CD$_3$OD, ppm): δ 0.94 (t, J=7.20 Hz, 3H), 1.58–1.68 (m, 2H), 2.01–2.62 (m, 2H), 6.82 (d, J=8.40 Hz, 1H), 7.55 (dd, J=2.40, 8.40 Hz, 1H), 7.60 (d, J=2.40 Hz, 1H). FAB-MS m/e=216 (M+1).

Step C: Preparation of methyl α-(2-n-propyl-4-aminosulfonylphenoxy)-3,4-methylenedioxyphenylacetate To a solution of 3.06 g (14.23 mmol) of the product of Step B dissolved in 25 mL of anhydrous DMF was added 4.87 g (15.0 mmol) of cesium carbonate and the reaction mixture was magnetically stirred under a nitrogen atmosphere at room temperature for 15 minutes. Methyl α-bromo-3,4-methylenedioxyphenylacetate (4.08 g, 15.0 mmol) was then added and the reaction mixture was stirred for an additional 3 hours. The reaction mixture was then partitioned between EtOAc (80 mL) and 10% aqueous citric acid (300 mL). The organic layer was separated, washed with saturated aqueous NaHCO$_3$, saturated aqueous NaCl, dried (MgSO$_4$), filtered and evaporated. The residue was dried in vacuo to afford 5.90 g (5.79 theoretical) of the title compound which was used in the next step without further purification.

$^1$H-NMR (400 MHz, CD$_3$OD, ppm): δ 0.97 (t, J=7.20 Hz, 3H), 1.64–1.76 (m, 2H), 2.74 (t, J=7.20 Hz, 2H), 3.70 (s, 3H), 5.87 (s, 1H), 5.97 (s, 2H), 6.85 (d, J=8.00 Hz, 1H), 6.93 (d, J=8.40 Hz, 1H), 7.03 (d, J=1.60 Hz, 1H), 7.06 (dd, J=1.60, 8.00 Hz, 1H), 7.65 (dd, J=2.40, 8.40 Hz, 1H), 7.69 (d, J=2.40 Hz, 1H). FAB-MS m/e=408 (M+1).

Step D: Preparation of methyl α-(2-n-propyl-4-methylaminosulfonylphenoxy)-3,4-methylenedioxyphenylacetate To a solution of 2.19 g (5.38 mmol) of the product of Step C dissolved in 20 mL of anhydrous THF was added 2.41 mL (16.1 mmol) of 1,8-diazabicyclo[5.4.0]undec-7-ene and the reaction mixture was magnetically stirred under a nitrogen atmosphere for 25 minutes at room temperature. Iodomethane (1.00 mL; 16.1 mmol) was added and the reaction mixture was stirred an additional 15 hours at room temperature. The reaction mixture was diluted with EtOAc and a precipitate formed which was redissolved by addition of methanol. The mixture was further diluted with warm EtOAc (150 mL total), refridgerated overnight and a solid separated which was removed by filtration. The filtrate was evaporated in vacuo and the residue was purified on a silica gel flash chromatography column eluted with 5% EtOAc-CHCl$_3$. Combination of the purified fractions and evaporation in vacuo afforded 0.164 g of the title compound and a number of impure fractions which were reserved for repurification. $^1$H-NMR (400 MHz, CD$_3$OD, ppm): δ 0.97 (t, J=7.20 Hz, 3H), 1.65–1.77 (m, 2H), 2.48 (s, 3H), 2.74 (t, J=7.20 Hz, 2H), 3.71 (s, 3H), 5.87 (s, 1H), 5.98 (s, 2H), 6.85 (d, J=8.00 Hz, 1H), 6.96 (d, J=8.80 Hz, 1H), 7.04 (d, J=1.60 Hz, 1H), 7.07 (dd, J=1.60, 8.00 Hz, 1H), 7.58–7.61 (m, 2H). ESI-MS m/e=421 (M$^+$).

Step E: Preparation of α-(2-n-propyl-4-methylaminosulfonylphenoxy)-3,4-methylenedioxyphenylacetic acid To a solution of 0.372 g (0.884 mmol) of the product of Step D dissolved in 3.0 mL of methanol was added 212 μL (1.06 mmol) of a 5.0N aqueous sodium hydroxide solution which resulted in a cloudy suspension. The reaction was warmed to assist solution, methanol (1 mL) was added followed by dichloromethane (0.5 mL), however a clear solution was not obtained. Additional 5N sodium hydroxide solution was added (212 μL), and finally 0.5 mL of THF was added which resulted in a clear solution. After stirring an additional 15 hours at room temperature, TLC analysis ($CHCl_3$-MeOH-$NH_4OH$ 80:15:1) indicated complete hydrolysis of the starting material and the reaction was adjusted to pH=7 with 6N HCl. The reaction mixture was then concentrated in vacuo and the residue was purified on a silica gel flash chromatography column eluted with $CHCl_3$-MeOH-HOAc (92:7:1). Combination of the purified fractions and drying in vacuo afforded 0.335 g (93%) of the title compound as an amorphous solid.

$^1$H-NMR (400 MHz, $CD_3OD$, ppm): δ 0.96 (t, J=7.20 Hz, 3H), 1.66–1.78 (m, 2H), 2.48 (s, 3H), 2.73–2.77 (m, 2H), 5.74 (s, 1H), 5.97 (s, 2H), 6.85 (d, J=7.60 Hz, 1H), 6.98 (d, J=9.20 Hz, 1H), 7.07–7.10 (m, 2H), 7.59–7.62 (m, 2H). ESI-MS m/e=407 ($M^+$).

EXAMPLE 101

N-(4-iso-propylbenzenesulfonyl)-α-(2-n-propyl-4-methylaminosulfonylphenoxy)-3,4-methylenedioxyphenylacetamide potassium salt To a solution of 0.298 g (0.73 mmol) of the product of Example 100 dissolved in 4.0 mL of anhydrous THF was added 0.237 g (1.46 mmol) of 1,1'-carbonyldiimidazole and the reaction mixture was magnetically stirred and refluxed for 2 hours under a nitrogen atmosphere. The reaction mixture was then cooled to room temperature, 0.219 g (1.10 mmol) 4-iso-propylbenzenesulfonamide and 164 μL (1.10 mmol) 1,8-diazabicyclo[5.4.0]undec-7-ene were added and the reaction was stirred and heated at reflux for an additional 10 minutes. The reaction mixture was then cooled to room temperature, partitioned between 10% aqueous citric acid and EtOAc and extracted. The organic layer which separated was washed with saturated aqueous NaCl, dried ($MgSO_4$), filtered and evaporated. The residue was redissolved in 1.0 mL of methanol and treated with 2.20 mL (3 eq) of a 1.1M aqueous solution of potassium hydroxide. The mixture was then diluted with 5 mL of water and filtered through a 0.45 micron filter. The filtrate was desalted and purified on a Waters Millipore Delta Prep 3000 liquid chromatograph equipped with an M1000 Prep-Pak module containing a 47×300 mm Delta-Pak C18 15 μm 100A column cartridge. Two solvent resevoirs were employed: solvent system A (95-5 water-acetonitrile), and solvent system B (5-95 water-acetonitrile), and the column effluent was monitored simultaneously at 210 and 280 nm with a Waters model 490 UV-visible detector. The column was preequillibrated with solvent system A and the filtrate was injected. The product was desalted by elution with 0.5 L of solvent system A (50 mL/min) then a gradient elution was begun which had as initial conditions 100% solvent system A-0% solvent system B and reached after 15 minutes 60% solvent system A-40% solvent system B, and the fractions were collected with an ISCO Foxy 200 fraction collector. The purified fractions were combined in round bottom flasks, frozen in a –78° C. dry ice-acetone bath, and lyophilized. Combination of the purified product afforded 0.284 g (62%) of the title compound as a white lyophilized powder.

$^1$H-NMR (400 MHz, $CD_3OD$, ppm): δ 0.89 (t, J=7.60 Hz, 3H), 1.21 (d, J=6.80 Hz, 3H), 1.22 (d, J=6.80 Hz, 3H), 1.57–1.64 (m, 2H), 2.45 (s, 3H), 2.56–2.63 (m, 1H), 2.70–2.76 (m, 1H), 5.37 (s, 1H), 5.93 (d, J=1.20 Hz, 1H), 5.94 (d, J=1.20 Hz, 1H), 6.76 (d, J=8.40 Hz, 1H), 6.85 (d, J=8.80 Hz, 1H), 7.02–7.04 (m, 2H), 7.21 (d, J=8.40 Hz, 2H), 7.47 (dd, J=2.40, 8.80 Hz, 1H), 7.52 (d, J=2.40 Hz, 1H), 7.65 (d, J=8.40 Hz, 2H). ESI-MS m/e=627 (M +1).

EXAMPLE 102

N-(4-iso-propylbenzenesulfonyl)-α-[4-(cyanomethyl)-2-n-propylphenoxy)]-3,4-methylenedioxyphenylacetamide Step A: Preparation of N-(4-iso-propylbenzenesulfonyl)-α-(4-bromomethyl-2-n-propylphenoxy)-3,4-methylenedioxyphenylacetamide To a solution of 0.200 g (0.381 mmol) of the product of Example 65 dissolved in 1.5 mL of diethyl ether was added 0.837 mL (0.837 mmole) of 1.0M phosphorus tribromide in methylene chloride solution under nitrogen at 0° C. The reaction mixture was stirred at 0° C. for 2 hours when TLC analysis (80:15:1 $CHCl_3$-MeOH-$NH_4OH$) indicated that the reaction was nearly complete. The reaction was quenched at 0° C. with water and then partitioned with EtOAc. The aqueous portion was separated and the EtOAc portion was washed with brine (2×10 mL). The EtOAc portion was then dried over $MgSO_4$, filtered, evaporated to a residue, and then used in the next step of the reaction scheme.

Step B: Preparation of N-(4-iso-propylbenzenesulfonyl)-α-(4-cyanomethyl-2-n-propylphenoxy)-3,4-methylenedioxyphenylacetamide To a solution of the crude product of Step A dissolved in 1.5 mL of methyl sulfoxide was added 0.050 g (0.762 mmol) of potassium cyanide at room temperature under nitrogen. The reaction mixture was stirred at room temperature for 1 h when TLC analysis (80:15:1 $CHCl_3$-MeOH-$NH_4OH$) indicated that the reaction was complete. The reaction mixture was diluted with EtOAc and 10% aqueous $NaHSO_4$ solution. The aqueous phase was separated and the EtOAc portion was washed with brine (2×10 mL). The EtOAc portion was then dried over $MgSO_4$, filtered, evaporated to a residue, and purified. Purification was done by reversed phase HPLC (Waters Millipore Delta Prep 4000 with Delta-Pak C18 15 μm 100 A column cartridge) with a solvent system of 30:70 water-acetonitrile and 0.1% TFA buffer. The purified fractions collected were combined in a round bottom flask, frozen in a –78° C. dry ice-acetone bath, and lyophilized. The resulting lyophilized powder afforded 0.071 g (35% 2-step yield).

$^1$H-NMR (400 MHz, $CD_3OD$, ppm): δ0.88 (t, J=7.37 Hz, 3H), 1.25 (d, J=6.92 Hz, 3H), 1.27 (d, J=6.97 Hz, 3H), 1.55 (m,2H), 2.60 (m, 2H), 2.99 (m, 1H), 3.75 (s, 2H), 5.40 (s, 1H), 5.96 (s, 2H), 6.53 (d, J=8.39 Hz, 1H), 6.78 (d, J=8.03 Hz, 1H), 6.86–6.96 (m, 3H), 7.10 (s, 1H), 7.37 (d, J=6.64 Hz, 2H), 7.78 (d, J=8.48 Hz, 2H). MS (ESI): $C_{29}H_{30}N_2O_6S$ 534.63 Found: [535.1, M+1].

EXAMPLE 103

N-(4-iso-propylbenzenesulfonyl)-α-[4-(tetrazol-5-ylmethyl)-2-n-propylphenoxy)]-3,4-methylenedioxyphenylacetamide A solution of 0.120 g (0.224 mmol) of the product of Example 102 and 0.139 g (0.673 mmol) of trimethyltin azide dissolved in 1.5 mL of toluene was heated in a sealed pressure reaction tube and stirred for 5 hours at 120° C. Analytical HPLC analysis (30:70 water-acetonitrile with 0.1% TFA) indicated that the reaction had gone to completion. The reaction mixture was cooled to room temperature and a 2M HCl solution was added. The reaction mixture was partitioned with EtOAc and the aqueous portion was separated. The EtOAc portion was washed with brine (2×10 mL), dried over $MgSO_4$, filtered, evaporated to a residue, and purified. Purification was done by reversed phase HPLC (Waters Millipore Delta Prep 4000 with Delta-Pak C18 15 μm 100 A column cartridge) with a solvent system of 30:70 water-acetonitrile and 0.1% TFA buffer. The purified fractions collected were combined in a round bottom flask, frozen in a −78° C. dry ice-acetone bath, and lyophilized. The resulting lyophilized powder afforded 0.0306 g (24% yield).
$^1$H-NMR (400 MHz, $CD_3OD$, ppm): δ 0.86 (t, J=7.47 Hz, 3H), 1.25 (d, J=6.82 Hz, 6H), 1.54 (m, 2H), 2.58 (m, 2H), 2.96 (m, 1H), 4.19 (s, 2H), 5.38 (s, 1H), 5.96 (s, 2H), 6.51 (d, J=8.30 Hz, 1H), 6.76 (d, J=8.53 Hz, 1H), 6.84–6.89 (m, 3H), 7.04 (s, 1H), 7.35 (d, J=8.30 Hz, 2H), 7.76 (d, J=8.35 Hz, 2H). MS (ESI): $C_{29}H_{31}N_5O_6S$ 577.66 Found: [578.2, M+1].

EXAMPLE 104

N-(4-iso-propylbenzenesulfonyl)-α-[N-(4-carbomethoxyphenylamino)]-3,4-methylenedioxyphenylacetamide Step A: Preparation of ethyl α-[N-(4-carbomethoxyphenylamino)]-3,4-methylenedioxyphenylacetate To a solution of 5.034 g (33.4 mmol) of methyl 4-aminobenzoate dissolved in 50.0 mL of DMF was added 10.526 g (36.7 mmol) of ethyl α-bromo-3,4-methylenedioxyphenylacetate. The reaction mixture was heated to 85° C. and stirred in a sealed pressure reaction tube for 16 hours. TLC analysis (25% EtOAc:Hexanes) indicated that the reaction had gone to completion. The reaction mixture was transferred to a seperatory funnel and partitioned between EtOAc and water. The aqueous portion was separated and the organic portion was washed with brine (2×25 mL), dried over $MgSO_4$, filtered, and evaporated to a residue. Purification was done by flash chromatography eluting with 20% EtOAc:Hexanes. The purified fractions collected were combined and evaporated to afford 7.90 g of the titled product. MS (ESI): $C_{19}H_{19}NO_6$ 357.36 Found: [357.9, M+1].

Step B: Preparation of α-[N-(4-carbomethoxyphenylamino)]-3,4-methylenedioxyphenylacetic acid To a solution of 2.12 g (5.93 mmoles) of the product of Step A dissolved in 10 mL of methanol was added 6.52 mL (6.52 mmoles) of 1.0N KOH solution in methanol. The reaction mixture was stirred at room temperature for 1 hour. TLC analysis (25% EtOAc:Hexanes) indicated that no more starting material was present in the reaction mixture. The reaction mixture was diluted with EtOAc and quenched with 10% $NaHSO_4$ aqueous solution. The aqueous phase was separated and the organic portion was washed with brine (2×15 mL), and evaporated to a residue. Purification was done by reversed phase HPLC (Waters Millipore Delta Prep 4000 with Delta-Pak C18 15 μm 100 A column cartridge) with a solvent system of 50:50 water-acetonitrile and 0.1% TFA buffer. The purified fractions collected were combined in a round bottom flask, frozen in a −78° C. dry ice-acetone bath, and lyophilized. The resulting lyophilized powder afforded 1.11 g (57% yield) of the titled product. MS (CI): $C_{17}H_{15}NO_6$ 329.13 Found: [330.5, M+1].

Step C: Preparation of N-(4-iso-propylbenzenesulfonyl)-α-[N-(4-carbomethoxyphenylamino)]-3,4-methylenedioxyphenyl-acetamide To a solution of 0.180 g (0.547 mmol) of the product of Step B dissolved in 1.5 mL of methylene chloride was added 0.080 g (0.656 mmole) of 4-dimethylaminopyridine, 0.147 g (0.766 mmol) of 1-ethyl-3-(3-dimethylaminopropyl)carbodiimide hydrochloride, and 0.120 g (0.602 mmole) of 4-isopropylbenzenesulfonamide respectively. The reaction mixture was stirred at room temperature under nitrogen for 24 hours. TLC analysis (80:15:1 $CHCl_3$—$CH_3OH$—$NH_4OH$) indicated that the reaction had gone to completion after 24 hours. The reaction mixture was diluted with EtOAc and transferred to a seperatory funnel. The organic portion was washed with 2N HCl (2×10 mL) and brine (1×10 mL), dried over $MgSO_4$, filtered, and evaporated to a residue. Purification was done by reversed phase HPLC (Waters Millipore Delta Prep 4000 with Delta-Pak C18 15 μm 100 A column cartridge) with a solvent system of 40:60 water-acetonitrile and 0.1% TFA buffer. The purified fractions collected were combined in a round bottom flask, frozen in a −78° C. dry ice-acetone bath, and lyophilized. The resulting lyophilized powder afforded 0.060 g (21% yield) of the titled product.
$^1$H-NMR (400 MHz, $CD_3OD$, ppm): δ 1.25 (d, J=6.96 Hz, 3H), 1.26 (d, J=6.87 Hz, 3H), 2.97 (sept., J=7.06 Hz, 1H), 3.80 (s, 3H), 4.86 (s, 1H), 5.94(s, 2H), 6.45 (d, J=8.81 Hz, 2H), 6.87–6.75 (m, 3H), 7.36 (d, J=8.39 Hz, 2H), 7.65 (d, J=8.85 Hz, 2H), 7.78 (d, J=8.48 Hz, 2H). MS (ESI): $C_{26}H_{26}N_2O_7S$ 510.57 Found: [511.0, M+1].

EXAMPLE 105

N-(4-iso-propylbenzenesulfonyl)-α-[N-(4-carboxyphenylamino )]-3,4-methylenedioxyphenylacetamide Following the hydrolysis procedure described in Example 58 the titled compound is prepared from N-(4-iso-propylbenzenesulfonyl)-α-[N-(4-carbometho xyphenylamino )]-3,4-methylenedioxyphenylacetamide.

EXAMPLES 106–121

Examples 106 through 121 were prepared following the procedures described in Example 40.

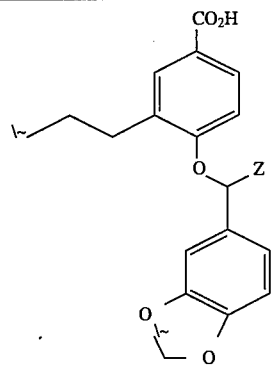

| Ex. # | Z | Mass Spectrum (M+1) |
|---|---|---|
| 106 | $CONHSO_2$-3-pyridyl | (M+1) 513 |
| 107 | $CONHSO_2$-(2-Me)-3-quininolinyl | (M+1) 563 |
| 108 | $CONHSO_2$-3-quininolinyl | (M+1) 549 |
| 109 | $CONHSO_2$-(4-OH)-3-pyridyl | (M+1) 529 |
| 110 | $CONHSO_2$-(4-OEt)Ph | $(M+NH_4^+)$ 599 |

-continued

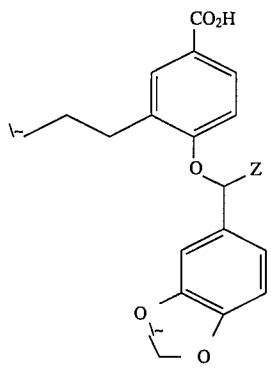

| Ex. # | Z | Mass Spectrum (M+1) |
|---|---|---|
| 111 | CONHSO$_2$-(4-CONH$_2$)Ph | (M+1) 542 |
| 112 | CONHSO$_2$-[4-CO(N(Me)$_2$)]Ph | (M+1) 569 |
| 113 | CONHSO$_2$-(4-SEt)-3-pyridyl | (M+1) 559 |
| 114 | CONHSO$_2$-(4-OEt)-3-pyridyl | (M+1) 543 |
| 115 | CONHSO$_2$-(4-amine, 2,5-di-OMe)Ph | (M+1) 573 |
| 116 | CONHSO$_2$-(2,5-di-OMe)Ph | (M+1) 558 |
| 117 | CONHSO$_2$-(3,4-di-OMe)Ph | (M+1) 558 |
| 118 | CONHSO$_2$-[5-(4-morpholinyl)]-2-benzothiophene | (M+1) 639 |
| 119 | CONHSO$_2$-(4-OMe)-2-benzothiophene | (M+1) 585 |
| 120 | CONHSO$_2$-[4-((CH$_2$)$_2$NHCBz))]Ph | (M+1) 675 |
| 121 | CONHSO$_2$-(2,5-di-OMe, 4-NHCONHiPr)Ph | (M+1) 658 |
| 122 | CONHSO$_2$-(2,4-di-OMe)Ph | — |
| 123 | CONHSO$_2$-(2,4,6-tri-OMe)Ph | — |

EXAMPLES 124–129

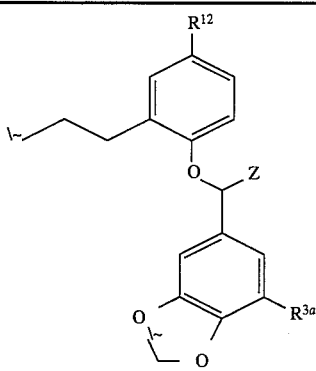

| Ex # | R$^{12}$ | R$^{3a}$ | Z | Mass Spectrum (M+1) |
|---|---|---|---|---|
| 124 | CO$_2$H | H | CONHSO$_2$-8-quininolinyl | 579 |
| 125 | CO$_2$H | H | CONHSO$_2$-3-quininolinyl | 579 |
| 126 | CONH$_2$ | OMe | CONHSO$_2$-8-quininolinyl | 578 |
| 127 | CONH$_2$ | OMe | CONHSO$_2$-(4-t-butyl)Ph | 553 |
| 128 | CONH$_2$ | OMe | CONHSO$_2$-(4-amine, 2,5-di-OMe)Ph | 572 |
| 129 | CO$_2$H | H | CONHSO$_2$NH-(4-iPr)Ph | 555 |

EXAMPLE 130

N-[N'-(4-iso-propylbenzene)amino sulfonyl]-α-[(4-carboxy-2-n-propyl)phenoxy]-3,4-methylenedioxyphenylacetamide Step A: Preparation of N-(4-isopropylbenzene)-N'-tert-butylsulfamide To a solution of p-isopropylaniline (1.69 g, 11.77 mmol) in CH$_2$Cl$_2$ (0.5 ml) was added N,N-diisopropylethylamine (2 ml) followed by the dropwise addition of a solution of N-t-butylsulfamoyl chloride (1.01 g, 5.88 mmol) [prepared according to the procedure described by W. L. Matier and W. T. Comer, J. Med. Chem., 15:5, 538 (1972)] in CH$_2$Cl$_2$ (0.4 ml) via a syringe at 0° C. The reaction mixture was then magnetically stirred at room temperature for 18 hrs. The reaction was diluted with CH$_2$Cl$_2$ and quenched with aqueousIN HCl. The organic phase was separated, washed with water, saturated aqueous NaCl, dried (MgSO$_4$), filtered, evaporated and dried in vacuo to yield an impure solid. The residue was purified by triturating with Hex:EtOAc (4:1) to yield 930 mg (58%) of the titled product as a white solid.

$^1$H-NMR (300 MHz, CD$_3$OD, ppm): δ 1.1–1.3 (m, 15H), 2.7–2.9 (m, 1H), 6.9–7.2 (m, 4H). ESI-MS m/e=271 (M+1).

Step B: Preparation of N-4-isopropylbenzenesulfamide

A solution of 0.9 g (3.32 mmol) of the product of Step A in trifluoroacetic acid (15 ml) was magnetically stirred at room temperature until TLC indicated the reaction was complete. The solvent was removed in vacuo, washed with cold Et$_2$O, and filtered to yield 553 mg (78%) of the titled product as a white solid.

$^1$H-NMR (300 MHz, CD$_3$OD, ppm): δ 1.1–1.3 (d, 6H), 1.7–1.9 (m, 1H), 7.1 (s, 4H). CI-MS, m/e=232 (M+NH$_4^+$).

Step C: Preparation of N-[N'-(4-iso-propylbenzene)aminosulfonyl]-α-[(4-carbomethoxy-2-n-propyl)phenoxy]-3,4-methylenedioxyphenylacetamide The compound from Step B was reacted with the carboxylic acid, obtained in Step B of Example 56, according to the procedure described in Step C of Example 25 to provide the titlted compound.

$^1$H-NMR (300 MHz, CD$_3$OD, ppm): δ 0.8–0.9 (t, 3H), 1.1–1.3 (d, 6H), 1.4–1.7 (m, 2H), 2.5–2.9 (m, 2H), 2.7–2.9 (m, 1H), 3.8 (s, 3H), 5.3 (s, 1H), 5.9 (s, 2H), 6.5–6.7 (dd, 2H), 6.8–7.1 (m, 6H), 7.5–7.6 (dd, 1H), 7.7 (s, 1H). ESI-MS, m/e=659 (M+1).

Step D: Preparation of N-[N'-(4-iso-propylbenzene)aminosulfonyl]-α-[(4-carboxy-2-n-propyl)phenoxy]-3,4-methylenedioxyphenylacetamide The titled compound was prepared following the procedure described in Example 40.

$^1$H-NMR (300 MHz, CD$_3$OD, ppm): δ 0.8–0.9 (t, 3H), 1.1–1.3 (d, 6H), 1.4–1.7 (m, 2H), 2.5–2.9 (m, 2H), 2.7–2.9 (m, 1H), 5.3 (s, 1H), 5.9 (s, 2H), 6.5–6.7 (dd, 2H), 6.8–7.1 (m, 6H), 7.5–7.6 (dd, 1H), 7.7 (s, 1H).

EXAMPLE 131

N-(4-iso-propylbenzenesulfonyl)-α-[4-methanesulfonylamino-2-n-propylphenoxy]-3,4-methylenedioxyphenylacetamide α-(4-Amino-2-n-propylphenoxy)-3,4-methylenedioxyphenylacetate (Product of Step C Example 99) was reacted with methanesulfonyl chloride in a mixture of pyridine and methylene chloride to provide α-[4-(N-methanesulfonyl)amino-2-n-propylphenoxy]-3,4-methylenedioxy- phenylacetate, which upon further elaboration following the procedures described in Example 99 provided the titled compound.

$^1$H-NMR (300 MHz, CDCl$_3$, ppm): δ 0.8–0.9 (t, 3H), 1.1–1.3 (d, 6H), 1.4–1.7 (m, 2H), 2.4–2.69 (m, 2H), 2.72 (s, 3H), 2.75–2.9 (m, 1H), 5.3 (s, 1H), 5.85 (s, 2H), 6.6–6.7 (dd, 2H), 6.8–7.1 (m, 6H), 7.6–7.75 (dd, 1H), 7.9 (s, 1H).

EXAMPLE 132

N-(4-iso-propylbenzenesulfonyl)-α-[(4-(N,N-dimethylcarbamoyl)amino-2-n-propylphenoxy]-3,4-methylenedioxy-phenylacetamide The title compound was prepared by reacting the amine from Example 99 (Step C) with N,N-dimethylcarbamoyl chloride.

$^1$H-NMR (300 MHz, CDCl$_3$, ppm): δ 0.95 (t, 3H), 1.1–1.3 (d, 6H), 1.45–1.8 (m, 2H), 2.5–2.7 (m, 2H), 2.75–2.9 (m, 1H), 3.0 (s, 6H), 5.3 (s, 1H), 5.85 (s, 2H), 6.6–6.7 (dd, 2H), 6.8–7.1 (m, 6H), 7.6–7.75 (dd, 1H), 7.9 (d, 2H).

EXAMPLE 133

N-(4-iso-propylbenzenesulfonyl)-α-[4-methoxycarbonylamino-2-n-propylphenoxy]-3,4-methylene dioxyphenylacetamide The title compound was prepared by reacting the amine from Example 99 (Step C) with ethylchloroformate.

$^1$H-NMR (300 MHz, CDCl$_3$, ppm): δ 0.9 (t, 3H), 1.1–1.3 (m, 9H), 1.45–1.7 (m, 2H), 2.45–2.7 (m, 2H), 2.8–3.0 (m, 1H), 4.1–4.25 (q, 2H), 5.3 (s, 1H), 5.9 (s, 2H), 6.5–6.75 (m, 2H), 6.8–7.0 (m, 6H), 7.6–7.75 (dd, 1H), 7.8 (d, 2H).

EXAMPLE 134

Methyl 3-allyl-4-hydroxybenzoate

Step A: Preparation of methyl 4-allyloxybenzoate

To a nitrogen flushed 5 L three neck round bottom flask fitted with a mechanical stirrer, condenser, and a nitrogen inlet was charged 608 g (4 mol) of methyl 4-hydoxybenzoate, 520 ml (727 g, 6.00 mol, 1.5 eq) of allyl bromide, 663 g (9.6 mol of anhydrous potassium carbonate, and 2.3 L of acetone. The mixture was refluxed with vigorous stirring for 90 min. Additional potassium carbonate, (50 g) was added, and 25 g added again after an additional 50 min. After 20 min (total reaction time of 160 min), the suspension was allowed to cool to ambient temperature and stirred overnight. The mixture was filtered and the cake washed with 3 L of acetone. The solution was concentrated to obtain 788.6 g (theoretical yield 768.9 g) of a pale yellow, almost colorless oil which was used without purification in the next step. The product was a single spot on TLC (silica-1:1 EtOAc/Hex) and the MNR was consistent with methyl 4-allyloxybenzoate.

Step B: Preparation of methyl 3-allyl-4-hydroxybenzoate

To a nitrogen flushed magnetically stirred 3 L single neck round bottom flask fitted with a condenser, and a nitrogen inlet was charged the methyl 4-allyloxybenzoate, 400 mL of 1,2-dichlorobenzene, and 10 g of BHT. The solution was heated and distillate collected untill the head temperature reached that of 1,2-dichlormbenzene (180° C.). The solution was then refluxed for 6.5 hr, then cooled to 140° C. and aged ovenight. The hot solution was then poured into 2.5 L of hexanes and the resulting suspension aged overnight with stirring. The suspension was filtered, and the cake washed with hexanes. The solid was air dried affording 747.7 g (97.3% yield) as a white solid having a faint odor of o-dichlorobenzene.

$^1$H-NMR (300 MHz, CDCl$_3$, ppm): δ 3.42 (dt J=6.4,1.4 Hz, 2H), 3.87 (s, 3H), 5.11–5.18 (m, 2H), 5.87 (bs, 1H), 5.93–6.06 (m,1H), 6.83 (d, J=7.9 Hz, 1H), 7.79–7.85 (m, 2H).

EXAMPLE 135

Methyl 4-hydoxy-3-n-propylbenzoate

Step A: preparation of methyl 4-hydoxy-3-n-propylbenzoate

A solution of 363 g of methyl 3-allyl-4-hydoxybenzoate in 1.5 L of methanol was hydrogenated for 1 hr in a Parr$^R$ type shaker at 40 psi and ambient temperature using 1.5 g of 10% palladium on carbon as the catalyst. The reaction was filterd through Sulka-Floc$^R$ and the cake washed with 1 L of methanol. The combined filtrate was concentrated and the oil flushed with ether. Hexanes (1.5 L) were added and the resulting suspension cooled to 0° C. The product was collected by filtration, washed with hexanes and dried affording 176.6 g of methyl 4-hydoxy-3-n-propylbenzoate. A second crop of 166.4 g was obtained by concentrating the filtrate, diluting with hexanes and filtering, bringing the total to 343 g (94.3% yield).

$^1$H-NMR (300 MHz, CDCl$_3$, ppm): δ 0.94 (t J=7.4 Hz, 3H), 1.63 (m, 2H), 2.59 (t J=7.7 Hz, 2H), 3.86 (s, 3H), 5.87 (s, 1H), 6.84 (d J=8.4 Hz, 1H), 7.76 (dd J=8.4, 2.2 Hz, 1H), 7.81 (d J=2.2 Hz, 1H).

EXAMPLE 136

Ethyl 3,4-methylenedioxy-d,l-mandelate

Step A α-Trimethylsilyloxy-3,4-methylenedioxyphenylacetonitrile

To a nitrogen flushed magnetically stirred 3 L single neck round bottom flask fitted with a nitrogen inlet was charged 285g (1.9 mol) of piperonal, 200 g (2.0 mol) of trimethylsilylycyanide, 0.2 g of potassium cyanide, 0.2 g of 18-crown-6 and 500 mL of methylene chloride. The mixture was stirred at ambient temperature for 75 min, during which time the reaction exothermed to 35° C. A second charge of 5 g of piperonal was added and the reaction stirred an additional 75 min. The reaction mixture was diluted with ether and 250 mL of saturated sodiuim bicarbonate solution was added. The mixture was stirred for 20 min before partitioning. The organic layer was washed with another 250 mL portion of saturated sodiuim bicarbonate, twice with brine (300 mL), dried with sodium sulfate, filtered and concentrated leaving 489.6 g (481.4 g theoretical yield) of the title compound as a pale yellow oil. This was used as is without purification in the next step.

Step B: Preparation of ethyl 3,4-methylenedioxy-d,l-mandelate

To a nitrogen flushed magnetically stirred 3 L single neck round bottom flask fitted with a gas inlet was charged the product obtained from the previous step and 1 L of absolute ethanol. The solution was cooled to 0° C and HCl gas gently bubbled through the solution for 1 hr. After a few minutes the reaction solidified to a white mass which was aged at room temperature ovenight. 1 L of methylene chloride, and 1 L of water were added. The mixture was shaken for ca 5 min dissolving some of the white solid. The mixture was decanted and the procedure repeated several more times until all of the solid had been dissolved. The layers were separated and the aqueous layer back extracted once with methylene chloride. The combined organic layer was washed with brine, dried with magnesium sulfate and filtered through a pad of silica. The solution was concentrated, flushed with ether and diluted with hexanes. The white slurry was cooled to 0° C. then filtered. The cake was washed with 1:2 ether/hexanes followed by hexanes. The product was dried affording 347.2 g of the title compound as a white solid. A second crop of 24 g was obtained by concentrating the mother liquors, bringing the total to 371.4 g (85.8% yield).

$^1$H-NMR (300 MHz, CDCl$_3$, ppm); δ 1.22 (t, J=7.2 Hz, 3H), 3.41.(d, J=5.6 Hz, 1H), 4.10–4.31 (m, 2H), 5.03 (d, J=5.6 Hz, 1H), 5.94 (s, 2H), 6.77 (d, J=8.5 Hz, 1H), 6.85–6.90 (m, 2H).

EXAMPLE 137

Ethyl α-bromo-3,4-methylenedioxyphenylacetate

Step A Preparation of ethyl α-bromo-3,4-methylenedioxyphenylacetate

To a nitrogen flushed 5 L three neck round bottom flask fitted with a mechanical stirrer, a dropping funnel and a nitrogen inlet was charged 433.8 g (1.93 mol) of ethyl 3,4-methylenedioxy-d,l-mandelate and 3.5 L of ether. The suspension was cooled to 0°–5° C. and a solution of 179 g (0.66 mol) of PBr3 in 500 mL of ether was added over a period of 30 min. The reaction was aged for 2.5 hr at 0°–5° C. during which time, an additional 24.2 g (0.09 mol) of PBr$_3$ was added. The solid initially present slowly dissolved leaving a clear yellow solution. The reaction was quenched by careful addition of 800 mL of saturated sodiuim bicarbonate solution and 200 mL of water. The layers were separated and the aqueous layer extracted once with ether. The combined organic phase was washed once with saturated sodiuim bicarbonate solution, 10% sodium bisulfite solution, brine, dried with magnesium sulfate, and filtered through a pad of silica. The solution was concentrated to 507.6 g (91.4%) of a pale yellow oil. Essentially a single spot on TLC (silica-1:1 Et$_2$O/Hex), NMR indicates a small amount of ether is present. This was used as is without purification in the next step.

$^1$H-NMR (300 MHz, CDCl$_3$, ppm): δ 1.27 (t,J=7.2 Hz, 3H), 4.10–4.35 (m, 2H), 5.26 (s, 1H), 5.96 (s, 2H), 6.72 (d, J=8. Hz, 1H), 6.94 (dd, J=8.0, 1.8 Hz, 1H), 7.11 (d, J=1.8 Hz, 1H).

EXAMPLE 138

α-(4-Carbomethoxy-2-n-propylphenoxy)-3,4-methylenedioxyphenyl)acetic acid sodium salt Step A: Preparation of ethyl α-(4-carbomethoxy-2-n-propylphenoxy)-3,4-methylenedioxyphenylacetate To a 2 L three necked 24/40 round bottom flask equipped with a mechanical stirrer, a nitrogen inlet and a dropping funnel was first added a solution of 36.0 g (0.185 mol) of methyl 4-hydroxy-3-n-propylbenzoate dissolved in 700 mL of anhydrous DMF followed by 66.4 g (0.204 mol) of cesium carbonate. The flask was purged with nitrogen and the reaction mixture was stirred at room temperature for 2 hours. A solution of 58.5 g (0.204 mol) of ethyl α-bromo-3,4-methylenedioxyphenylacetate dissolved in 100 mL of DMF was then added via an addition funnel over a 15 minute period. The reaction mixture was stirred an additional 1 hour at room temperature then quenched by addition to 5 L of a 5% aqueous citric acid solution. The organic product was extracted into diethylether (2×4 L), the organic layers were separated, washed with saturated aqueous NaCl, dried (MgSO$_4$), filtered, and evaporated. The residue was applied to a silica gel (2 kg; 70–230 mesh) column equilibrated in 10% CH$_2$Cl$_2$-hexane. The column was then eluted successively with 12 L of 10% CH$_2$Cl$_2$-hexane, 12 L of 5% EtOAc-hexane, 4 L of 7.5% EtOAc-hexane, 12 L of 10% EtOAc-hexane, and finally 8 L of 20% EtOAc-hexane. Combination of the purified fractions and evaporation in vacuo afforded 76.3 g (74.2 theoretical) of the title compound as a pale yellow oil which was used without further purification in the next step.

Step B: Preparation of α-(4-carbomethoxy-2-n-propylphenoxy)-3,4-methylenedioxyphenylacetic acid sodium salt A 1 L 3 necked 24/40 round bottom flask equipped with a mechanical stirrer, a dropping funnel, and a nitrogen inlet was charged with a solution of 76.3 g 0.185 mol) of the semi-purified product of Step A dissolved in 500 mL of methanol. The flask was purged with nitrogen, the stirrer was started, and 37 mL of a 5.0N aqueous solution of sodium hydroxide was added over a 30 minute period via an addition funnel. The reaction mixture was stirred at room temperature for an additional 30 minutes at which point TLC analysis (CH$_2$Cl$_2$-MeOH-NH$_4$OH 90:10:1) indicated that the starting material had been consumed. The reaction mixture was adjusted to pH=4 with 6N HCl, and the bulk of the organic solvent was removed in vacuo. The precipitated organic product and the aqueous layer were next partitioned between CH$_2$Cl$_2$ (1 L) and water (1 L) which produced a copious emulsion. The reaction mixture was then aged overnight in a refridgerator which resulted in crystallization of the organic product. The crystalline solid was separated from the two phase mixture by filtration and washed with CH$_2$Cl$_2$. The solid was slurfled again in diethylether, filtered, washed with hexane, and then dried in a vacuum to afford 65 g (85.3%) of the title compound as a white crystalline solid.

$^1$H-NMR (400 MHz, CD$_3$OD, ppm): δ 0.93 (t, J=7.2 Hz, 3H), 1.62–1.75 (m, 2H), 2.63–2.70 (m, 1H), 2.77–2.81 (m, 1H), 3.84 (s, 3H), 5.54 (s, 1H), 5.94 (s, 2H), 6.81 (d, J=7.6 Hz, 1H), 6.89 (d, J=9.2 Hz, 1H), 7.08 (d, J=1.6 Hz, 1H), 7.11 (br s, 1H), 7.78–7.81 (m, 2H). Microanalysis for C$_{20}$H$_{20}$O$_7$Na$_{0.75}$1.25 H$_2$O.

Calc'd: C=58.29; H=5.50; Na=4.18
Found: C=58.19; H=5.17; Na=3.93

EXAMPLE 139

N-(4-iso-propylbenzenesulfonyl)-α-(4-carbomethoxy-2-n-propylphenoxy)-3,4-methylenedioxyphenylacetamide Step A: Preparation of ethyl α-(4-carbomethoxy-2-n-propylphenoxy)-3,4-methylenedioxyphenylacetate To a nitrogen flushed 5 L three neck round bottom flask fitted with a mechanical stirrer, condenser, and a nitrogen inlet was charged 326 g (1.68 mol) of methyl 4-hydoxy-3-n-propylbenzoate, 507.6 g (1.73 mol)of ethyl α-bromo-3,4-methylenedioxyphenylacetate from above, 235 g (1.70 mol) of anhydrous potassium carbonate, and 1.7 L of acetone. The mixture was refluxed with vigorous stirring for 9 hr. The suspension was allowed to cool to ambient temperature and stirred overnight. The mixture diluted with 2 L of ether, cooled to 0° C. and filtered through Super-Cel$^R$. The cake washed with ether and the combined filtrate concentrated. The residue was redissolved in ether and the organic layer washed with once with 1 N HCl, saturated sodiuim bicarbonate solution, 10% sodium bisulfite solution, brine, dried with magnesium sulfate, treated with charcoal and filtered through a plug of silica. The pale yellow solution was concentrated to 697.3 g (theoretical 678 g) of a thick yellow oil which was used without purification in the next step. NMR was consistent with the title compound.

$^1$H-NMR (300 MHz, CDCl$_3$, ppm): δ 0.95 (t, J=7.3 Hz, 3H), 1.17 (t, J=7.1 Hz, 3H), 1.61–1.81 (m, 2H), 2.63–2.80 (m, 2H), 3.85 (s, 3H), 4.07–4.23 (m, 2H), 5.58 (s, 1H), 5.96 (s, 2H), 6.71 (d, J=8.5 Hz, 1H), 6.76 (d, J=8.0 Hz, 1H), 7.02 (d,d, J=8.0,1.7 Hz, 1H), 7.05 (d, J=1.7 Hz, 1H), 7.79 (d,d, J=8.5, 2.2 Hz, 1H), 7.84 (d, J=2.2 Hz, 1H).

Step B: Preparation of α-(4-carbomethoxy-2-n-propylphenoxy)-3,4-methylenedioxyphenylacetic acid To a nitrogen flushed 5 L 3 neck round bottom flask equipped with a mechanical stirrer, a dropping funnel, and a nitrogen inlet was charged with 697.3 g (1.68 mol) of the crude product of Step A and 2 L of methanol. 500 mL of 5.0N (1.5 eq) aqueous sodium hydroxide was added over a 20 minute period via an addition funnel. The reaction mixture was stirred at room temperature for an additional 1 hr at which point TLC analysis ($CH_2Cl_2$-MeOH-$NH_4OH$ 90:10:1) indicated that the starting material had been consumed. The reaction mixture neutralized with 420 mL of 6N HCl, and the bulk of the organic solvent was removed in vacuo. The residue was dissolved in ether and extracted with a combination of aqueous NaOH and $NaHCO_3$. The aqueous layer was extracted with ether and the combined organic layer was washed with aqueous $NaHCO_3$. The aqueous layer was acidified with HCl and extracted with ether. The ether solution was dried with magnesium sulfate, filtered, and concentrated to afford 708.9 g (theoretical 625 g) of the title compound as a viscous orange oil. NMR indicated that it was ca 85% product by weight (15% ether) thus providing a corrected yield of 602.6 g (96.4% yield)

$^1$H-NMR (300 MHz, $CD_3OD$, ppm): δ 0.93 (t, J=7.4 Hz, 3H), 1.56–1.77 (m, 2H), 2.68 (t, 2H), 3.84 (s, 3H), 5.57 (s, 1H), 5.95 (s, 2H), 6.42 (bs, 1H), 6.71 (d, J=8.5 Hz, 1H), 6.79 (d, J=7.9 Hz, 1H), 6.99–7.05 (m, 2H), 7.78 (d,d, J=8.5, 2.2 Hz, 1H), 7.82 (d, J=2.2, 1H).

Step C: Preparation of N-(4-iso-propylbenzenesulfonyl)-α-(4-carbomethoxy-2-n-propylphenoxy)-3,4-methylenedioxyphenylacetamide potassium salt To a nitrogen flushed 5 L 3 neck round bottom flask equiped with a mechanical stirrer, a dropping funnel, a condenser and a nitrogen inlet was charged 1 L of THF and 350 g (2.16 mol, 1.42 eq) of carbonyl diimidazole (CDI). The mixture was heated to reflux and a solution of 663.6 g (1.52 mol) of acid from Step B and 1 L of THF was added dropwise over a period of 30 min. The reaction was monitored for coversion of the acid to the acyl imidazolide by NMR. An additional 85 g of CDI was added over 45 min. The solution was cooled and 291 g (1.48 mol) 4-iso-propylbenzenesulfonamide was added as a solid in one portion and the solution aged 20 min. DBU 230 mL (234 g, 1.54 mol) was added dropwise over 10 min resulting in an exotherm to 45° C. The reaction was aged at room temperature for 3 hr then concentrated in vacuo. The residue was partitioned between 2.75 L of 2.5N HCl and 3 L of ether. The aqueous layer was extracted with 1 L of ether, and the combined organic layer washed with 2N HCl and saturated potassium bicarbonate solution. The etherial layer was transferred to a 5 L 3 neck round bottom flask equipped with a mechanical stirrer. 1 L of aqueous potassium bicarbonate solution was added and the mixture stirred overnight at room temperature. The resulting thick suspension was filtered and the cake washed with 500 mL of water followed by 1 L of ether. The product was then slurried in the funnel with additional ether and sucked dry yielding 741 g of a tan solid The solid was recharged to a 5 L 3 neck round bottom flask equipped with a mechanical stirrer to which was added 1 L of ethyl acetate and 500 mL of saturated potassium bicarbonate solution. The slurry was stirred at room temperature for 1 hr, diluted with 3 L of ether, and the slurried stirred at room temperature overnight. The product was filtered, washed with 500 mL of water and 1 L of ether and dried in vacuo. The yield was 592 g of the title compound as a white crystalline solid. A second crop of 47.6 g was obtained from the mother liqours bringing the total to 639.6 g (74% of theory)

$^1$H-NMR (300 MHz, $CD_3OD$, ppm): δ 0.88 (t, J=7.4 Hz, 3H), 1.21 (d, J=6.9 Hz, 6H), 1.52–1.66 (m, 2H), 2.50–2.76 (m, 2H), 2.90 (sept, J=6.9 Hz, 1H), 3.84 (s, 3H), 5.35 (s, 1H), 5.94 (s, 2H), 6.69 (d, J=8.6 Hz, 1H), 6.76 (d, J=8.5 Hz, 1H), 7.04 (m, 2H), 7.20 (d, J=8.4 Hz, 2H), 7.61 (dd, J=8.5, 2.20, Hz, 1H), 7.67 (d, J=8.4 Hz, 2H), 7.71 (d, J=2.1 Hz, 1H).

EXAMPLE 140

N-(4-iso-propylbenzenesulfonyl)-α-(4-carboxy-2-n-propylphenoxy)-3,4-methylenedioxyphenylacetamide dipotassium salt Method A:

Step A: Preparation of N-(4-iso-propylbenzenesulfonyl)-α-(4-carboxy-2-n-propylphenoxy)-3,4-methylenedioxyphenylacetamide dipotassium salt A mixture of 204 g (0.345 mol) of the product of Example 139, 420 mL of 1.0N KOH in methanol and 500 mL of water was stirred at 60° C. under a nitrogen atmosphere. After 3 hours TLC analysis (90:10:1 $CH_2Cl_2$-MeOH-$NH_4OH$) indicated that ester hydrolysis was complete. The reaction mixture was cool slightly, then concentrated on a rotary evaporator to a weight of 500 g. 2.5 L of isopropanol was added and the solution reconcentrated to an oil. The residue was flushed with an additional 2–3 L of isopropanol untill crystallization began. The slurry was concentrated to ca 1.5 L and cooled to 30° C., filtered and washed with 300 mL of IPA and 500 mL of ether. The product was dried affording 185 g of semi-pure title compound as a white crystalline solid. A second crop of 17 g was obtained from the filtrate after cooling. The material was recrystallized as follows: 168 g was dissolved in 3 L of absolute ethanol at reflux, filtered hot, and the flask and funnel rinsed with an additional 500 mL of ethanol. 70 mL of water was added and the solution cooled to 0° C. over 2 hr then aged at 0° C. for 6 hr. The product was collected by filtration, washed with ethanol, then air. The yield was 160.8 g of the title compound as a white crystalline solid.

$^1$H-NMR (400 MHz, $CD_3OD$, ppm): δ 0.88 (t,J=7.2 Hz, 3H), 1.21 (d, J=7.0 Hz, 3H), 1.22 (d, J=7.0 Hz, 3H), 1.56–1.63 (m, 2H), 2.52–2.59 (m, 1H), 2.67–2.74 (m, 1H), 2.91 (sept, J=7.0 Hz, 1H), 5.33 (s, 1H), 5.92 (d, J=1.2 Hz, 1H), 5.93 (d, J=1.2 Hz, 1H), 6.72 (d, J=8.5 Hz, 1H), 6.76 (d, J=8.5 Hz, 1H), 7.04 (d, J=7.5 Hz, 1H), 7.05 (s, 1H), 7.21 (d, J=8.5 Hz, 2H), 7.64 (dd, J=2.0, 8.5 Hz, 1H), 7.67 (d, J=8.5 Hz, 2H), 7.73 (d, J=2.0 Hz, 1H). Microanalysis for $C_{28}H_{27}NSO_8K_2 \cdot 3.4\ H_2O$.

KF=9.00 (calc for 3.4 $H_2O$=9.04)

Calc'd: C=49.67; H=5.03; N=2.07; K=11.55; S=4.74.

Found: C=49.30; H=4.95; N=2.06; K=11.85; S=4.82

Method B:

Step A Preparation of N-(4-iso-propylbenzenesulfonyl)-α-(4-carboxy-2-n-propylphenoxy)-3,4-methylenedioxyphenylacetamide A mixture of 205 g (0.345 mol) of the product of Example 139, 425 mL of 1.0N KOH in methanol and 500 mL of water was stirred at 60° C. under a nitrogen atmosphere. After 1.75 hours TLC analysis (90:10:1 $CH_2Cl_2$-MeOH-$NH_4OH$) indicated that ester hydrolysis was complete. The reaction mixture was cooled slightly, then concentrated on a rotary evaporator. The concentrate was acidified with 400 mL of 2N HCl and extracted first with 6 L of ether-EtOAc-$CH_2Cl_2$ 4:1:1, then with 3 L of 1:2 EtOAc-$CH_2Cl_2$. The organic layers were washed with 250 mL of 2N $HC_1$, then with 3×500 mL of water, dried with magnesium sulfate, filtered, and concentrated, during which, the product began to crystallize. The solution was concentrated to a white slurry of ca 750 mL, diluted with 1 L of hexanes, cooled to 0° C., aged 1 hr then filtered. The product was air dried affording 170.0 g (91% yield) of the title compound as a white crystalline solid.

$^1$H-NMR (400 MHz, CD$_3$OD, ppm): δ 0.88 (t,J=7.2 Hz, 3H), 1.21 (d, J=7.00 Hz, 3H), 1.22 (d, J=7.0 Hz, 3H), 1.56–1.63 (m, 2H), 2.52–2.59 (m, 1H), 2.67–2.74 (m, 1H), 2.91 (sept, J=7.0 Hz, 1H), 5.33 (s, 1H), 5.92 (d, J=1.2 Hz, 1H), 5.93 (d, J=1.2 Hz, 1H), 6.72 (d, J=8.5 Hz, 1H), 6.76 (d, J=8.5 Hz, 1H), 7.04 (d, J=7.5 Hz, 1H), 7.05 (s, 1H), 7.21 (d, J=8.5 Hz, 2H), 7.64 (dd, J=2.0, 8.5 Hz, 1H), 7.67 (d, J=8.5 Hz, 2H), 7.73 (d, J=2.0 Hz, 1H). Microanalysis for C$_{28}$H$_{29}$NO$_8$S
Calc'd: C=62.33; H=5.42; N=2.60; S=5.94.
Found: C=62.15; H=5.48; N=2.54; S=5.99

Step.B: Preparation of N-(4-iso-propylbenzenesulfonyl)-α-(4-carboxy-2-n-propylphenoxy)-3,4-methylenedioxyphenylacetamide dipotassium salt 159.7 g (0.296 mol) of acid from Step A was suspended in 3 L of absolute ethanol. To this was added 590 mL of 1.0N KOH in methanol over 20 min while simultaneously warming the mixture to 50° C. The clear and colorless solution was cooled to 0° C. during which it was seeded with 20 mg of the title compound. The suspension was stirred for 2 hr at 0° C., 1 L of ether was added and the suspension filtered. The solid was dried affording 168.4 g of the title compound as a white crystalline solid. A second crop of 22.3 g of comparable quality material was obtained by concentrating the mother liquors to ca. 1 L, diluting with 1 L of ether, filtering, and recrystallizing the solid (27 g) so obtained from 200 mL of 98% ethanol. Thus affording after drying a total of 190.7 g (96.8% yield corr'd for water content) of the title compound. Microanalysis for C$_{28}$H$_{27}$K$_2$NO$_8$S·2.75 H$_2$O.
KF=7.45 (calc for 2.75 H$_2$O=7.44)
Calc'd: C=50.55; H=4.92; N=2.11; K=11.75;
Found: C=50.69; H=4.56; N=2.05; K=11.20; S=4.71

EXAMPLE 141

(−)-N-(4-iso-propylbenzenesulfonyl)-α-(4-carboxy-2-n-propylphenoxy)-3,4-methylenedioxyphenylacetamide dipotassium salt Step A: Preparation of N-(4-iso-propylbenzenesulfonyl)-α-(4-carboxy-2-n-prop ylphenoxy)-3,4-methylenedioxyphenylacetamide di-R-(+)-α-methylbenzylamine salt 32.4 g of the acid from Example 139 was dissolved in 500 mL of isopropanol, and 15.5 mL of R-(+)-α-methylbenzyl amine was added. The solution was allowed to stand at room temperature overnight. The mixture was filtered and the cake washed with a small amount of isopropanol. The solid was recrystallized 4 more times from isopropanol affording 4.5 g of the title compound.

Step B: Preparation of (−)-N-(4-iso-propylbenzenesulfonyl)-α-(4-carboxy-2-n-propylphenoxy)-3,4-methylenedioxyphenylacetamide dipotassium salt.

The α-methylbenzylamine salt from the above example was partitioned between ethyl acetate and 10% aqueous NaHSO$_4$, the organic layer was separated, dried with MgSO$_4$, filtered and concentrated. The residue was dissolved in methanol-water at room temperature, and basicified with ca. 12 mL of 1N NaOH in methanol, diluted with water and filtered through a 0.45 micron membrane filter. The solution was desalted and purified on a Waters Millipore Delta Prep 4000 liquid chromatograph equipped with an M1000 Prep-Pak module containing a 47×300 mm Delta-Pak C18 15 μm 100A column cartridge. Two solvent resevoirs were employed: solvent system A (95-5 water-acetonitrile), and solvent system B (5-95 water-acetonitrile), and the column effluent was monitored simultaneously at 210 and 280 nm with a Waters model 490 UV-visible detector. The sample was pump-injected onto the column and desalted by elution (50 mL/min) with several column volumes of solvent system A. A gradient elution was then begun which had as initial conditions 100% solvent system A-0% solvent system B and reached after 30 minutes 50% solvent system A-50% solvent system B, and the fractions were collected with an ISCO Foxy 200 fraction collector. The purified fractions were combined in round bottom flasks, frozen in a −78° C. dry ice-acetone bath, and lyophilized. Combination of the purified product afforded 4.8 g of the title compound as a white lyophilized powder.

$^1$H-NMR (400 MHz, CD$_3$OD, ppm): δ 0.88 (t, J=7.2 Hz, 3H), 1.21 (d, J=7.0 Hz, 3H), 1.22 (d, J=7.0 Hz, 3H), 1.56–1.63 (m, 2H), 2.52–2.59 (m, 1H), 2.67–2.74 (m, 1H), 2.91 (sept, J=7. Hz, 1H), 5.33 (s, 1H), 5.92 (d, J=1.2 Hz, 1H), 5.93 (d, J=1.2 Hz, 1H), 6.72 (d, J=8.50 Hz, 1H), 6.76 (d, J=8.5 Hz, 1H), 7.04 (d, J=7.5 Hz, 1H), 7.05 (s, 1H), 7.21 (d, J=8.5 Hz, 2H), 7.64 (dd, J=2.0, 8.5 Hz, 1H), 7.67 (d, J=8.5 Hz, 2H), 7.73 (d, J=2.0 Hz, 1H). Microanalysis for C$_{28}$H$_{27}$NSO$_8$K$_2$OH$_2$O.
Calc'd: C=53.06; H=4.61; N=2.21; K=12.34.
Found: C=52.81; H=4.56; N=2.17; K=12.02. [α]D=−48.9° (c=0.90, H$_2$O).

EXAMPLE 142

N-(4-iso-propylbenzenesulfonyl)-α-[[4-[N-[2-(carbethoxy)ethyl]-carbamoyl]]-2-propylphenoxy]-2-(3,4-methylenedioxyphenyl)acetamide The titled compound was prepared using procedures similar to those described in Example 82 except that β-alanine ethyl ester (liberated from the corresponding hydrochloride in situ) was the amine starting material. The crude product was flash chromatographed over silica gel (gradient elution, 1–5% MeOH/CH$_2$Cl$_2$) to give the desired product as a white foam in 78% yield; homogeneous by TLC (1%0 MeOH/CH$_2$Cl$_2$); mp 167°–168° C.; MS (ESI) 639 (M+H)$^+$.
Analysis (C$_{33}$H$_{38}$N$_2$O$_9$S·0.75H$_2$O):
Calcd: C, 60.78; H, 6.10; N, 4.30
Found: C, 60.69 H, 5.88 N, 4.30

$^1$H NMR (400 MHz, CD$_3$OD, ppm): δ 8.36 (t, 1H, J=5 Hz), 7.72 (d, 2H, J=8.4 Hz), 7.58 (d, 1H, J=2.3 Hz), 7.46 (dd, 1H, J=8.5, 2.3 Hz), 7.30 (d, 2H J=8.4 Hz), 6.93–6.98 (m, 2H), 6.77 (d, 1H, J=7.9 Hz), 6.65 (d, 1H, J=8.7 Hz), 5.95 (s, 2H), 5.47 (s, 1H), 4.13 (q, 2H, J=7.1 Hz), 3.57–3.63 (m, 2H), 2.93–2.98 (m, 1H), 2.68 (m, 2H), 2.62 (t, 2H, J=6.9 Hz), 1.60 (m, 2H), 1.21–1.25 (m, 6H), 0.88 (t, 3H, J=7.4 Hz).

EXAMPLE 143

N-( 4- iso-propylbenzenesulfonyl)-2-[[4-[N-(2-carboxyethyl)carbamoyl]]-2-propylphenoxy]-2-(3,4-methylenedioxyphenyl)acetamide The product from Example 142 was saponified (excess NaOH in MeOH, 60° C., 4 h) to give the titled product as a white solid in quantitative yield; mp 199°–201° C.; MS (ESI) 611 (M+H)$^+$.
Analysis (C$_{31}$H$_{34}$N$_2$O$_9$S·0.4H$_2$O):

Calcd: C, 60.25; H, 5.67; N, 4.55 Found: C, 60.49 H, 5.48 N, 4.18 $^1$H NMR (400 MHz, CD$_3$OD, ppm): δ 7.76 (dd, 2H, J=1.8, 8.5 Hz), 7.58 (d, 1H, J=2.3 Hz), 7.46 (dd, 1H, J=2.4, 8.6 Hz), 7.35 (d, 2H J=8.4 Hz), 6.92 (dd, 1H, J=1.7, 8.0 Hz), 6.87 (d, 1H, J=1.6 Hz), 6.78 (d, 1H, J=8.0 Hz), 6.56 (d, 1H, J=8.7 Hz), 5.96 (s, 2H), 5.51 (s, 1H), 3.58 (m, 2H), 2.95 (m, 1H), 2.68 (m, 2H), 2.61 (t, 2H, J=7.2 Hz), 1.58 (m, 2H), 1.21–1.25 (m, 6H), 0.88 (t, 3H, J=7.4 Hz).

EXAMPLE 144

N-(4-iso-propylbenzenesulfonyl)-2-[[4- [N-(2-carbamoyl-ethyl)-carbamoyl]]-2-propylphenoxy]-2-(3,4-methylene-dioxyphenyl)acetamide The titled compound was prepared using procedures similar to those described in Example 82. The crude product was flash chromatographed over silica gel (gradient elution, 2–10% MeOH/CH$_2$Cl$_2$) to yield the desired product as a white foam in 42% yield; homogeneous by TLC ($^{10}$/$_{90}$ MeOH/CH$_2$Cl$_2$), mp 110°–112° C.; MS (ESI) 610 (M+H)$^+$.

Analysis (C$_{31}$H$_{35}$N$_3$O$_8$S·0.75H$_2$O):
Calcd: C, 59.73; H, 5.90; N, 6.76
Found: C, 59.74 H, 5.61 N, 6.62
$^1$H NMR (400 MHz, CD$_3$OD, ppm): δ 7.77 (d, 2H, J=8.3 Hz), 7.59 (d, 1H, J=2.3 Hz), 7.46 (dd, 1H, J=2.4, 8.6 Hz), 7.36 (d, 2H J=8.7 Hz), 6.92 (dd, 1H, J=1.5, 8.0 Hz), 6.87 (d, 1H, J=1.6 Hz), 6.78 (d, 1H, J=8.1 Hz), 6.58 (d, 1H, J=8.6 Hz), 5.97 (s, 2H), 5.50 (s, 1H), 3.59 (t, 2H, J=7.0 Hz), 2.98 (m, 1H), 2.68 (m, 2H), 2.51 (t, 2H, J=6.9 Hz), 1.60 (m, 2H), 1.21–1.28 (m, 6H), 0.89 (t, 3H, J=7.4 Hz).

EXAMPLE 145

N-(4-iso-prop ylbenzenesulfonyl)-2-[4-[N-((2,2,2-trifluoroethyl)-carbamoyl]-2-propylphenoxy]-2-(3,4-methylenedioxyphenyl)acetamide The titled compound was prepared using procedures similar to those described in Example 82 except that trifluoroethylamine was used as the amine starting material. The crude product was flash chromatographed over silica gel (gradient elution, 1–4% MeOH/CH$_2$Cl$_2$) to give the desired product as a white foam in 79% yield; homogeneous by TLC ($^5$/$_{95}$ MeOH/CH$_2$Cl$_2$), mp 110–112° C.; MS (ESI) 621 (M+H)$^+$.

Analysis (C$_{30}$H$_{31}$F$_3$N$_2$O$_7$S·0.5H$_2$O): Calcd: C, 57.22; H, 5.12; N, 4.46 Found: C, 57.33 H, 4.87 N, 4.52
$^1$H NMR (400 MHz, CD$_3$OD, ppm): δ 7.71 (d, 2H, J=8.3 Hz), 7.63 (d, 1H, J=2.4 Hz), 7.52 (dd, 1H, J=2.2, 8.4 Hz), 7.29 (d, 2H J=8.3 Hz), 6.97 (m, 2H), 6.77 (d, 1H, J=7.9 Hz), 6.68 (d, 1H, J=8.7 Hz), 5.96 (s, 2H), 5.47 (s, 1H), 4.05 (dq, 2H, J=3.0, 9.2 Hz), 2.92 (m, 1H), 2.68 (m, 2H), 1.61 (m, 2H), 1.19–1.30 (m, 6H), 0.89 (t, 3H, J=7.3 Hz).

EXAMPLE 146

N-(4-iso-propylbenzenesulfonyl)-α-(4-N-t-butyloxy-carbonyl-aminosulfonyl-2-n-propylphenoxy)-3,4-methylenedioxyphenylacetamide Step A: Preparation of methyl α-(4-N-t-butyloxycarbony-lamino-sulfonyl-2-n-propylphenoxy)-3,4-methylenediox-yphenylacetate To a stirred solution of 76 mg (0.187 mmol) of methyl α-(2-n-propyl-4-aminosulfonylphenoxy)-3,4-methylene-dioxyphenylacetate (the product of Example 100 Step C), 29 μL (0.206 mmol) of triethylamine and 2.3 mg (0.0187 mmol) of DMAP hydrochloride in 1 mL of methylene chloride was added 47 mg (0.215 mmol) of di-tert-butyldicarbonate. After 1.5 hours, TLC analysis (5% methanol/methylene chloride) indicated that the coupling was complete and the reaction mixture was diluted with ethyl acetate, partitioned with water, washed another time with water, and washed with brine. The organic layer was then dried over magnesium sulfate, filtered, and the filtrate concentrated and dried in vacuo to afford 95 mg (100%) of the title compound as an amorphous solid. $^1$H-NMR (400 MHz, CDCl$_3$, ppm) δ 0.97 (t, J=7.40 Hz,3H), 1.35 (s, 9H), 1.62–1.75 (m, 2H), 2.66–2.79 (m, 2H), 3.71 (s, 3H), 5.60 (s, 1H), 5.98 (s, 2H), 6.75 (d,J=9.2 Hz, 1H), 6.81 (d,J=8.0 Hz, 1H), 6.99–7.04 (m, 2H), 7.74–7.76 (m, 2H).

Step B: Preparation of methyl α-(4-N-t-butyloxycarbony-lamino-sulfonyl-2-n-propylphenoxy)-3,4-methylene-dioxy-phenylacetic acid To a stirred solution of 95 mg (0.187 mmol) of the product of Step A in 0.75 mL of methylene chloride and 0.75 mL of methanol was added 45 μL (0.225 mmol) of 5N sodium hydroxide. After 5 hours, TLC analysis (5% methanol/methylene chloride) indicated slow ester hydrolysis and an additional 45 μL (0.225 mmol) of 5N sodium hydroxide was added. The reaction mixture stirred 2 days, at which time TLC analysis (5% methanol/methylene chloride) indicated the ester hydrolysis was complete. The reaction was extracted with ethyl acetate following acidification to pH=4–5 with 10% citric acid and dilution with water. The extract was washed with brine, dried over magnesium sulfate, filtered and the filtrate was evaporated in vacuo and dried to afford 75 mg (82%) of the title compound as an amorphous solid.

$^1$H-NMR (400 MHz, CD$_3$OD, ppm) δ 0.96 (t,J=7.40 Hz, 3H), 1.34 (s, 9H), 1.62–1.75 (m, 2H), 2.75 (t,J=7.40 Hz, 2H), 5.78 (s, 1H), 5.97 (s, 2H), 6.84 (d,J=8.00 Hz, 1H), 6.99 (d,J=9.20 Hz, 1H), 7.06–7.10 (m, 2H), 7.72–7.74 (m, 2H). APCI-MS m/e=511 (M+NH$_4$).

Step C: Preparation of N-(4-iso-propylbenzenesulfonyl)-α-(4-N-t-butyloxycarbonylaminosulfonyl-2-n-propylphe-noxy)-3,4-methylenedioxyphenylacetamide A solution of 68 mg (0.138 mmol) of the product of Step B and 34 mg (0.207 mmol) of 1,1'-carbonyldiimidazole in 0.8 mL of dry tetrahydrofuran was refluxed in an oil bath. After 2 hours, TLC analysis (20% methanol/methylene chloride) indicated the desired intermediate had formed. The reaction mixture was then cooled to room temperature and 41 mg (0.207 mmol) of dry 4-iso-propylbenzenesulfona-mide and 31 μL (0.207 mmol) of DBU were added. The reaction mixture was refluxed again for 25 minutes, allowed to cool, after which TLC analysis (20% methanol/methylene chloride) indicated the desired product had been formed. The reaction mixture was poured into 10% citric acid and extracted with ethyl acetate. The extract was washed with brine, dried over magnesium sulfate, and evaporated in vacuo. The residue was purified by silica-gel flash chromatography eluting first with 3% methanol/methylene chloride and then with 5% methanol/methylene chloride. The purified fractions were combined and evaporated to afford 11 mg (12%) of the title compound as an amorphous solid.

$^1$H-NMR (400 MHz, CD$_3$OD,ppm) δ 0.88 (t,J=7.40 Hz,3H), 1.24 (d,J=7.20 Hz,3H), 1.25 (d,J=7.20 Hz,3H), 1.35 (s,9H), 1.56–1.68 (m,2H), 2.60–2.69 (m,1H), 2.70–2.77 (m,1H), 2.95 (sept., J=7.20 Hz,1H), 5.46 (s,1H), 5.95 (s,2H), 6.77 (d,J=8.40 Hz,1H), 6.81 (d,J=8.40 Hz,1H), 7.00–7.03 (m,2H), 7.27 (d,J=8.00 Hz,2H), 7.60 (dd,=2.40, 8.40 Hz,1H), 7.64 (d,J=8.00 Hz,2H), 7.68 (d,J=2.4 Hz,1H). ESI-MS m/e=697 (M+Na).

EXAMPLE 147

N-(4-iso-propylbenzenesulfonyl)-α-(4-amino-sulfonyl-2-n-propylphenoxy)-3,4-methylenedioxyphenylacetamide A solution of 18 mg (0.0267 mmol) of the product of Example 146 in 0.8 mL of dimethylsulfoxide was heated to reflux for 3 minutes and cooled to room temperature. After heating, TLC analysis (20% methanol/methylene chloride) indicated the reaction was complete. The reaction was diluted with 6 mL of water and filtered through a 0.45 mm membrane filter. The filtrate was purified using a Waters 600E HPLC system with a 9.4×250 mm 5 mm Zorbax-RX C8 at 40° C. eluting at 5.0 mL/min first using 100% B (95-5 water-acetonitrile) with 0.1% TFA for 12 minutes and then switching 65% A (95-5 acetonitrile-water) 35% B (95-5 water-acetonitrile) each with 0.1% TFA where the column effluent was monitored simultaneously at 210 and 277 nM with a Waters model 490 UV-visible detector. The purified fractions were combined in a round bottom flask, frozen in a −78° C. dry ice-acetone bath and lyophylized to afford 10.7 mg (71%) of the title compound as an amorphous powder. $^1$H-NMR (400 MHz, CD$_3$OD,ppm) δ 0.90 (t,J=7.20 Hz, 3H), 1.26 (d,J=6.80 Hz, 3H), 1.27 (d,J=6.80 Hz, 3H), 1.54–1.68 (m, 2H), 2.60–2.72 (m, 2H), 3.00 (septet, J=6.80 Hz, 1H), 5.54 (s, 1H), 5.97 (s, 2H), 6.65 (d,J=8.40 Hz, 1H), 6.78 (d,J=8.00 Hz, 1H), 6.84 (d,J=1.60 Hz, 1H), 6.91 (dd,J=1.60, 8.00 Hz, 1H), 7.37 (d,J=8.40 Hz, 2H), 7.53 (dd,J=2.40, 8.40 Hz, 1H), 7.66 (d,J=2.4 Hz, 1H), 7.76 (d,J=8.40 Hz, 2H). ESI-MS m/e=575 (M+H).

EXAMPLE 148

N-(4-iso-propylbenzenesulfonyl)-α-(4-(N-methylcarbamyl)-aminosulfonyl-2-n-propylphenoxy)-3,4-methylenedioxyphenylacetamide Step A: Preparation of methyl α-(4-(N -methylcarbamyl)-aminosulfonyl-2-n-propylphenoxy)-3,4-methylene-dioxyphenylacetate To a stirred solution of 500 mg(1.23 mmol) of methyl α-(4-aminosulfonyl-2-n-propylphenoxy)-3,4-methylenedioxyphenylacetate (the product of Example 100, Step C) in dry dimethylformamide (2 mL) was added 80 µL (1.35 mmol) of methyl isocyanate followed by 6 mg (0.06 mmol) of cuprous chloride. The reaction mixture was stirred overnight, after which TLC analysis (5% methanol/methylene chloride) indicated the reaction had not proceeded to completion. Subsequently, an additional 80 µL (1.35 mmol) of methyl isocyanate, 6 mg (0.06 mmol) of cuprous chloride as well as 342 µL (2.46 mmol) of triethylamine was added and the reaction mixture was again stirred overnight. TLC analysis (5% methanol/methylene chloride) indicated the reaction had proceeded to completion. The reaction mixture was poured into 1N HCl and extracted with ethyl acetate. The extract was washed with brine, dried over magnesium sulfate, filtered and the filtrate concentrated in vacuo and dried to afford 570 mg(100%) of the title compound as an amorphous solid.

$^1$H-NMR (400 MHz, CD$_3$OD, ppm) δ0.96 (t,J=7.20 Hz, 3H), 1.64–1.77 (m, 2H), 2.65 (s, 3H), 2.74 (t,J=7.00 Hz, 2H), 3.71 (s, 3H), 5.88 (s, 1H), 5.98 (s, 2H), 6.85 (d,j=8.00 Hz, 1H), 6.95 (d,J=8.40 Hz, 1H), 7.04 (dd,J=1.60, 8.40 Hz, 1H), 7.07 (d,J=1.60 Hz, 1H), 7.72–7.76 (m, 2H). ESI-MS m/e=464 (M+1 ).

Step B: Preparation of α-(4-(N -methylcarbamyl)aminosulfonyl-2-n-propylphenoxy)-3,4-methylenedioxyphenylacetic acid To a stirred solution of 570 mg (1.23 mmol) of the product of Step A in 6 mL of methanol was added 540 µL (2.71 mmol) of 5N sodium hydroxide. The reaction mixture was allowed to stir overnight after which TLC analysis (90:10:1 chloroform/methanol/acetic acid) indicated the saponification had proceeded to completion. The reaction mixture was acidified to pH=2 using 6N HCl poured into water, and extracted with ethyl acetate. The extract was dried over magnesium sulfate, filtered and evaporated in vacuo to give the crude product. Purification of the crude product by silica-gel flash chromatography using (92:7:1 chloroform/methanol/acetic acid) afforded 384 mg (70%) of the title compound as an amorphous solid.

$^1$H-NMR (400 MHz, CD$_3$OD, ppm): δ 0.96 (t,J=7.40 Hz, 3H), 1.62–1.77 (m, 2H), 2.65 (s, 3H), 2.74 (t,J=7.60 Hz, 2H), 5.76 (s, 1H), 5.98 (s, 2H), 6.85 (d,J=8.00 Hz, 1H), 6.95 (d,J=8.40 Hz, 1H), 7.06 (d,J=1.60 Hz, 1H), 7.08 (dd,J=1.60, 8.00 Hz, 1H), 7.72–7.75 (m, 2H). CI-MS m/e=538 (M+1).

Step C: Preparation of N-(4-iso-propylbenzenesulfonyl)-α-(4-(N-methylcarbamyl)aminosulfonyl-2-n-propylphenoxy)-3,4-methylenedioxyphenylacetamide A solution of 384 mg (0.853 mmol) of the product of Step B and 208 mg (1.28 mmol) of 1,1'-carbonyldiimidazole in 2 mL of dry tetrahydrofuran was refluxed 2 minutes by placing the reaction mixture into a preheated oil bath. After brief refluxing and gas evolution, TLC analysis (90:10:1 chloroform/methanol/acetic acid) indicated that the desired intermediate had formed. The reaction mixture was then cooled to room temperature and 255 mg (1.28 mmol) of dry 4-iso-propylbenzenesulfonamide, 10 mg (0.085 mmol) of CDI followed by 191 µL (1.28 mmol) of DBU was added. The reaction mixture was refluxed for 3 minutes, allowed to cool and stir at room temperature 1 hour after which TLC analysis (96:3:1 chloroform/methanol/acetic acid) indicated the desired product had been formed. The reaction mixture was poured into 10% citric acid and extracted with ethyl acetate. The extract was washed with brine, dried over magnesium sulfate, and evaporated in vacuo. The residue was partially purified by silica-gel flash chromatography eluting first with ethyl acetate and then with (92:7:1 chloroform/methanol/acetic acid). The purified fractions were combined to afford 48 mg (9%) of the title compound. Upon standing, material precipitated from the ethyl acetate fractions to afford an addition 55 mg (10%) of the title compound. The remainder of semi-purified material was combined and purified using a Waters Delta Prep 4000 HPLC applying the residue in 6 mL total volume (4.5 mL methanol and 1.5 mL water) to an M1000 Prep-Pak module containing a 47×300 mm 15 µM DeltaPak C18 column and eluting isocratically at 50 mL/min using 60% A (95-5 acetonitile-water) and 40% B (95-5 water-acetonitrile) each with 0.1% TFA. The column effluent was monitored simultaneously at 210 and 277 nM with a Waters model 490 UV-visible detector and the purified fractions were combined in a round bottom flask, frozen in a −78° C. dry ice-acetone bath and lyophylized. The HPLC purified lyophylizate 155 mg (29%), the silica gel purified amorphous solid 48 mg (9%) and the precipitated amorphous solid 55 mg (10%) were combined to afford 258 mg (48%) of the title compound.

$^1$H-NMR (400 MHz, CD$_3$OD, ppm): δ 0.89 (t,J=7.40 Hz, 3H), 1.26 (d,J=6.80 Hz, 3H), 1.27 (d,J=6.80 Hz, 3H), 1.55–1.65 (m, 2H), 2.63–2.70 (m, 5H), 3.00 (septet,J= 6.80 Hz, 1H), 5.56 (s, 1H), 5.97 (s, 2H), 6.67 (d,J=8.40 Hz, 1H), 6.79 (d,J=7.60 Hz, 1H), 6.84 (d,J=1.60 Hz, 1H), 6.91 (dd,J=1.60, 7.60 Hz, 1H), 7.38 (d,=8.40 Hz, 2H), 7.62 (dd,J=2.40, 8.40 Hz, 1H), 7.71 (d,J=2.40 Hz, 1H), 7.77 (d,J=8.40 Hz, 2H). CI-MS m/e=632 (M+1).

Step D: Preparation of N-(4-iso-propylbenzenesulfonyl)-α-(4-(N-methylcarbamyl)aminosulfonyl-2-n-propylphenoxy)-3,4-methylenedioxyphenylacetamide dipotassium salt.

To a solution of 250 mg (0.396 mmol) of the product of Step C in 3 mL of methanol was added 1.58 mL (1.58 mmol) of a 1N potassium hydroxide in methanol solution. The reaction mixture was stirred 15 minutes at RT, diluted with 7 mL of water and filtered through a 0.45 gM membrane filter. The filtrate was purified using a Waters Delta Prep 3000 HPLC by applying the compound in a 15 mL total volume (8 mL methanol and 7 mL water) to an M1000 Prep-Pak module containing a 47×300 mm 15 μM DeltaPak C18 column and eluting at 50 mL/min first using 100% B (95-5 water-acetonitrile) for 10 minutes and then a 30 minute linear gradient to 60% A (95-5 acetonitile-water) and 40% B (95-5 water-acetonitrile). The column effluent was monitored simultaneously at 210 and 277 nM with a Waters model 490 UV-visible detector and the purified fractions were combined in a round bottom flask, frozen in a −78° C. dry ice-acetone bath and lyophilized to afford 221 mg (79%) of the title compound as a white lyophilized powder.

$^1$H-NMR (400 MHz, CD$_3$OD,ppm): δ 0.89 (t,J=7.40 Hz, 3H), 1.22 (d,J=6.80 Hz, 3H), 1.23 (d,J=6.80 Hz, 3H), 1.53–1.68 (m, 2H), 2.54–2.62 (m, 4H), 2.67–2.74 (m, 1H), 2.91 (septet, J=6.80 Hz, 1H), 5.34 (s, 1H), 5.92 (s, 2H), 6.73–6.79 (m, 2H), 7.00–7.02 (m, 2H), 7.20 (d,J=8.00 Hz, 2H), 7.57 (dd,J=1.80, 8.60 Hz, 1H), 7.61–7.64 (m, 3H). ESI-MS m/e=701 (M+1).

EXAMPLE 149

N-(4-iso-propylbenzenesulfonyl)-α-(4-(methylsulfonylcarbamyl)-2-n-propylphenoxy)-3,4-methylenedioxyphenylacetamide dipotassium salt Step A: Preparation of N-(4-iso-propylbenzenesulfonyl)-α-(4-(methylsulfonylcarbamyl)-2-n-propylphenoxy)-3,4-methylenedioxyphenylacetamide A solution of 146 mg (0.271 mmol) of N-(4-iso-propyl-benzenesulfonyl)-α-(4-carboxy-2-n-propylphenoxy)-3,4-methylenedioxyphenylacetamide (free acid form of the product of Example 58) and 66 mg (0.406 mmol) of 1,1'-carbonyldiimidazole in 1 mL of dry tetrahydrofuran was refluxed for 1.5 hours. The reaction mixture was cooled to room temperature and 39 mg (0.406 mmol) of methanesulfonamide and 101 μL (0.667 mmol) of DBU were added and the mixture was refluxed again. The reaction progress was monitored by analytical HPLC analysis using a Waters 600E HPLC system with a 4.6×250 mm 5 μM Zorbax C18 column at 40° C. and eluting isocratically 1.5 mL/min using 60% A (95-5 acetonitrile-water) 40% B (95-5 water-acetonitrile) each with 0.1% TFA where the column effluent was monitored simultaneously at 210 and 277 nM with a Waters model 490 UV-visible detector. After 1.0 hour of additional refluxing, analytical HPLC analysis indicated that the coupling was complete. The reaction mixture poured into 1N HCl and extracted with ethyl acetate, washed with brine, dried over magnesium sulfate, filtered, and the filtrate evaporated in vacuo to afford 160 mg (96%) of the title compound as an amorphous solid.

$^1$H-NMR (400 MHz, CD$_3$OD,ppm): δ 0.90 (t,J=7.40 Hz, 3H), 1.25 (d,J=6.80 Hz, 3H), 1.26 (dd=6.80 Hz, 3H), 1.53–1.66 (m, 2H), 2.58–2.63 (m, 2H), 3.00 (septet, J=6.80 Hz, 1H), 3.33 (s, 3H), 5.54 (s, 1H), 5.97 (s, 2H), 6.61 (d,J=8.80 Hz, 1H), 6.79 (d,J=8.00 Hz, 1H), 6.87 (dd=1.60 Hz, 1H), 6.93 (dd,J=1.60, 8.80 Hz, 1H), 7.36 (d,J=8.40 Hz, 2H), 7.56 (d,J=2.40, 8.80 Hz, 1H), 7.70 (d,J=2.40 Hz, 1H), 7.77 (d,J=8.40 Hz, 2H). CI-MS m/e= 634 (M+NH$_4$).

Step B: Preparation of N-(4-iso-propylbenzenesulfonyl)-α-(4-(methylsulfonylcarbamyl)-2-n-propylphenoxy)-3,4-methylenedioxyphenylacetamide dipotassium salt To a solution of 160 mg (0.260 mmol) of the product of Step B in 1 mL of methanol was added 1.04 mL (1.04 mmol) of a 1N potassium hydroxide in methanol solution. The reaction mixture was stirred 15 minutes at RT, diluted with 4 mL of water and filtered through a 0.45 μM membrane filter. The filtrate was purified using a Waters Delta Prep 3000 HPLC by applying the compound in a 10 mL total volume (6 mL methanol and 4 mL water) to an M1000 Prep-Pak module containing a 47×300 mm 15 μM DeltaPak C18 column and eluting at 50 mL/min first using 100% B (95-5 water-acetonitrile) for 10 minutes and then a 30 minute linear gradient to 60% A (95-5 acetonitile-water) and 40% B (95-5 water-acetonitrile). The column effluent was monitored simultaneously at 210 and 277 nM with a Waters model 490 UV-visible detector and the purified fractions were combined in a round bottom flask, frozen in a −78° C. dry ice-acetone bath and lyophilized to afford 138 mg (77%) of the title compound as a white lyophilized powder.

$^1$H-NMR (400 MHz, CD$_3$OD,ppm): δ 0.87 (t,J=7.40 Hz, 3H), 1.21 (d,=6.80 Hz, 6H), 1.52–1.67 (m, 2H), 2.51–2.58 (m, 1H), 2.67–2.74 (m, 1H), 2.91 (septet,J=6.80 Hz, 1H), 3.07 (s, 3H), 5.33 (s, 1H), 5.92 (s, 2H), 6.70 (d,J=8.80 Hz, 1H), 6.74 (dd,J=2.20, 6.20 Hz, 1H), 7.02–7.04 (m, 2H), 7.21 (d,J=8.40 Hz, 2H), 7.65 (d,J=8.40 Hz, 2H), 7.70 (dd,J=2.20, 8.40 Hz, 1H), 7.78 (d,=2.00 Hz, 1H). ESI-MS m/e=693 (M+1).

EXAMPLE 150

N-(4-iso-propyl benzenesulfonyl)-α-(4-sulfamylcarbamyl)-2-n- propylphenoxy)-3,4-methylenedioxyphenylacetamide dipotassium salt Step A: Preparation of N-(4-iso-propylbenzenesulfonyl)-α-(4-(sulfamylcarbamyl)-2-n-propylphenoxy)- 3,4-methylenedioxyphenylacetamide A solution of 158 mg (0.293 mmol) of N-(4-iso-propyl-benzenesulfonyl)-α-(4-carboxy-2-n-propylphenoxy)-3,4-methylenedioxyphenylacetamide (free acid form of the product of Example 58) and 71 mg (0.440 mmol) of 1,1'-carbonyldiimidazole in 1 mL of dry tetrahydrofuran was refluxed for 3.5 hours. The reaction mixture was cooled to room temperature and 141 mg (1.47 mmol) of sulfamide and 110 μL (0.733 mmol) of DBU were added and the mixture was refluxed again. The reaction progress was monitored by analytical HPLC analysis using a Waters 600E HPLC system with a 4.6×250 mm 5 μM Zorbax-RX C8 at 40° C. and eluting isocratically 1.5 mL/min using 60% A (95-5 acetonitrile-water) 40% B (95-5 water-acetonitrile) each with 0.1% TFA where the column effluent was monitored at 254 nM with a Waters model 490 UV-visible detector. After 2.0 hour of additional refluxing, analytical HPLC analysis indicated that the coupling was complete. The reaction mixture was diluted with 2.5 mL of methanol and 2 mL of water, filtered and the filtrate partially purified was purified using a Varian 5500 HPLC by applying the compound in a 4.5 mL total volume (2.5 mL methanol and 2 mL water) onto two in series 21.2×250 mm Zorbax ODS C18 columns and eluting at 15 mL/min with 60% acetonitrile and 40% water both with 0.1% TFA. The column effluent was monitored 254 nM with a Kratos Spectroflow 783 UV detector. Combination and evaporation of the purified fractions afforded 50 mg (28%) of the title compound. The mixed fractions were combined and subjected to a second preparative HPLC chromatography using a linear gradient over 35 minutes from 65% water and 35% acetonitrile both with 0.1% TFA to 65% acetonitrile and 35% water both with 0.1% TFA, holding all other conditions from the previous chromatography. The purified fractions were combined and concentrated to afford 57 mg (31%) of the title compound, which was combined with the previously purified material to provide a total of 107 mg (59%) of the title compound as an amorphous solid.

$^1$NMR (400 MHz, CD$_3$OD,ppm): δ 0.89 (tJ=7.40 Hz, 3H), 1.25 (d,J=6.80 Hz, 3H), 1.26 (d,J=6.80 Hz, 3H), 1.53–1.66 (m, 2H), 2.58–2.73 (m, 2H), 2.98 (septet, J=6.80 Hz, 1H), 5.54 (s, 1H), 5.97 (s, 2H), 6.62 (d,J=8.80 Hz, 1H), 6.79 (d,J=8.00 Hz, 1H), 6.86 (d,J=1.60 Hz, 1H), 6.92 (dd,J=1.60, 8.00 Hz, 1H), 7.36 (d,J=8.50 Hz, 2H), 7.56 (d,J=2.40, 8.80 Hz, 1H), 7.69 (dJ =2.40 Hz, 1H), 7.77 (d,J=8.50 Hz, 2H). ESI-MS m/e=618 (M+1 ).

Step B: Preparation of N-(4-iso-propylbenzenesulfonyl)-α-(4-(aminosulfonylamino-N'- 1 -oxomethyl)-2-n-propyl-phenoxy)-3,4-methylenedioxyphenylacetamide dipotassium salt To a solution of 107 mg (0.173 mmol) of the product of Step B in 1.5 mL of methanol was added 0.691 mL (0.691 mmol) of a 1N solution of potassium hydroxide in methanol. The reaction mixture was stirred 15 minutes at RT, diluted with 1 mL of water and filtered through a 0.45 µM membrane filter. The filtrate was purified using a Varian 5500 HPLC by applying the compound in a 4.0 mL total volume (3 mL methanol and 1 mL water) onto two in series 21.2×250 mm Zorbax ODS C18 columns and eluting at 15 mL/min first using 95% water and 5% acetonitrile for 10 minutes and then a 30 minute linear gradient to 60% acetonitrile and 40% water. The column effluent was monitored 254 nM with a Kratos Spectroflow 783 UV detector and the purified fractions were combined in a round bottom flask, frozen in a –78° C. dry ice-acetone bath and lyophylized to afford 84 mg (73%) of the title compound as a white lyophilized powder.

$^1$H-NMR (400 MHz, CD$_3$OD,ppm): δ 5 0.87 (t,J=7.40 Hz, 3H), 1.20 (d,J=6.80 Hz, 3H), 1.21 (d,J=6.80 Hz, 3H), 1.53–1.66 (m, 2H), 2.51–2.59 (m, 1H), 2.67–2.74 (m, 1H), 2.91 (septet,J=6.80 Hz, 1H), 3.07 (s, 3H), 5.33 (s, 1H), 5.92 (s, 2H), 6.71–6.75 (m, 2H), 7.01–7.04 (m, 2H), 7.19–7.22 (m, 2H), 7.64–7.70 (m, 3H), 7.77 (d,J=2.4 Hz, 1H). ESI-MS m/e=694 (M+1 ).

EXAMPLE 151

N-(4-iso-propylbenzenesulfonyl)-α-(4-cyano-2-n-propylphenoxy)-3,4-methylenedioxyphenylacetamide potassium salt Step A: Preparation of 3-allyl-4-hydroxybenzonitrile To a stirred solution of 25.00 g (210.1 mmol) of 4-cyanophenol in 100 mL of acetone was added 30.49 g (220.6 mmol) of powdered potassium carbonate followed by 19.09 mL (220.6 mmol) of allyl bromide and the reaction mixture refluxed overnight. TLC analysis (15% ethyl acetate/hexane) indicated that the alkylation was complete and the reaction mixture was filtered, the filtrated evaporated in vacuo to afford 33.20 g (99%) of a light yellow oil. The 33.20 (209 mmol) of crude O-allyl ether was dissolved in 100 mL of 1,2-dichlorobenzene and stirred at reflux for 56 hours until TLC analysis (15% ethyl acetate/hexane) indicated essentially no starting material remained. The reaction mixture was poured into 300 mL of hexane, cooled in a freezer overnight, and the precipitate was filtered and dried in vacuo to provide 29.76 g (90%) of the title compound as a light tan amorphous solid.

$^1$H-NMR (300 MHz, CDCl$_3$, ppm): δ 3.36 (d,=6.30 Hz,2H), 5.09–5.19 (m, 2H), 5.79 (bs, 1H), 5.86–6.00 (m, 1H), 6.82 (dd,J=1.80, 7.20 Hz, 1H), 7.38–7.41 (m, 2H). El-MS m/e=159 (M$^+$)

Step B: preparation of 4-hydroxy-3-n-propylbenzonitrile

A Parr hydrogenation shaker was charged with a solution of 29.76 g (187 mmol) of the product of Step A in 100 mL of ethanol and 3.00 g of a 10% palladium on carbon catalyst was added. The flask was mounted in the hydrogenation appartus, freed of air, pressurized with hydrogen (40 psig) and shaken 80 minutes. At the end of this preiod, TLC analysis (15% ethyl acetate/hexane) indicated that the reaction was complete and the reaction mixture was filtered and evaporated. The product was dried in vacuo to afford 30.01 g (99%) of the title compound as a yellow oil.

$^1$H-NMR (300 MHz, CDCl$_3$, ppm): δ 0.92 (t,J=7.40 Hz, 3H), 1.53–1.65 (m, 2H), 2.54 (t,J=7.60 Hz, 2H), 6.77 (d,J=8.10 Hz, 1H), 7.32–7.37 (m, 2H). El-MS m/e=161 (M$^+$)

Step C: Preparation of methyl α-(2-n-propyl-4-cyanophenoxy)-3,4-methylenedioxyphenylacetate To a stirred solution of 4.50 g (27.95 mmol) of the product of Step B in 30 mL of acetone was added 4.64 g (33.54 mmol) of powdered potassium carbonate and the reaction mixture was stirred for 10 minutes. Methyl α-bromo-3,4-methylenedioxyphenylacetate (8.01 g; 29.35 mmol) was then added and the reaction mixture refluxed overnight. The reaction mixture was cooled, filtered, and the filtrate evaporated in vacuo, dried in a vacuum to afford 10.30 g (9.87 g theoretical) of the title compound which was used without purification in the next step.

$^1$H-NMR (300 MHz, CDCl$_3$, ppm): δ 0.92 (t,J=7.40 Hz,3H), 1.58–1.68 (m, 2H), 2.60–2.71 (m, 2H), 5.53 (s, 1H), 5.95 (s, 2H), 6.68 (d,J=8.10 Hz, 1H), 6.78 (d,J=7.80 Hz, 1H), 6.95–6.98 (m, 2H), 7.35–7.39 (m, 2H). El-MS m/e=353 (M$^+$).

Step D: Preparation of methyl α-(2-n-propyl-4-cyanophenoxy)-3,4-methylenedioxyphenylacetic acid To a solution of 3.5 g (8.64 mmol) of the product of Step C in 30 mL of methanol was added 2.07 mL (10.37 mmol) of 5.0N aqueous sodium hydroxide solution. After stirring overnight, TLC analysis (80:15:1 chloroform/methanol/ammonium hydroxide) indicated that the saponification was complete. The reaction mixture was acidified to pH 3 with 6N aqueous HCl and concentrated in vacuo.

With heating and sonnication, the residue was redissolved in ethyl acetate, washed with brine, dried over magnesium sulfate, filtered, and the filtrate evaporated in vacuo to afford 2.92 g (99%) of the title compound as an amorphous solid which was used without further purification in the next step.

$^1$H-NMR (300 MHz, CD$_3$OD, ppm): δ 0.90 (t,J=7.40 Hz, 3H), 1.58–1.68 (m, 2H), 2.66 (t,J=7.60 Hz, 2H), 5.72 (s,1H), 5.92 (s, 2H), 6.60 (d,J=8.10 Hz, 1H), 6.90–6.93 (m, 1H), 7.00–7.04 (m, 2H), 7.45–7.47 (m,H). El-MS m/e=339 (M$^+$).

Step E: Preparation of N-(4-iso-propylbenzenesulfonyl)-α-(4-cyano-2-n-propylphenoxy)-3,4-methylenedioxyphenyl-acetamide To a stirred solution of 2.92 g (8.61 mmol) of the product of Step D in 40 mL of methylene chloride was added 2.31 g (12.05 mmol) of 1-(3-dimethylaminopropyl)-3-ethylcarbodiimide hydrochloride, 1.26 g (10.33 mmol)of 4-dimethylaminopyridine, and 1.89 g (9.47 mmol) of 4-iso-propylbenzenesulfonamide. The reaction mixture was stirred overnight and after TLC analysis (80:15:1 chloroform/ methanol/ammonium hydroxide) was poured into 1N HCl and extracted with ethyl acetate. The extract was washed with brine, dried over magnesium sulfate, filtered, and evaporated in vacuo. The residue was partially purified with silica gel flash chromatography eluting first with 40% ethyl acetate-hexane and then with 3% methanol-methylene chloride to flush the column. All of the product fractions were contaminated and were chromatographed. The 3.86 g of semi-purified material was dissolved in 15 mL of acetonitrile and 15 mL of water and filtered through a 0.45 µM membrane filter. The compound was purified using a Waters Delta Prep 3000 HPLC by applying the filtered solution to an M1000 Prep-Pak module containing a 47×300 mm 15 mM DeltaPak C18 column and eluting at 50 mL/min first using 50% A (95-5 acetonitile-water) and 50% B (95-5 water-acetonitrile) with 0.1% TFA for 15 minutes and then 70% A (95-5 acetonitile-water) and 30% B (95-5 water-acetonitrile) both with 0.1% TFA. The column effluent was monitored simultaneously at 210 and 277 nM with a Waters model 490 UV-visible detector and the purified fractions were combined in a round bottom flask and concentrated in vacuo to afford 1.45 g (38%) of the title compound as an amorphous solid.

$^1$H-NMR (500 MHz, CD$_3$OD, ppm): δ 0.89 (t,J=7.50 Hz, 3H), 1.26 (d,J=7.00 Hz, 3H), 1.27 (d,J=7.00 Hz, 3H), 1.53–1.61 (m, 2H), 2.59–2.66 (m, 2H), 3.00 (septet,J=7.00 Hz, 1H), 5.55 (s, 1H), 5.97 (s, 2H), 6.60 (d,J=7.50 Hz, 1H), 6.79 (d,J=8.00 Hz, 1H), 6.85 (d,J=2.50 Hz, 1H), 6.92 (dd,J=2.00, 8.20 Hz, 1H), 7.31 (dd,J=2.50, 8.00 Hz, 1H), 7.38 (d,J=8.50 Hz, 2H), 7.45 (d,J=2.00 Hz, 1H), 7.78 (d,J=8.50 Hz, 2H).

Step F: Preparation of N-(4-iso-propylbenzenesulfonyl)-α-(4-cyano-2-n-propylphenoxy)-3,4-methylenedioxy-phenylacetamide potassium salt To a stirred solution of 393 mg (0.756 mmol) of the the product of Step E in 1 mL of methanol was added 2.26 mL (2.27 mmol) of a 1N potassium hydroxide solution in methanol. The reaction mixture was stirred 15 minutes, diluted with water and filtered through a 0.45 µM membrane filter. The filtrate was purified using a Varian 5500 HPLC by applying the compound in a 4.0 mL total volume (3 mL methanol and 1 mL water) onto two in series 21.2×250 mm Zorbax ODS columns and eluting at 15 mL/min first using 85% water and 15% acetonitrile for 10 minutes and then a 30 minute linear gradient to 50% acetonitrile and 50% water. The column effluent was monitored 254 nM with a Kratos Spectroflow 783 UV detector and the purified fractions were combined in a round bottom flask, frozen in a −78° C. dry ice-acetone bath and lyophylized to afford 177 mg (42%) of the title compound as a white lyophilized powder.

$^1$H-NMR (500 MHz, CD$_3$OD, ppm): δ 0.88 (t,J=7.50 Hz, 3H), 1.23 (s, 3H), 1.24 (s, 3H), 1.55–1.62 (m, 2H), 2.53–2.59 (m, 1H), 2.67–2.73 (m, 1H), 3.90–2.94 (m, 1H), 5.37 (s, 1H), 5.94 (s, 2H), 6.76–6.78 (m, 2H), 7.02–7.04 (m, 2H), 7.21 (d,J=8.50 Hz, 2H), 7.27 (dd,J=2.00, 8.50 Hz, 1H), 7.38 (d,J=2.00 Hz, 1H), 7.66 (d,J=8.50 Hz, 2H). ESI-MS m/e =559 (M+1).

EXAMPLE 152

N-(4-iso-propylbenzenesulfonyl)-α-(4-(tetrazol-5-yl)-2-n-propyl-phenoxy)-3,4-methylenedioxyphenylacetamide dipotassium salt Step A: Preparation of N-(4-iso-propylbenzenesulfonyl)-α-(4-(tetrazol-5-yl)-2-n-propylphenoxy)-3,4-methylenedioxy-phenylacetamide A stirred solution of 600 mg (1.15 mmol) of the product of Example 151, Step F and 284 mg (1.38 mmol) of trimethyltin azide in 2 mL of toluene was heated with an oil bath at reflux overnight. The reaction was evaporated in vacuo, purified by silica gel flash chromatography eluting with methylene chloride/methanol/acetic acid 100:3:1, and the purified fractions concentrated in vacuo to afford 244 mg (38%) of the title compound as an amorphous solid.

$^1$H-NMR (500 MHz, CD$_3$OD,ppm): δ0.90–0.94 (m, 2H), 1.16–1.19 (m, 6H), 1.60–1.68 (m, 2H), 2.64–2.75 (m, 2H), 2.89–2.95 (m, 1H), 5.56 (s, 1H), 5.96 (s, 2H), 6.73 (d,J=8.50 Hz, 1H), 6.79 (d,J=8.00 Hz, 1H), 6.89 (d,J=2.00 Hz, 1H), 6.94 (dd,J=2.00, 8.00 Hz, 1H), 7.34 (dd,J=1.50, 8.50 Hz, 2H), 7.64 (dd,J=2.00, 8.50 Hz, 1H), 7.76 (d,J=2.00 Hz, 1H), (dd,J=2.00, 8.50 Hz, 2H). ESI-MS m/e=564 (M+1).

Step B: Preparation of N-(4-iso-propylbenzenesulfonyl)-α-(4-tetrazo-5-yl- 2-n-propylphenoxy)- 3,4-methylenedioxy-phenylacetamide dipotassium salt To a stirred solution of 240 mg (0.426 mmol) of the product of Step A in 3 ml of methanol was added 2.41 mL (2.41 mmol) of a 1N potassium hydroxide solution in methanol. The reaction mixture was stirred 15 minutes, diluted with 4 mL of water and filtered through a 0.45 µM membrane filter. The filtrate was purified using a Varian 5500 HPLC by applying the compound in a 8.0 mL total volume (4 mL methanol and 4 mL water) onto two in series 21.2×250 mm Zorbax ODS columns and eluting at 15 mL/min first using 90% water and 10% acetonitrile for 5 minutes and then a 30 minute linear gradient to 40% acetonitrile and 60% water. The column effluent was monitored 254 nM with a Kratos Spectroflow 783 UV detector and the purified fractions were combined in a round bottom flask, frozen in a −78° C. dry ice-acetone bath and lyophylized to afford 196 mg (72%) of the title compound as a white lyophilized powder.

$^1$H-NMR (500 MHz, CD$_3$OD,ppm): δ 5 0.91 (t,J=7.20 Hz, 3H), 1.15 (d,J=7.0 Hz, 3H), 1.16 (d,J=7.0 Hz, 3H), 1.62–1.68 (m, 2H), 2.58–2.64 (m, 1H), 2.74–2.80 (m, 1H), 2.86 (septet,J=7.00 Hz, 1H), 5.36 (s, 1H), 5.93 (d,J=1.20 Hz, 1H), 5.94 (d,J=b 1.20Hz, 1H), 6.76 (d,J=7.50 Hz, 1H), 6.82 (d,J=8.50 Hz, 1H), 7.04–7.07 (m, 2H), 7.20 (d,J=8.50 Hz, 2H), 7.65–7.69 (m, 3H), 7.78(d,J=2.00 Hz, 1H). ESI-MS m/e=640 (M+1).

EXAMPLE 153

N-(4-iso-propylbenzenesulfonyl)-α-(4-N-methyl-N-methoxycarbamyl-2-n-propylphenoxy)-3,4-methylenedioxyphenylacetamide Step A: N-(4-iso-propylbenzenesulfonyl)-α-(4-N-methyl-N-methoxycarbamyl- 2-n-propylphenoxy )-3,4-methylenedioxyphenylacetamide To a 0° C. suspension of 2.00 g (3.25 mmol) of the product of Example 58 and 951 mg (9.75 mmol) N,O-dimethylhydroxylamine hydrochloride in 15 mL of methylene chloride and 1.36 mL (9.75 mmol) of triethylamine was added 1.49 g (9.75 mmol) of 1-hydroxybenzotriazole hydrate and 1.87 g (9.75 mmol) of 1-(-3-dimethylaminopropyl)-3-ethylcarbodiimide hydrochloride. The reaction mixture was stirred 16 hour and allowed to warm to room temperature after which TLC analysis (10% methanol/methylene chloride) indicated that the coupling reaction was complete. The reaction was diluted with ethyl acetate (30 mL) and partitioned with water (150 mL). The organic layer was washed with 1N HCl (50 mL), brine (50 mL), dried over MgSO₄, filtered, evaporated in vacuo affording 1.64 g (87%) of the title compound as an amorphous powder.

¹H-NMR(400 MHz, d₆-DMSO,ppm): δ 0.82 (t,J=7.20 Hz, 3H), 1.17 (d,J=7.20 Hz, 6H), 1.43–1.58 (m, 2H), 2.48–2.60 (m, 2H), 2.93 (septet, J=7.20 Hz, 1H), 3.19 (s, 1H), 3.51 (s, 3H), 5.66 (s, 1H), 6.03 (dd,J=1.20Hz, 1H), 6.04 (d,J=1.20 Hz, 1H), 6.47 (d,J=8.40 Hz, 1H), 6.91–6.98 (m, 3H), 7.25 (dd,J=2.00, 8.40 Hz, 1H), 7.38 (d,J=2.00 Hz, 1H), 7.41 (d,J=8.40 Hz, 2H), 7.69 (d,J=8.40 Hz, 2H). ESI-MS m/e=583 (M+1).

EXAMPLE 154

N-(4-iso-propylbenzenesulfonyl)-α-(4-acyl-2-n-propylphenoxy)- 3,4-methylenedioxyphenylacetamide dipotassium salt Step A: Preparation of N-(4-iso-propylbenzenesulfonyl)-α-(4-acyl-2-n-propylphenoxy).3,4-methylenedioxyphenylacetmide To a 0° C. stirred suspension of 594 mg (1.02 mmol) of the product of Example 153 in 8 mL of dry tetrahydrofuran was added 1.19 mL (3.57 mmol) of methylmagnesium chloride as a 3.0M solution in tetrahydrofuran. Following the addition of the Grignard reagent, a homogenous reaction mixture was achieved which was then allowed to warm to room temperature. After stirring 3 hours, TLC analysis (10% methanol/methylene chloride) indicated that the coupling reaction was complete. The reaction mixture was poured into 5% 6N HCl/ethanol (20 mL) and then partitioned between brine (60 mL) and ethyl acetate (30 mL). The extract was dried over magnesium sulfate, filtered and the filtrate concentrated in vacuo affording 373 mg (68%) of the title compound as an amorphous powder.

¹H-NMR (400 MHz, CD₃OD,ppm): δ 0.88 (t,J=7.20 Hz, 3H), 1.21 (d,J=6.80 Hz, 6H), 1.54–1.66 (m, 2H), 2.51 (s, 3H), 2.55–2.63(m, 1H), 2.67–2.75 (m, 1H), 2.91 (septet, dJ=6.80 Hz, 1H), 5.43 (s, 1H), 5.94 (d,J=1.20 Hz, 2H), 6.74–6.77 (m, 2H), 7.01–7.03 (m, 2H), 7.23 (d,J=8.40 Hz, 2H), 7.65–7.69 (m, 3H), 7.73 (dd,J=2.40 Hz, 1H). CI-MS m/e=538 (M+1).

Step B: Preparation of N-(4-iso-propylbenzenesulfonyl)-α-(4-acyl-2-n-propylphenoxy)-3,4-methylenedioxyphenylacetamide potassium salt The titled compound is prepared using the product of Step A according to the procedure described in Example 152, Step B.

What is claimed is:

1. A compound of structural formula I:

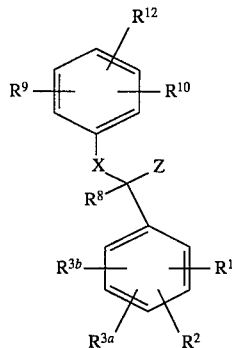

I or a pharmaceutically acceptable salt thereof, wherein:
R³ᵃ and R³ᵇ are independently:
(a) H,
(b) F, Cl, Br, or I,
(c) —NO₂,
(d) —NH₂,
(e) —NH(C₁-C₄)-alkyl,
(f) —N[(C₁-C₄)-alkyl]₂,
(g) —SO₂NHR⁷,
(h) —CF₃,
(i) (C₁-C₆)-alkyl,
(j) —OR⁷,
(k) —S(O)ₙ—(C₁-C₄)-alkyl,
(l) —NHCO—(C₁-C₄)-alkyl,
(m) —NHCO—O(C₁-C₄)-alkyl,
(n) —CH₂O—(C₁-C₄)-alkyl,
(o) —O—(CH₂)ₘ—OR⁷,
(p) —CONR⁷R¹¹,
(q) —COOR⁷, or
(r) —phenyl;

R¹ and R² on adjacent carbon atoms are joined together to form a ring structure:

A represents:
a) —Y—C(R⁴)=C(R⁵)—,
b) —Y—[C(R⁶)(R⁶)]ₛ—Y—,
c) —Y—C(R⁶)(R⁶)—C(R⁶)(R⁶)—,
d) —C(R⁴)=C(R⁵)—Y—, or
e) —C(R⁶)(R⁶)—C(R⁶)(R⁶)—Y—;

n is 0, 1, or 2;
m is 2, 3 or 4;
s is 1 or 2;
Y is —O—, or —S(O)ₙ—;
R⁴ and R⁵ are independently;
(a) H,
(b) (C₁-C₆)-alkyl or (C₂-C₆)-alkenyl each of which is unsubstituted or substituted with one or two substituents selected from the group consisting of:
i) —OH,
ii) —O—(C₁-C₄)-alkyl,
iii) —S(O)ₙ—(C₁-C₄)-alkyl,
—NR⁷—(C₁-C₄)-alkyl,
v) —NHR⁷,
vi) —COOR⁷,
vii) —CONHR⁷,
viii) —OCOR¹¹, or
ix) —CONR⁷R¹¹,
(c) (C₃-C₇)-cycloalkyl,
(d) F, Cl, Br, I,
(e) CF₃,
(f) —COOR⁷,
(g) —CONR⁷R¹¹,
(h) —NR⁷R¹¹,
(i) —NR⁷CONR⁷R¹¹,
(j) —NR⁷COOR¹¹,
(k) —SO₂NR⁷R¹¹,
(l) —O—(C₁-C₄)-alkyl,
(m) —S(O)ₙ—(C₁-C₄)-alkyl, or
(n) —NHSO₂R¹¹;

R6 is:
(a) H,
(b) (C₁-C₄)-alkyl unsubstituted or substituted with one of the following substituents:
i) —OH, ii) —NR⁷R¹¹,
iii) —COOR⁷,
iv) —CONHR⁷, or
v) —CONR⁷R¹¹
Cl, or F;

R⁷ is:
(a) H,
(b) $(C_1-C_6)$-alkyl,
(c) phenyl,
(d) $(C_1-C_6)$-alkylphenyl, or
(e) $(C_3-C_7)$-cycloalkyl;

R⁸ is:
(a) H,
(b) $(C_1-C_6)$-alkyl, unsubstituted or substituted with a substituent selected from the group consisting of:
 (i) —phenyl,
 (ii) —$(C_3-C_7)$-cycloalkyl,
 (iii) —NR⁷R¹¹,
 (iv) —morpholin-4-yl,
 (v) —OH,
 (vi) —CO₂R⁷, or
 (vii) —CON(R⁷)₂,
(c) phenyl, unsubstituted or substituted with a substituent selected from the group consisting of:
 i) $(C_1-C_4)$-alkyl
 ii) —O—$(C_1-C_4)$-alkyl
 iii) —CONR⁷R¹¹,
 iv) F, Cl, Br or I, or
 v) —COOR⁷;

R⁹ and R¹⁰ are independently:
(a) H,
(b) $(C_1-C_6)$-alkyl, unsubstituted or substituted with $(C_3-C_7)$-cycloalkyl or —CO₂R⁷,
(c) $(C_2-C_6)$-alkenyl,
(d) $(C_2-C_6)$-alkynyl,
(e) Cl, Br, F, I,
(f) $(C_1-C_6)$-alkoxy,
(g) perfluoro-$(C_1-C_6)$-alkyl,
(h) $(C_3-C_7)$-cycloalkyl, unsubstimted or substituted with $(C_1-C_6)$-alkyl,
(i) phenyl,
(j) $(C_1-C_6)$-alkyl-$S(O)_n$—$(CH_2)_n$—,
(k) hydroxy-$(C_1-C_6)$-alkyl,
(l) —CF₃,
(m) —CO₂R⁷,
(n) —OH,
(o) —NR⁷R¹¹,
(p) —[$(C_1-C_6)$-alkyl]NR⁷R¹¹,
(q) —NO₂,
(r) —$(CH_2)_n$—SO₂—N(R⁷)₂,
(s) —NR⁷CO—$(C_1-C_4)$-alkyl, or
(t) —CON(R⁷)₂;

R⁹ and R 10 on adjacent carbons can join together to form a fused phenyl ring, unsubstituted or substituted with a substituent selected from the group consisting of: $(C_1-C_6)$-alkyl, $(C_1-C_6)$-alkoxy, $(C_3-C_7)$-cycloalkyl and $(C_1-C_6)$-alkyl-$(C_3-C_7)$-cycloalkyl, R¹¹ is
(a) $(C_1-C_6)$-alkyl, unsubstituted or substituted with a substituent selected from the group consisting of:
 i) —OR⁷,
 ii) —N[R⁷]₂,
 iii) —NH₂,
 iv) —COOR⁷,
 v) —N[CH₂CH₂]₂Q,
 vi) —CF₃, or
 vii) —CON(R⁷)₂;
(b) aryl, wherein aryl is defined as phenyl or naphthyl which is unsubstituted or substituted with one or two substituents selected from the group consisting of:
 i) $(C_1-C_4)$-alkyl,
 ii) —O—$(C_1-C_4)$-alkyl,
 iii) —CO[NR⁷]₂,
 iv) F, Cl, Br or I,
 v) —COOR⁷,
 vi) —NH₂,
 vii) —NH[$(C_1-C_4)$-alkyl],
 viii) —N[$(C_1-C_4)$-alkyl]₂, or
 ix) —CON[CH₂CH₂]₂Q;
(c) —$(C_1-C_4)$-alkylaryl, wherein aryl is as defined above,
(d) $(C_3-C_7)$-cycloalkyl,

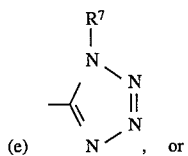
(e) , or (f) CF₃;

R⁷ and R¹¹ on the same nitrogen atom they can join together to form a ring selected from the group consisting of: morpholinyl, piperazinyl, or pyrrolyl, or Q is O, S or —NR⁷;

R¹² is
(a) H
(b) $(C_1-C_6)$-alkyl, unsubstituted or substituted with one or two substituents consisting of:
 —OH,
 ii) —O—$(C_1-C_4)$-alkyl,
 iii) —O—$(C_1-C_4)$-cycloalkyl,
 iv) —$S(O)_n$—$(C_1-C_4)$-alkyl,
 v) —NR⁷R¹¹,
 vi) —COOR⁷,
 vii) —CONHR⁷,
 viii) —OCOR¹¹,
 ix) —CONR⁷R¹¹,
 x) NR⁷CONR⁷R¹¹,
 xi) —NR⁷COOR¹¹,
 xii) —C(R⁶)(OH)—C(R⁶)(R⁷)(OH),
 xiii) —SO₂NR⁷R¹¹, or

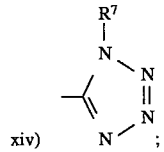
xiv) ;

(c) $(C_3-C_7)$-cycloalkyl,
(d) —OR⁷
(e) —COOR⁷,
(f) —CONH₂,
(g) —CONR¹⁶OH,
(h) —CONR⁷R¹¹,
(i) —CONR⁷CO₂R⁷,
(j) —NH₂,
(k) —NR⁷R¹¹,
(l) —NR⁷CONR⁷R¹¹,
(m) —NR⁷COOR¹¹,
(n) —C(R⁶)(OH)—C(R⁶)(R⁷)(OH),
(o) —SO₂NR⁷R¹¹, (p) —S(O)$_2$NR$^7$COR$^{11}$,
(q) —S(O)$_2$NR$^7$CO$_2$R$^{11}$,
(r) —S(O)$_2$NR$^7$CONR$^7$R$^{11}$,
(s) —NHSO$_2$R$^{11}$,
(t) —NR$^7$SO$_2$NR$^7$R$^{11}$,
(u) —CONHSO$_2$R$^{11}$,
(v) —CO-amino acid, wherein amino acid is defined as an L- or D-amino acid selected from the group consisting of Ala, Ile, Phe, Asp, Pro and Val and which can be further substituted as a (C$_1$–C$_6$)-alkyl ester or an amide, or (w) 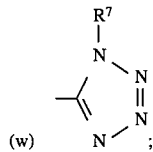

X is
(a) —O—,
(b) —S(o)$_n$—,
(c) —NR$^7$—,
(d) —CH$_2$O—,
(e) —CH$_2$S(O)$_n$—,
(f) —CH$_2$NR$^7$—,
(g) —OCH$_2$—,
(h) —N(R$^7$)CH$_2$—,
(i) —S(O)$_n$CH$_2$—, or
(j) —single bond;

Z is:
(a) —CO$_2$H,
(b) —CO$_2$R$^{13}$,
(c) —CONH—(tetrazol-5-yl),
(d) —CONHSO$_2$OR$^{11}$,
(e) —CONHSO$_2$NR$^7$R$^{11}$,
(f) —CONHSO$_2$-aryl, wherein aryl is defined as phenyl or naphthyl which is unsubstituted or substituted with one, two or three substituents selected from the group consisting of:
  i) (C$_1$–C$_4$)-alkyl,
  ii) —O—(C$_1$–C$_4$)-alkyl,
  iii) —CONR$^7$R$^{11}$,
  iv) F, Cl, Br or I,
    —COOR$^7$,
  vi) —NH$_2$,
  vii) —NH[(C$_1$–C$_4$)-alkyl],
  viii) —N[(C$_1$–C$_4$)-alkyl]$_2$,
  ix) —phenyl,
  x) —OH,
  xi) —OCH$_2$CH$_2$OH,
  xii) —CF$_3$;
(g) —CONHSO$_2$—(C$_1$–C$_8$)-alkyl, wherein the alkyl group is unsubstituted or substituted as defined in R$^4$(b),
(h) —CONHSO$_2$—(C$_1$–C$_4$)-perfluoroalkyl,
(i) —tetrazol-5-yl,
(j) —CONHSO$_2$-heteroaryl, wherein heteroaryl is defined as carbazolyl, furyl, thienyl, pyrrolyl, isothiazolyl, imidazolyl, isoxazolyl, thiazolyl, oxazolyl, pyrazolyl, pyrazinyl, pyridyl, pyrimidyl, purinyl or quinolinyl, which is unsubstituted or substituted with one, two or three substituents selected from the group consisting of:
  i) (C$_1$–C$_4$)-alkyl,
  ii) —O—(C$_1$–C$_4$)-alkyl,
  iii) —CONR$^7$R$^{11}$,
  iv) F, Cl, Br or I,
  v) —COOR$^7$,
  vi) —NR$^7$CONR$^7$R$^{11}$, and
  vii) —NR$^7$COOR$^{11}$;
(k) —SO$_2$NHCO-aryl, wherein aryl is defined in Z(f) above,
(l) —SO$_2$NHCO—(C$_1$–C$_8$)-alkyl, wherein the alkyl group is unsubstituted or substituted as defined in R$^4$(b),
(m) —SO$_2$NHCO—(C$_1$–C$_4$)-perfluoroalkyl,
(n) —SO$_2$NHCO-heteroaryl, wherein heteroaryl is as defined in Z(j) above, or
(o) SO$_2$NHCON(R$^{11}$)$_2$ wherein the R$^{11}$ groups are the same or different;

R$^{13}$ is:
(a) (C$_1$–C$_4$)-alkyl,
(b) CHR$^{14}$—O—COR$^{15}$
(c) CH$_2$CH$_2$—N[(C$_1$–C$_2$)-alkyl]$_2$,
(d) CH$_2$CH$_2$—N[CH$_2$CH$_2$]$_2$O,
(e) (CH$_2$CH$_2$O)$_y$—O—[(C$_1$–C$_4$)-alkyl], wherein y is 1 or 2,
(f) phenyl, naphthyl, CH$_2$-phenyl or CH$_2$-naphthyl, where phenyl or naphthyl is substituted or unsubstituted with CO$_2$—(C$_1$–C$_4$)-alkyl, (g) 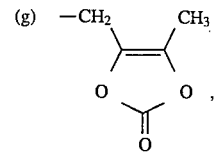

(h) 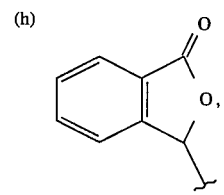

(i) 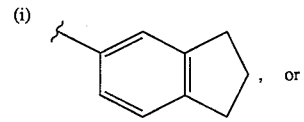, or (j) 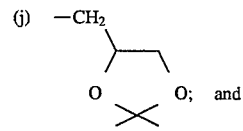; and

R$^{14}$ and R$^{15}$ independently are (C$_1$–C$_6$)-alkyl or phenyl;
R$^{16}$ is H, (C$_1$–C$_6$)-alkyl or (C$_1$–C$_6$)-alkylphenyl; and
(a) with the proviso that when the compound of structural formula I is defined as Z is CO$_2$H or CO$_2$R$^{13}$, where R$^{13}$ is (C$_1$–C$_6$)-alkyl; X is O; R$^9$ is H or (C$_1$–C$_6$)-alkyl, unsubstituted or substituted with hydroxy; R$^{10}$ is H; R$^{12}$ is OR$^7$, where R$^7$ is H or (C$_1$–C$_6$)-alkyl; R$^{3a}$ is H, F, Cl, Br, or I; and R$^{3b}$ is F, Cl, Br, I, or OR$^7$, where R$^7$ is (C$_1$–C$_6$)-alkyl; that R$^1$ and R$^2$ are not both hydrogen nor in the alternative does R$^1$ and R$^2$ together represent —CR$^4$=CR$^5$—CR$^4$=CR$^5$—, where R$^4$ and R$^5$ are H; or
(b) when the compound of structural formula I is defined as Z is CO$_2$H or CO$_2$R$^{13}$, where R$^{13}$ is (C$_1$–C$_6$)-alkyl; X is a single bond; and R$^1$ and R$^{12}$ are OR$^7$, where R$^7$ is H, then R$^{3a}$, R$^{3b}$, R$^9$ and R$^{10}$ are not defined as Cl; or
(c) when the compound of structural formula I is defined as Z is CO$_2$R$^{13}$, where R$^{13}$ is H or (C$_1$–C$_6$)- alkyl; X is S(O)$_n$; n is 0, 1, or 2; and R$^1$ and R$^2$ represent the ring structure A which is —O—CH$_2$—O— and fused at the 3,4-position of the phenyl ring; then at least one of R$^{3a}$, R$^{3b}$, R$^8$, R$^9$, R$^{10}$ and R$^{12}$ is other than hydrogen; or (d) when the compound of structural formula I is defined as Z is CO$_2$H or CO$_2$R$^{13}$, where R$^{13}$ is (C$_1$–C$_6$)-alkyl; X is —OCH$_2$—; and R$^1$ and R$^2$ represent the ring structure A which is —O—CH$_2$13 O— and fused at the 3,4-position of the phenyl ring; R$^{3a}$, R$^{3b}$ and R$^8$ are hydrogen; R$^{12}$ is OR$^7$, where R$^7$ is (C$_1$–C$_6$)-alkyl; then at least one of R$^9$ and R$^{10}$ is other than hydrogen and C$_1$-alkyl; or (e) when the compound of structural formula I is defined as Z is CO$_2$H or CO$_2$R$^{13}$, where R$^{13}$ is (C$_1$–C$_6$)-alkyl; X is —OCH$_2$—; and R$^1$ and R$^2$ represent the ring structure A which is —O—CH$_2$—O— and fused at the 3,4-position of the phenyl ring, R$^{3a}$, R$^{3b}$, R$^8$ are H; and either of R$^9$ or R$^{10}$ is (C$_1$–C$_6$)-alkoxy and the other of R$^9$ or R$^{10}$ is hydrogen, then R$^{12}$ is other than hydrogen; or (f) when the compound of structural formula I is defined as Z is CO$_2$H; X is —NR$^7$—; and R$^1$ and R$^2$ represent the ring structure A which is —O—CH$_2$—O— and fused at the 3,4-position of the phenyl ring; and R$^{3a}$, R$^{3b}$, R$^8$, R$^9$ and R$^{10}$ are H; then R$^7$ is other than hydrogen C$_1$-alkyl and R12 is other than H or OC$_2$H$_5$.

2. The compound of claim 1 of structural formula II:

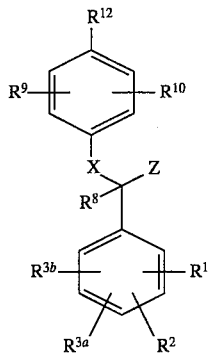

or a pharmaceutically acceptable salt thereof, wherein:

R$^{3a}$ and R$^{3b}$ are independently:
(a) H,
(b) F, Cl, Br, or I,
(c) —NO$_2$,
(d) —NH$_2$,
(e) —NH(C$_1$–C$_4$)-alkyl,
(f) —N[(C$_1$–C$_4$)-alkyl]$_2$,
(g) —SO$_2$NHR$^7$,
(h) —CF$_3$,
(i) (C$_1$–C$_6$)-alkyl,
(j) 'OR$^7$,
(k) —S(O)$_n$—(C$_1$–C$_4$)-alkyl,
(l) —NHCO—(C$_1$–C$_4$)-alkyl,
(m) —NHCO—O(C$_1$–C$_4$)-alkyl,
(n) —CH$_2$O—(C$_1$–C$_4$)-alkyl,
(o) —O—(CH$_2$)$_m$—OR$^7$,
(p) —CONR$^7$R$^{11}$, or
(q) —COOR$^7$;

R$^1$ and R$^2$ on adjacent carbon atoms are joined together to form a ring structure:

A represents:
a) —Y—C(R$^4$)=C(R$^5$)—,
b) —Y—[C(R$^6$)(R$^6$)]$_s$—Y—,
c) —y—C(R$_6$)(R$_6$)—C(R$_6$)(R$_6$)—,
d) —C(R$^4$)=C(R$^5$)—Y—, or
e) —C(R$^6$)(R$^6$)—C(R$^6$)(R$^6$)—Y—;

m is 2, 3 or 4,
n is 0, 1 or 2,
s is 1 or 2,

Y is —O—, or —S(O)$_n$—;

R$^4$ and R$^5$ are independently:
(a) H,
(b) (C$_1$–C$_6$)-alkyl or (C$_2$–C$_6$)-alkenyl each of which is unsubstituted or substituted with one or two substituents selected from the group consisting of:
  i) —OH,
  ii) —O—(C$_1$–C$_4$)-alkyl,
  iii) —S(O)$_n$—(C$_1$–C$_4$)-alkyl,
  iv) —NR$^7$—(C$_1$–C$_4$)-alkyl,
  v) —NHR$^7$,
  vi) —COOR$^7$,
  vii) —CONHR$^7$,
  viii) —OCOR$^{11}$, or
  ix) —CONR$^7$R$^{11}$,
(c) (C$_3$–C$_7$)-cycloalkyl,
(d) F, Cl, Br, I,
(e) CF$_3$,
(f) —COOR$^7$,
(g) —CONR$^7$R$^{11}$,
(h) —NR$^7$R$^{11}$,
(i) —NR$^7$COOR$^{11}$,
(j) —NR$^7$COOR$^{11}$,
(k) —SO$_2$NR$^7$R$^{11}$,
(l) —O—(C$_1$–C$_4$)-alkyl,
(m) —S(O)$_n$—(C$_1$–C$_4$)-alkyl, or
(n) —NHSO$_2$R$^{11}$;

R$^6$ is:
(a) H,
(b) (C$_1$–C$_4$)-alkyl, unsubstituted or substituted with one or two substituents selected from the group consisting of:
  i) —OH,
  ii) —NR$^7$R$^{11}$,
  iii) —COOR$^7$,
  iv) —CONHR$^7$, or
  v) —CONR$^7$R$^{11}$
(c) C, or F;

R7 is:
(a) H,
(b) (C$_1$–C$_6$)-alkyl,
(c) phenyl,
(d) (C$_1$–C$_6$)-alkylphenyl, or
(e) (C$_3$–C$_7$)-cycloalkyl;

R8 is:
(a) H,
(b) (C$_1$–C$_6$)-alkyl, unsubstituted or substituted with one or two substiments selected from the group consisting of:
  (i) —phenyl,
  (ii) —(C$_3$–C$_7$)-cycloalkyl,
  (iii) —NR$^7$R$^{11}$, (iv) —morpholin-4-yl,
(v) —OH,
(vi) —CO$_{2R}^7$, or
(vii) —CON(R$^7$)$_2$, or
(c) phenyl;

R$^9$ and R$^{10}$ are independently:
(a) H,
(b) (C$_1$–C$_6$)-alkyl, unsubstituted or substituted with (C$_3$–C$_7$)-cycloalkyl or —CO$_2$R$^7$,
(c) (C$_2$–C$_6$)-alkenyl,
(d) (C$_2$–C$_6$)-alkynyl,
(e) Cl, Br, F, I,
(f) (C$_1$–C$_6$)-alkoxy,
(g) perfluoro-(C$_1$–C$_6$)-alkyl,
(h) (C$_3$–C$_7$)-cycloalkyl, unsubstituted or substituted with (C$_1$–C$_6$)-alkyl,
(i) phenyl,
(j) (C$_1$–C$_6$)-alkyl-S(O)$_n$—(CH$_2$)$_n$—,
(k) hydroxy-(C$_1$–C$_6$)-alkyl,
(l) —CF$_3$,
(m) —CO$_2$R$^7$,
(n) —OH,
(o) —NR$^7$R$^{11}$,
(p) [(C$_1$–C$_6$)-alkyl]NR$^7$R$^{11}$,
(q) —NO$_2$,
(r) —(CH$_2$)$_n$—SO$_2$—N(R$^7$)$_2$,
(s) —NR$^7$CO—(C$_1$–C$_4$)-alkyl, or
(t) —CON(R$^7$)$_2$;

R$^9$ and R$^{10}$ on adjacent carbons can join together to form a fused phenyl ring, unsubstituted or substituted with a substituent selected from the group consisting of: (C$_1$–C$_6$)-alkyl, (C$_1$–C$_6$)-alkoxy, (C$_3$–C$_7$)-cycloalkyl and (C$_1$–C$_6$)-alkyl-(C$_3$–C$_7$)-cycloalkyl, R$^{11}$ is
(a) (C$_1$–C$_6$)-alkyl, unsubstituted or substituted with a substituent selected from the group consisting of:
 i) —OR$^7$,
 ii) —N[R$^7$]$_2$,
 iii) —NH$_2$,
 iv) —COOR$^7$,
 v) —N[CH$_2$CH$_2$]$_2$Q,
 vi) —CF$_3$, or
 vii) —CON(R$^7$)$_2$;
(b) aryl, wherein aryl is defined as phenyl or naphthyl which is unsubstituted or substituted with one, two or three substituents selected from the group consisting of:
 i) (C$_1$–C$_4$)-alkyl,
 ii) —O—(C$_1$–C$_4$)-alkyl,
 iii) —CO[NR$^7$]$_2$,
 iv) F, Cl, Br or I,
 v) —COOR$^7$,
 vi) —NH$_2$,
 vii) —NH[(C$_1$–C$_4$)-alkyl],
 viii) —N[(C$_1$–C$_4$)-alkyl]$_2$, or
 ix) —CON[CH$_2$CH$_2$]$_2$Q;
(c) —(C$_1$–C$_4$)-alkylaryl, wherein aryl is as defined above,
(d) (C$_3$–C$_7$)-cycloalkyl, (e)

$$\underset{N}{\overset{R^7}{|}}\underset{}{N}\!-\!\underset{}{\underset{N\diagdown N}{\overset{\diagup\!\!\diagup\,N}{}}}$$

, or (f) CF$_3$;

R$^7$ and R$^{11}$ on the same nitrogen atom they can join together to form a ring selected from the group consisting of: morpholinyl, piperazinyl, or pyrrolyl, or Q is O, S or —NR$^7$;

R$^{12}$ is
(a) H
(b) (C$_1$–C$_6$)-alkyl, unsubstituted or substituted with one or two substituents selected from the group consisting of:
 i) —OH,
 ii) —O—(C$_1$–C$_4$)-alkyl,
 iii) —O—(C$_1$–C$_4$)-cycloalkyl,
 iv) —S(O)$_n$—(C$_1$–C$_4$)-alkyl,
 v)
 vi) —COOR$^7$,
 vii) —CONHR$^7$,
 viii) —OCOR$^7$R$^{11}$,
 ix) —NR$^7$CONR$^7$R$^{11}$,
 xi) —NR$^7$COOR$^{11}$,
 xii) —C(R$^6$)(OH)—C(R$^6$)(R$^7$)(OH),
 xiii) —SO$_2$NR$^7$R$^{11}$, or xiv) $\underset{N}{\overset{R^7}{|}}\!-\!\underset{N\diagdown N}{\overset{\diagup\!\!\diagup\,N}{}}$ ;

(c) (C$_3$–C$_7$)-cycloalkyl,
(d) —OR$^7$,
(e) —COOR$^7$,
(f) —CONH$_2$,
(g) —CONR$^{16}$OH,
(h) —CONR$^7$R$^{11}$,
(i) —CONR$^7$CO$_2$R$^7$,
(j) —NH$_2$,
(k) —NR$^7$R$^{11}$,
(l) —NR$^7$CONR$^7$R$^{11}$,
(m) —NR$^7$COOR$^{11}$,
(n) —C(R$^6$)(OH)—C(R$^6$)(R$^7$)(OH),
(o) —SO$_2$NR$^7$R$^{11}$,
(p) —S(O)$_2$NR$^7$COR$^{11}$,
(q) —S(O)$_{2l\ NR}^7$O$_2$R$^{11}$,
(r) —S(O)$_2$NR$^7$CONR$^7$R$^{11}$,
(s) —NHSO$_2$R$^{11}$,
(t) —NR$^7$SO$_2$NR$^7$R$^{11}$,
(u) —CONHSO$_2$R$^{11}$,
(v) —CO-amino acid, wherein amino acid is defined as an L - or D-amino acid selected from the group consisting of Ala, Ile, Phe, Asp, Pro and Val and which can be further substituted as a (C$_1$–C$_6$)-alkyl ester or an amide, or

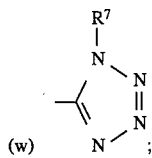
(w)

X is
(a) —O—,
(b) —S(O)$_n$—,
(c) —NR$^7$—,
(d) —CH$_2$O—,
(e) —CH$_2$S(O)$_n$—,
(f) —CH$_2$NR$^7$—,
(g) —OCH$_2$—,
(h) —N(R$^7$)CH$_2$—,
(i) —S(O)$_n$CH$_2$—, or
(j) —single bond;

Z is:
(a) —CO$_2$H,
(b) —CO$_2$R$^{13}$,
(c) —CONH—(tetrazol-5-yl),
(d) —CONHSO$_2$OR$^{11}$,
(e) —CONHSO$_2$NR$^7$R$^{11}$,
(f) —CONHSO$_2$-aryl, wherein aryl is defined as phenyl or naphthyl which is unsubstituted or substituted with one, two or three substituents selected from the group consisting of:
  i) (C$_1$-C$_4$)-alkyl,
  ii) —O—(C$_1$-C$_4$)-alkyl,
  iii) —CONR$^7$R$^{11}$,
  iv) F, Cl, Br or I,
  v) —COOR$^7$,
  vi) —NH$_2$,
  vii) —NH[(C$_1$-C$_4$)-alkyl],
  viii) —N[(C$_1$-C$_4$)-alkyl]$_2$,
  ix) —phenyl,
  x) —OH,
  xi) —OCH$_2$CH$_2$OH,
  xii) —CF$_3$;
(g) —CONHSO$_2$—(C$_1$-C$_8$)-alkyl, wherein the alkyl group is unsubstituted or substituted as defined in R$^4$(b),
(h) —CONHSO$_2$—(C$_1$-C$_4$)-perfluoroalkyl,
(i) —tetrazol-5-yl,
(j) —CONHSO$_2$-heteroaryl, wherein heteroaryl is defined as carbazolyl, furyl, thienyl, pyrrolyl, isothiazolyl, imidazolyl, isoxazolyl, thiazolyl, oxazolyl, pyrazolyl, pyrazinyl, pyridyl, pyrimidyl, purinyl or quinolinyl, which is unsubstituted or substituted with one, two or three substituents selected from the group consisting of:
  i) (C$_1$-C$_4$)-alkyl,
  ii) —O—(C$_1$-C$_4$)-alkyl,
  iii) —CONR$^7$R$^{11}$,
  iv) F, Cl, Br or I,
  v) —COOR$^7$,
  vi) —NR$^7$CONR$^7$R$^{11}$, and
  vii) —NR$^7$COOR$^{11}$;
k) —SO$_2$NHCO—aryl, wherein aryl is defined in Z(f) above,
(l) —SO$_2$NHCO—(C$_1$-C$_8$)-alkyl, wherein the alkyl group is unsubstituted or substituted as defined in R$^4$(b),
(m) —SO$_2$NHCO—(C$_1$-C$_4$)-perfluoroalkyl,
(n) —SO$_2$NHCO-heteroaryl, wherein heteroaryl is as defined in Z(j) above, or
(o) —SO$_2$NHCON(R$^{11}$)$_2$ wherein the R$^{11}$ groups are the same or different;

R$^{13}$ is:
(a) (C$_1$-C$_4$)-alkyl,
(b) CHR$^{14}$—O—COR$^{15}$,
(c) CH$_2$CH$_2$—N[(C$_1$-C$_2$)-alkyl]$_2$,
(d) CH$_2$CH$_2$—N[CH$_2$CH$_2$]$_2$O,
(e) (CH$_2$CH$_2$O)$_y$—O—[(C$_1$-C$_4$)-alkyl], wherein y is 1 or 2,
(f) phenyl, naphthyl, CH$_2$-phenyl or CH$_2$-naphthyl, where phenyl or naphthyl is substituted or unsubstituted with CO$_2$—(C$_1$-C$_4$)-alkyl, (g) 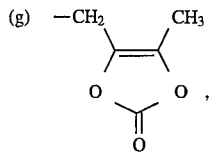

(h) 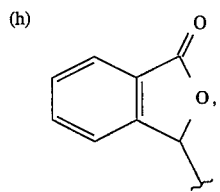

(i) 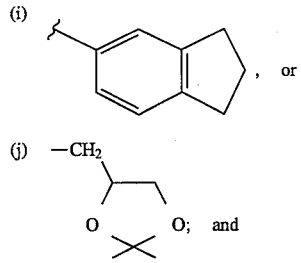, or (j) 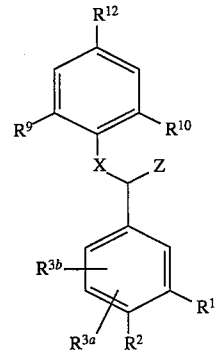; and

R$^{14}$ and R$^{15}$ independently are (C$_1$-C$_6$)-alkyl or phenyl; and
R$^{16}$ is H, (C$_1$-C$_6$)-alkyl, or (C$_1$-C$_6$)-alkylphenyl.

3. The compound of claim 32 of structural formula III:

III or a pharmaceutically acceptable salt thereof, wherein:
R$^{3a}$ and R$^{3b}$ are independently:
(a) H,
(b) F, Cl, Br, or I,
(c) —NO$_2$,
(d) (C$_1$-C$_6$)-alkyl,
(e) —OR$^7$,
(f) —NHCO—(C$_1$-C$_4$)-alkyl,
(g) —NHCO—O(C$_1$-C$_4$)-alkyl,
(h) —O—(CH$_2$)m—OR$^7$,
(i) —CONR$^7$R$^{11}$, or
(j) —COOR$^7$;

$R^1$ and $R^2$ on adjacent carbon atoms are joined together to form a ring structure:

;

A represents:
  a) $-Y-C(R^4)=C(R^5)-$,
  b) $-Y-[C(R^6)(R^6)]s-Y-$,
  c) $-Y-C(R^6)(R^6)-C(R^6)(R^6)-$,
  d) $-C(R^4)=C(R^5)-Y-$, or
  e) $-C(R^6)(R^6)-C(R^6)(R^6)-Y-$;

m is 2, 3 or 4,
n is 0, 1 or 2,
s is 1 or 2,
Y is $-O-$, or $-S-$;
$R^4$ and $R^5$ are independently:
  (a) H,
  (b) $(C_1-C_6)$-alkyl,
  (c) $(C_3-C_7)$-cycloalkyl,
  (d) F, Cl, Br, I,
  (e) $-NR^7COOR^{11}$,
  (f) $-SO_2NR^7R^{11}$,
  (g) $-O-(C_1-C_4)$-alkyl,
  (h) $-S(O)_n-(C_1-C_4)$-alkyl, or
  (i) $-NHSO_2R^{11}$;
$R^6$ is:
  (a) H, or
  (b) $(C_1-C_4)$-alkyl, or
  (c) Cl, or F;
$R^7$ is:
  (a) H,
  (b) $(C_1-C_6)$-alkyl,
  (c) phenyl, or
  (d) benzyl;
$R^8$ is:
  (a) H,
  (b) $(C_1-C_6)$-alkyl, or
  (c) phenyl;
$R^9$ and $R^{10}$
  (a) H,
  (b) $(C_1-C_6)$-alkyl, unsubstituted or substituted with $(C_3-C_7)$-cycloalkyl,
  (c) Cl, Br, F, I,
  (d) $(C_1-C_6)$-alkoxy, or
  (e) hydroxy-$(C_1-C_6)$-alkyl;
$R^{11}$ is
  (a) $(C_1-C_6)$-alkyl, unsubstituted or substituted with a substituent selected from the group consisting of:
    i) $-OR^7$,
    ii) $-N[R^7]_2$,
    iii) $-NH_2$,
    iv) $-COOR^7$,
    v) $-N[CH_2CH_2]_2Q$,
    vi) $-CF_3$, or
    vii) $-CON(R^7)_2$;
  (b) aryl, wherein aryl is defined as phenyl or naphthyl which is unsubstituted or substituted with one or two substituents selected from the group consisting of:
    i) $(C_1-C_4)$-alkyl,
    ii) $-O-(C_1-C_4)$-alkyl,
    iii) $-CO[NR^7]_2$,
    iv) F, Cl, Br, or I,
    v) $-COOR^7$,
    vi) $-NH_2$,
    vii) $-NH[(C_1-C_4)$-alkyl$]$,
    viii) $-N[(C_1-C_4)$-alkyl$]_2$,
    ix) $-CON[CH_2CH_2]_2Q$, or
  (c) $-(C_1-C_4)$-alkylaryl, wherein aryl is as defined above,
  (d) $(C_3-C_7)$-cycloalkyl, (e) 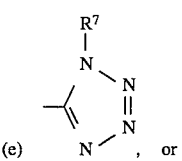, or (f) $CF_3$;

$R^7$ and $R^{11}$ on the same nitrogen atom they can join together to form a ring selected from the group consisting of: morpholinyl, piperazinyl, or pyrrolyl, or Q is O, S or $-NR^7$;
$R^{12}$ is
  (a) H,
  (b) $(C_1-C_6)$-alkyl, wherein alkyl is defined as unsubstituted or substituted with one or two substituents selected from the group consisting of:
    i) $-OH$,
    ii) $-O-(C_1-C_4)$-alkyl,
    iii) $-O-(C_1-C_4)$-cycloalkyl,
    iv) $-S(O)_n-(C_1-C_4)$-alkyl,
    iv) $-NR^7-(C_1-C_4)$-alkyl,
    v) $-NR^7R^{11}$,
    vi) $-COOR^7$,
    vii) $-CONHR^7$,
    viii) $-OCOR^{11}$,
    ix) $-CONR^7R^{11}$,
    x) $-NR^7CONR^7R^{11}$,
    xi) $-NR^7COOR^{11}$,
    xii) $-C(R^6)(OH)-C(R^6)(R^7)(OH)$,
    xiii) $-SO_2NR^7R^{11}$, or xiv) 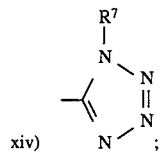;

(c) $-COOR^7$,
  (d) $-CONH_2$,
  (e) $-CONR^{16}OH$,
  (f) $-CONR^7R^{11}$,
  (g) $-CONR^7CO_2R^7$,
  (h) $-C(R^6)(OH)-C(R^6)(R^7)(OH)$, or
  (i) $-CONHSO_2R^{11}$,
  (j) $-SO_2NR^7R^{11}$,
  (k) $-NR^7SO_2NR^7R^{11}$,
  (l) $-CO$-amino acid, wherein amino acid is defined as an L- or D-amino acid selected from the group consisting of Ala, Ile, Phe, Asp, Pro and Val and which can be further substituted as a $(C_1-C_6)$-alkyl ester or an amide, or

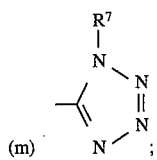

X is
(a) —O—,
(b) —NR$^7$—, or
(c) —single bond;

Z is:
(a) —CO$_2$H,
(b) —CO$_2$R$^{13}$,
(c) —CONH(tetrazol-5-yl),
(d) —CONHSO$_2$NR$^7$R$^{11}$,
(e) —CONHSO$_2$-aryl, wherein aryl is defined as phenyl or naphthyl which is unsubstituted or substituted with one, two or three substiments selected from the group consisting of:
  i) (C$_1$-C$_4$)-alkyl,
  ii) —O—(C$_1$-C$_4$)-alkyl,
  iii) —CONR$^7$R$^{11}$,
  iv) F, Cl, Br or I,
  v) —COOR$^7$,
  vi) —NH$_2$,
  vii) —NH[(C$_1$-C$_4$)-alkyl],
  viii) —N[(C$_1$-C$_4$)-alkyl]$_2$,
  ix) —phenyl;
(f) —CONHSO$_2$—(C$_1$-C$_8$)-alkyl, wherein alkyl is unsubstituted
(g) —CONHSO$_2$-heteroaryl, wherein heteroaryl is defined as carbazolyl, furyl, thienyl, pyrrolyl, isothiazolyl, imidazolyl, isoxazolyl, thiazolyl, oxazolyl, pyrazolyl, pyrazinyl, pyridyl, pyrimidyl, purinyl, or quinolinyl, which is unsubstituted or substituted with one, two or three substituents selected from the group consisting of:
  i) (C$_1$-C$_4$)-alkyl,
  ii) —O—(C$_1$-C$_4$)-alkyl,
  iii) —CONR$^7$R$^{11}$,
  iv) F, Cl, Br or I,
  v) —COOR$^7$,
  vi) —NR$^7$CONR$^7$R$^{11}$, and
  vii) —NR$^7$COOR$^{11}$;
(h) —tetrazol-5-yl;

R$^{13}$ is: (C$_1$-C$_4$)-alkyl; and
R$^{16}$ is H, (C$_1$-C$_6$)-alkyl, or (C$_1$-C$_6$)-alkylphenyl.

4. The compound of claim 3 of structural formula IV:

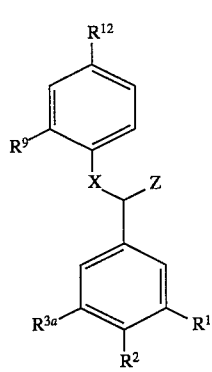

or a pharmaceutically acceptable salt thereof, wherein:

R$^1$ and R$^2$ taken together form the ring structure:

A represents —Y—[C(R$^6$)(R$^6$)]$_s$—Y—;
s is 1 or 2;
Y is —O—;
R$^{3a}$ is:
(a) H,
(b) F, Cl, Br, or I,
(c) (C$_1$-C$_6$)-alkyl,
(d) —OR$^7$,
(e) —O—(CH$_2$)$_m$—OR$_7$,
(f) —CONR$_7$R$^{11}$, or
(g) —COOR$^7$;

m is 2, 3 or 4;

R$^4$ and R$^5$ are independently:
(a) H,
(b) (C$_1$-C$_6$)-alkyl,
(c) (C$_3$-C$_7$)-cycloalkyl,
(d) F, Cl, Br, I,
(e) —NR$^7$COOR$^{11}$,
(f) —SO$_2$NR$^7$R$^{11}$,
(g) —O—(C$_1$-C$_4$)-alkyl,
(h) —S(O)$_n$—(C$_1$-C$_4$)-alkyl, or
(i) —NHSO$_2$R$^{11}$;

n is 0, 1 or 2,

R$^6$ is:
(a) H, or
(b) (C$_1$-C$_4$)-alkyl, or
(c) Cl, or F;

R$^7$ is:
(a) H,
(b) (C$_1$-C$_6$)-alkyl,
(c) phenyl, or
(d) benzyl;

R$^8$ is:
(a) H,
(b) (C$_1$-C$_6$)-alkyl, or
(c) phenyl;

R$^9$ is:
(a) H,
(b) (C$_1$-C$_6$)-alkyl, unsubstituted or substituted with (C$_3$-C$_7$)-cycloalkyl,
(c) Cl, Br, F, I,
(d) (C$_1$-C$_6$)-alkoxy, or
(e) hydroxy-(C$_1$-C$_6$)-alkyl;

R$^{11}$ is
(a) (C$_1$-C$_6$)-alkyl, unsubstituted or substituted with a substituent selected from the group consisting of:
  i) —OR$^7$,
  ii) —N[R$^7$]$_2$,
  iii) —NH$_2$,
  iv) —COOR$^7$,
  v) —N[CH$_2$CH$_2$]$_2$Q,
  vi) —CF$_3$, or
  —CON(R$^7$)$_2$;
(b) aryl, wherein aryl is defined as phenyl or naphthyl which is unsubstituted or substituted with one or two substitutents selected from the group consisting of:
  i) (C$_1$-C$_4$)-alkyl,
  ii) —O—(C$_1$-C$_4$)-alkyl,
  iii) —CO[NR$^7$]$_2$, iv) F, Cl, Br or I,
v) —COOR$^7$,
vi) —NH$_2$,
vii) —NH[(C$_1$–C$_4$)-alkyl],
viii) —N[(C$_1$–C$_4$)-alkyl]$_2$, or
ix) —CON[CH$_2$CH$_2$]$_2$Q;

(c) —(C$_1$–C$_4$)-alkylaryl, wherein aryl is as defined above, (d) (C$_3$–C$_7$)-cycloalkyl,

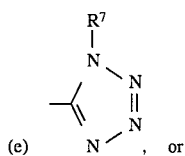

(e)         , or

R$^7$ and R$^{11}$ on the same nitrogen atom they can join together to form a ring selected from the group consisting of: morpholinyl, piperazinyl, or pyrrolyl, or Q is O, S or —NR$^7$;

R$^{12}$ is (a) H,
(b) (C$_1$–C$_6$)-alkyl, wherein alkyl is defined as unsubstituted or substituted with one or two substituents selected from the group consisting of:
  i) —OH,
  ii) —O—(C$_1$–C$_4$)-alkyl,
  iii) —O—O—(C$_1$–C$_4$)-cycloalkyl,
  iv) —S(O)$_n$—(C$_1$–C$_4$)-alkyl,
  iv) —NR$^7$—(C$_1$–C$_4$)-alkyl,
  v) —NR$^7$R$^{11}$,
  vi) —COOR$^7$,
  vii) —CONHR$^7$,
  viii) —OCOR$^{11}$,
  ix) —CONR$^7$R$^{11}$,
  x) —NR$^7$CONR$^7$R$^{11}$,
  xi) —NR$^7$COOR$^{11}$,
  xii) —C(R$^6$)(OH)—C(R$^6$)(R$^7$)(OH), or
  xiii) —SO$_2$NR$^7$R$^{11}$,

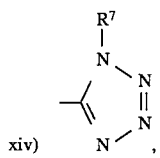

xiv)         , (c) —COOR$^{7l}$.
(d) —CONH$_2$,
(e) —CONR$^{16}$OH,
(f) —CONR$^7$R$^{11}$,
(g) —CONR$^7$CO$_2$R$^7$,
(h) —C(R$^6$)(OH)—C(R$^6$)(R$^7$)(OH), or
(i) —CONHSO$_2$R$^{11}$,
(j) —SO$_2$NR$^7$R$^{11}$,
(k) —NR$^7$ SO$_2$NR$^7$R$^{11}$,
(l) —CO-amino acid, wherein amino acid is defined as an L- or D-amino acid selected from the group consisting of Ala, Ile, Phe, Asp, Pro and Val and which can be further substituted as a (C$_1$–C$_6$)-alkyl ester or an amide, or

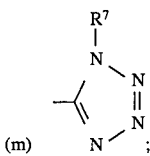

(m)         ;

X is
(a) —O—,
(b) —NR$^7$—, or
(c) —single bond;

Z is:
(a) —CO$_2$H,
(b) —CO$_2$R$^{13}$,
(c) —CONH-(tetrazol-5-yl ),
(d) —CONHSO$_2$NR$^7$R$^{11}$,
(e) —CONHSO$_2$-aryl, wherein aryl is defined as phenyl or naphthyl which is unsubstituted or substituted with one, two or three substituents selected from the group consisting of:
  i) (C$_1$–C$_4$)-alkyl,
  ii) —O—(C$_1$–C$_4$)-alkyl,
  iii) —CONR$^7$R$^{11}$,
  iv) F, Cl, Br or I,
  v) —COOR$^7$,
  vi) —NH$_2$,
  vii) —NH[(C$_1$–C$_4$)-alkyl],
  viii) —N[(C$_1$–C$_4$)-alkyl]2,
  ix) —phenyl;
(f) —CONHSO$_2$-(C$_1$–C$_8$)-alkyl, wherein alkyl is unsubstituted
(g) —CONHSO$_2$-heteroaryl, wherein heteroaryl is defined as carbazolyl, furyl, thienyl, pyrrolyl, isothiazolyl, imidazolyl, isoxazolyl, thiazolyl, oxazolyl, pyrazolyl, pyrazinyl, pyridyl, pyrimidyl, purinyl, or quinolinyl, which is unsubstituted or substituted with one, two or three substituents selected from the group consisting of:
  i) (C$_1$–C$_4$)-alkyl,
  ii) —O—(C$_1$–C$_4$)-alkyl,
  iii) —CONR$^7$R$^{11}$,
  iv) F, Cl, Br or I,
  v) —COOR$^7$,
  vi) —NR$^7$CONR$^7$R$^{11}$, and
  vii) —NR$^7$COOR$^{11}$;
(h) —tetrazol-5-yl;

R$^{13}$ is: (C$_1$–C$_4$)-alkyl; and

R$^{16}$ is H, (C$_1$–C$_6$)-alkyl, or (C$_1$–C$_6$)-alkylphenyl.

5. The compound of claim 4 of structrual formula VI:

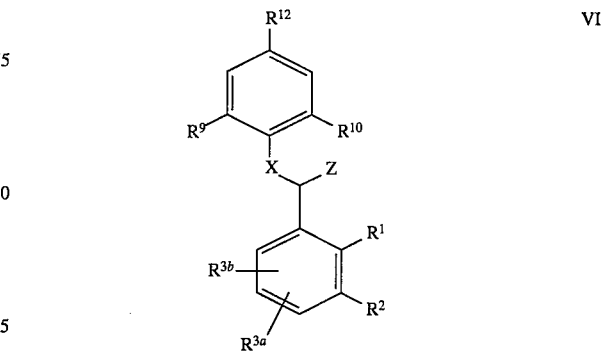

VI or a pharmaceutically acceptable salt thereof, wherein:

$R^1$ and $R^2$ are represented by the following ring structure:

A represents: —Y—[C($R^6$)($R^6$)]$_s$—Y—;
s is 1 or 2,
Y is —O—, or —S—;
$R^{3a}$ and $R^{3b}$ are independently;
  (a) H,
  (b) F, Cl, Br, or I,
  (c) —$NO_2$,
  (d) ($C_1$–$C_6$)-alkyl,
  (e) —$OR^7$,
  (f) —NHCO–($C_1$–$C_4$)-alkyl,
  (g) —NHCO—O($C_1$–$C_4$)-alkyl,
  (h) —O—$(CH_2)_m$—$OR^7$,
  (i) —$CONR^7R^{11}$, or
  (j) —$COOR^7$;
m is 2, 3 or 4,
$R^4$ and $R^5$ are independently:
  (a) H,
  (b) ($C_1$–$C_6$)-alkyl,
  (c) ($C_3$–$C_7$)-cycloalkyl,
  (d) F, Cl, Br, I,
  (e) —$NR^7COOR^{11}$,
  (f) —$SO_2NR^7R^{11}$,
  (g) —O—($C_1$–$C_4$)-alkyl,
  (h) —S(O)$_n$—($C_1$–$C_4$)-alkyl, or
  (i) —$NHSO_2R^{11}$;
n is 0, 1 or 2,
$R^6$ is:
  (a) H, or
  (b) ($C_1$–$C_4$)-alkyl, or
  (c) Cl or F;
$R^7$ is:
  (a) H,
  (b) ($C_1$–$C_6$)-alkyl,
  (c) phenyl, or
  (d) benzyl;
$R^8$ is:
  (a) H,
  (b) ($C_1$–$C_6$)-alkyl, or
  (c) phenyl;
$R^9$ and $R^{10}$ are independently;
  (a) H,
  (b) ($C_1$–$C_6$)-alkyl, unsubstituted or substituted with ($C_3$–$C_7$)-cycloalkyl,
  (c) Cl, Br, F, I,
  (d) ($C_1$–$C_6$)-alkoxy, or
  (e) hydroxy-($C_1$–$C_6$)-alkyl;
$R^{11}$ is
  (a) ($C_1$–$C_6$)-alkyl, unsubstituted or substituted with a substituent selected from the group consisting of:
    i) —$OR^7$,
    ii) —$N[R^7]_2$,
    iii) —$NH_2$,
    iv) —$COOR^7$,
    v) —$N[CH_2CH_2]_2Q$,
    vi) —$CF_3$, or
    vii) —$CON(R^7)_2$;
  (b) aryl, wherein aryl is defined as phenyl or naphthyl which is unsubstituted or substituted with one or two substituents selected from the group consisting of:
    i) ($C_1$–$C_4$)-alkyl,
    ii) —O—($C_1$–$C_4$)-alkyl,
    iii) —$CO[NR^7]_2$,
    iv) F, Cl, Br or I,
    v) —$COOR^7$,
    vi) '$NH_2$,
    vii) —NH[($C_1$–$C_4$)-alkyl],
    viii) —N[($C_1$–$C_4$)-alkyl]$_2$, or
    ix) —$CON[CH_2CH_2]_2Q$;
  (c) —($C_1$–$C_4$)-alkylaryl, wherein aryl is as defined above,
  (d) ($C_3$–$C_7$)-cycloalkyl,

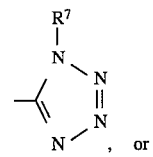

(e)           , or (f) $CF_3$;
$R^7$ and $R^{11}$ on the same nitrogen atom they can join together to form a ring selected from the group consisting of: morpholinyl piperazinyl, or pyrrolyl, or
Q is O, S or —$NR^7$;
$R^{12}$ is
  (a) H,
  (b) ($C_1$–$C_6$)-alkyl, wherein alkyl is defined as unsubstituted or substituted with one or two substituents selected from the group consisting of:
    i) —OH,
    ii) —O—($C_1$–$C_4$)-alkyl,
    iii) —O—($C_1$–$C_4$)-cycloalkyl,
    iv) —S(O)$_n$—($C_1$–$C_4$)-alkyl,
    iv) —$NR^7$—($C_1$–$C_4$)-alkyl,
    v) —$NR^7R^{11}$,
    vi) —$COOR^7$,
    vii) —$CONHR^7$,
    viii) —$OCOR^{11}$,
    ix) —$CONR^7R^{11}$,
    x) —$NR^7CONR^7R^{11}$,
    xi) —$NR^7COOR^{11}$,
    xii) —C($R^6$)(OH)—C($R^6$)($R^7$)(OH),
    xiii) —$SO_2NR^7R^{11}$, or

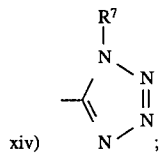

xiv)         ;

(c) —$COOR^7$,
  (d) —$CONH_2$,
  (e) —$CONR^{16}OH$,
  (f) —$CONR^7R^{11}$,
  (g) —$CONR^7CO_2R^7$,
  (h) —C($R^6$)(OH)—C($R^6$)($R^7$)(OH), or
  (i) —$CONHSO_2R^{11}$,
  (j) —$SO_2NR^7R^{11}$,
  (k) —$NR^7SO_2NR^7R^{11}$,
  (l) —CO-amino acid, wherein amino acid is defined as an L- or D-amino acid selected from the group consisting of Ala, Ile, Phe, Asp, Pro and Val and which can be further substituted as a ($C_1$–$C_6$)-alkyl ester or an amide, or

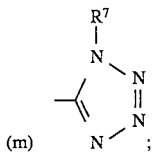

X is
(a) —O—,
(b) —NR⁷—, or
(c) —single bond;

Z is:
(a) —CO₂H,
(b) —CO₂R¹³,
(c) —CONH—(tetrazol-5- yl),
(d) —CONHSO₂NR⁷R¹¹,
(e) —CONHSO₂-aryl, wherein aryl is defined as phenyl or naphthyl which is unsubstituted or substituted with one, two or three substituents selected from the group consisting of:
  i) (C₁-C₄)-alkyl,
  ii) —O—(C₁-C₄)-alkyl,
  iii) —CONR⁷R¹¹,
  iv) F, Cl, Br or I,
  v) —COOR⁷,
  vi) —NH₂,
  vii) —NH[(C₁-C₄)-alkyl],
  viii) —N[(C₁-C₄)-alkyl]₂,
  ix) —phenyl;
(f) —CONHSO₂—(C₁-C₈)-alkyl, wherein alkyl is unsubstituted,
(g) —CONHSO₂—heteroaryl, wherein heteroaryl is defined as carbazolyl, furyl, thienyl, pyrrolyl, isothiazolyl, imidazolyl, isoxazolyl, thiazolyl, oxazolyl, pyrazolyl, pyrazinyl, pyridyl, pyrimidyl, purinyl, or quinolinyl, which is unsubstituted or substituted with one, two or three substituents selected from the group consisting of:
  i) (C₁-C₄)-alkyl,
  ii) —O—(C₁-C₄)-alkyl,
  iii) —CONR⁷R¹¹,
  iv) F, Cl, Br or I,
  v) —COOR⁷,
  vi) —NR⁷CONR⁷R¹¹, and
  vii) —NR⁷COOR¹¹;
(h) —tetrazol-5-yl;

R¹³ is: (C₁-C₄)-alkyl; and
R¹⁶ is H, (C₁-C₆)-alkyl, or (C₁-C₆)-alkylphenyl.

6. The compound claim 1 of Formula I selected from the group consisting of:
2-[(2,6-dipropyl-4-hydroxymethyl)phenoxy]-2-(3,4-ethylenedioxyphenyl)acetic acid;
2-[(2,6-dipropyl-4-hydroxymethyl)phenoxy]-2-(3,4-methylenedioxyphenyl)acetic acid;
2-[(2,6-dipropyl-4-(2-hydroxyethyl)phenoxy]-2-(3,4-methylenedioxyphenyl)acetic acid;
2-[(4-carboxy-2,6-dipropyl)phenoxy]-2-[3,4-methylenedioxyphenyl]acetic acid;
(N-4-t-butylbenzenesulfonyl)-2-(4-methoxycarbonyl-2-propylphenoxy)-2-(3,4-methylenedioxyphenyl)acetamide;
N-(4-phenylbenzenesulfonyl)-2-(4-methoxycarbonyl-2-propylphenoxy)-2-(3,4-methylenedioxyphenyl)acetamide;
N-(4-chlorobenzenesulfonyl)-2-(4-methoxycarbonyl-2-propylphenoxy)-2-(3,4-methylenedioxyphenyl)acetamide;
N-(4-methylbenzenesulfonyl)-2-(4-methoxycarbonyl-2-propylphenoxy)-2-(3,4-methylenedioxyphenyl)acetamide;
N-(5-iso-butylthien-2-ylsulfonyl)-2-(4-methoxycarbonyl-2-propylphenoxy)-2-(3,4-methylenedioxyphenyl)acetamide;
N-(4-methoxybenzenesulfonyl)-2-(4-methoxycarbonyl-2-propylphenoxy)-2-( 3,4-methylenedioxyphenyl)acetamide;
N-(4-dimethylaminobenzenesulfonyl)-2-(4-methoxycarbonyl-2-propylphenoxy)-2-(3,4-methylenedioxyphenyl)acetamide;
N-(2-methylbenzenesulfonyl)-2-(4-methoxycarbonyl-2-propylphenoxy)-2-(3,4-methylenedioxyphenyl)acetamide;
N-(2-methoxycarbonylbenzenesulfonyl)-2-(4-methoxycarbonyl-2-propylphenoxy)-2-(3,4-methylenedioxyphenyl)acetamide;
N-(2-chlorobenzenesulfonyl)-2-(4-methoxycarbonyl-2-propylphenoxy)-2-(3,4-methylenedioxyphenyl)acetamide;
N-(3-chlorobenzenesulfonyl)-2-(4-methoxycarbonyl-2-propylphenoxy)-2-(3,4-methylenedioxyphenyl)acetamide;
N-(phenylmethanesulfonyl)-2-(4-methoxycarbonyl-2-propylphenoxy)-2-(3,4-methylenedioxyphenyl)acetamide;
N-(dansylsulfonyl)-2-(4-methoxycarbonyl-2-propylphenoxy)-2-(3,4-methylenedioxyphenyl)acetamide;
N-(8-quinolinesulfonyl)-2-(4-methoxycarbonyl-2-propylphenoxy)-2-(3,4-methylenedioxyphenylacetamide;
N-(4-t-butylbenzenesulfonyl)-2-(4-carboxy-2-propylphenoxy)-2-(3,4-methylenedioxyphenyl)acetamide;
N-(benzenesulfonyl)-2-(4-carboxy-2-propylphenoxy)-2-(3, 4-methylenedioxyphenyl)acetamide;
N-(4-phenylbenzenesulfonyl)-2-(4-carboxy-2-propylphenoxy)-2-(3,4-methylenedioxyphenyl)acetamide;
N-(4-chlorobenzenesulfonyl)-2-(4-carboxy-2-propylphenoxy)-2-(3,4-methylenedioxyphenyl)acetamide;
N-(4-methylbenzenesulfonyl)-2-(4-carboxy-2-propylphenoxy)-2-(3,4-methylenedioxyphenyl)acetamide;
N-(5-isobutylthien-2-ylsulfonyl)-2-(4-carboxy-2-propylphenoxy)-2-(3,4-methylenedioxyphenyl)acetamide;
N-(4-methoxybenzenesulfonyl)-2-(4-carboxy-2-propylphenoxy)-2-(3,4-methylenedioxyphenyl)acetamide;
N-(4-dimethylaminobenzenesulfonyl)-2-(4-carboxy-2-propylphenoxy)-2-2-(3,4-methylenedioxyphenyl)acetamide;
N-(2-methylbenzenesulfonyl)-2-(4-carboxy-2-propylphenoxy)-2-(3,4-methylenedioxyphenyl)acetamide;
N-(2-methoxycarbonylbenzenesulfonyl)-2-(4-carboxy-2-propylphenoxy)-2-(3,4-methylenedioxyphenyl)acetamide;
N-(2-chlorobenzenesulfonyl)-2-(4-carboxy-2-propylphenoxy)-2-(3,4-methylenedioxyphenyl)acetamide;
N-(3-chlorobenzenesulfonyl)-2-(4-carboxy-2-propylphenoxy)-2-(3,4-methylenedioxyphenyl)acetamide;
N-(phenylmethanesulfonyl)-2-(4-carboxy-2-propylphenoxy)-2-(3,4-methylenedioxyphenyl)acetamide;
N-(dansylsulfonyl)-2-(4-carboxy-2-propylphenoxy)-2-(3,4-methylenedioxyphenyl)acetamide;
N-(8-quinolinesulfonyl)-2-(4-carboxy-2-propylphenoxy)-2-(3,4-methylenedioxyphenyl)acetamide;
N-(8-quinolinesulfonyl)-2-(4-carboxamido-2-propylphenoxy)-2-(3,4-methylenedioxyphenyl)acetamide;
α-(4-carbomethoxy-2-n-propylphenoxy)-3,4-methylenedioxyphenylacetic acid;
N-(4-iso-propylbenzenesulfonyl)-α-(4-carbomethoxy-2-n-propylphenoxy)-3,4-methylenedioxyphenylacetamide;
N-(4-iso-propylbenzenesulfonyl)-α-(4-carboxy-2-n-propylphenoxy)-3,4-methylenedioxyphenylacetamide dipotassium salt;
α-(2-iso-butyl-4-carbomethoxyphenoxy)-3,4-methylenedioxy-phenylacetic acid;

N-(4-iso-propylbenzenesulfonyl)-α-(2-iso-butyl-4-carbomethoxyphenoxy)-3,4-methylenedioxyphenylacetamide;

N-(4-iso-propylbenzenesulfonyl)-α-(2-iso-butyl-4-carboxyphenoxy)-3,4-methylenedioxyphenylacetamide;

N-(4-iso-propylbenzenesulfonyl)-α-(2-n-propyl-4-methoxycarbonylphenoxy)-α-methyl-3,4-methylenedioxyphenylacetamide;

N-(4-iso-propylbenzenesulfonyl)-α-(2-n-propyl-4-carboxyphenoxy)-α-methyl-3,4-methylenedioxyphenylacetamide dipotassium salt;

N-(4-iso-propylbenzenesulfonyl)-α-(2-n-propyl-4-carboxamidophenoxy)-3,4-methylenedioxyphenylacetamide;

N-(4-iso-propylbenzenesulfonyl)-α-(2-n-propyl-4-hydroxymethylphenoxy)-3,4-methylenedioxyphenylacetamide;

N-(4-iso-propylbenzenesulfonyl)-α-(4-formyl-2-n-propylphenoxy)-3,4-methylenedioxyphenylacetamide;

α-(4-acetyl-2-n-propylphenoxy)-3,4-methylenedioxyphenylacetic acid;

N-(4-iso-propylbenzenesulfonyl)-α-(4-acetyl-2-n-propylphenoxy)-3,4-methylenedioxyphenylacetamide;

α-(2-n-propylphenoxy)-3,4-methylenedioxyphenylacetic acid

N-(4-iso-propylbenzenesulfonyl)-α-(2-n-propylphenoxy)-3,4-methylenedioxyphenylacetamide;

α-(3-methoxyphenoxy)-3,4-methylenedioxyphenylacetic acid;

α-(2-(2-hydroxyethyl)phenoxy)-3,4-methylenedioxyphenylacetic acid;

α-(2-(2-carbomethoxyethyl)phenoxy)-3,4-methylenedioxyphenylacetic acid;

α-(4-hydroxymethyl-2-n-propylphenoxy)-3,4-methylenedioxyphenylacetic acid;

α-(2-(2-hydroxyethyl)-2-n-propylphenoxy)-3,4-methylenedioxyphenyl-acetic acid;

N-(4-iso-propylbenzenesulfonyl)-α-(2-(2-carbomethoxyethyl)phenoxy)-3,4-methylenedioxyphenylacetamide;

N-(4-iso-propylbenzenesulfonyl)-α-(2-(2-carboxyethyl)phenoxy)-3,4-methylenedioxyphenylacetamide;

α-(2-(2-carboxyethyl)phenoxy)-3,4-methylenedioxyphenylacetic acid;

N-(4-iso-propylbenzenesulfonyl)-2-(4-carbomethoxy-2-n-propylphenoxy)-2-(5-methoxy-3,4-methylenedioxyphenyl)acetamide;

N-(4-iso-propylbenzenesulfonyl)-2-(4-carboxy-2-propylphenoxy)-2-(5-methoxy-3,4-methylenedioxyphenyl)acetamide;

N-(4-iso-propylbenzenesulfonyl)-2-(4-(N-(4-iso-propylbenzenesulfonyl)carboxamido)-2-propylphenoxy)-2-(5-methoxy-3,4-methylenedioxyphenyl)acetamide;

N-(4-iso-propylbenzenesulfonyl)-2-(4-carboxamido-2-propylphenoxy)-2-(5-methoxy-3,4-methylenedioxyphenyl)acetamide;

N-(4-iso-propylbenzenesulfonyl)-2-(4-(N-methylcarboxamido)-2-propylphenoxy)-2-(5-methoxy-3,4-methylenedioxyphenyl)acetamide;

N-(4-iso-propylbenzenesulfonyl)-2-(4-(N-2-hydroxyethylcarboxamido)-2-propylphenoxy)-2-(5-methoxy-3,4-methylenedioxyphenyl)acetamide;

N-(4-iso-propylbenzenesulfonyl)-2-(4-(N-morpholinylcarboxamido)-2-propylphenoxy)-2-(5-methoxy-3,4-methylenedioxyphenyl)acetamide;

N-(4-iso-propylbenzenesulfonyl)-2-(4-(N-3-methylbutylcarboxamido)-2-propylphenoxy)-2-(5-methoxy-3,4-methylenedioxyphenyl)acetamide;

N-(4-iso-propylbenzenesulfonyl)-2-(4-(N-carboxymethylcarboxamido)-2-propylphenoxy)-2-(5-methoxy-3,4-methylenedioxyphenyl)acetamide;

N-(4-iso-propylbenzenesulfonyl)-2-(4-(N-(L-Ala-OEt)carboxamido)-2-propylphenoxy)-2-(5-methoxy-3,4-methylenedioxyphenyl)acetamide;

N-(4-iso-propylbenzenesulfonyl)-2-(4-(N-2-ethoxycarbonylethyl-carboxamido)-2-propylphenoxy)-2-(5-methoxy-3,4-methylenedioxyphenyl)acetamide;

N-(4-iso-propylbenzenesulfonyl)-2-(4-(N-(L-Ala)carboxamido)-2-propylphenoxy)-2-(5-methoxy-3,4-methylenedioxyphenyl)acetamide;

N-(4-iso-propylbenzenesulfonyl)-2-(4-(N-2-carboxyethylcarboxamido)-2-propylphenoxy)-2-(5-methoxy-3,4-methylenedioxyphenyl)acetamide;

N-(4-iso-propylbenzenesulfonyl)-2-(4-(N-3-hydroxypropyl-carboxamido)-2-propylphenoxy)-2-(5-methoxy-3,4-methylenedioxyphenyl)acetamide;

N-(4-iso-propylbenzenesulfonyl)-2-(4-(N-tetrazol-5-ylcarboxamido)-2-propylphenoxy)-2-(5-methoxy-3,4-methylenedioxyphenyl)acetamide;

N-(4-iso-propylbenzenesulfonyl)-2-(4-(N-3-(morpholin-4-yl)propylcarboxamido)-2-propylphenoxy)-2-(5-methoxy-3,4-methylenedioxyphenyl)acetamide;

N-(4-iso-propylbenzenesulfonyl)-2-(4-(N-(D-Ala-OMe)carboxamido)-2-propylphenoxy)-2-(5-methoxy-3,4-methylenedioxyphenyl)acetamide;

N-(4-iso-propylbenzenesulfonyl)-2-(4-(N-(D-Ala)carboxamido)-2-propylphenoxy)-2-(5-methoxy-3,4-methylenedioxyphenyl)acetamide;

N-(4-iso-propylbenzenesulfonyl)-2-(4-(N-(3-carboxymethylpropyl)-carboxamido)-2-propylphenoxy)-2-(5-methoxy-3,4-methylenedioxyphenyl)acetamide;

N-(4-iso-propylbenzenesulfonyl)-2-(4-(N-(3-carboxypropyl)-carboxamido)-2-n-propylphenoxy)-2-(5-methoxy-3,4-methylenedioxyphenyl)acetamide;

N-(4-iso-propylbenzenesulfonyl)-2-(4-(N-iso-propylcarbamoyl)amino-2-n-propylphenoxy)-2-(3,4-methylenedioxyphenyl)acetamide;

α-(2-n-propyl-4-methylaminosulfonylphenoxy)-3,4-methylenedioxyphenylacetic acid; and N-(4-iso-propylbenzenesulfonyl)-α-(2-n-propyl-4-methylaminosulfonylphenoxy)-3,4-methylenedioxyphenylacetamide potassium salt;

N-(4-iso-propylbenzenesulfonyl)-α-[4-(cyanomethyl)-2-n-propylphenoxy)]-3,4-methylenedioxyphenylacetamide;

N-(4-iso-propylbenzenesulfonyl)-α-[4-(tetrazol-5-ylmethyl)-2-n-propylphenoxy)]-3,4-methylenedioxyphenylacetamide;

N-(4-iso-propylbenzenesulfonyl)-α-[N-(4-carbomethoxyphenylamino)]-3,4-methylenedioxyphenylacetamide;

N-(4-iso-propylbenzenesulfonyl)-α-[N-(4-carboxyphenylamino)]-3,4-methylenedioxyphenylacetamide;

N-(3-pyridinesulfonyl)-2-(4-carboxy-2-propylphenoxy)-2-(3,4-methylenedioxyphenyl)acetamide;

N-(2-methyl-3-quinolinesulfonyl)-2-(4-carboxy-2-propylphenoxy)-2-(3,4-methylenedioxyphenyl)acetamide;

N-(3-quinolinesulfonyl)-2-(4-carboxy-2-propylphenoxy)-2-(3,4-methylenedioxyphenyl)acetamide;

N-(4-hydroxy-3-pyridinesulfonyl)-2-(4-carboxy-2-propylphenoxy)-2-(3,4-methylenedioxyphenyl)acetamide;

N-(4-ethoxybenzenesulfonyl)-2-(4-carboxy-2-propylphenoxy)-2-(3,4-methylenedioxyphenyl)acetamide;

N-(4-carboxamidobenzenesulfonyl)-2-(4-carboxy-2-propylphenoxy)-2-(3,4-methylenedioxyphenyl)acetamide;

N-[4-(N,N-dimethylcarboxamido)benzenesulfonyl]-2-(4-carboxy-2-propylphenoxy)-2-(3,4-methylenedioxyphenyl)acetamide;

N-(4-ethylthio-3-pyridinesulfonyl)-2-(4-carboxy-2-propylphenoxy)-2-(3,4-methylenedioxyphenyl)acetamide;

N-(4-ethoxy-3-pyridinesulfonyl)-2-(4-carboxy-2-propylphenoxy)-2-(3,4-methylenedioxyphenyl)acetamide;
N-[(4-amino-2,5-dimethoxy)benzenesulfonyl]-2-(4-carboxy-2-propylphenoxy)-2-(3,4-methylenedioxyphenyl)acetamide;
N-[(2,5-dimethoxy)benzenesulfonyl]-2-(4-carboxy-2-propylphenoxy)-2-(3,4-methylenedioxyphenyl)acetamide;
N-[(3,4-dimethoxy)benzenesulfonyl]-2-(4-carboxy-2-propylphenoxy)-2-(3,4-methylenedioxyphenyl)acetamide;
N-[2-[5-(morpholin-4-yl)benzothiophene]sulfonyl ]-2-(4-carboxy-2-propylphenoxy)-2-(3,4-methylenedioxyphenyl)acetamide;
N-[[2-(4-methoxy)benzothiophene]sulfonyl]-2-(4-carboxy-2-propylphenoxy)-2-(3,4-methylenedioxyphenyl)acetamide;
N-[4-[2-(benzyloxycarbonylamino)ethyl]benzenesulfonyl]-2-(4-carboxy-2-propylphenoxy)-2-(3,4-methylenedioxyphenyl)acetamide;
N-[[2,5-dimethoxy-4-((N-iso-propylcarbamoyl)amino)]benzene-sulfonyl]-2-(4-carboxy-2-propylphenoxy)-2-(3,4-methylenedioxyphenyl)acetamide;
N-[(2,4-dimethoxy)benzenesulfonyl]-2-(4-carboxy-2-propylphenoxy)-2-(3,4-methylenedioxyphenyl)acetamide;
N-[(2,4,6-trimethoxy)benzenesulfonyl]-2-(4-carboxy-2-propylphenoxy)-2-(3,4-methylenedioxyphenyl)acetamide;
N-(8-quinolinesulfonyl)-2-(4-carboxy-2-propylphenoxy)-2-(3,4-methylenedioxyphenyl)acetamide;
N-(3-quinolinesulfonyl)-2-(4-carboxy-2-propylphenoxy)-2-(3,4-methylenedioxyphenyl)acetamide;
N-(8-quinolinesulfonyl)-2-(4-carboxamido-2-propylphenoxy)-2-(5-methoxy-3,4-methylenedioxyphenyl)acetamide;
N-(4-tert-butylbenzenesulfonyl)-2-(4-carboxamido-2-propylphenoxy)-2-(5-methoxy-3,4-methylenedioxyphenyl)acetamide;
N-(4-amino-2,5-dimethoxybenzenesulfonyl)-2-(4-carboxamido-2-propylphenoxy)-2-(5-methoxy-3,4-methylenedioxyphenyl)acetamide;
N-(4-iso-propylbenzenesulfonyl)-2-(4-carboxy-2-propylphenoxy)-2-(3,4-methylenedioxyphenyl)acetamide;
N-(4-iso-propylbenzenesulfonyl)-2-[[4-[N-[2-(carbethoxy)ethyl]-carbamoyl]]-2-propylphenoxy]-2-(3,4-methylenedioxyphenyl)acetamide;
N-(4-iso-propylbenzenesulfonyl)-2-[[4-[N-(2-carboxyethyl)carbamoyl]]-2-propylphenoxy]-2-(3,4-methylenedioxyphenyl)acetamide;
N-(4-iso-propylbenzenesulfonyl)-2-[[4-[N-(2-carbamoylethyl)-carbamoyl]]-2-propylphenoxy]-2-(3,4-methylenedioxyphenyl)acetamide;
N-(4-iso-propylbenzenesulfonyl)-2-[4-[N-(2,2,2-trifluoroethyl)-carbamoyl]-2-propylphenoxy]-2-(3,4-methylenedioxyphenyl)acetamide.

7. A compound which is:
N-(4-iso-propylbenzenesulfonyl)-α-(4-carboxy-2-n-propylphenoxy)-3,4-methylenedioxyphenylacetamide dipotassium salt.

8. A compound which is:
N-(8-quinolinylsulfonyl)-2-(4-carboxy-2-propylphenoxy)-3,4-methylenedioxyphenylacetamide.

9. A compound which is:
N-(4-dimethylaminobenzenesulfonyl)-2-(4-carboxy-2-n-propylphenoxy)-3,4-methylenedioxyphenylacetamide.

10. A compound which is:
(−)-N-(4-iso-propylbenzenesulfonyl)-α-(4-carboxy-2-n-propylphenoxy)-3,4-methylenedioxyphenylacetamide dipotassium salt.

11. A method of treating a condition in a mammal, the treatment of which is effected or facilitated by a decrease in endothelin mediated actions, comprising the administration, in an amount that is effective for antagonizing the effect of endothelin, of a compound of Formula I as recited in claim 1.

12. The method as recited in claim 11, wherein the condition is selected from the group consisting of: hypertension, pulmonary hypertension, Raynaud's disease, myocardial infarction, angina pectoris, congestive heart failure, acute renal failure, cerebral infarction, cerebral vasospasm, arteriosclerosis, vascular restenosis, asthma, benign prostatic hyperplasia, inflammatory bowel diseases, endotoxic shock, endotoxin-induced multiple organ failure or disseminated intravascular coagulation, or cyclosporin-induced renal failure or hypertension.

13. The method as recited in claim 12, wherein the condition is hypertension.

14. The method as recited in claim 13, wherein the mammal is human.

15. The method as recited in claim 12, wherein the condition is benign prostatic hyperplasia.

16. The method as recited in claim 15, wherein the mammal is human.

17. A method of treating cardiovascular disorders by administering to a person in need of such treatment a therapeutically effective amount of a compound of Formula I as recited in claim 1.

18. A method of treating benign prostatic hyperplasia by administering to a person in need of such treatment a therapeutically effective amount of an endothelin receptor antagonist.

19. The method as recited in claim 12 comprising a pharmaceutical composition of therapeutically effective amount of the compound of formula I and a pharmaceutically acceptable carrier.

20. A pharmaceutical composition useful in the treatment of hypertension which comprises a pharmaceutically acceptable carrier and a pharmaceutically effective amount of a compound of claim 1.

21. A method of treating a condition in a mammal, the treatment of which is effected or facilitated by a decrease in endothelin mediated actions, comprising the administration, in an amount that is effective for antagonizing the effect of endothelin, of a compound of Formula I as recited in claim 1 and a pharmaceutically acceptable carrier.

22. A pharmaceutical composition useful in the treatment of a condition which is effected or facilitated by a decrease in endothelin mediated actions, which comprises a pharmaceutically acceptable carrier and a pharmaceutically effective amount of a compound of claim 1.

23. A pharmaceutical composition useful in the treatment of renal failure which is effected or facilitated by a decrease in endothelin mediated actions, which comprises a pharmaceutically acceptable carrier and a pharmaceutically effective amount of a compound of claim 1.

* * * * *